US010786235B2

(12) United States Patent
Sorensen et al.

(10) Patent No.: US 10,786,235 B2
(45) Date of Patent: *Sep. 29, 2020

(54) METHOD AND APPARATUS FOR CLOSING A FISSURE IN THE ANNULUS OF AN INTERVERTEBRAL DISC, AND/OR FOR EFFECTING OTHER ANATOMICAL REPAIRS AND/OR FIXATIONS

(71) Applicant: Anchor Innovation Medical, Inc., Basking Ridge, NJ (US)

(72) Inventors: Peter Sorensen, Basking Ridge, NJ (US); Daniel Morgan, Basking Ridge, NJ (US); Bret A. Ferree, Cincinnati, OH (US); Christopher Runnells, Basking Ridge, NJ (US)

(73) Assignee: Anchor Innovation Medical, Inc., Basking Ridge, NJ (US)

( * ) Notice: Subject to any disclaimer, the term of this patent is extended or adjusted under 35 U.S.C. 154(b) by 124 days.

This patent is subject to a terminal disclaimer.

(21) Appl. No.: 15/827,322

(22) Filed: Nov. 30, 2017

(65) Prior Publication Data
US 2018/0085112 A1 Mar. 29, 2018

Related U.S. Application Data

(63) Continuation-in-part of application No. 14/461,992, filed on Aug. 18, 2014, now Pat. No. 9,949,734, (Continued)

(51) Int. Cl.
*A61B 17/04* (2006.01)
*A61N 1/05* (2006.01)
(Continued)

(52) U.S. Cl.
CPC ...... *A61B 17/0401* (2013.01); *A61B 17/0469* (2013.01); *A61B 17/0482* (2013.01);
(Continued)

(58) Field of Classification Search
CPC ............ A61B 17/0401; A61B 17/0409; A61B 17/0411; A61B 2017/0414;
(Continued)

(56) References Cited

U.S. PATENT DOCUMENTS 4,235,238 A 11/1980 Ogiu et al.
4,386,606 A * 6/1983 Tretinyak .......... A61M 5/31501
604/220

(Continued)

FOREIGN PATENT DOCUMENTS

DE 10340150 3/2005
WO WO 03/088876 10/2003
(Continued)

OTHER PUBLICATIONS

Deer, Timothy R. et al., The Appropriate Use of Neurostimulation: Avoidance and Treatment of Complications of Neurostimulation Therapies for the Treatment of Chronic Pain, Neuromodulation, vol. 17, 2014, pp. 571-598.

(Continued)

*Primary Examiner* — Katrina M Stransky
*Assistant Examiner* — Brigid K Byrd
(74) *Attorney, Agent, or Firm* — Pandiscio & Pandiscio

(57) ABSTRACT

Apparatus for attaching a suture to an object, the apparatus comprising: an anchor comprising a body having a distal end and a proximal end, and a vertical bore extending through the body substantially perpendicular to the longitudinal axis of the body; wherein the anchor further comprises a recess formed on one side of the body and a U-shaped slot formed on the opposing side of the body, whereby to form a flexible finger extending distally within the body, and further wherein the distal end of the finger is spaced from an opposing portion of the body; and wherein at least one of the flexible finger and the body comprises a cutout extending (Continued)

therethrough, with the cutout cooperating with the U-shaped slot and the recess so as to together form a suture loading hole extending through the body, with the suture loading hole being sized to receive a suture therein.

33 Claims, 93 Drawing Sheets

Related U.S. Application Data which is a continuation-in-part of application No. 14/068,406, filed on Oct. 31, 2013, now Pat. No. 9,433,404.

(60) Provisional application No. 61/866,955, filed on Aug. 16, 2013, provisional application No. 61/915,433, filed on Dec. 12, 2013, provisional application No. 61/984,431, filed on Apr. 25, 2014, provisional application No. 61/720,593, filed on Oct. 31, 2012, provisional application No. 62/427,879, filed on Nov. 30, 2016.

(51) Int. Cl.
 *A61B 17/34* (2006.01)
 *A61F 2/46* (2006.01)
 *A61F 2/44* (2006.01)
 *A61B 17/06* (2006.01)

(52) U.S. Cl.
 CPC ........ *A61B 17/3472* (2013.01); *A61F 2/4611* (2013.01); *A61N 1/0558* (2013.01); *A61B 2017/042* (2013.01); *A61B 2017/0409* (2013.01); *A61B 2017/0414* (2013.01); *A61B 2017/0417* (2013.01); *A61B 2017/0438* (2013.01); *A61B 2017/0446* (2013.01); *A61B 2017/0451* (2013.01); *A61B 2017/0456* (2013.01); *A61B 2017/0459* (2013.01); *A61B 2017/0464* (2013.01); *A61B 2017/0496* (2013.01); *A61B 2017/06052* (2013.01); *A61F 2/442* (2013.01); *A61F 2002/4435* (2013.01)

(58) Field of Classification Search
 CPC ..... A61B 2017/0404–0406; A61B 2017/0459; A61B 2017/0458; A61B 2017/0438
 See application file for complete search history.

(56) References Cited

U.S. PATENT DOCUMENTS

| | | |
|---|---|---|
| 4,413,359 A | 11/1983 | Akiyama et al. |
| 4,512,338 A | 4/1985 | Balko et al. |
| 4,663,358 A | 5/1987 | Hyon et al. |
| 4,669,473 A | 6/1987 | Richards et al. |
| 4,772,287 A | 9/1988 | Ray et al. |
| 4,834,757 A | 5/1989 | Brantigan |
| 4,904,260 A | 2/1990 | Ray et al. |
| 4,932,969 A | 6/1990 | Frey et al. |
| 5,015,255 A | 5/1991 | Kuslich |
| 5,041,129 A | 8/1991 | Hayhurst et al. |
| 5,047,055 A | 9/1991 | Bao et al. |
| 5,100,422 A | 3/1992 | Berguer et al. |
| 5,147,374 A | 9/1992 | Fernandez |
| 5,171,278 A | 12/1992 | Pisharodi |
| 5,192,326 A | 3/1993 | Bao et al. |
| 5,258,043 A | 11/1993 | Stone |
| 5,304,194 A | 4/1994 | Chee et al. |
| 5,342,394 A | 8/1994 | Matsuno et al. |
| 5,370,660 A | 12/1994 | Weinstein et al. |
| 5,390,683 A | 2/1995 | Pisharodi |
| 5,413,585 A | 5/1995 | Pagedas |
| 5,425,772 A | 6/1995 | Brantigan |
| 5,489,307 A | 2/1996 | Kuslich et al. |
| 5,540,715 A | 7/1996 | Katsaros et al. |
| 5,545,229 A | 8/1996 | Parsons et al. |
| 5,549,679 A | 8/1996 | Kuslich |
| 5,562,736 A | 10/1996 | Ray et al. |
| 5,645,597 A | 7/1997 | Krapiva |
| 5,681,310 A | 10/1997 | Yuan et al. |
| 5,702,454 A | 12/1997 | Baumgartner |
| 5,716,416 A | 2/1998 | Lin |
| 5,735,877 A | 4/1998 | Pagedas |
| 5,800,549 A | 9/1998 | Bao et al. |
| 5,800,550 A | 9/1998 | Sertich |
| 5,810,848 A | 9/1998 | Hayhurst |
| 5,824,093 A | 10/1998 | Ray et al. |
| 5,827,328 A | 10/1998 | Butterman |
| 5,879,366 A | 3/1999 | Shaw et al. |
| 5,916,225 A | 6/1999 | Kugel |
| 5,976,174 A | 11/1999 | Ruiz |
| 5,976,186 A | 11/1999 | Bao et al. |
| 6,015,428 A | 1/2000 | Pagedas |
| 6,024,754 A | 2/2000 | Engelson |
| 6,066,160 A | 5/2000 | Colvin et al. |
| 6,224,630 B1 | 5/2001 | Bao et al. |
| 6,235,107 B1 | 5/2001 | Yuan |
| 6,245,106 B1 | 6/2001 | Makker et al. |
| 6,245,107 B1 | 6/2001 | Ferree |
| 6,371,990 B1 | 4/2002 | Ferree |
| 6,402,750 B1 | 6/2002 | Atkinson et al. |
| 6,419,704 B1 | 7/2002 | Ferree |
| 6,423,065 B2 | 7/2002 | Ferree |
| 6,425,919 B1 | 7/2002 | Lambrecht |
| 6,454,804 B1 | 9/2002 | Ferree |
| 6,482,235 B1 | 11/2002 | Lambrecht et al. |
| 6,491,724 B1 | 12/2002 | Ferree |
| 6,508,839 B1 | 1/2003 | Lambrecht et al. |
| 6,579,291 B1 | 6/2003 | Keith et al. |
| 6,592,625 B2 | 7/2003 | Cauthen |
| 6,645,247 B2 | 11/2003 | Ferree |
| 6,648,919 B2 | 11/2003 | Ferree |
| 6,648,920 B2 | 11/2003 | Ferree |
| 6,652,585 B2 | 11/2003 | Lange |
| 6,689,125 B1 | 2/2004 | Keith et al. |
| 6,719,797 B1 | 4/2004 | Ferree |
| 6,723,335 B1 | 4/2004 | Moehlenbruck et al. |
| 6,733,531 B1 | 5/2004 | Trieu |
| 6,743,255 B2 | 6/2004 | Ferree |
| 6,755,863 B2 | 6/2004 | Ferree |
| 6,764,489 B2 | 7/2004 | Ferree |
| 6,805,695 B2 | 10/2004 | Keith et al. |
| 6,821,276 B2 | 11/2004 | Lambrecht et al. |
| 6,835,205 B2 | 12/2004 | Atkinson et al. |
| 6,843,790 B2 | 1/2005 | Ferree |
| 6,852,128 B2 | 2/2005 | Lange |
| 6,878,167 B2 | 4/2005 | Ferree |
| 6,883,520 B2 | 4/2005 | Lambrecht et al. |
| 6,936,072 B2 | 8/2005 | Lambrecht et al. |
| 6,969,404 B2 | 11/2005 | Ferree |
| 6,984,247 B2 | 1/2006 | Cauthen |
| 6,997,956 B2 | 2/2006 | Cauthen |
| 7,004,945 B2 | 2/2006 | Boyd et al. |
| 7,004,970 B2 | 2/2006 | Cauthen, III et al. |
| 7,033,393 B2 | 4/2006 | Gainor et al. |
| 7,033,395 B2 | 4/2006 | Cauthen |
| 7,041,138 B2 | 5/2006 | Lange |
| 7,048,764 B2 | 5/2006 | Ferree |
| 7,048,766 B2 | 5/2006 | Ferree |
| 7,052,516 B2 | 5/2006 | Cauthen, III et al. |
| 7,060,100 B2 | 6/2006 | Ferree et al. |
| 7,094,258 B2 | 8/2006 | Lambrecht et al. |
| 7,124,761 B2 | 10/2006 | Lambrecht et al. |
| 7,144,397 B2 | 12/2006 | Lambrecht et al. |
| 7,189,235 B2 | 3/2007 | Cauthen |
| 7,198,047 B2 | 4/2007 | Lambrecht et al. |
| 7,201,774 B2 | 4/2007 | Ferree |
| 7,201,775 B2 | 4/2007 | Gorensek et al. |
| 7,201,776 B2 | 4/2007 | Ferree et al. |
| 7,220,281 B2 | 5/2007 | Lambrecht et al. |
| 7,223,289 B2 | 5/2007 | Trieu et al. |
| 7,226,481 B2 | 6/2007 | Kuslich |

(56) References Cited

U.S. PATENT DOCUMENTS

| | | |
|---|---|---|
| 7,232,455 B2 | 6/2007 | Pedlick et al. |
| 7,258,700 B2 | 8/2007 | Lambrecht et al. |
| 7,267,688 B2 | 9/2007 | Ferree |
| 7,273,497 B2 | 9/2007 | Ferree |
| 7,338,525 B2 | 3/2008 | Ferree |
| 7,341,590 B2 | 3/2008 | Ferree |
| 7,435,260 B2 | 10/2008 | Ferree |
| 7,445,634 B2 | 11/2008 | Trieu |
| 7,465,318 B2 | 12/2008 | Sennett et al. |
| 7,500,978 B2 | 3/2009 | Gorensek et al. |
| 7,513,911 B2 | 4/2009 | Lambrecht et al. |
| 7,524,333 B2 | 4/2009 | Lambrecht et al. |
| 7,547,326 B2 | 6/2009 | Bhatnagar et al. |
| 7,553,329 B2 | 6/2009 | Lambrecht et al. |
| 7,553,330 B2 | 6/2009 | Lambrecht et al. |
| 7,556,649 B2 | 7/2009 | Moehlenbruck et al. |
| 7,556,650 B2 | 7/2009 | Collins et al. |
| 7,563,282 B2 | 7/2009 | Lambrecht et al. |
| 7,601,157 B2 | 10/2009 | Boyd et al. |
| 7,601,172 B2 | 10/2009 | Segal et al. |
| 7,608,108 B2 | 10/2009 | Bhatnagar et al. |
| 7,615,076 B2 | 11/2009 | Cauthen, III et al. |
| 7,632,313 B2 | 12/2009 | Bhatnagar et al. |
| 7,658,765 B2 | 2/2010 | Lambrecht et al. |
| 7,670,379 B2 | 3/2010 | Cauthen |
| 7,670,380 B2 | 3/2010 | Cauthen, III |
| 7,682,393 B2 | 3/2010 | Trieu et al. |
| 7,682,400 B2 | 3/2010 | Zwirkoski |
| 7,717,961 B2 | 5/2010 | Lambrecht et al. |
| 7,727,241 B2 | 6/2010 | Gorensek et al. |
| 7,740,659 B2 | 6/2010 | Zarda et al. |
| 7,740,660 B2 | 6/2010 | Collins et al. |
| 7,749,230 B2 | 7/2010 | Yuan et al. |
| 7,749,273 B2 | 7/2010 | Cauthen, III et al. |
| 7,749,275 B2 | 7/2010 | Lambrecht et al. |
| 7,753,941 B2 | 7/2010 | Keith et al. |
| 7,776,096 B2 | 8/2010 | Cauthen |
| 7,789,912 B2 | 9/2010 | Manzi et al. |
| 7,789,913 B2 | 9/2010 | Collins et al. |
| 7,799,833 B2 | 9/2010 | Boyd |
| 7,824,414 B2 | 11/2010 | Evans |
| 7,828,807 B2 | 11/2010 | LeHuec et al. |
| 7,828,850 B2 | 11/2010 | Cauthen, III et al. |
| 7,837,733 B2 | 11/2010 | Collins et al. |
| 7,846,208 B2 | 12/2010 | Cauthen, III et al. |
| 7,856,277 B1 | 12/2010 | Thacker et al. |
| 7,857,855 B2 | 12/2010 | Ferree |
| 7,857,857 B2 | 12/2010 | Kim |
| 7,867,278 B2 | 1/2011 | Lambrecht et al. |
| 7,879,097 B2 | 2/2011 | Lambrecht et al. |
| 7,879,102 B2 | 2/2011 | Slivka et al. |
| 7,879,103 B2 | 2/2011 | Gertzman et al. |
| 7,883,527 B2 | 2/2011 | Matsuura et al. |
| 7,887,551 B2 | 2/2011 | Bojarski et al. |
| 7,891,085 B1 | 2/2011 | Kuzma et al. |
| 7,901,430 B2 | 3/2011 | Matsuura et al. |
| 7,905,923 B2 | 3/2011 | Keith et al. |
| 7,909,879 B2 | 3/2011 | Cauthen |
| 7,914,553 B2 | 3/2011 | Ferree |
| 7,922,768 B2 | 4/2011 | Cauthen, III et al. |
| 7,935,147 B2 | 5/2011 | Wales |
| 7,947,080 B2 | 5/2011 | Ferree |
| 7,951,201 B2 | 5/2011 | Cauthen et al. |
| 7,953,498 B1 | 5/2011 | Carbunaru et al. |
| 7,959,679 B2 | 6/2011 | Lambrecht et al. |
| 7,959,863 B2 | 6/2011 | Yamamoto et al. |
| 7,963,991 B2 | 6/2011 | Conner et al. |
| 7,963,992 B2 | 6/2011 | Cauthen, III et al. |
| 7,972,337 B2 | 7/2011 | Boyajian et al. |
| 7,993,343 B2 | 8/2011 | Lin et al. |
| 7,993,345 B2 | 8/2011 | Yuan et al. |
| 7,998,208 B2 | 8/2011 | Kohm et al. |
| 7,998,213 B2 | 8/2011 | Lambrecht et al. |
| 8,007,500 B2 | 8/2011 | Lin et al. |
| 8,012,211 B2 | 9/2011 | Kuslich |
| 8,021,425 B2 | 9/2011 | Lambrecht |
| 8,025,698 B2 | 9/2011 | Lambrecht |
| 8,029,536 B2 | 10/2011 | Sorensen et al. |
| 8,048,618 B2 | 11/2011 | Luk et al. |
| 8,062,337 B2 | 11/2011 | Bruneau et al. |
| 8,070,818 B2 | 12/2011 | Bhatnagar et al. |
| 8,075,618 B2 | 12/2011 | Trieu et al. |
| 8,075,619 B2 | 12/2011 | Ferree |
| RE43,143 E | 1/2012 | Hayhurst |
| 8,092,536 B2 | 1/2012 | Ahrens et al. |
| 8,100,973 B2 | 1/2012 | Sennett et al. |
| 8,105,382 B2 | 1/2012 | Olmos et al. |
| 8,109,978 B2 | 2/2012 | Ferree |
| 8,114,161 B2 | 2/2012 | Evans et al. |
| 8,162,993 B2 | 4/2012 | Ferree |
| 8,163,019 B2 | 4/2012 | Bao et al. |
| 8,177,810 B2 | 5/2012 | Ferree |
| 8,177,847 B2 | 5/2012 | Bhatnagar et al. |
| 8,197,544 B1 | 6/2012 | Manzi et al. |
| 8,211,126 B2 | 7/2012 | Yeh et al. |
| 8,224,451 B2 | 7/2012 | Jaax et al. |
| 8,224,465 B2 | 7/2012 | Tantawi et al. |
| 8,231,678 B2 | 7/2012 | Lambrecht |
| 8,246,630 B2 | 8/2012 | Manzi et al. |
| 8,252,031 B2 | 8/2012 | Carls et al. |
| 8,257,437 B2 | 9/2012 | Lambrecht et al. |
| 8,267,939 B2 | 9/2012 | Cipoletti et al. |
| 8,267,943 B2 | 9/2012 | Ferree |
| 8,285,397 B2 | 10/2012 | Grandhe |
| 8,295,945 B1 | 10/2012 | Thacker et al. |
| 8,317,802 B1 | 11/2012 | Manzi et al. |
| 8,317,868 B2 | 11/2012 | Bhatnagar et al. |
| 8,337,528 B2 | 12/2012 | Ferree |
| 8,337,529 B2 | 12/2012 | Ferree |
| 8,337,557 B2 | 12/2012 | Collins et al. |
| 8,442,649 B2 | 5/2013 | McDonald |
| 8,449,614 B2 | 5/2013 | Ferree |
| 8,450,288 B2 | 5/2013 | Boyd |
| 8,470,043 B2 | 6/2013 | Schaller et al. |
| 8,494,626 B2 | 7/2013 | Moffitt et al. |
| 8,494,657 B2 | 7/2013 | Carbunaru et al. |
| 8,506,633 B2 | 8/2013 | Trieu |
| 8,535,338 B2 | 9/2013 | Wates et al. |
| 8,554,342 B2 | 10/2013 | Thacker et al. |
| 8,568,481 B2 | 10/2013 | Olmos et al. |
| 8,594,785 B2 | 11/2013 | Bradley |
| 8,594,807 B2 | 11/2013 | Colvin |
| 8,603,118 B2 | 12/2013 | Yeh et al. |
| 8,603,170 B2 | 12/2013 | Cipoletti et al. |
| 8,612,023 B2 | 12/2013 | McDonald et al. |
| 8,679,179 B2 | 3/2014 | Ferree |
| 8,679,180 B2 | 3/2014 | Ferree |
| 9,089,323 B2 | 7/2015 | Bonutti et al. |
| 9,433,404 B2 | 9/2016 | Ferree |
| 9,949,734 B2 | 4/2018 | Sorensen et al. |
| 2002/0019649 A1 | 2/2002 | Sikora et al. |
| 2002/0032155 A1 | 3/2002 | Ferree |
| 2002/0128713 A1 | 9/2002 | Ferree |
| 2002/0151896 A1 | 10/2002 | Ferree |
| 2002/0151981 A1 | 10/2002 | Ferree |
| 2002/0156532 A1 | 10/2002 | Ferree |
| 2002/0156533 A1 | 10/2002 | Ferree |
| 2002/0161367 A1 | 10/2002 | Ferree |
| 2002/0165542 A1 | 11/2002 | Ferree |
| 2003/0004574 A1 | 1/2003 | Ferree |
| 2003/0040796 A1 | 2/2003 | Ferree |
| 2003/0074076 A1 | 4/2003 | Ferree et al. |
| 2003/0078579 A1 | 4/2003 | Ferree |
| 2003/0167062 A1 | 9/2003 | Gambale et al. |
| 2003/0185812 A1 | 10/2003 | Ferree |
| 2003/0191536 A1 | 10/2003 | Ferree |
| 2003/0195631 A1 | 10/2003 | Ferree |
| 2003/0204260 A1 | 10/2003 | Ferree |
| 2004/0002734 A1 | 1/2004 | Fallin et al. |
| 2004/0010318 A1 | 1/2004 | Ferree |
| 2004/0092945 A1 | 5/2004 | Ferree |
| 2004/0093087 A1 | 5/2004 | Ferree et al. |
| 2004/0093092 A1 | 5/2004 | Ferree |
| 2004/0097980 A1 | 5/2004 | Ferree |

(56) References Cited

U.S. PATENT DOCUMENTS

| | | |
|---|---|---|
| 2004/0138753 A1 | 7/2004 | Ferree |
| 2004/0143334 A1 | 7/2004 | Ferree |
| 2004/0148028 A1 | 7/2004 | Ferree et al. |
| 2004/0186573 A1 | 9/2004 | Ferree |
| 2004/0186577 A1 | 9/2004 | Ferree |
| 2004/0220101 A1 | 11/2004 | Ferree |
| 2004/0220102 A1 | 11/2004 | Ferree |
| 2004/0225290 A1 | 11/2004 | Ferree |
| 2004/0230310 A1 | 11/2004 | Ferree |
| 2004/0236342 A1 | 11/2004 | Ferree et al. |
| 2004/0244806 A1 | 12/2004 | Ferree |
| 2004/0249459 A1 | 12/2004 | Ferree |
| 2004/0249461 A1 | 12/2004 | Ferree |
| 2004/0249465 A1 | 12/2004 | Ferree |
| 2004/0260396 A1 | 12/2004 | Ferree et al. |
| 2005/0033338 A1 | 2/2005 | Ferree |
| 2005/0065089 A1 | 3/2005 | Ferree |
| 2005/0165484 A1 | 7/2005 | Ferree |
| 2005/0251208 A1 | 11/2005 | Elmer et al. |
| 2005/0256582 A1 | 11/2005 | Ferree |
| 2005/0261773 A1 | 11/2005 | Ferree |
| 2005/0288711 A1* | 12/2005 | Fallin ............... A61B 17/0401 606/232 |
| 2006/0004454 A1 | 1/2006 | Ferree et al. |
| 2006/0052870 A1 | 3/2006 | Ferree |
| 2006/0058844 A1 | 3/2006 | White et al. |
| 2006/0064169 A1 | 3/2006 | Ferree |
| 2006/0212121 A1 | 9/2006 | Ferree |
| 2006/0217747 A1 | 9/2006 | Ferree |
| 2006/0235535 A1 | 10/2006 | Ferree et al. |
| 2006/0247665 A1 | 11/2006 | Ferree |
| 2006/0247778 A1 | 11/2006 | Ferree et al. |
| 2006/0258977 A1* | 11/2006 | Lee ................... A61M 5/31596 604/82 |
| 2007/0027471 A1 | 2/2007 | Ferree |
| 2007/0038231 A1 | 2/2007 | Ferree |
| 2007/0055375 A1 | 3/2007 | Ferree |
| 2007/0067040 A1 | 3/2007 | Ferree |
| 2007/0135920 A1 | 6/2007 | Ferree |
| 2007/0142839 A1 | 6/2007 | Ferree |
| 2007/0156152 A1 | 7/2007 | Ferree |
| 2007/0168043 A1 | 7/2007 | Ferree |
| 2007/0179530 A1* | 8/2007 | Tieu ................... A61B 17/0487 606/232 |
| 2007/0219558 A1 | 9/2007 | Deutsch |
| 2007/0276494 A1 | 11/2007 | Ferree |
| 2007/0288040 A1 | 12/2007 | Ferree |
| 2008/0014179 A1 | 1/2008 | Ferree |
| 2008/0027459 A1 | 1/2008 | Ferree |
| 2008/0097479 A1 | 4/2008 | Boehlke et al. |
| 2008/0125779 A1 | 5/2008 | Ferree |
| 2008/0125780 A1 | 5/2008 | Ferree |
| 2008/0140123 A1 | 6/2008 | Ferree |
| 2008/0140126 A1 | 6/2008 | Ferree |
| 2008/0195119 A1 | 8/2008 | Ferree |
| 2008/0195151 A1 | 8/2008 | Ferree |
| 2008/0221686 A1 | 9/2008 | Ferree |
| 2008/0228230 A1 | 9/2008 | Ferree |
| 2008/0243220 A1 | 10/2008 | Barker |
| 2008/0243256 A1 | 10/2008 | Ferree |
| 2008/0311114 A1 | 12/2008 | Ferree |
| 2009/0012591 A1 | 1/2009 | Barker |
| 2009/0024165 A1 | 1/2009 | Ferree |
| 2009/0216306 A1 | 8/2009 | Barker |
| 2009/0220571 A1 | 9/2009 | Eaton et al. |
| 2009/0222073 A1 | 9/2009 | Flowers et al. |
| 2010/0016889 A1 | 1/2010 | Ferree |
| 2010/0049248 A1 | 2/2010 | Del Rio et al. |
| 2010/0069957 A1 | 3/2010 | Abuzaina et al. |
| 2010/0174328 A1 | 7/2010 | Seaton, Jr. et al. |
| 2010/0318091 A1 | 12/2010 | Linares |
| 2011/0034975 A1 | 2/2011 | Ferree |
| 2011/0178602 A1 | 7/2011 | Ferree |
| 2011/0190893 A1 | 8/2011 | Ferree |
| 2011/0218573 A1 | 9/2011 | Ferree |
| 2011/0264224 A1 | 10/2011 | Ferree |
| 2011/0288618 A1 | 11/2011 | Glen et al. |
| 2011/0288647 A1 | 11/2011 | Ferree |
| 2011/0295276 A1 | 12/2011 | Wales et al. |
| 2012/0071896 A1 | 3/2012 | Ferree |
| 2012/0089162 A1 | 4/2012 | Ferree |
| 2012/0116514 A1 | 5/2012 | Kuslich et al. |
| 2012/0203302 A1 | 8/2012 | Moffitt et al. |
| 2012/0277766 A1 | 11/2012 | Ferree |
| 2012/0283835 A1 | 11/2012 | Bentley et al. |
| 2013/0013005 A1 | 1/2013 | Ferree |
| 2013/0131728 A1 | 5/2013 | Ferree |
| 2013/0178899 A1 | 7/2013 | Chang et al. |
| 2013/0226271 A1 | 8/2013 | Ferree |
| 2013/0268040 A1 | 10/2013 | Barker |
| 2013/0274809 A1 | 10/2013 | Ferree |
| 2013/0317585 A1 | 11/2013 | Barker |
| 2013/0317587 A1 | 11/2013 | Barker |
| 2014/0005786 A1 | 1/2014 | Lambrecht |
| 2014/0031864 A1* | 1/2014 | Jafari ............... A61B 17/0487 606/232 |
| 2015/0051621 A1* | 2/2015 | Sorensen ........... A61B 17/0482 606/144 |
| 2015/0374367 A1 | 12/2015 | Hall et al. |
| 2016/0206314 A1 | 7/2016 | Scheib et al. |

FOREIGN PATENT DOCUMENTS

| | | |
|---|---|---|
| WO | WO 2006/028986 | 3/2006 |
| WO | WO 2007/001936 | 1/2007 |
| WO | WO 2010/132310 | 11/2010 |
| WO | WO 2011/057394 | 5/2011 |
| WO | WO 2012/135141 | 10/2012 |
| WO | WO 2015/024013 | 2/2015 |

OTHER PUBLICATIONS

Gazelka, Halena M. et al., Incidence of Clinically Significant Percutaneous Spinal Cord Stimulator Lead Migration, Neuromodulation, vol. 18, 2015, pp. 123-125.

Geurts, José W. et al., Spinal Cord Stimulation for Complex Regional Pain Syndrome Type I: A Prospective Cohort Study With Long-Term Follow-Up, Neuromodulation, vol. 16, 2013, pp. 523-529.

Henderson, Jaimie M. et al., Prevention of Mechanical Failures in Implanted Spinal Cord Stimulation Systems, Neuromodulation, vol. 9, No. 3, 2006, pp. 183-191.

Justiz III, Rafael et al., A Case Series Review of Spinal Cord Stimulation Migration Rates With a Novel Fixation Device, Neuromodulation, vol. 17, 2014, pp. 37-41.

Kumar, Krishna et al., Financial impact of spinal cord stimulation on the healthcare budget: a comparative analysis of costs in Canada and the United States, J Neurosurg Spine, vol. 10, 2009, pp. 564-573.

Kumar, Krishna et al., Spinal cord stimulation in treatment of chronic benign pain: challenges in treatment planning and present status, a 22-year experience, Neurosurgery, vol. 58, No. 3, 2006, pp. 481-496.

Medtronic Product Performance Report. http://professional.medtronic.com/ppr/spinal-cord-stimulation-systems/index.htm#.WLx9NDvyuUk.

Mekhail, Nagy A. et al., Retrospective review of 707 Cases of Spinal Cord Stimulation: Indications and Complications, Pain Practice, vol. 11, No. 2, 2011, pp. 148-153.

North, R. B. et al., Questions about Turner et al. Spinal cord stimulation for failed back surgery syndrome: outcomes in a worker's compensation setting, Pain, vol. 151, 2010, pp. 550-557.

Osborne, Michael D. et al., Spinal Cord Stimulator—Trial Lead Migration Study, Pain Medicine, vol. 12, 2011, pp. 204-208.

Turner, Judith A. et al., Spinal cord stimulation for patients with failed back surgery syndrome or complex regional pain syndrome: a systematic review of effectiveness and complications, Pain, vol. 108, 2004, pp. 137-147.

(56) References Cited

OTHER PUBLICATIONS

Verrils, Paul et al., A review of spinal cord stimulation systems for chronic pain, Journal of Pain Research, vol. 9, 2016, pp. 481-492.
Cameron, Tracy, Safety and efficacy of spinal cord stimulation for the treatment of chronic pain: a 20-year literature review, J Neurosurg (Spine 3), vol. 100, 2004, pp. 254-267.
North, Richard B. et al., Spinal Cord Stimulation for Chronic, Intractable Pain: Experience over Two Decades Clinical Study, Neurosurgery, vol. 32, No. 3, Mar. 1993, pp. 384-399.
Attaway, Stephen W., The Mechanics of Friction in Rope Rescue, International Technical Rescue Symposium (ITRS), 1999.
Boston Scientific, Clik™ Anchor, Precision Spinal Cord Stimulation System, 2011.
Boston Scientific, Percutaneous Leads Directions For Use, 2012.
Boston Scientific, Precision Spectra™ System Information For Prescribers, 2012.
Boston Scientific, Precision Spectra™: Innovation Focused On Pain Relief, 2013, http://hcp.controlyourpain.com/products-helping-patients/precision-spectra/.
Boston Scientific, Surgical Leads Directions For Use, 2012.
Mehta, Vishal M. et al., Cyclic Testing of 3 All-Inside Meniscal Repair Devices, The American Journal of Sports Medicine vol. X, No. X, 2009 pp. 1-5.
Ostrovsky, Gene, Boston Scientific's Clik Anchor for Faster, Easier SCS Lead Placements, Mar. 2011, http://www.medgadget.com/2011/03/boston_scientifics_clik_anchor_for_faste.
Yeung, Anthony T., YESS Transforaminal Endoscopic Technique, Desert Institute for Spine Care, Workshop, 2009.

\* cited by examiner

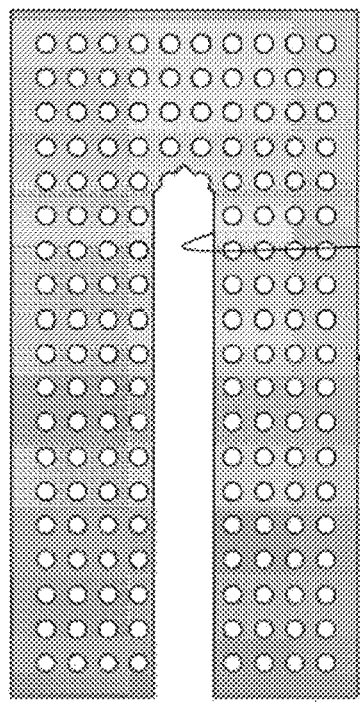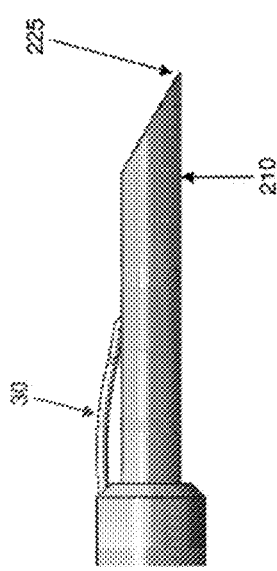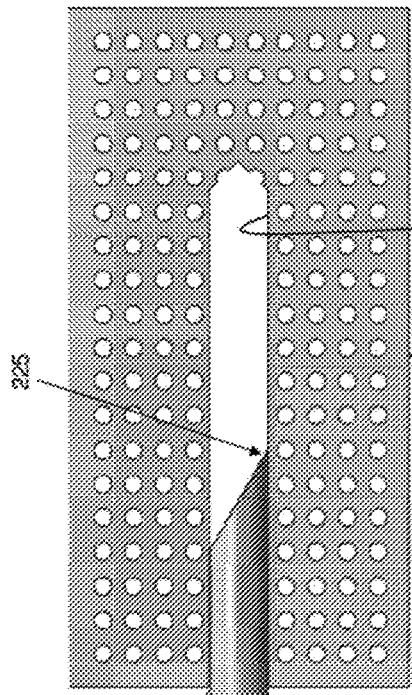
FIG. 34 Hole drilled orientating inserter.
FIG. 35 Place inserter into prepared hole.

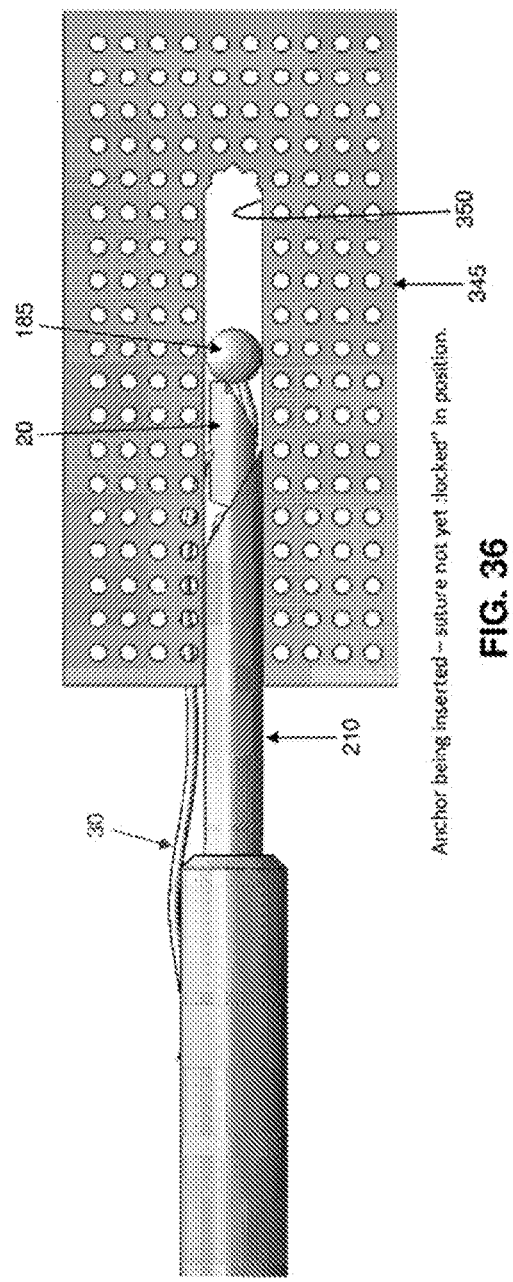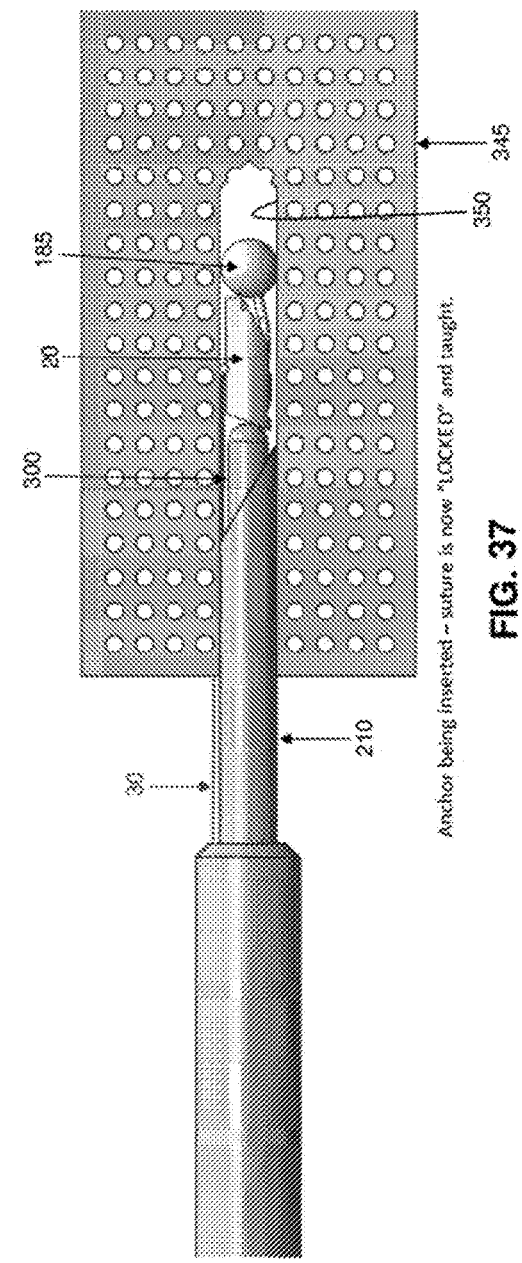

Continued advancement of plunger forces anchor ride up on the ball initiating rotation of anchor.

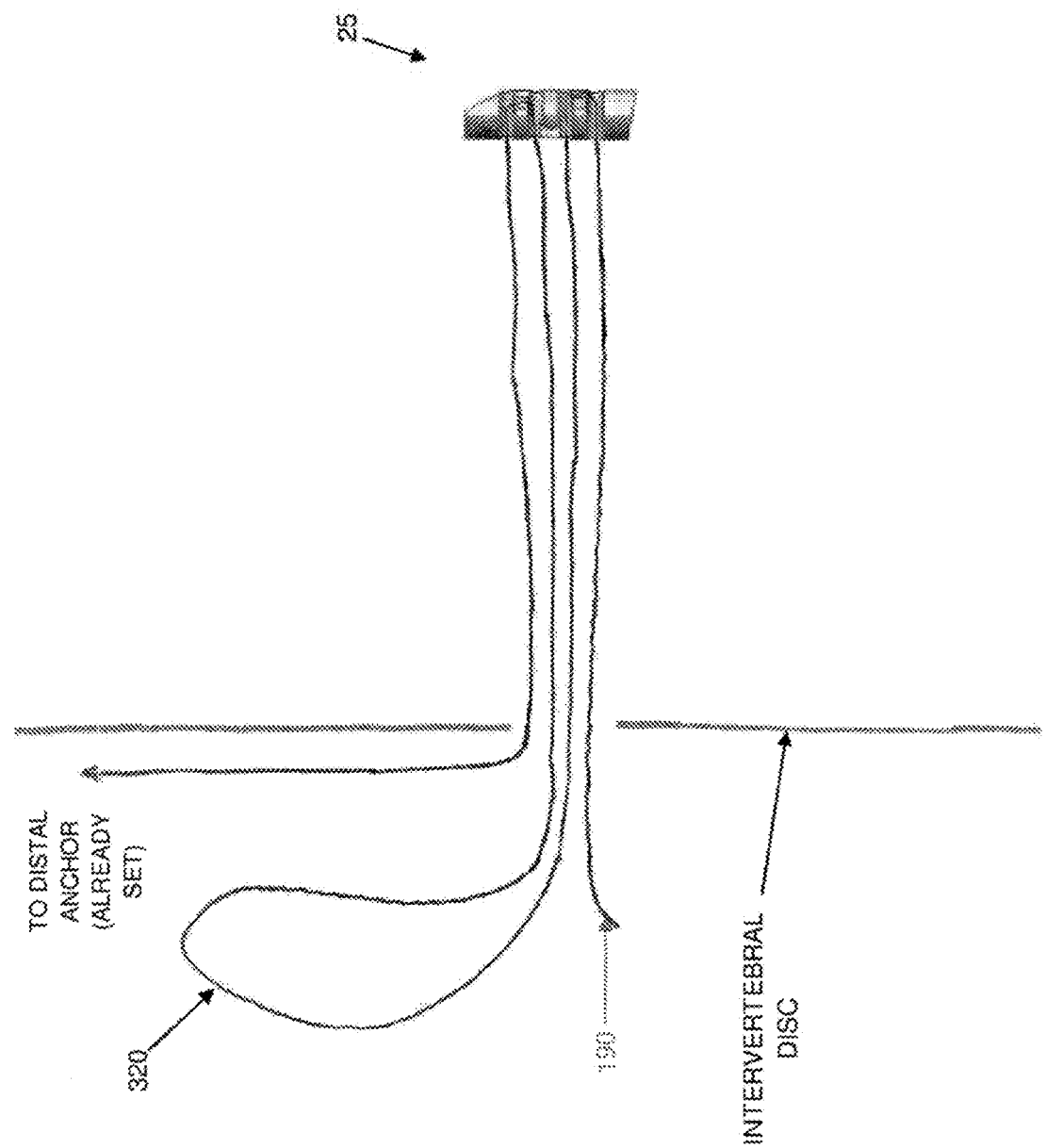

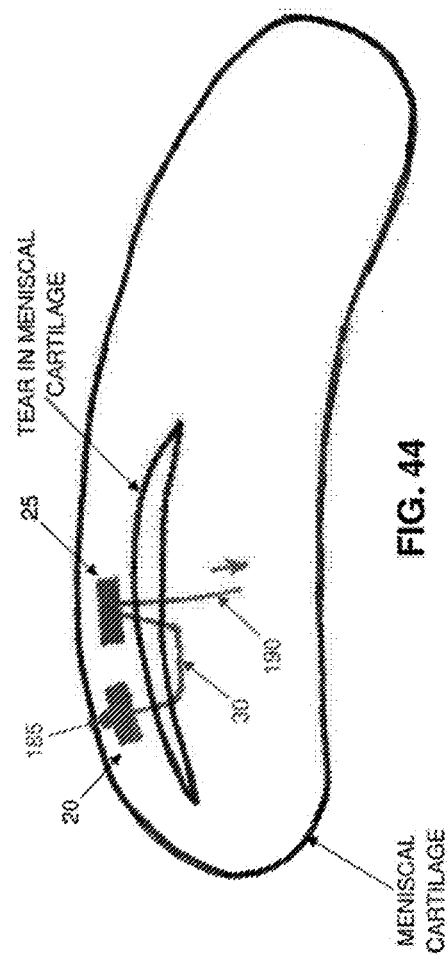
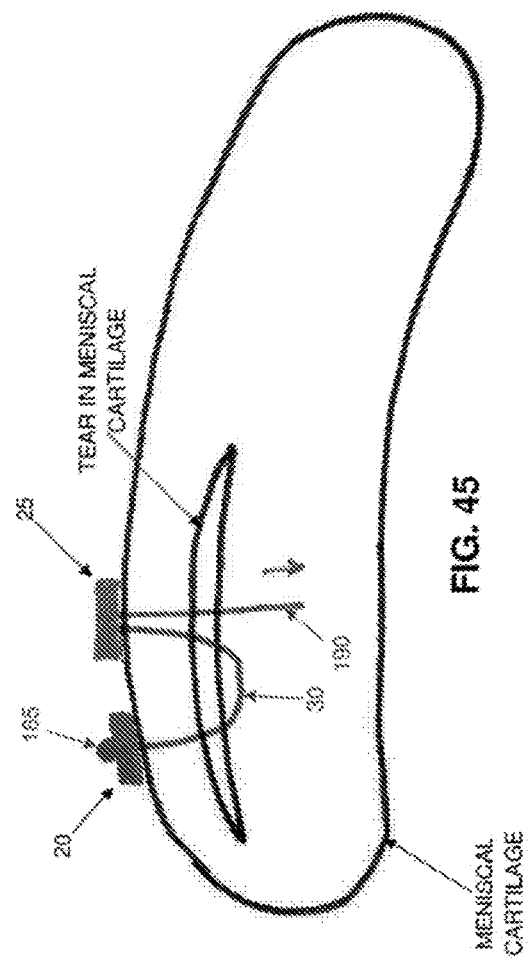

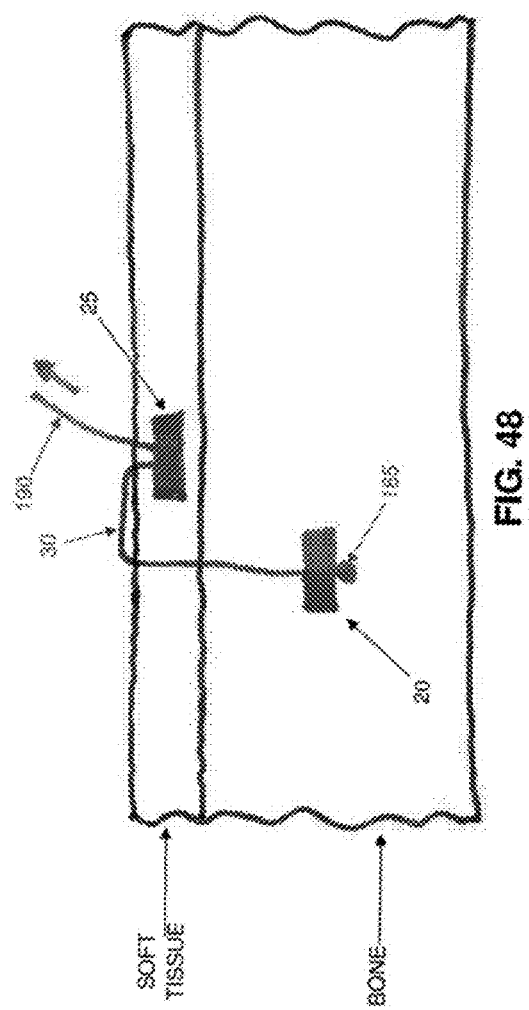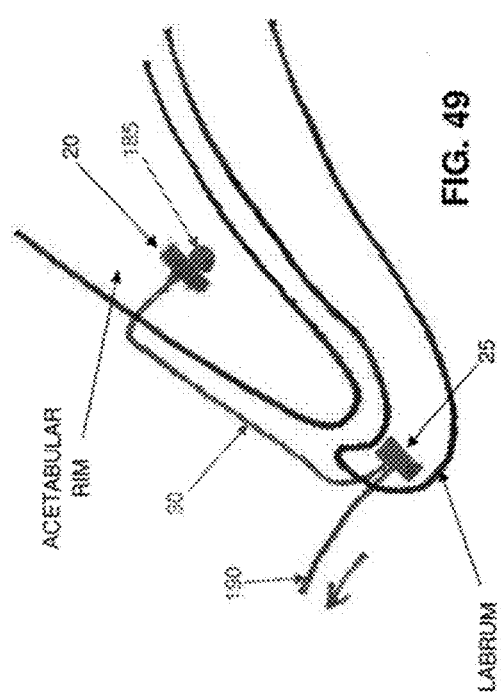

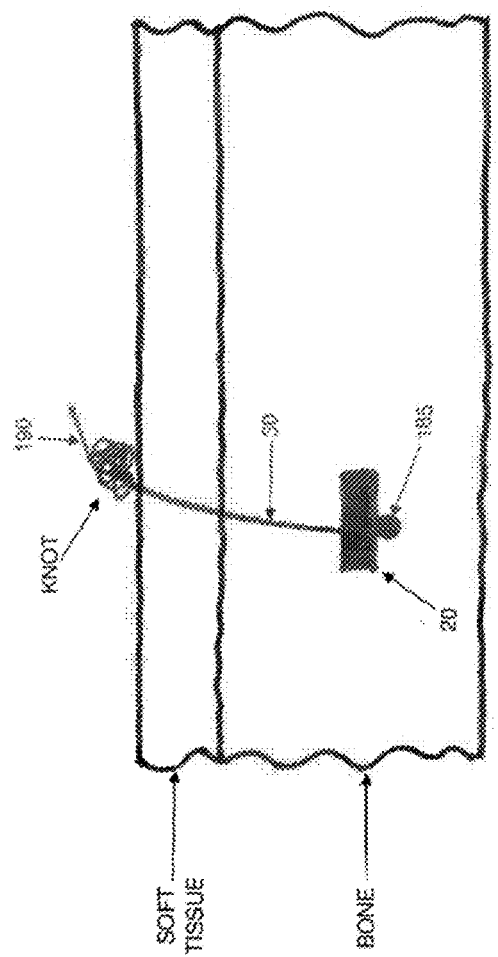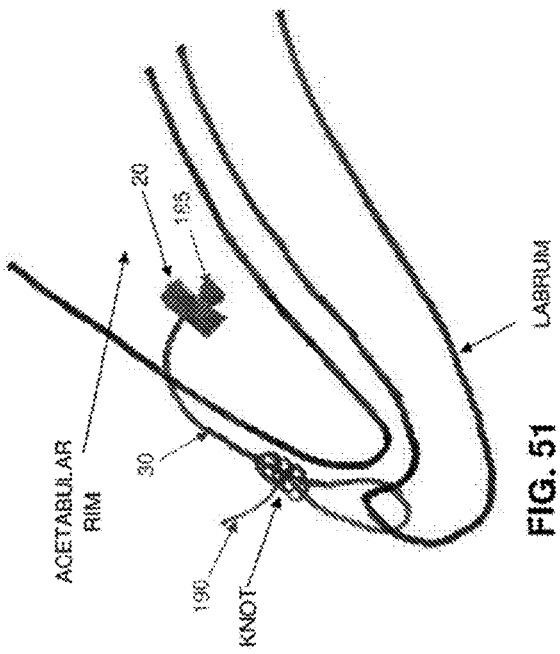

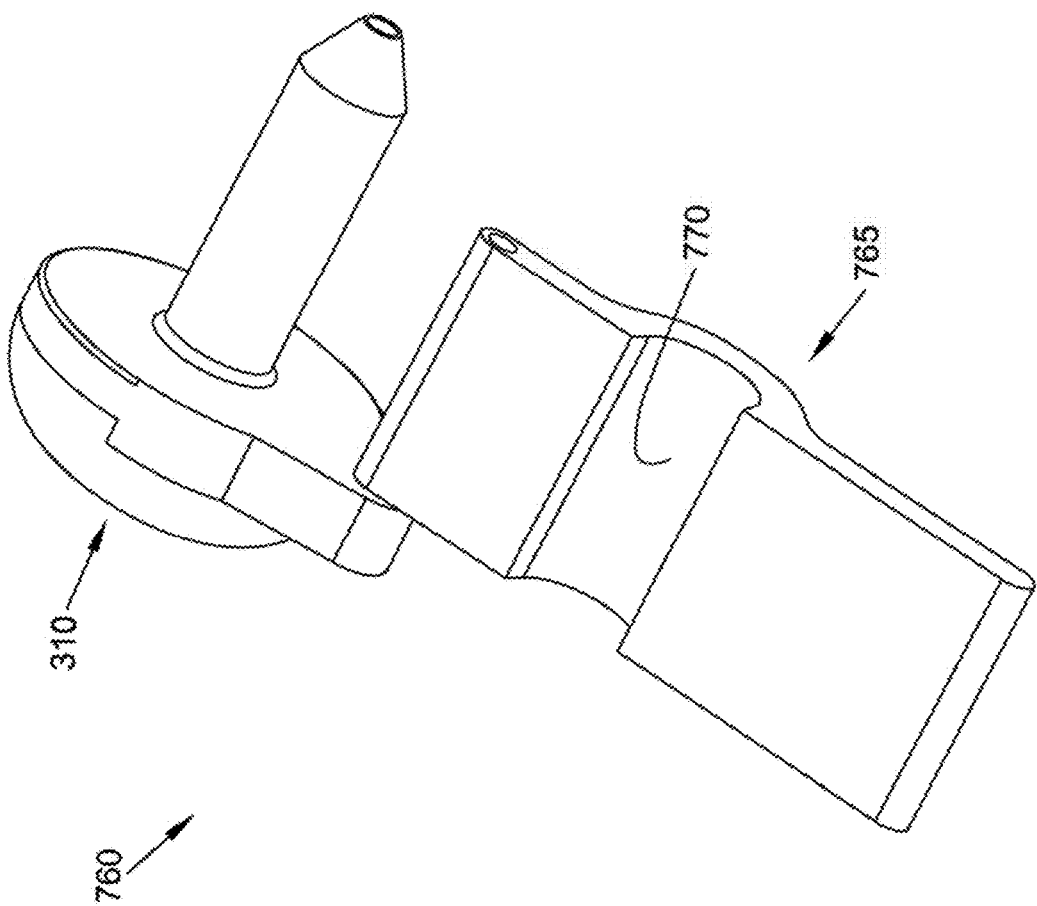

METHOD AND APPARATUS FOR CLOSING A FISSURE IN THE ANNULUS OF AN INTERVERTEBRAL DISC, AND/OR FOR EFFECTING OTHER ANATOMICAL REPAIRS AND/OR FIXATIONS

REFERENCE TO PENDING PRIOR PATENT APPLICATIONS

This patent application:

(1) is a continuation-in-part of prior U.S. patent application Ser. No. 14/461,992, filed Aug. 18, 2014 by Suture Concepts Inc. and Peter Sorensen et al. for METHOD AND APPARATUS FOR CLOSING A FISSURE IN THE ANNULUS OF AN INTERVERTEBRAL DISC, AND/OR FOR EFFECTING OTHER ANATOMICAL REPAIRS AND/OR FIXATIONS, which patent application in turn:

(i) claims benefit of prior U.S. Provisional Patent Application Ser. No. 61/866,955, filed Aug. 16, 2013 by Suture Concepts Inc. and Peter Sorensen et al. for METHOD AND APPARATUS FOR CLOSING A FISSURE IN THE ANNULUS OF AN INTERVERTEBRAL DISC, AND/OR FOR EFFECTING OTHER ANATOMICAL REPAIRS AND/OR FIXATIONS (ii) claims benefit of prior U.S. Provisional Patent Application Ser. No. 61/915,433, filed Dec. 12, 2013 by Suture Concepts Inc. and Peter Sorensen et al. for METHOD AND APPARATUS FOR CLOSING A FISSURE IN THE ANNULUS OF AN INTERVERTEBRAL DISC, AND/OR FOR EFFECTING OTHER ANATOMICAL REPAIRS AND/OR FIXATIONS (iii) claims benefit of prior U.S. Provisional Patent Application Ser. No. 61/984,431, filed Apr. 25, 2014 by Suture Concepts Inc. and Peter Sorensen et al. for METHOD AND APPARATUS FOR CLOSING A FISSURE IN THE ANNULUS OF AN INTERVERTEBRAL DISC, AND/OR FOR EFFECTING OTHER ANATOMICAL REPAIRS AND/OR FIXATIONS and (iv) is a continuation-in-part of prior U.S. patent application Ser. No. 14/068,406, filed Oct. 31, 2013 by Suture Concepts Inc. and Bret A. Ferree for METHOD AND APPARATUS FOR CLOSING FISSURES IN THE ANNULUS FIBROSUS, which in turn claims benefit of:

(a) prior U.S. Provisional Patent Application Ser. No. 61/720,593, filed Oct. 31, 2012 by Bret A. Ferree for METHOD AND APPARATUS FOR CLOSING FISSURES IN THE ANNULUS FIBROSUS; and (2) claims benefit of prior U.S. Provisional Patent Application Ser. No. 62/427,879, filed Nov. 30, 2016 by Suture Concepts Inc. and Peter Sorensen et al. for METHOD AND APPARATUS FOR CLOSING A FISSURE IN THE ANNULUS OF AN INTERVERTEBRAL DISC, AND/OR FOR EFFECTING OTHER ANATOMICAL REPAIRS AND/OR FIXATIONS.

The seven (7) above-identified patent applications are hereby incorporated herein by reference.

FIELD OF THE INVENTION

This invention relates to the treatment of degenerative disc disease in general, and more particularly to methods and apparatus for closing fissures in the annulus of an intervertebral disc. This invention also relates to methods and apparatus for effecting other anatomical repairs and/or fixations.

BACKGROUND OF THE INVENTION

The human spine is a column of articulating vertebrae separated by intervertebral discs. It provides support for the torso, and houses and protects the spinal cord in its spinal canal.

The human intervertebral disc is an oval-shaped to kidney-shaped structure of variable size depending on its location in the spine. The outer portion of the disc is known as the annulus fibrosus (or anulus fibrosus, annulus fibrosis, anulus fibrosis) or simply "the annulus". The inner portion of the disc is known as the nucleus pulposis or simply "the nucleus".

The annulus is made up of ten to twenty collagen fiber lamellae. The collagen fibers within a given lamella extend parallel to one another. Successive lamellae have their collagen fibers oriented in alternating directions. About 48 percent of the lamellae are incomplete, but this percentage varies with location and it increases with age. On average, the collagen fibers of a given lamella lie at an angle of about sixty degrees to the vertebral axis line, but this too varies with location. The orientations of the lamellae serve to control vertebral motion (i.e., one half of the lamellae tighten to check motion when the vertebra above or below the disc are turned in either direction).

The annulus contains the nucleus. The nucleus has a consistency generally similar to that of crabmeat. The nucleus serves to transmit and dampen axial loads. A high water content (approximately 70-80 percent) assists the nucleus in this function. The water content has a diurnal variation. The nucleus absorbs water while a person lies recumbent. Activity generates increased axial loads which squeeze water from the disc. The nucleus comprises roughly 50 percent of the entire disc. The nucleus contains cells (chondrocytes and fibrocytes) and proteoglycans (chondroitin sulfate and keratin sulfate). The cell density in the nucleus is on the order of 4,000 cells per microliter.

The intervertebral disc changes, or "degenerates", with age. As a person ages, the water content of the disc falls from approximately 85 percent at birth to approximately 70 percent in the elderly. The ratio of chondroitin sulfate to keratin sulfate decreases with age, while the ratio of chondroitin 6 sulfate to chondroitin 4 sulfate increases with age. The distinction between the annulus and the nucleus decreases with age. Generally, disc degeneration is painless.

Premature or accelerated disc degeneration is known as degenerative disc disease. A large portion of patients suffering from chronic lower back pain are thought to have this condition. As the disc degenerates, the nucleus and annulus functions are compromised. The nucleus becomes thinner and less able to handle compressive loads. The annulus fibers become redundant as the nucleus shrinks. The redundant annular fibers are less effective in controlling vertebral motion. This disc pathology can result in (i) tears of the annulus (both "full-thickness" tears and "partial-thickness" tears) as abnormal loads are transmitted to the annulus and the annulus is subjected to excessive motion between vertebrae, and (ii) disc herniation (i.e., extrusion of the nucleus) through complete (i.e., full-thickness) annular tears. Degenerative disc disease is frequently the cause of substantial pain for a patient.

Current surgical treatments for disc degeneration are generally "destructive", in the sense that they generally involve the removal or destruction of disc tissue.

One group of procedures, which includes microlumbar discectomy, removes the nucleus or a portion of the nucleus.

A second group of procedures destroys nuclear material. This group includes Chymopapin (an enzyme) injection, laser discectomy, and thermal therapy (i.e., heat treatment to denature proteins in the nucleus).

The foregoing two groups of procedures compromise the nucleus of the treated disc, and may exacerbate fissures in the annulus while accessing the nucleus.

A third group of procedures, which includes spinal fusion procedures, either removes the disc or effectively eliminates the disc's function by connecting together two or more vertebrae, e.g., by "fusing" the vertebrae together with bone. However, such spinal fusion procedures transmit additional stress to the adjacent discs, which typically results in premature degeneration of the adjacent discs over time.

In general, the "destructive" nature of current surgical treatments for disc degeneration can provide substantial pain relief for the patient, but it can also lead to further disc degeneration over time, which can result in new pain for the patient. By way of example but not limitation, procedures to remove the nucleus or a portion of the nucleus, and procedures to destroy nuclear material, compromise nucleus function and may exacerbate fissures in the annulus while accessing the nucleus, thereby leading to further disc degeneration. By way of further example but not limitation, spinal fusion procedures can induce premature disc degeneration in adjacent intervertebral discs.

Ideally, disc herniation (i.e., the extrusion of nucleus through full-thickness annular tears) should be treated by closing the fissures in the annulus. However, in practice, this is difficult to achieve.

By way of example but not limitation, it is difficult to close fissures in the annulus by conventional suturing. For one thing, the annulus is tough and thick and does not lend itself to manual suturing, particularly given the limited access corridors often imposed on the surgeon. For another thing, the loads imposed on the nucleus are large, so that inadequate closure of the fissures can lead to subsequent recurrence of the fissures. Furthermore, the area surrounding the intervertebral disc is crowded with delicate structures (e.g., nerves), so that the use of knots to secure suture can be problematic.

By way of further example but not limitation, it is difficult to close fissures in the annulus using conventional toggle anchors. More particularly, in U.S. Pat. No. 7,004,970, issued Feb. 28, 2006 to Cauthen III et al., there is disclosed a system for closing fissures in the annulus, wherein the system comprises first and second conventional toggle anchors connected together by filament, and wherein the filament comprises a cinch knot and a cinch line. See, for example, FIGS. 61A, 61B, 62A-62D and 63 of Cauthen III et al. With this system, the first conventional toggle anchor is passed through the annulus and into the nucleus on a first side of a fissure, the second conventional toggle anchor is passed through the annulus and into the nucleus on a second side of the fissure, and then the cinch line is pulled to draw together the two conventional toggle anchors and thereby close the fissure. However, this system suffers from significant drawbacks. First, it is difficult to reliably toggle conventional toggle anchors within the nucleus, which can result in poor setting of the conventional toggle anchors within the intervertebral disc and hence inadequate closure of the fissure. Second, it is difficult to set the cinch knot close to the surface of the annulus, particularly given the limited access corridors often imposed on the surgeon, which can result in inadequate closure of the fissure and interference with the delicate structures around the intervertebral disc, e.g., nerves, etc. Third, the cinch knot can easily slip, thereby undermining the closure of the fissure. For this reason, systems using conventional toggle anchors have achieved limited success in closing fissures within the annulus.

In Cauthen III et al., there is also disclosed a knotless system for tensioning the filament between the two conventional toggle anchors, wherein enlargements are formed on the filament and are pulled through a narrow opening formed on one of the conventional toggle anchors so as to provide a knotless ratchet securement. However, this knotless ratchet securement is limited to preset tension levels (i.e., it is not continuously adjustable) and has limited holding power, among other things.

Thus there is a need for a new and improved method and apparatus for closing fissures in the annulus of an intervertebral disc, whereby to treat degenerative disc disease.

In addition to the foregoing, in many other situations it may be necessary and/or desirable to effect anatomical repairs and/or fixations.

By way of example but not limitation, two pieces of soft tissue may need to be held in apposition to one another to effect a repair (e.g., so as to close an incision in the skin), or two pieces of cartilage may need to be held in apposition to one another to effect a repair (e.g., so as to close a tear in meniscal cartilage), or two pieces of bone may need to be held in apposition to one another so as to effect a repair (e.g., so as to fuse together bone).

By way of further example but not limitation, a piece of soft tissue may need to be held in apposition to bone to effect a repair (e.g., so as to attach soft tissue to bone), or a piece of cartilage may need to be held in apposition to bone to effect a repair (e.g., so as to attach labrum to bone or to attach meniscal cartilage to bone).

By way of further example but not limitation, a prosthesis may need to be held in apposition to soft tissue or bone, or soft tissue or bone may need to be held in apposition to a prosthesis, and/or any first object may need to be held in apposition to any second object.

In these and other situations, it would also be advantageous to provide a new and improved method and apparatus for effecting anatomical repairs and/or fixations.

SUMMARY OF THE INVENTION

The present invention provides a new and improved method and apparatus for closing fissures in the annulus of an intervertebral disc, whereby to treat degenerative disc disease.

The present invention also provides a new and improved method and apparatus for effecting other anatomical repairs and/or fixations.

More particularly, among other things, the present invention facilitates the reconstruction of the annulus by providing a novel method and apparatus for closing fissures in the annulus of an intervertebral disc. Among other things, such reconstruction prevents recurrent herniation following a microlumbar discectomy. The invention may also be used in the treatment of herniated discs, annular tears of the disc, and/or other disc degeneration, while enabling surgeons to preserve (or even augment or replace) the contained nucleus. The method and apparatus of the present invention may be used to treat discs throughout the spine, including the cervical, thoracic, and lumbar spines of humans and animals.

Preferred embodiments of the present invention include a flexible longitudinal fixation component (e.g., a filament) extending across a soft tissue defect, such as a fissure in the annulus. A pair of transverse anchor components (e.g., bar anchors), selectively connected to the flexible longitudinal fixation component, are preferably placed behind an inner layer of the annulus on opposite sides of the fissure, so as to anchor the flexible longitudinal fixation component to the annulus, with the flexible longitudinal fixation component extending axially through the annulus and laterally across the fissure so as to hold the fissure closed, whereby to prevent nucleus material from passing out the fissure and pressing on the adjacent nerves, including the spinal cord. Significantly, with the present invention, the transverse anchor components can be passed through the annulus and into the nucleus of the intervertebral disc using a direct "needle plunge" action, which facilitates passage through the tough, thick annulus, and which is highly compatible with the limited access corridors often imposed on the surgeon. Furthermore, the present invention allows the tension of the flexible longitudinal fixation component to be adjusted as necessary so as to effect proper fissure closure, and then set in place without requiring the use of knots.

And the flexible longitudinal fixation component (e.g., the filament) may be anchored to one of the upper and lower vertebral bodies adjacent to the intervertebral disc being treated.

In one preferred form of the present invention, two novel transverse anchor components (e.g., bar anchors) are provided. One novel anchor component (sometimes hereinafter referred to as the distal anchor) is provided with an associated inserter and the two, in conjunction with the flexible longitudinal fixation component (e.g., filament) provide enhanced toggling of the anchor component within dense structures such as a vertebral body and/or an intervertebral disc. The second novel anchor component (sometimes hereinafter referred to as the proximal anchor) is provided with novel means for knotlessly securing the flexible longitudinal fixation component to that anchor component, whereby to allow the tension of the flexible longitudinal fixation component to be reliably set between the two anchor components without requiring the use of knots.

The present invention may also be used to effect other anatomical repairs and/or fixations.

By way of example but not limitation, the present invention may be used to hold two pieces of soft tissue in apposition to one another to effect a repair (e.g., so as to close an incision in the skin), or the present invention may be used to hold two pieces of cartilage in apposition to one another to effect a repair (e.g., so as to close a tear in meniscal cartilage), or the present invention may be used to hold two pieces of bone in apposition to one another so as to effect a repair (e.g., so as to fuse together bone).

By way of further example but not limitation, the present invention may be used to hold a piece of soft tissue in apposition to bone to effect a repair (e.g., so as to attach soft tissue to bone), or the present invention may be used to hold a piece of cartilage in apposition to bone to effect a repair (e.g., so as to attach labrum to bone or to attach meniscal cartilage to bone).

By way of further example but not limitation, the present invention may be used to hold a prosthesis in apposition to soft tissue or bone, or to hold soft tissue or bone in apposition to a prosthesis, and/or to hold any first object in apposition to any second object.

In one preferred form of the present invention, there is provided apparatus for attaching a first object to a second object, said apparatus comprising:

a distal anchor comprising a generally cylindrical body, a distal end and a proximal end, wherein said distal end comprises an inclined distal end surface, and a vertical bore extending through said generally cylindrical body, perpendicular to the longitudinal axis of said generally cylindrical body;

a proximal anchor comprising a generally cylindrical body, a distal end and a proximal end, a top surface and a bottom surface, a first vertical bore extending through said generally cylindrical body from said top surface to said bottom surface, perpendicular to the longitudinal axis of the generally cylindrical body, a second vertical bore spaced distally from said first vertical bore and extending from said top surface to said bottom surface parallel to said first vertical bore, a third vertical bore spaced distally from said second vertical bore and extending from said top surface to said bottom surface parallel to said first vertical bore, and a fourth vertical bore spaced distally from said third vertical bore and extending from said top surface to said bottom surface parallel to said first vertical bore; and a suture having a proximal end and a distal end, with an enlargement formed at said distal end, wherein said suture extends through said vertical bore of said distal anchor, through said fourth vertical bore of said proximal anchor, through said third vertical bore of said proximal anchor, through said second vertical bore of said proximal anchor and through said first vertical bore of said proximal anchor.

In another preferred form of the present invention, there is provided a method for connecting a first object to a second object, said method comprising:

providing apparatus comprising:
  a distal anchor comprising a generally cylindrical body, a distal end and a proximal end, wherein said distal end comprises an inclined distal end surface, and a vertical bore extending through said generally cylindrical body, perpendicular to the longitudinal axis of said generally cylindrical body;
  a proximal anchor comprising a generally cylindrical body, a distal end and a proximal end, a top surface and a bottom surface, a first vertical bore extending through said generally cylindrical body from said top surface to said bottom surface, perpendicular to the longitudinal axis of the generally cylindrical body, a second vertical bore spaced distally from said first vertical bore and extending from said top surface to said bottom surface parallel to said first vertical bore, a third vertical bore spaced distally from said second vertical bore and extending from said top surface to said bottom surface parallel to said first vertical bore, and a fourth vertical bore spaced distally from said third vertical bore and extending from said top surface to said bottom surface parallel to said first vertical bore; and
  a suture having a proximal end and a distal end, with an enlargement formed at said distal end, wherein said suture extends through said vertical bore of said distal anchor, through said fourth vertical bore of said proximal anchor, through said third vertical bore of said proximal anchor, through said second vertical bore of said proximal anchor and through said first vertical bore of said proximal anchor;

advancing said distal anchor into the first object, with said suture and said enlargement advancing with said distal anchor;

while holding said suture and said enlargement in place, further advancing said distal anchor so that said inclined distal end surface of said distal anchor engages said enlargement and causes said distal anchor to turn relative to the first object;

advancing said proximal anchor into the second object;

pulling proximally on the portion of said suture extending between said second vertical bore of said proximal anchor and said third vertical bore of said proximal anchor so as to cause said proximal anchor to turn relative to the second object;

passing said proximal end of said suture between (i) the portion of said suture extending between said second vertical bore of said proximal anchor and said third vertical bore of said proximal anchor and (ii) said proximal anchor, so as to form a half hitch in said suture; and pulling proximally on said proximal end of said suture so as to set said half hitch.

In another preferred form of the present invention, there is provided apparatus for attaching a suture to an object, said apparatus comprising:

an anchor comprising a generally cylindrical body, a distal end and a proximal end, wherein said distal end comprises an inclined distal end surface, and a vertical bore extending through said generally cylindrical body, perpendicular to the longitudinal axis of said generally cylindrical body; and a suture having a proximal end and a distal end, with an enlargement formed at said distal end, wherein said suture extends through said vertical bore of said anchor.

In another preferred form of the present invention, there is provided a method for attaching a suture to an object, said method comprising:

providing apparatus comprising:
an anchor comprising a generally cylindrical body, a distal end and a proximal end, wherein said distal end comprises an inclined distal end surface, and a vertical bore extending through said generally cylindrical body, perpendicular to the longitudinal axis of said generally cylindrical body; and a suture having a proximal end and a distal end, with an enlargement formed at said distal end, wherein said suture extends through said vertical bore of said anchor;

advancing said anchor into said object, with said suture and said enlargement advancing with said anchor;

while holding said suture and said enlargement in place, further advancing said anchor so that said inclined distal end surface of said anchor engages said enlargement and causes said anchor to turn relative to said object.

In another preferred form of the present invention, there is provided apparatus for attaching a suture to an object, said apparatus comprising:

an anchor comprising a generally cylindrical body, a distal end and a proximal end, a vertical bore extending through said generally cylindrical body, perpendicular to the longitudinal axis of said generally cylindrical body, a recess formed on one side of said generally cylindrical body and a U-shaped slot formed on the opposing side of said generally cylindrical body whereby to form a flexible finger extending distally within said generally cylindrical body, and further wherein said distal end of said finger is spaced from an opposing portion of said generally cylindrical body; and a suture extending through said vertical bore, said recess and said U-shaped slot.

In another preferred form of the present invention, there is provided a method for attaching a suture to an object, said method comprising providing apparatus comprising:
an anchor comprising a generally cylindrical body, a distal end and a proximal end, a vertical bore extending through said generally cylindrical body, perpendicular to the longitudinal axis of said generally cylindrical body, a recess formed on one side of said generally cylindrical body and a U-shaped slot formed on the opposing side of said generally cylindrical body whereby to form a flexible finger extending distally within said generally cylindrical body, and further wherein said distal end of said finger is spaced from an opposing portion of said generally cylindrical body; and a suture extending through said vertical bore, said recess and said U-shaped slot;

advancing said anchor into the object; and
pulling on said proximal end of said suture.

In another preferred form of the present invention, there is provided apparatus for attaching a suture to an object, said apparatus comprising:

an anchor comprising a body having a distal end and a proximal end, and a vertical bore extending through said body substantially perpendicular to the longitudinal axis of said body;

wherein said anchor further comprises a recess formed on one side of said body and a U-shaped slot formed on the opposing side of said body, whereby to form a flexible finger extending distally within said body, and further wherein said distal end of said finger is spaced from an opposing portion of said body; and wherein at least one of said flexible finger and said body comprises a cutout extending therethrough, with said cutout cooperating with said U-shaped slot and said recess so as to together form a suture loading hole extending through said body, with said suture loading hole being sized to receive a suture therein.

In another preferred form of the present invention, there is provided a method for attaching a suture to an object, said method comprising providing apparatus comprising:
an anchor comprising a body having a distal end and a proximal end, and a vertical bore extending through said body substantially perpendicular to the longitudinal axis of said body;

wherein said anchor further comprises a recess formed on one side of said body and a U-shaped slot formed on the opposing side of said body, whereby to form a flexible finger extending distally within said body, and further wherein said distal end of said finger is spaced from an opposing portion of said body; and wherein at least one of said flexible finger and said body comprises a cutout extending therethrough, with said cutout cooperating with said U-shaped slot and said recess so as to together form a suture loading hole extending through said body, with said suture loading hole being sized to receive a suture therein; and a suture comprising a proximal end and a distal end; and
passing said suture through said vertical bore of said anchor, forming a loop, passing said suture back through said vertical bore of said anchor, and passing said suture through said suture loading hole.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIGS. 32-38 and 38A-38G are schematic views showing use of the novel system of FIGS. 1 and 2 to close a fissure in the annulus of an intervertebral disc;

FIGS. 42-51 are schematic views showing examples of additional anatomical repairs and/or fixations which may be effected using the present invention;

FIG. 98 is a schematic view showing yet another form of stop for selectively preventing deployment of an anchor from an inserter.

DETAILED DESCRIPTION OF THE PREFERRED EMBODIMENTS

The present invention comprises the provision and use of a novel system for closing a fissure in the annulus of an intervertebral disc, whereby to treat degenerative disc disease.

The present invention also provides a new and improved method and apparatus for effecting other anatomical repairs and/or fixations.

Figure 1:
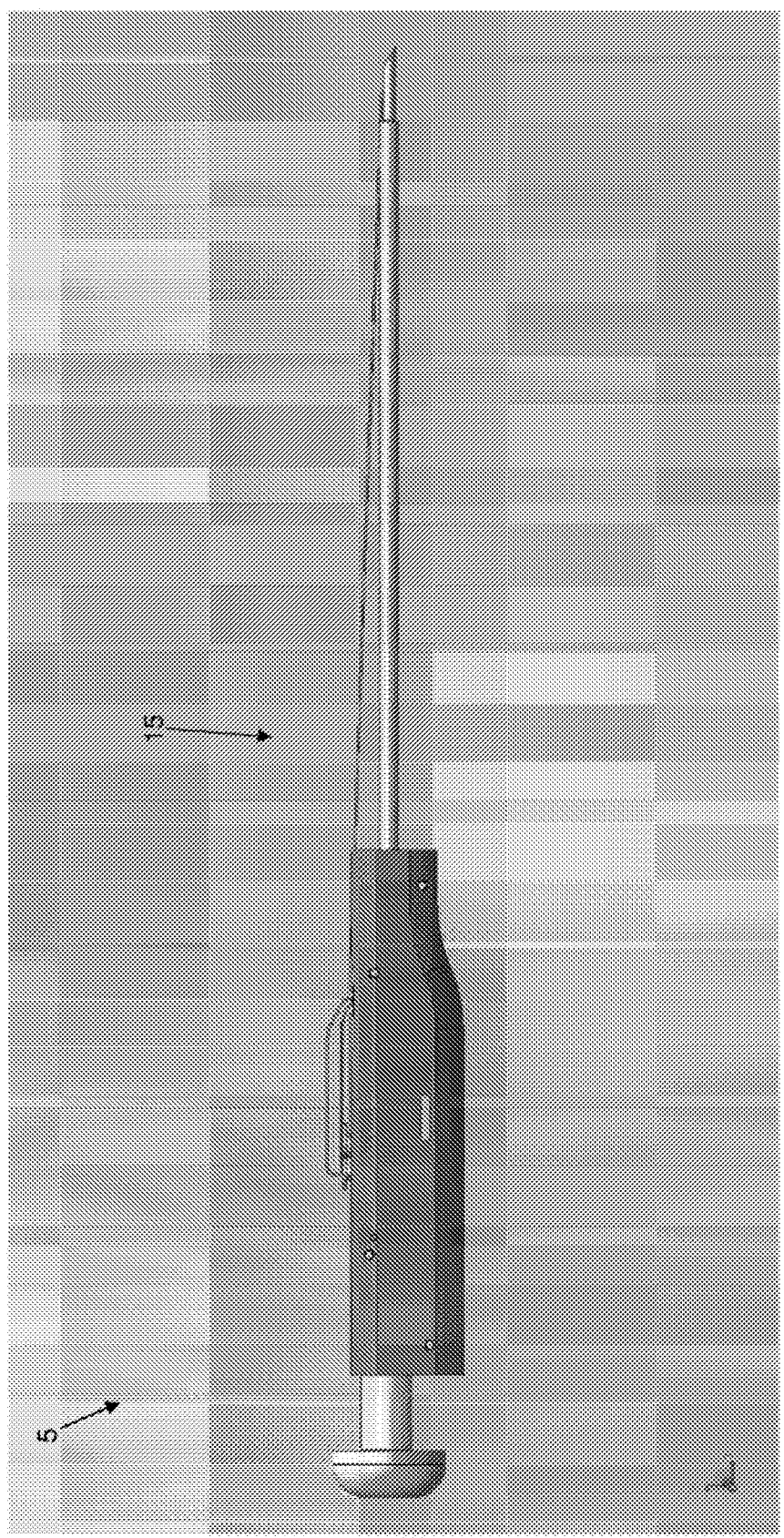
FIGS. 1 and 2 are schematic views showing a novel system for closing a fissure in the annulus of an intervertebral disc, whereby to treat degenerative disc disease, and/or for effecting other anatomical repairs and/or fixations.
Figure 2:
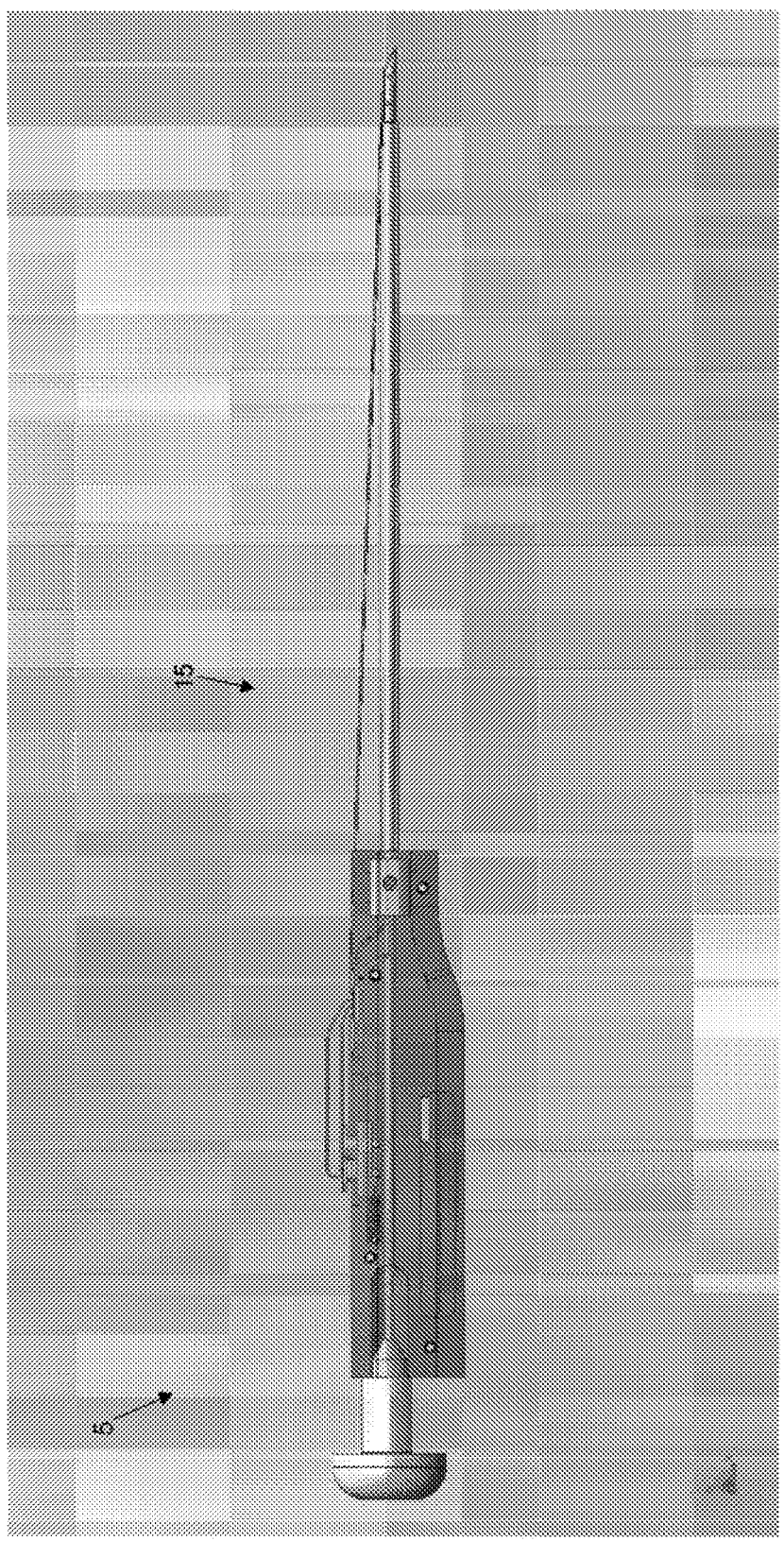
Figure 3:
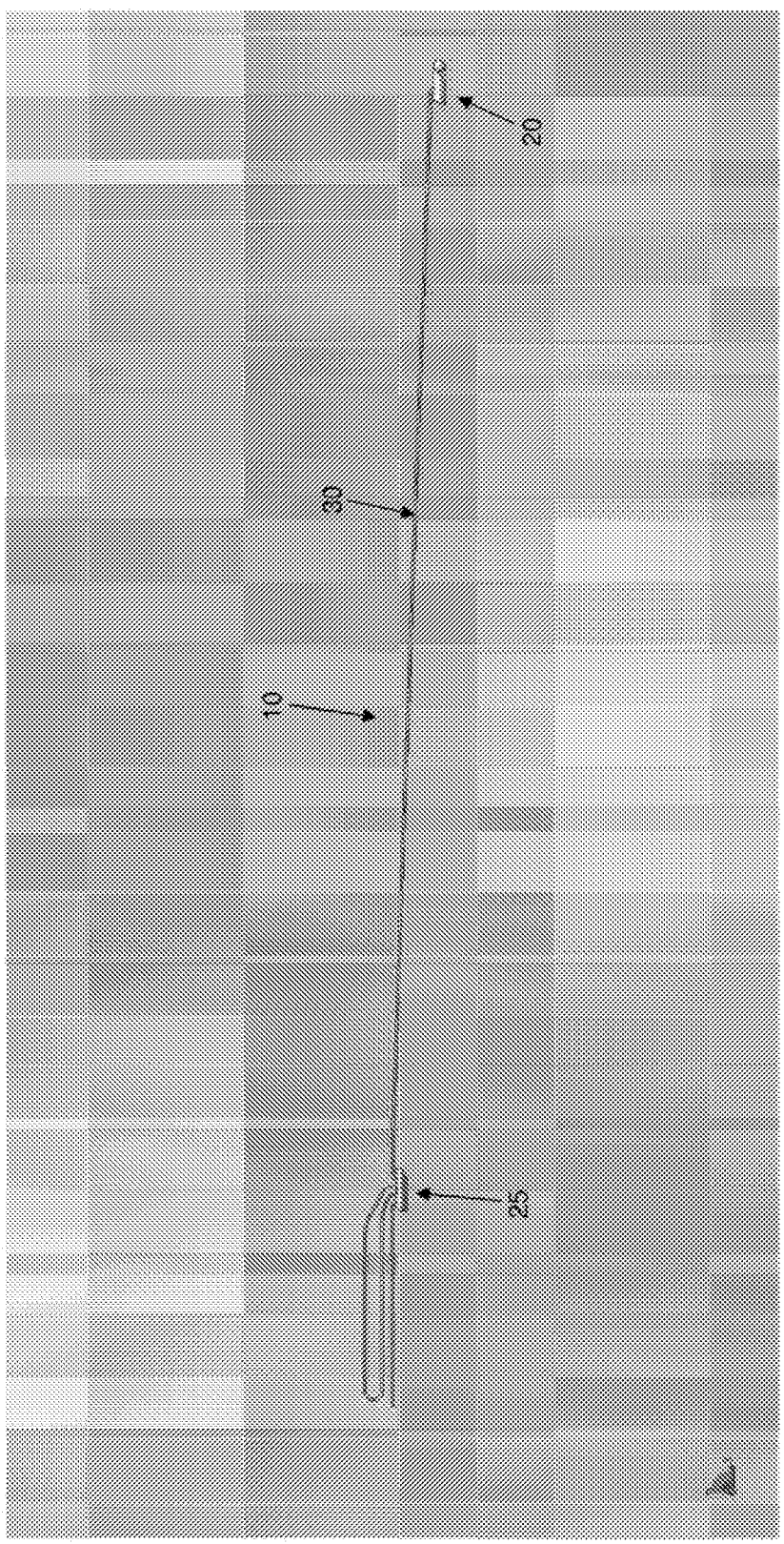
FIG. 3 is a schematic view showing the anchor assembly of the novel system of FIGS. 1 and 2.
Figure 4:
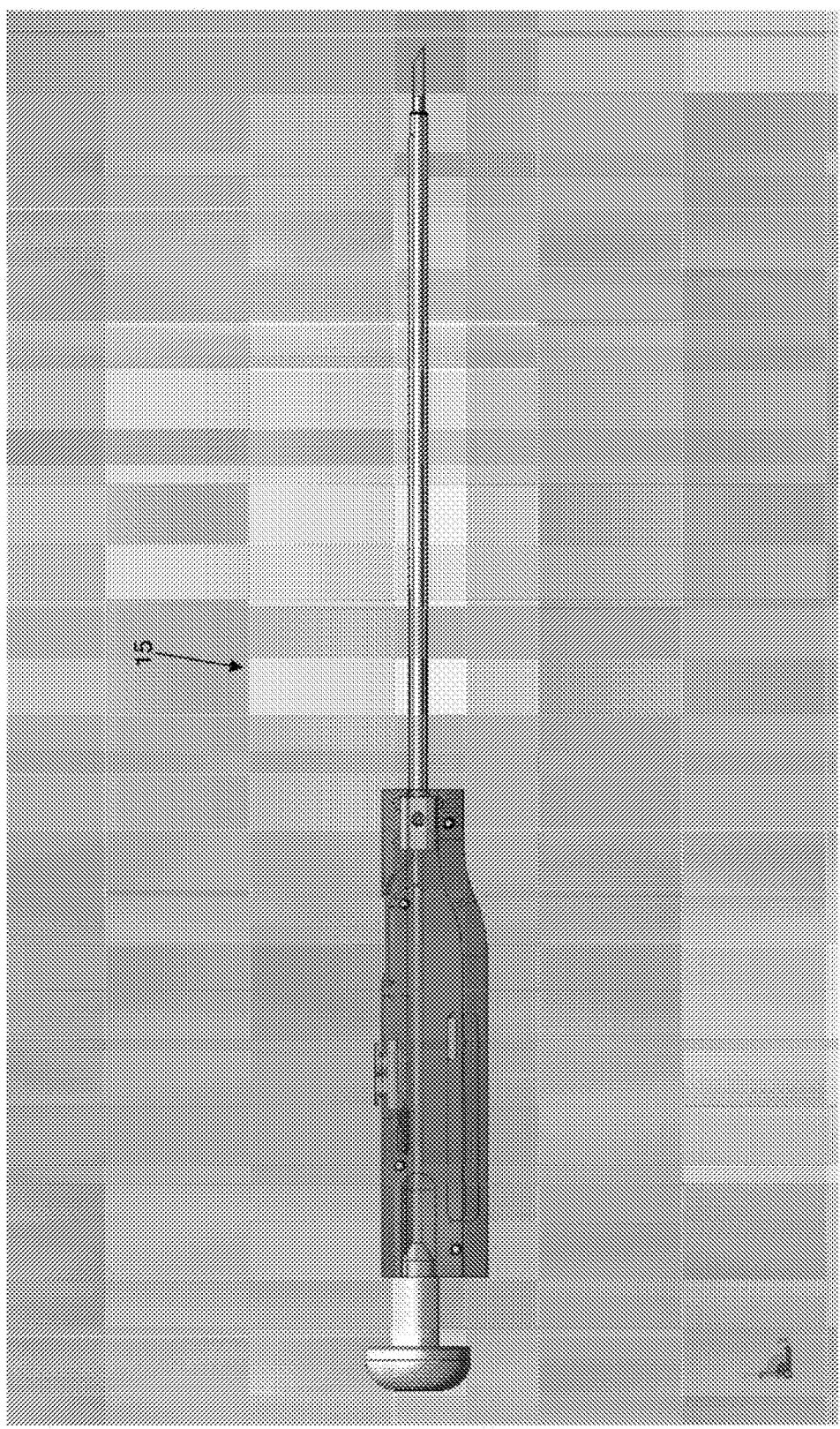
FIG. 4 is a schematic view showing the inserter of the novel system of FIGS. 1 and 2.
Figure 5:
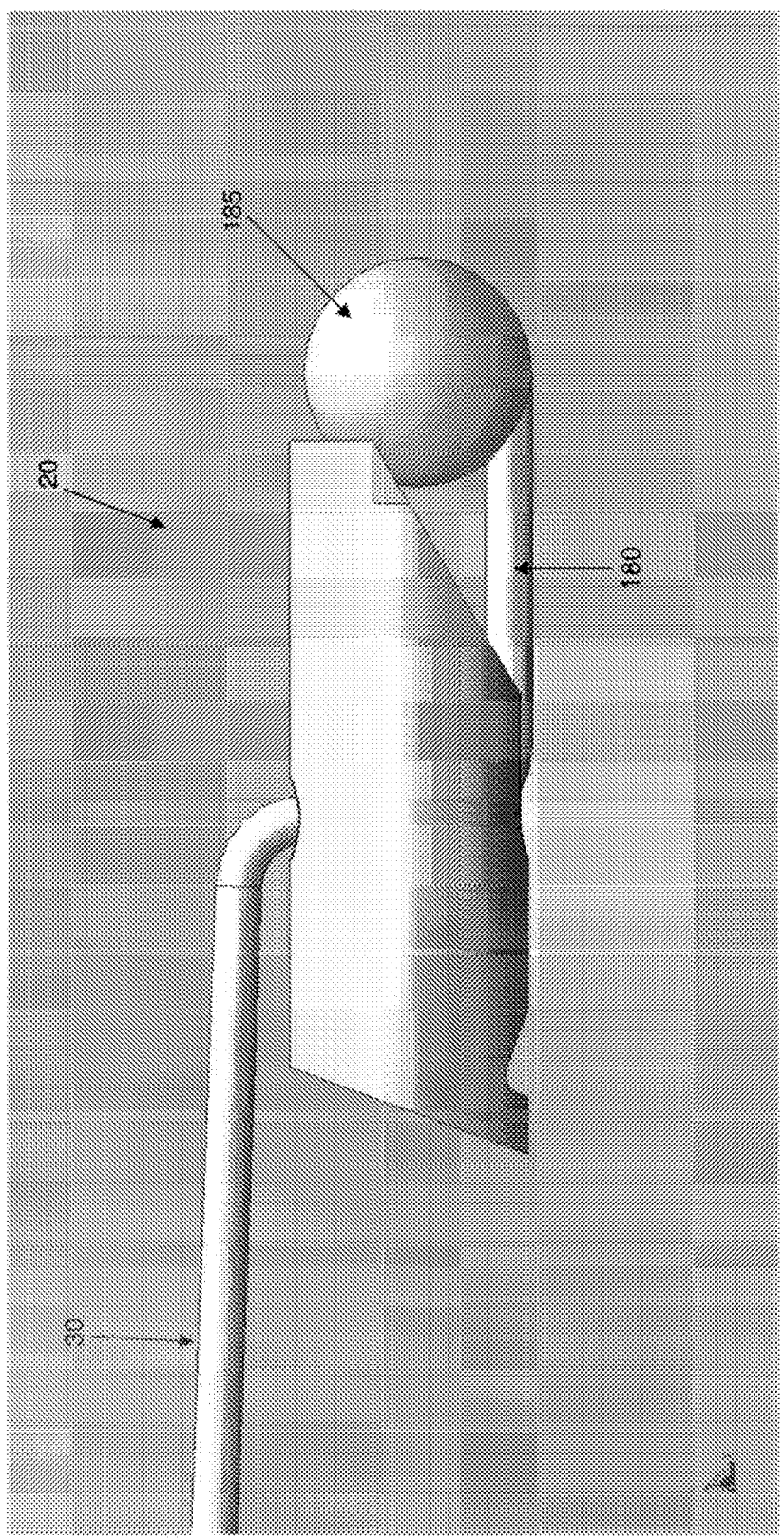
FIGS. 5-25 are schematic views showing further details of the anchor assembly of FIG. 3.

Novel System for Closing a Fissure in the Annulus of an Intervertebral Disc and/or for Effecting Other Anatomical Repairs and/or Fixations More particularly, and looking first at FIGS. 1 and 2, there is shown a novel system 5 for, among other things, closing a fissure in the annulus of an intervertebral disc. System 5 generally comprises an anchor assembly 10 (FIGS. 1-3) and an inserter 15 (FIGS. 1, 2 and 4).

Novel Anchor Assembly

Looking now at FIGS. 3 and 5-8, anchor assembly 10 generally comprises a distal anchor 20, a proximal anchor 25, and a suture 30 connecting distal anchor 20 and proximal anchor 25.

Novel Distal Anchor

As seen in FIGS. 5, 6 and 9-16, distal anchor 20 comprises a generally cylindrical body 35 having a distal end 40, a proximal end 45 and a generally circular side wall 50. Distal end 40 terminates in a flat distal surface 55 and an inclined distal surface 60. Flat distal surface 55 is preferably sufficiently large to render distal end 40 of distal anchor 20 substantially blunt. Inclined distal surface 60 is pitched at an appropriate angle (e.g., 30 degrees, 45 degrees, etc.) so as to cause distal anchor 20 to turn during deployment, as will hereinafter be discussed. Proximal end 45 terminates in an inclined proximal surface 65. Inclined proximal surface 65 is pitched at an appropriate angle (e.g., 70 degrees) so as to cause distal anchor 20 to set during deployment, as will hereinafter be discussed. A vertical bore 70 passes through distal anchor 20. Vertical bore 70 is sized to slidably receive suture 30 therein. A horizontal slot 75 extends between inclined distal end surface 60 and vertical bore 70. Horizontal slot 75 is preferably also sized to slidably receive suture 30 therein and helps keep distal anchor 20 and suture 30 from binding when they are disposed within inserter 15. A pair of distal notches 80 are preferably formed in distal end 40 and intersect inclined distal surface 60. A proximal notch 85 is preferably formed near to, but proximal to, proximal end surface 65. Proximal notch 85 cooperates with inclined proximal surface 65 to form a pointed heel 87 which enhances setting of distal anchor 20, as will hereinafter be discussed. In one preferred form of the invention, distal anchor 20 is formed out of PEEK or carbon-filled PEEK, has a length of about 0.20 inch and a width of about 0.063 inch. However, it should be appreciated that distal anchor 20 may also be formed out of other suitable materials and/or have other dimensions.

Novel Proximal Anchor

As seen in FIGS. 7, 8 and 17-25, proximal anchor 25 comprises a generally cylindrical body 90 having a distal end 95, a proximal end 100 and a generally circular side wall 105. Distal end 95 terminates in a flat distal surface 110 and an inclined distal surface 115. Flat distal surface 110 is preferably sufficiently large to render distal end 95 of proximal anchor 25 substantially blunt. Inclined distal surface 115 is pitched at an appropriate angle (e.g., 30 degrees, 45 degrees, etc.) so as to assist proximal anchor 25 in turning during deployment, as will hereinafter be discussed. Proximal end 100 terminates in an inclined proximal surface 120. Inclined proximal surface 120 is pitched at an appropriate angle (e.g., 20 degrees from the vertical) so as to assist proximal anchor 25 in setting during deployment, as will hereinafter be discussed. Four vertical bores 125, 130, 135 and 140 pass through proximal anchor 25. Vertical bores 125, 130, 135 and 140 are sized to slidably receive suture 30 therein. A top horizontal slot 145 extends between vertical bores 130 and 135. Top horizontal slot 145 is preferably also sized to slidably receive suture 30 therein and helps keep proximal anchor 25 and suture 30 from binding when they are disposed within inserter 15. A bottom horizontal slot 150 extends between vertical bores 125 and 130. If desired, bottom horizontal slot 150 may be stepped, and may comprise a wider outer portion 155 and a narrower inner portion 160. Wider outer portion 155 may be sized to slidingly receive suture 30 therein so as to help keep proximal anchor 25 and suture 30 from binding when they are disposed within inserter 15, but narrower inner portion 160 may be sized to snugly receive suture 30 therein, whereby to provide a light hold on suture 30 when suture 30 is disposed therein. A bottom horizontal slot 165 extends between vertical bores 135 and 140. If desired, bottom horizontal slot 165 may also be stepped, and may comprise a wider outer portion 170 and a narrower inner portion 175. Wider outer portion 170 may be sized to slidingly receive suture 30 therein so as to help keep proximal anchor 25 and suture 30 from binding when they are disposed within inserter 15, but narrower inner portion 175 may be sized to snugly receive suture 30 therein, whereby to provide a light hold on suture 30 when suture 30 is disposed therein.

The Suture

Figure 6:
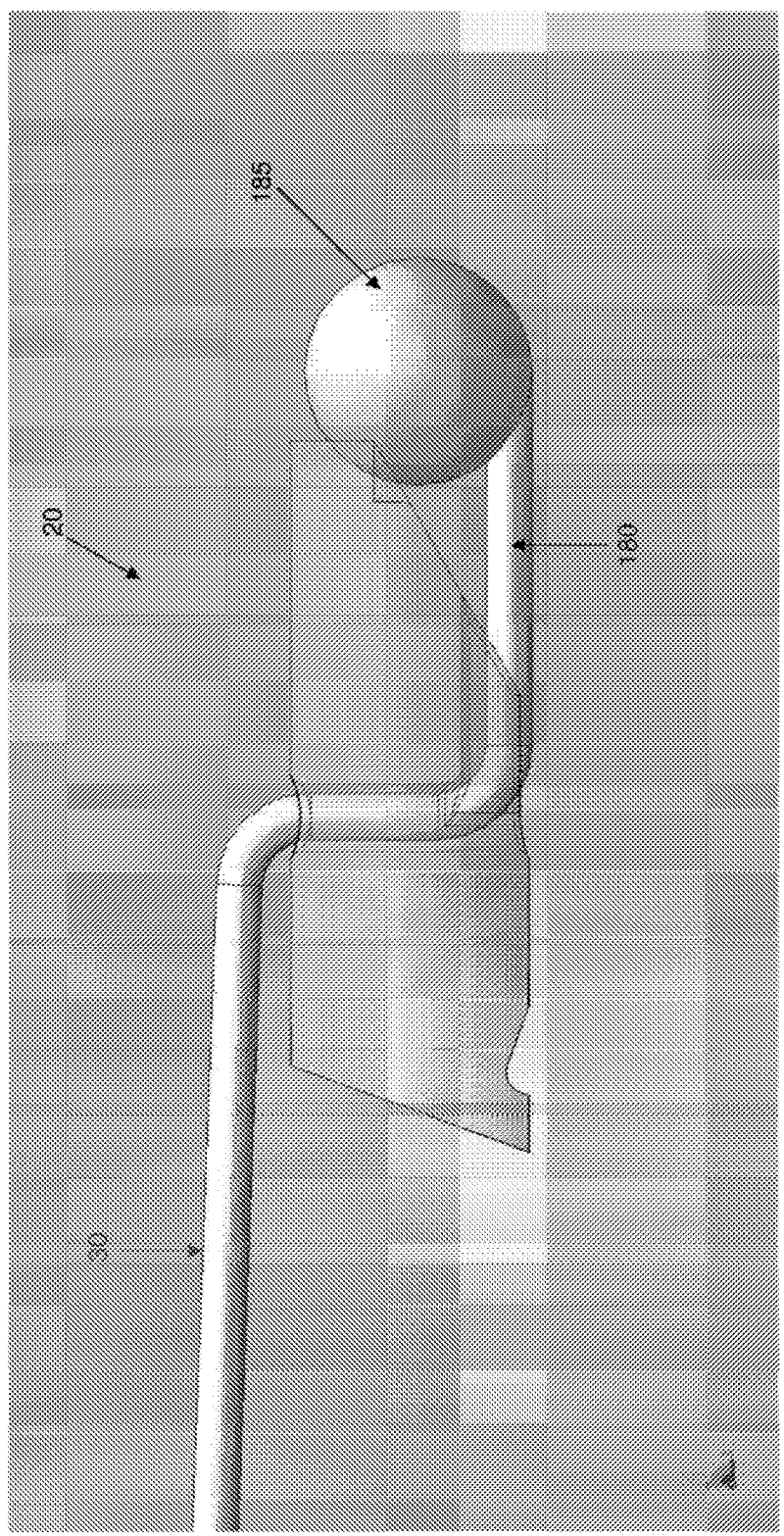
Figure 7:
Figure 8:
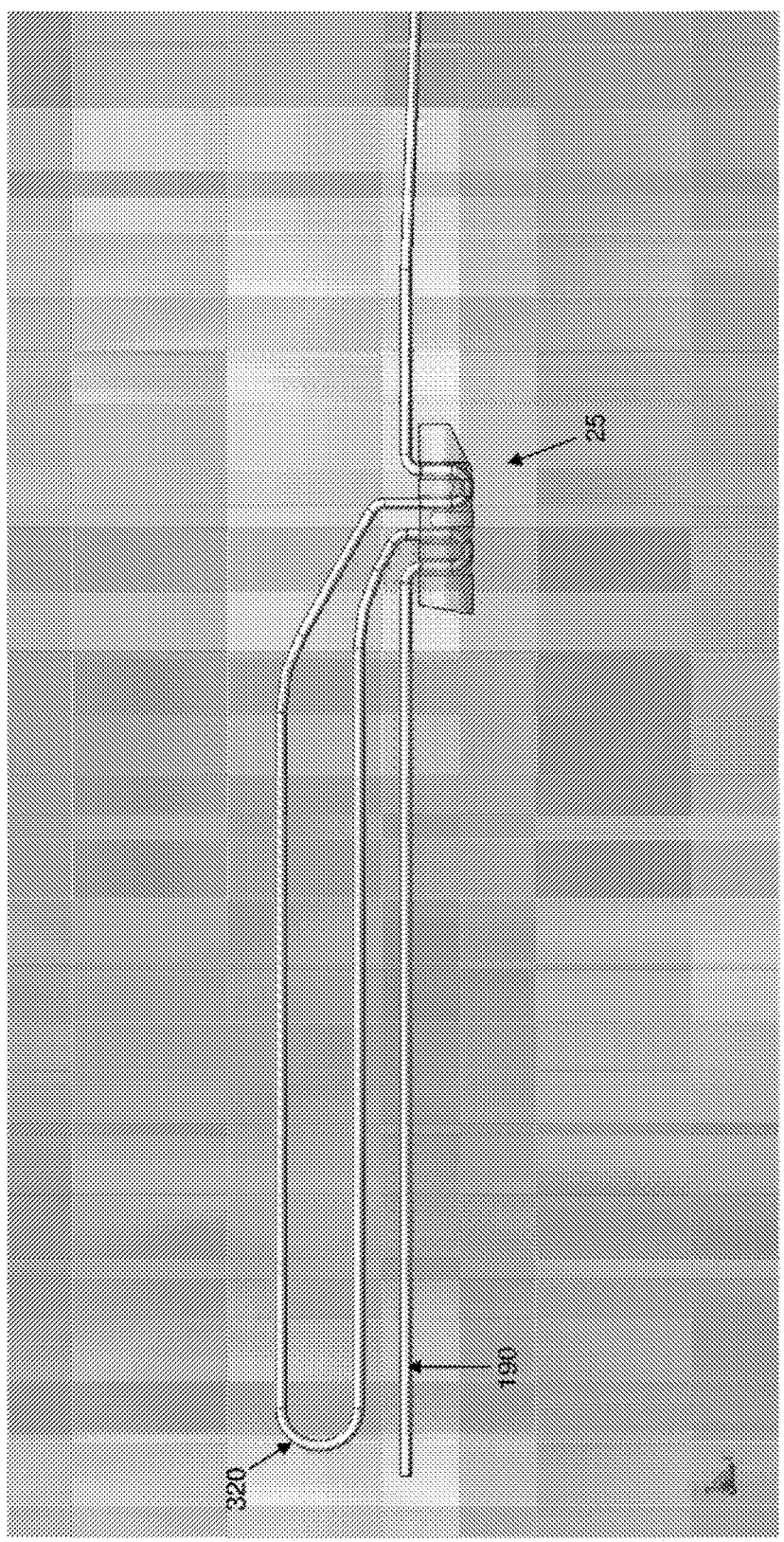
Figure 9:
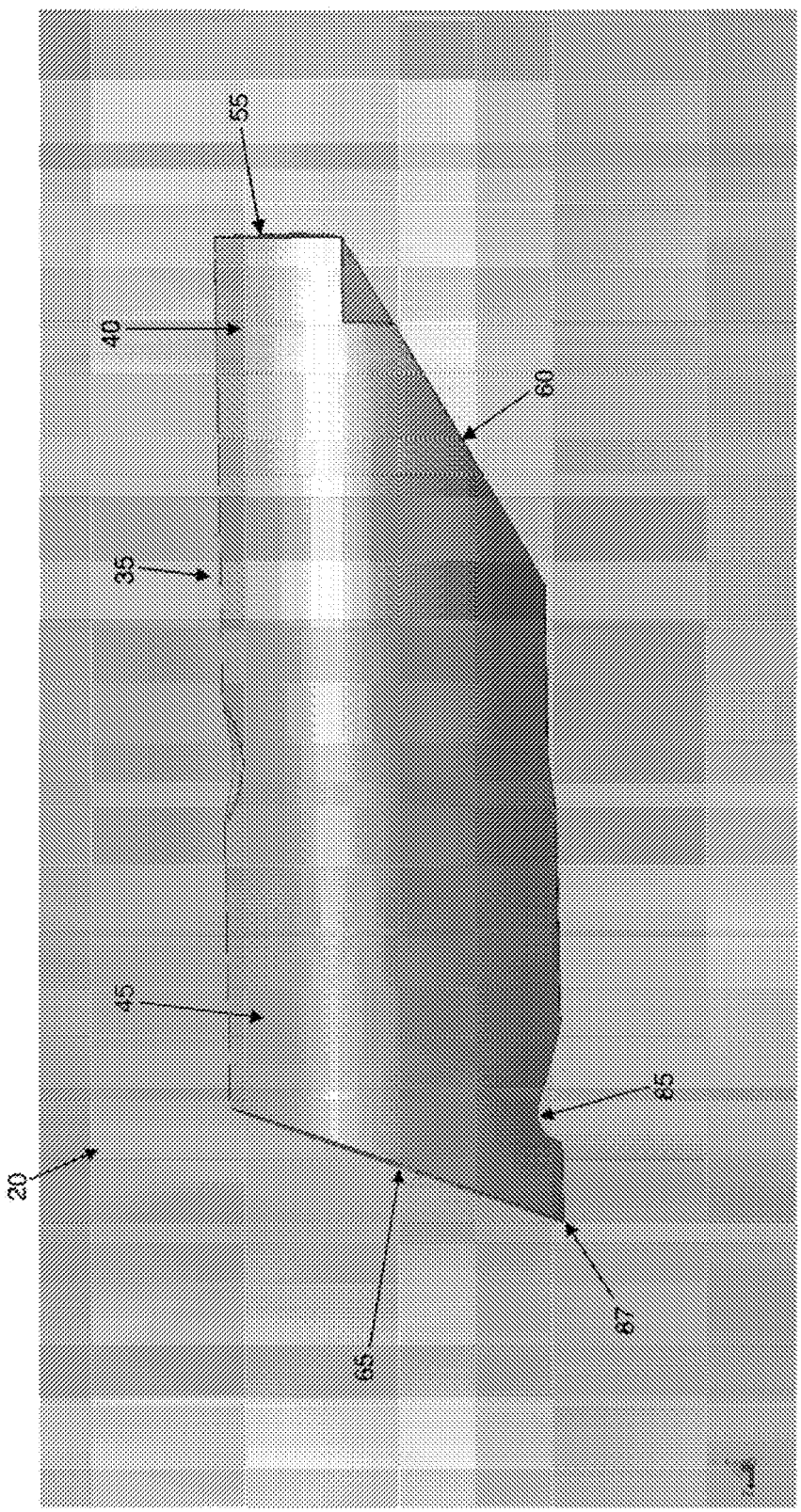
Figure 10:
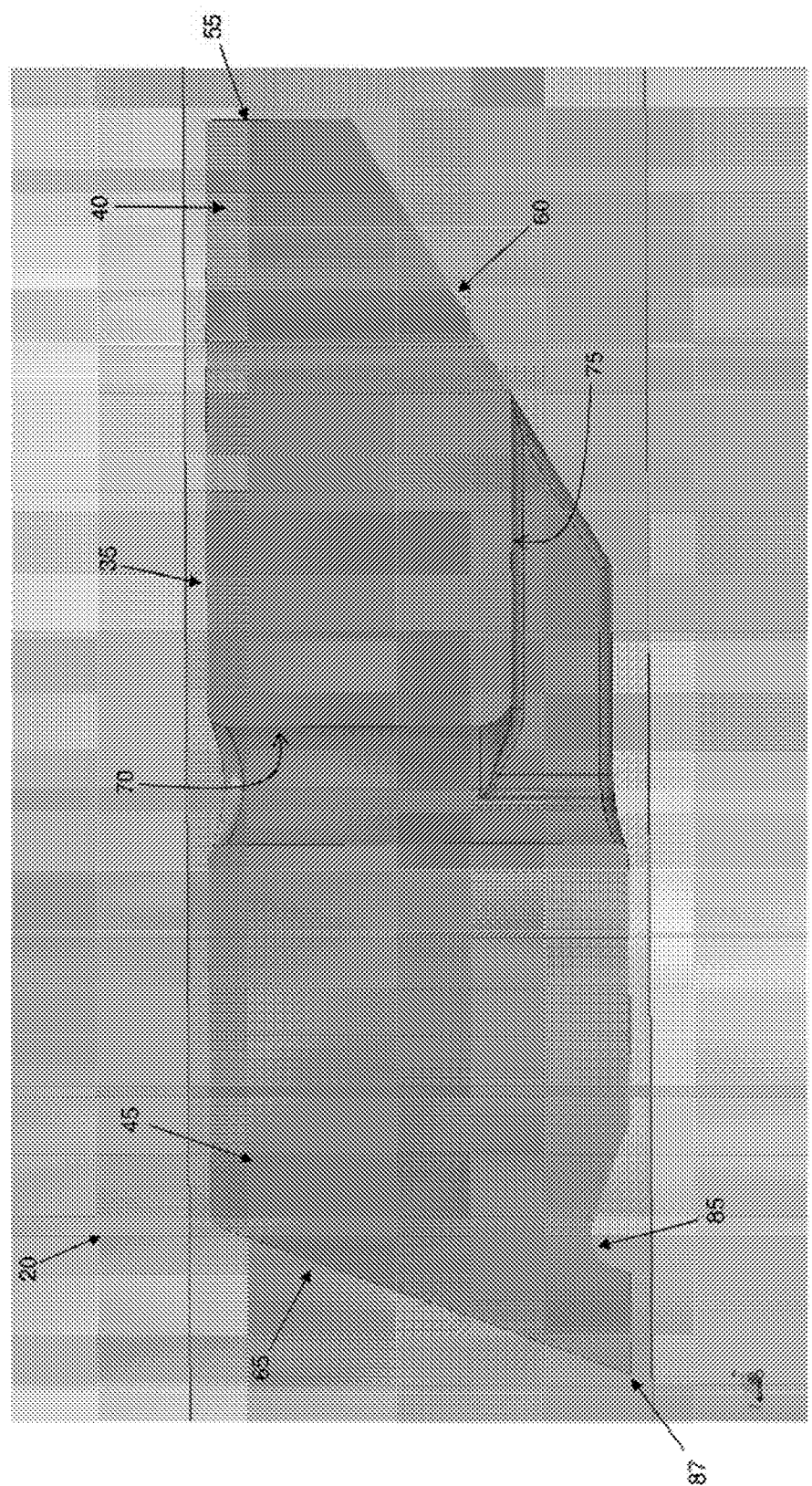
Figure 11:
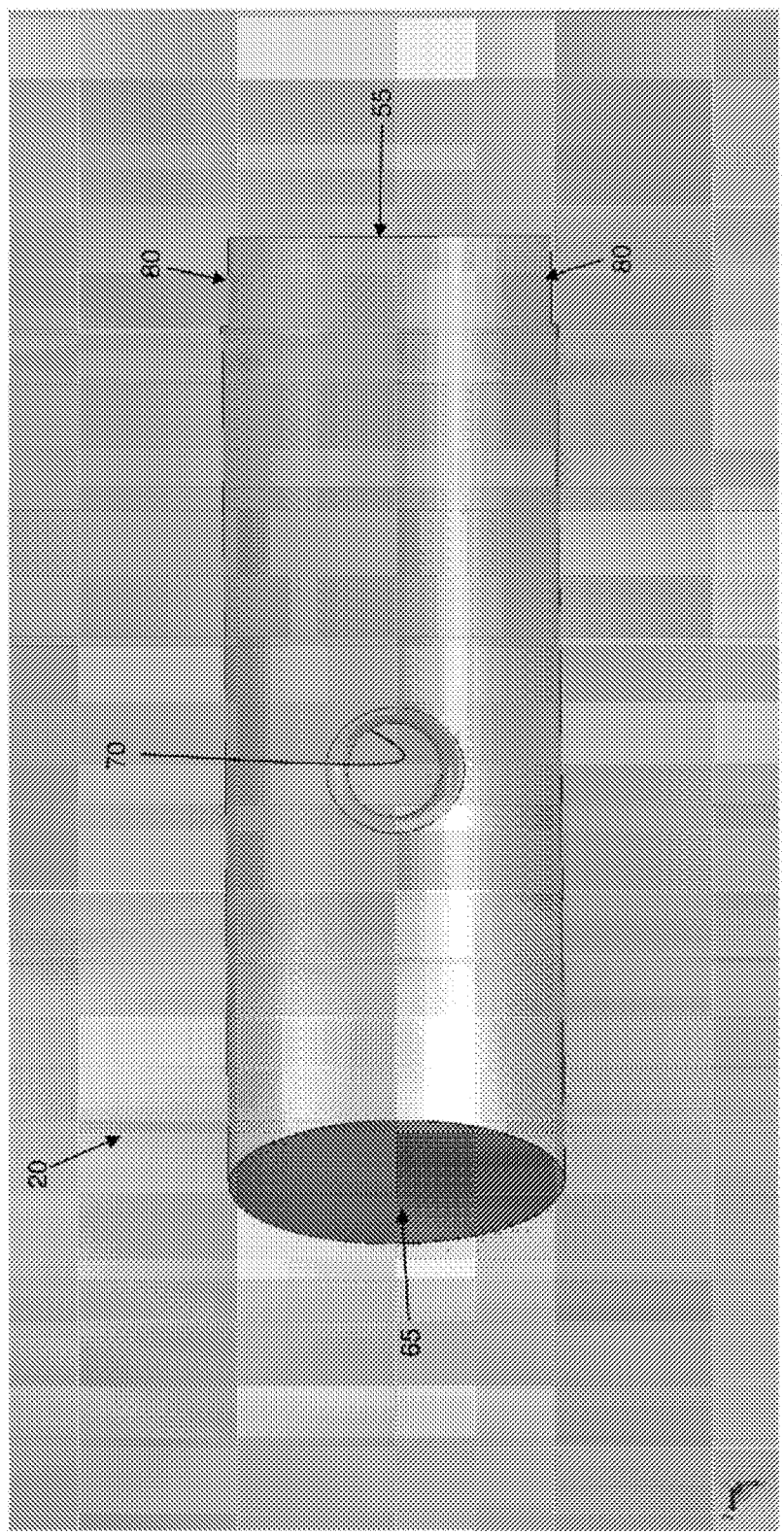
Figure 12:
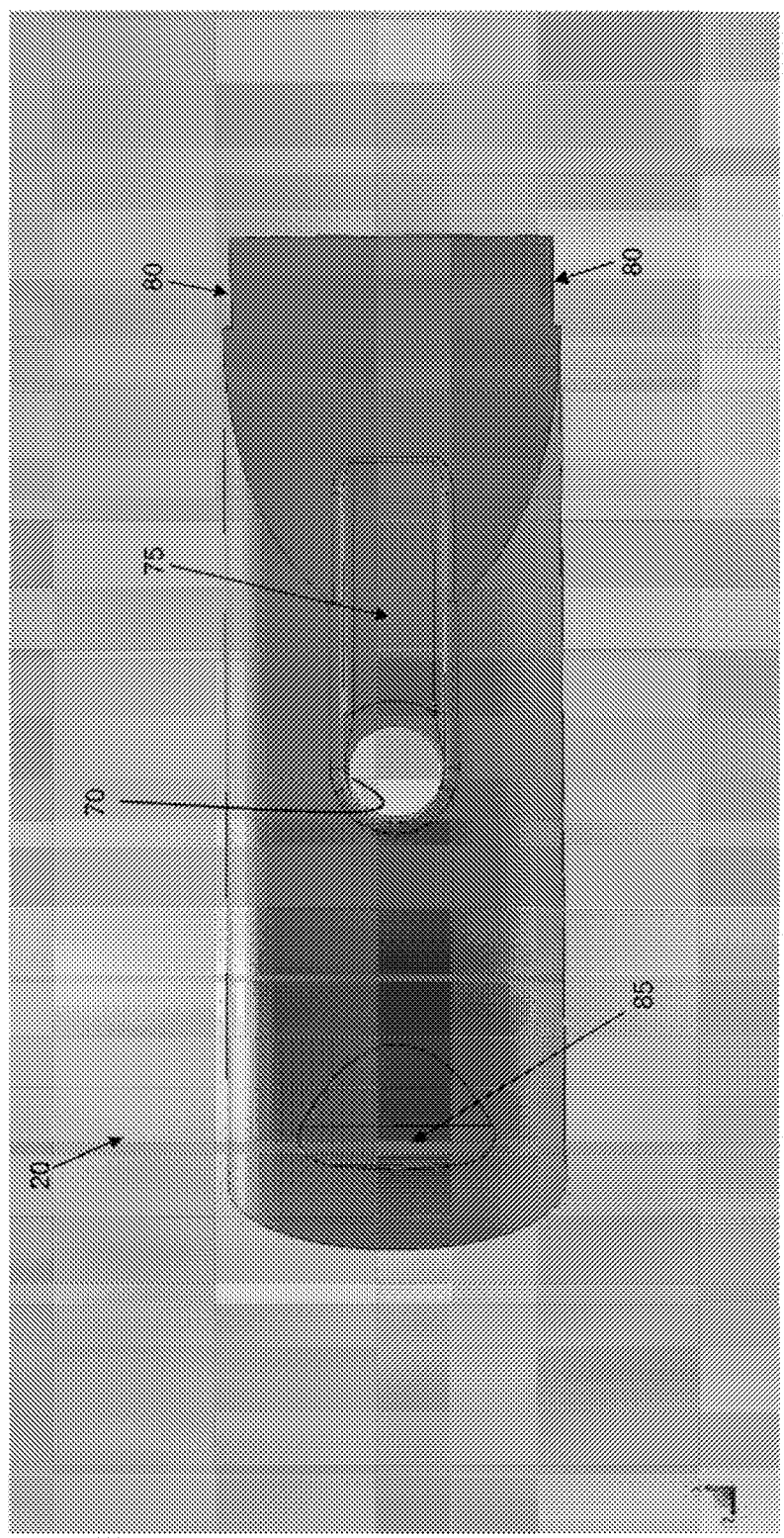
Figure 13:
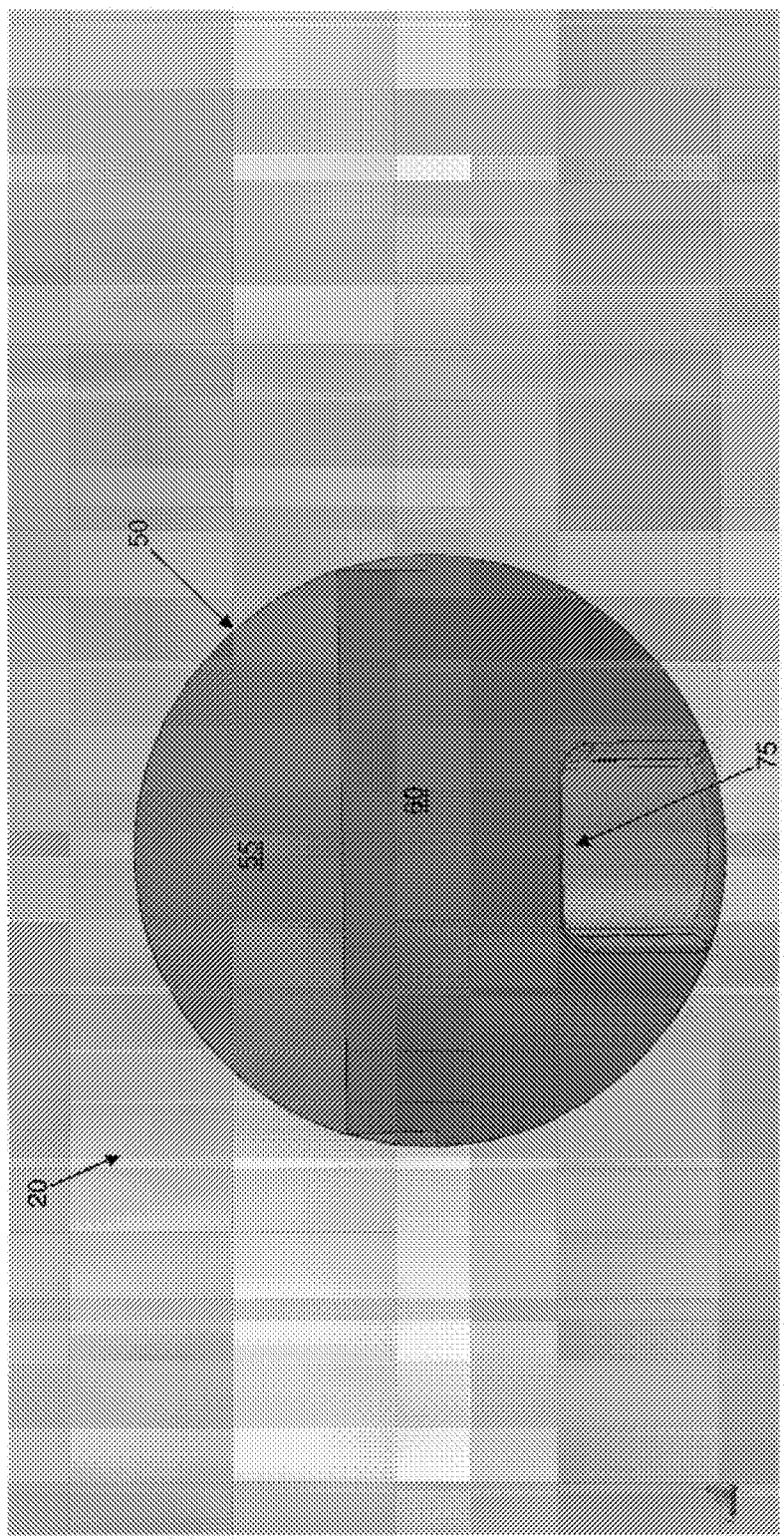
Figure 14:
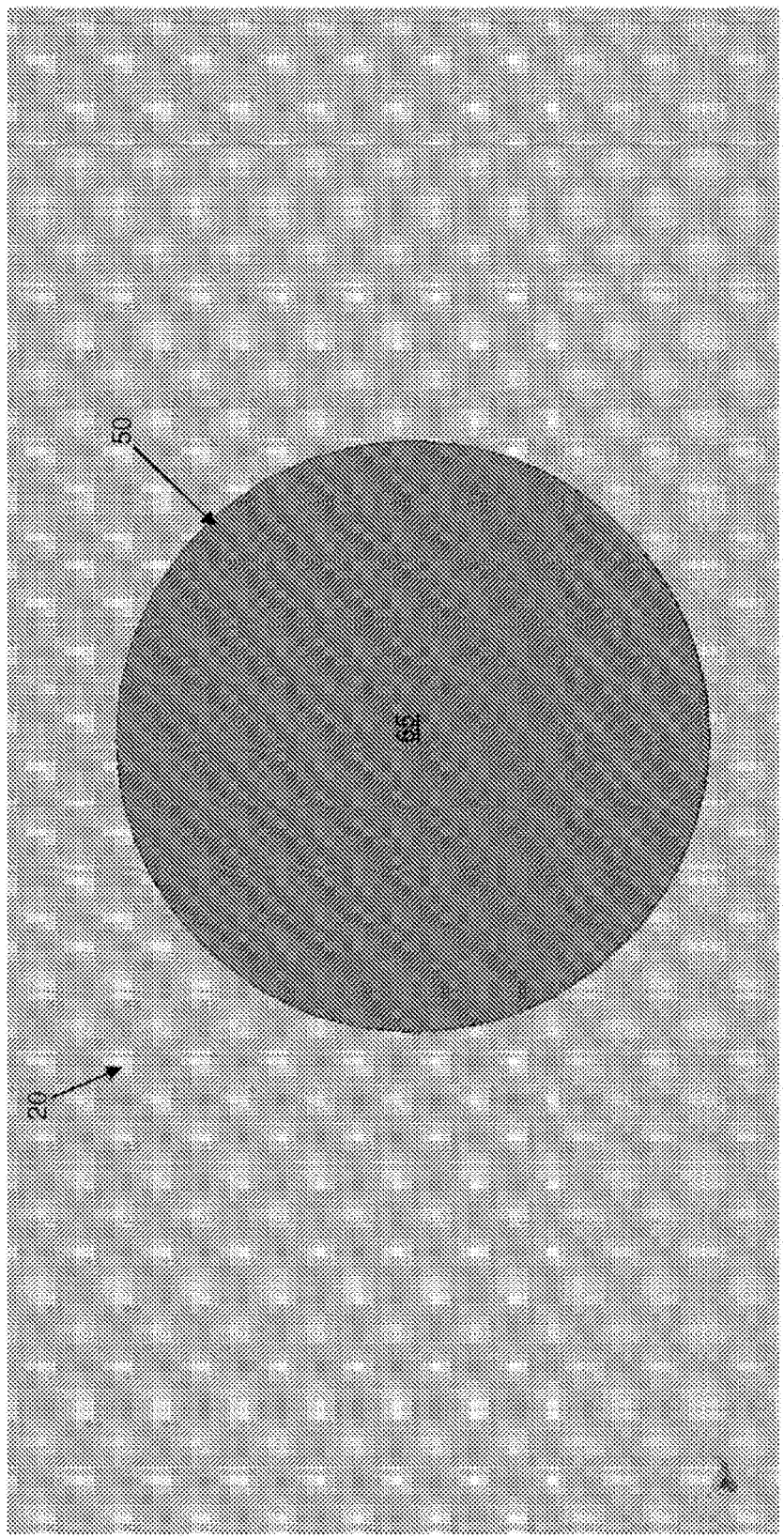
Figure 15:
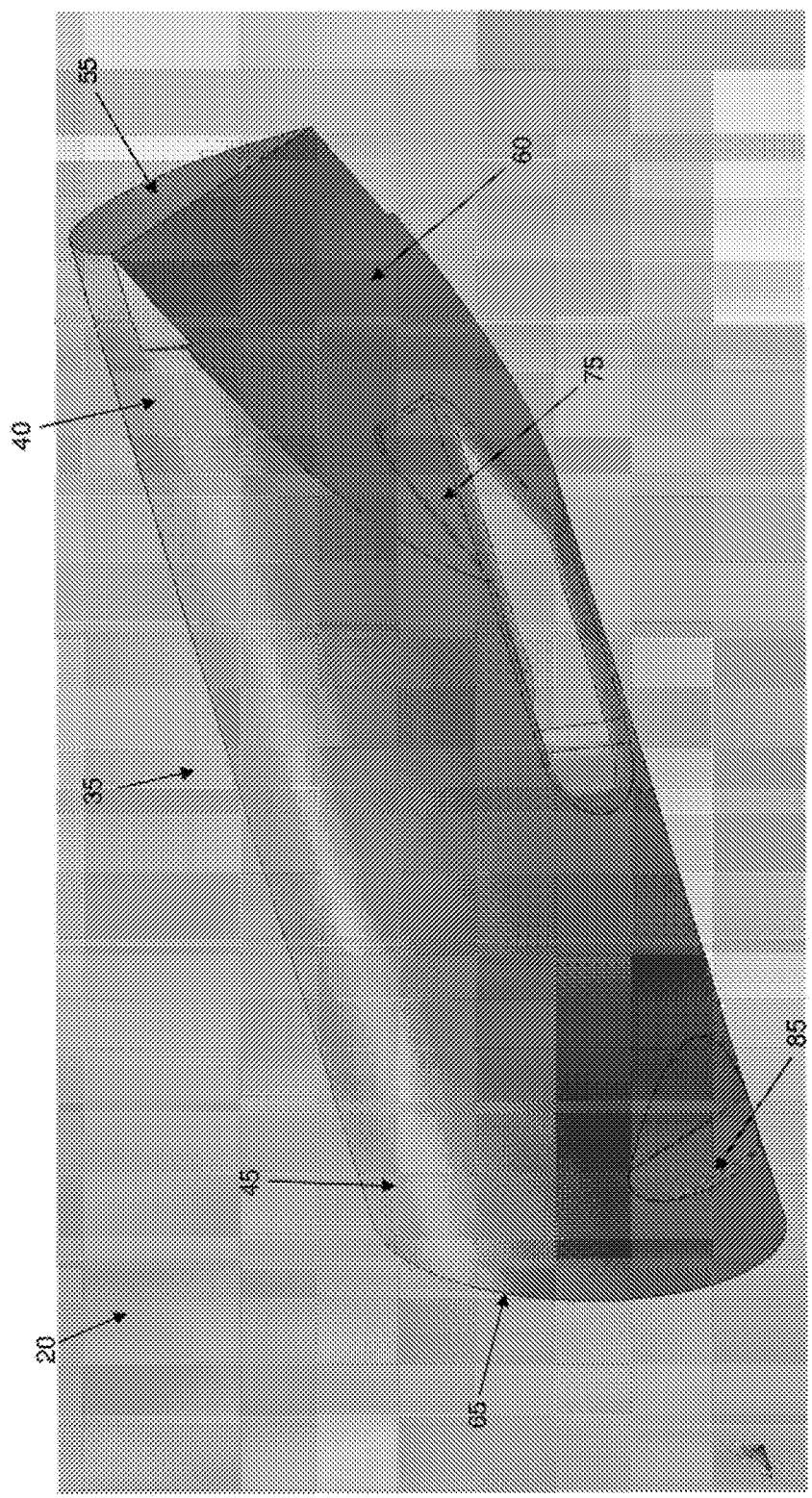
Figure 16:
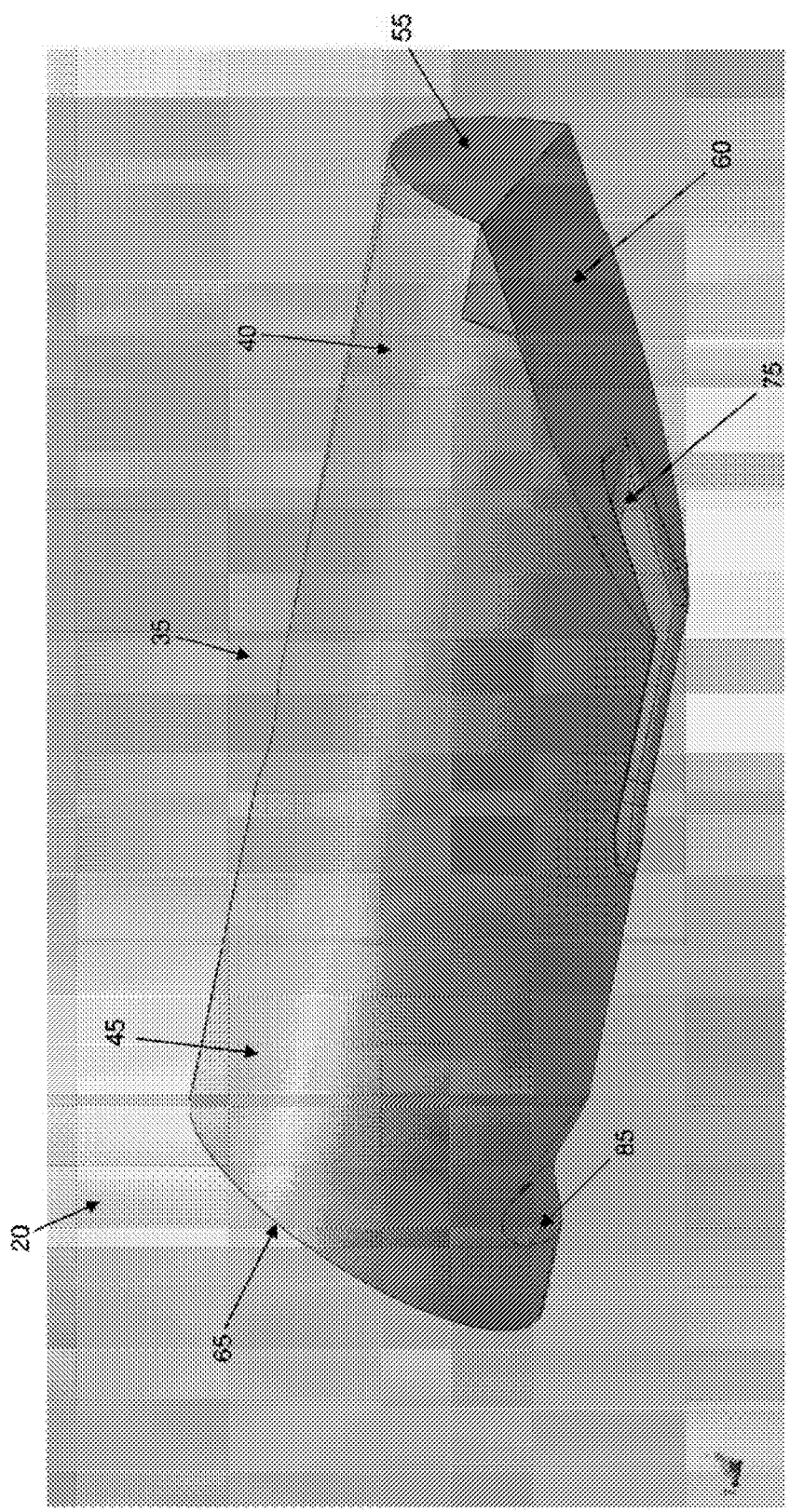
Figure 17:
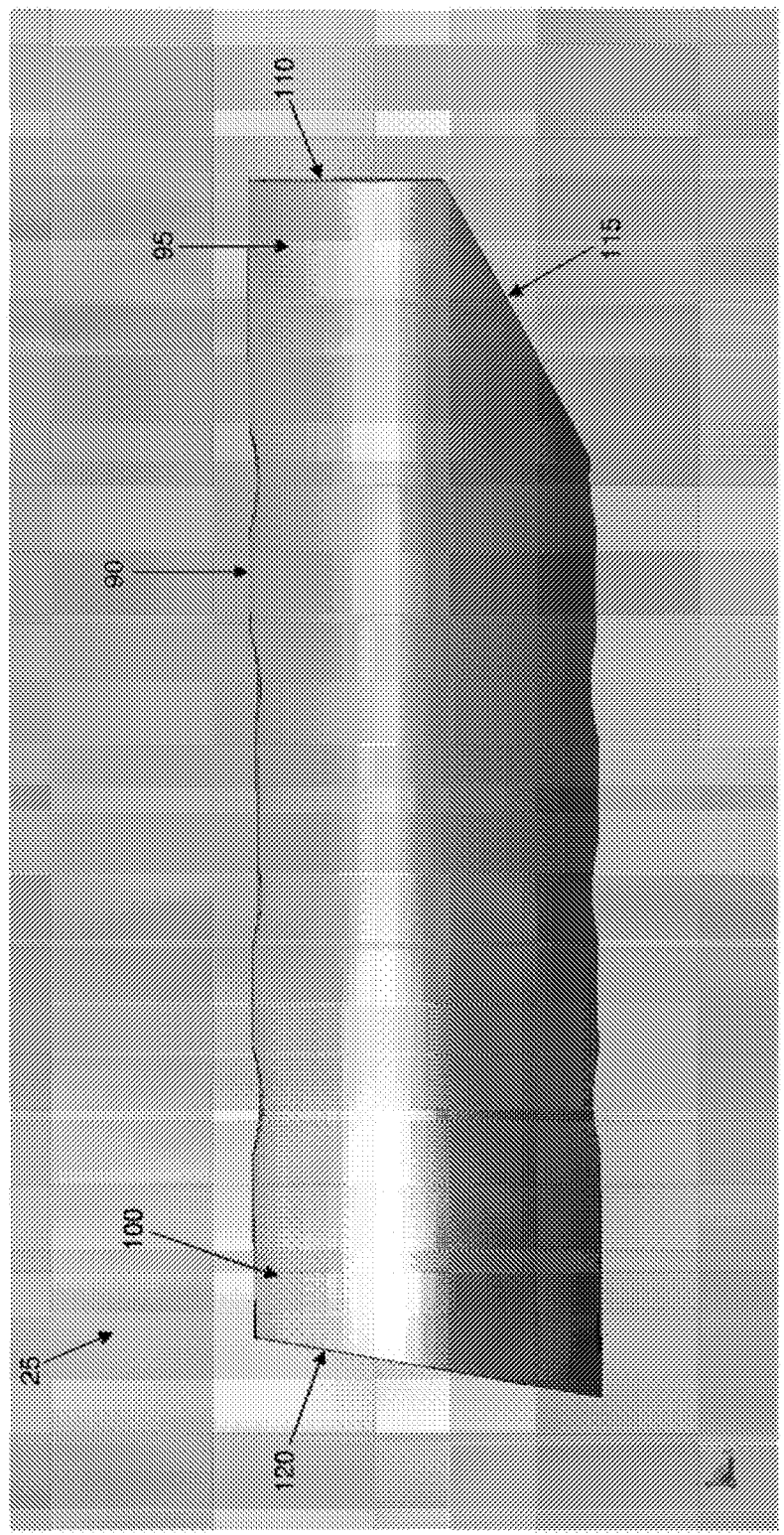
Figure 18:
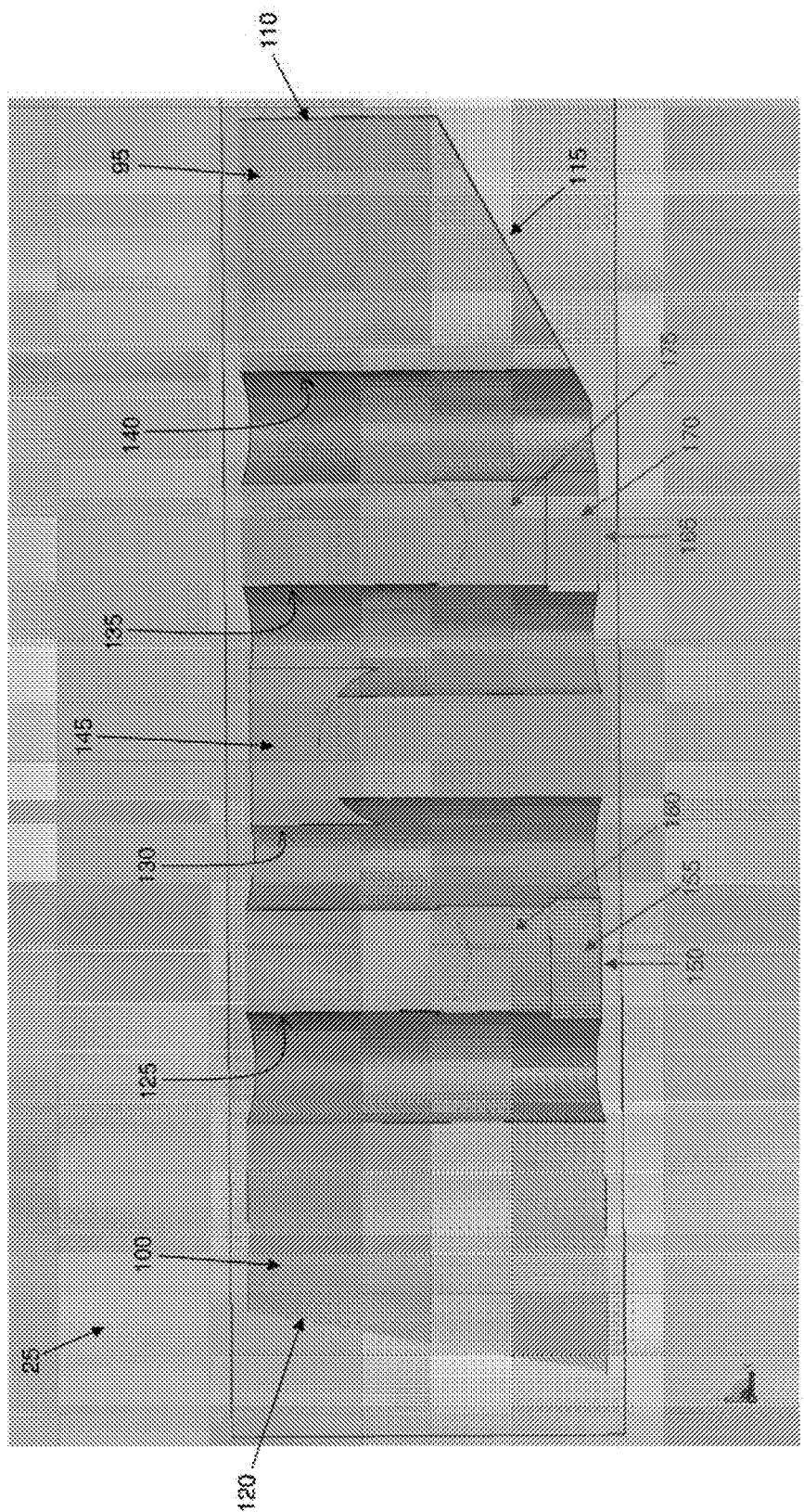
Figure 19:
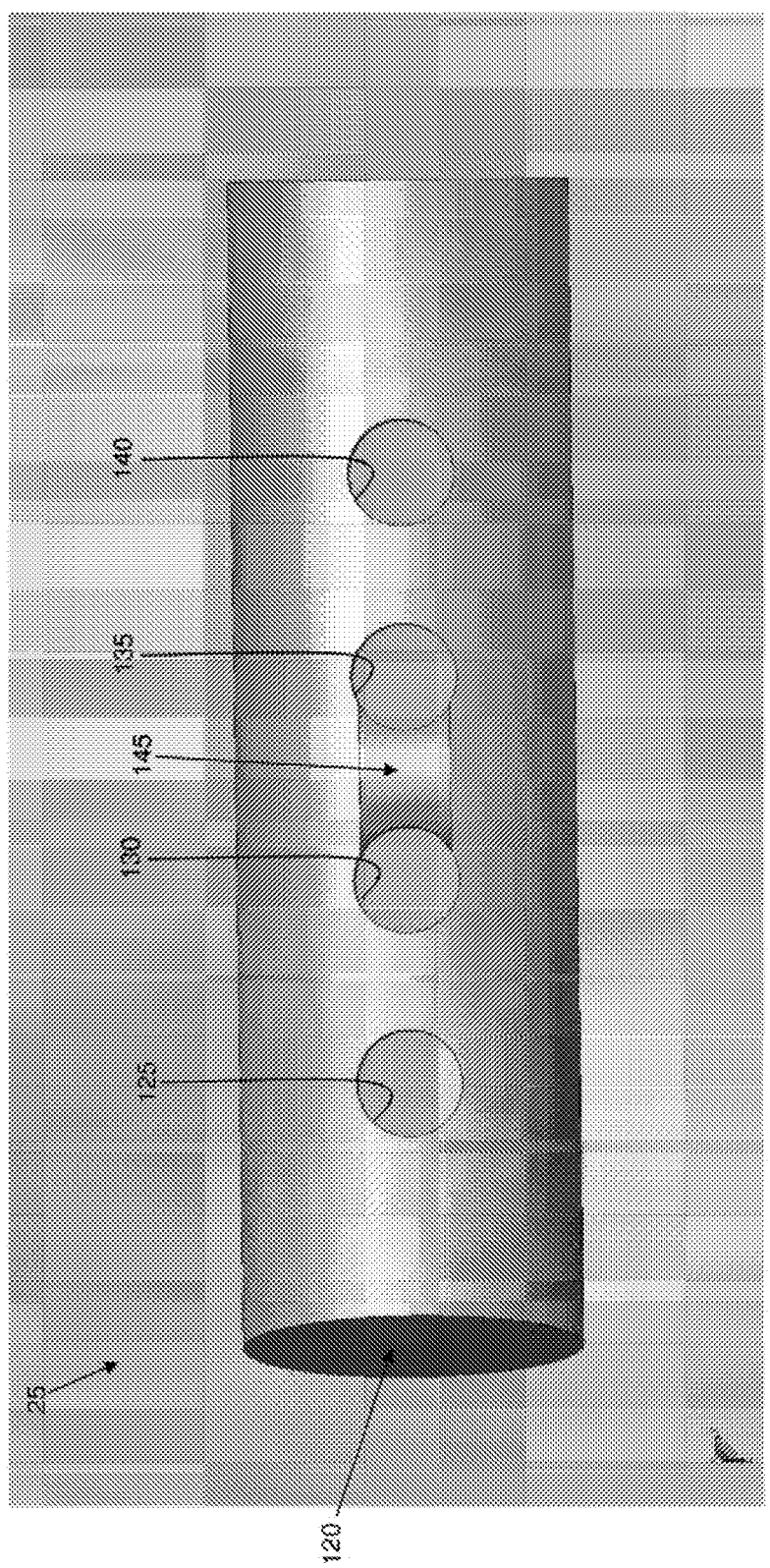
Figure 20:
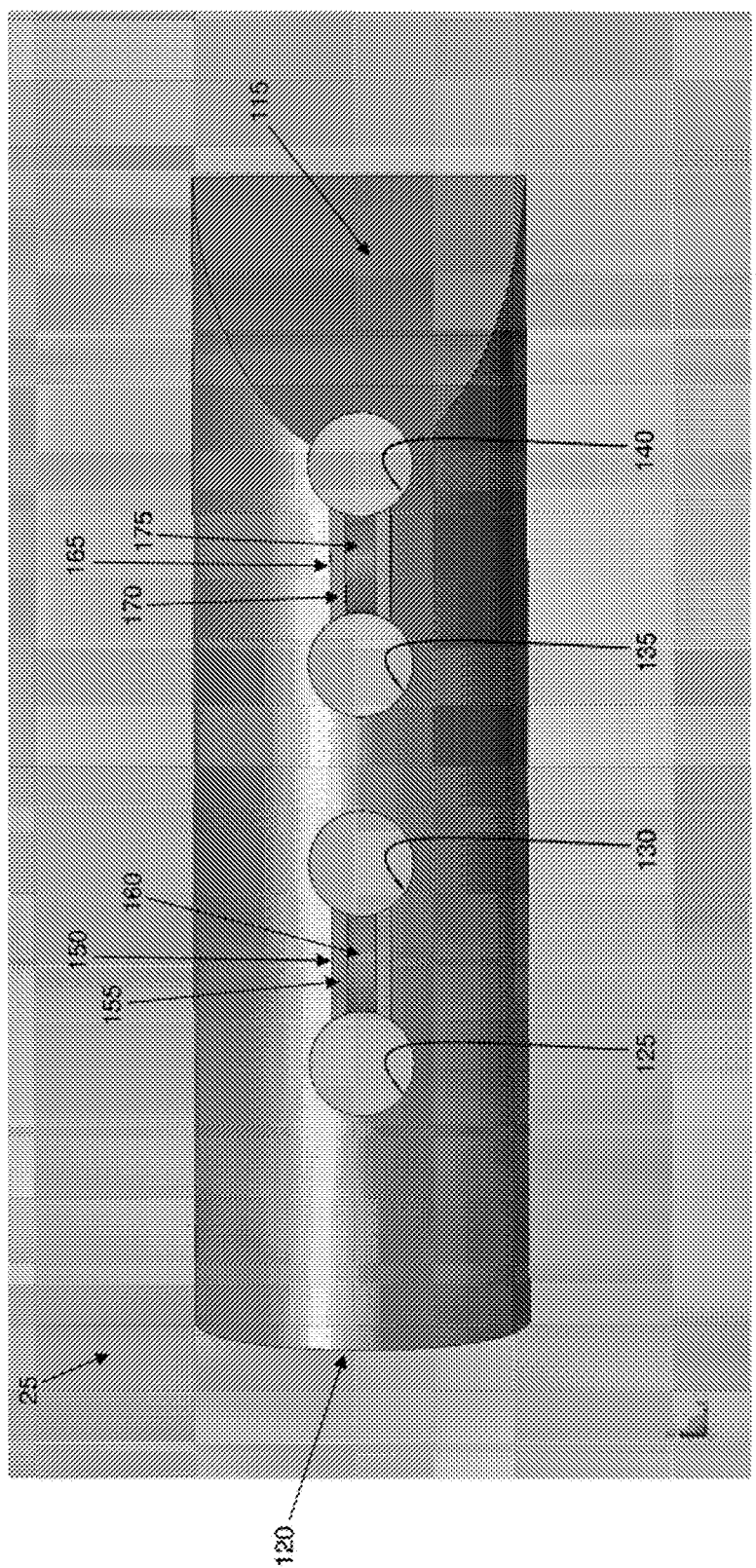
Figure 21:
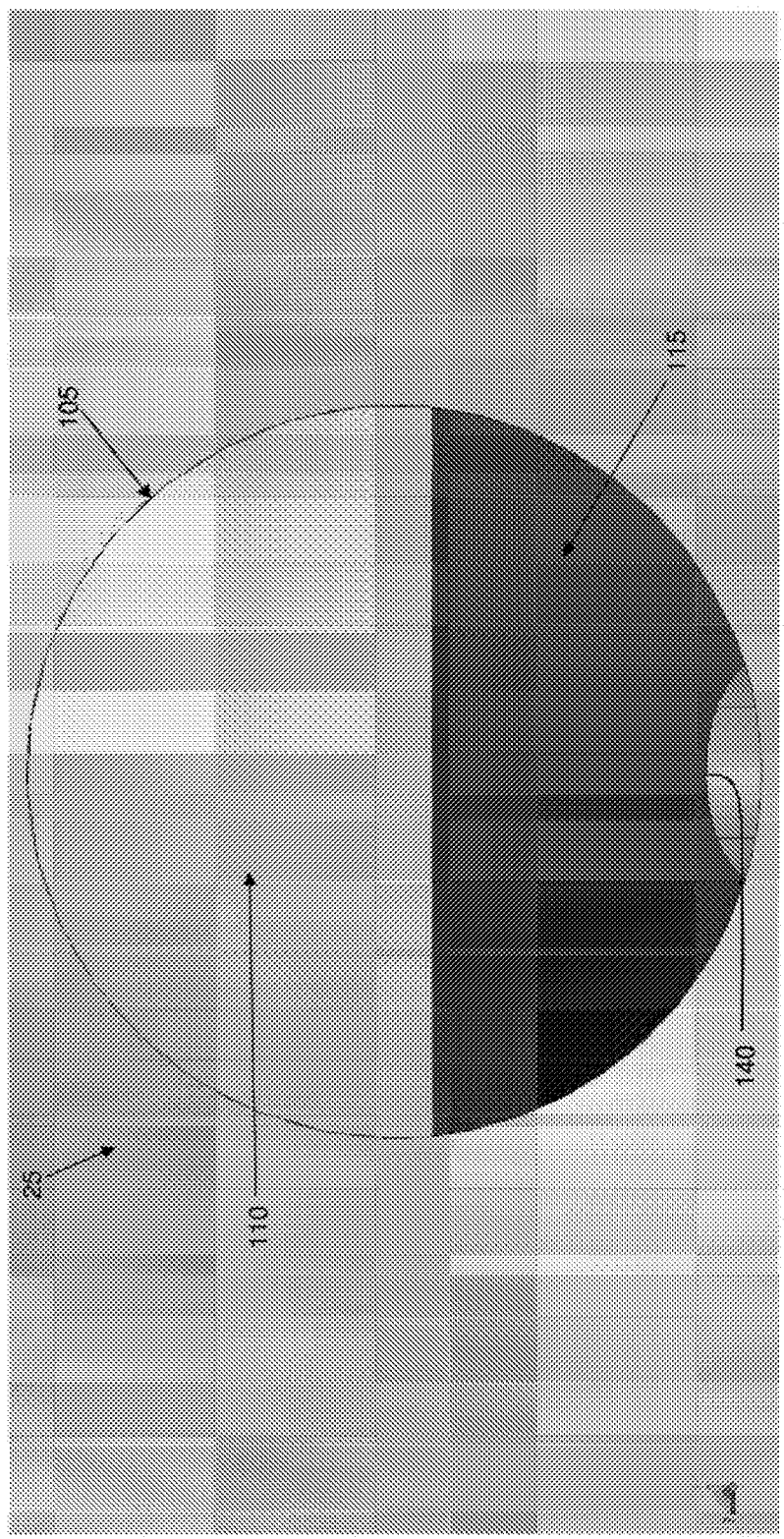
Figure 22:
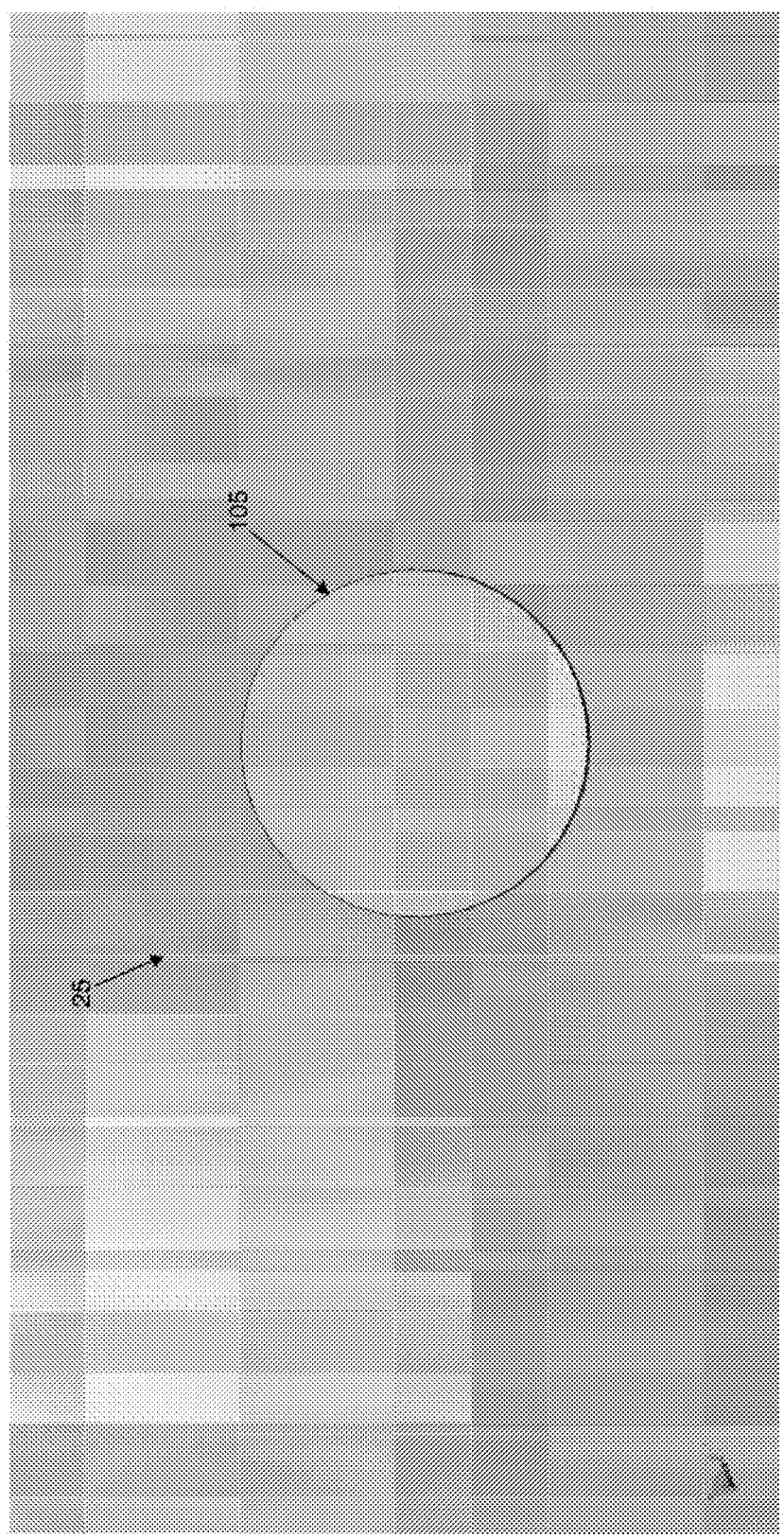
Figure 23:
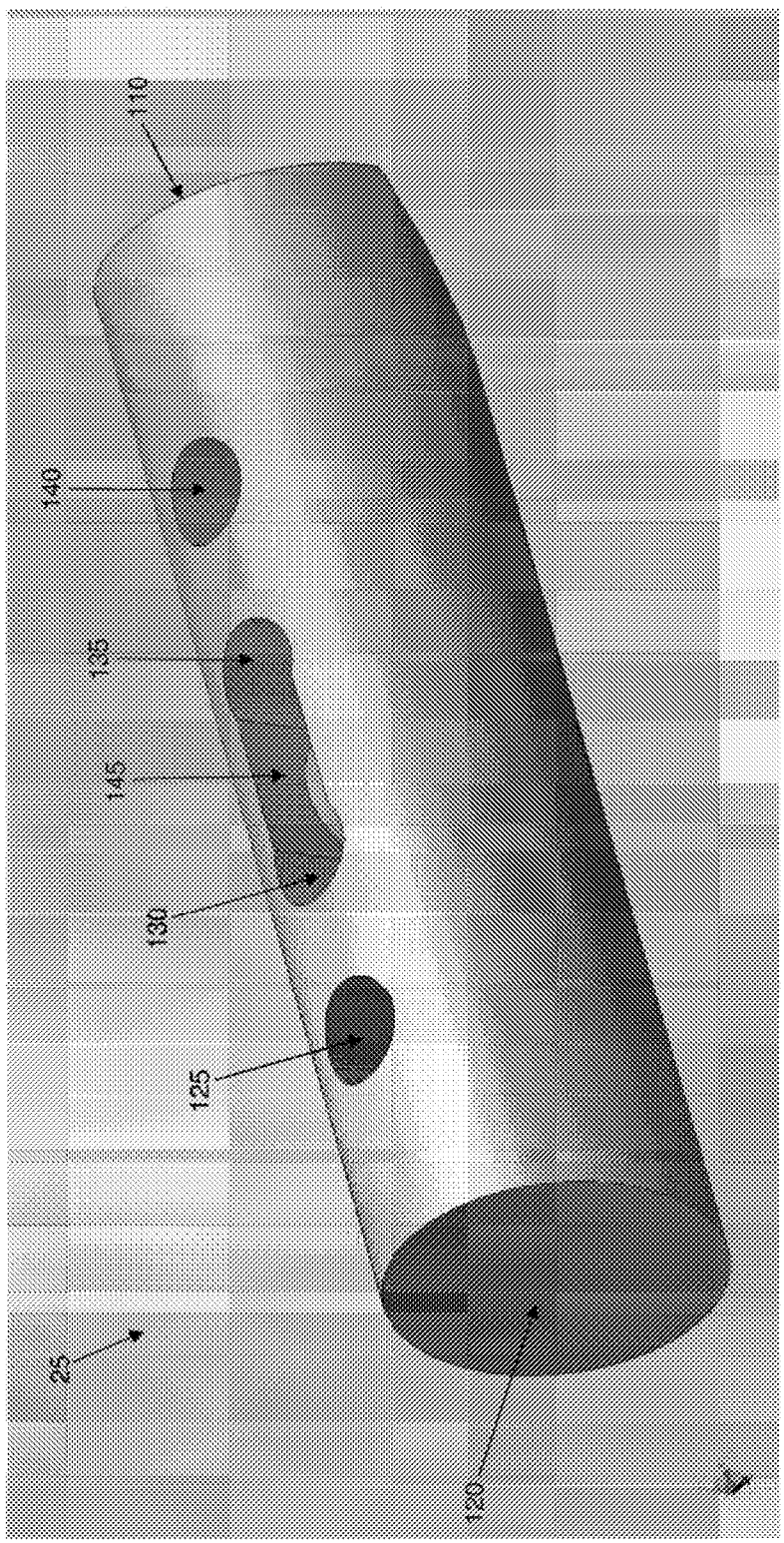
Figure 24:
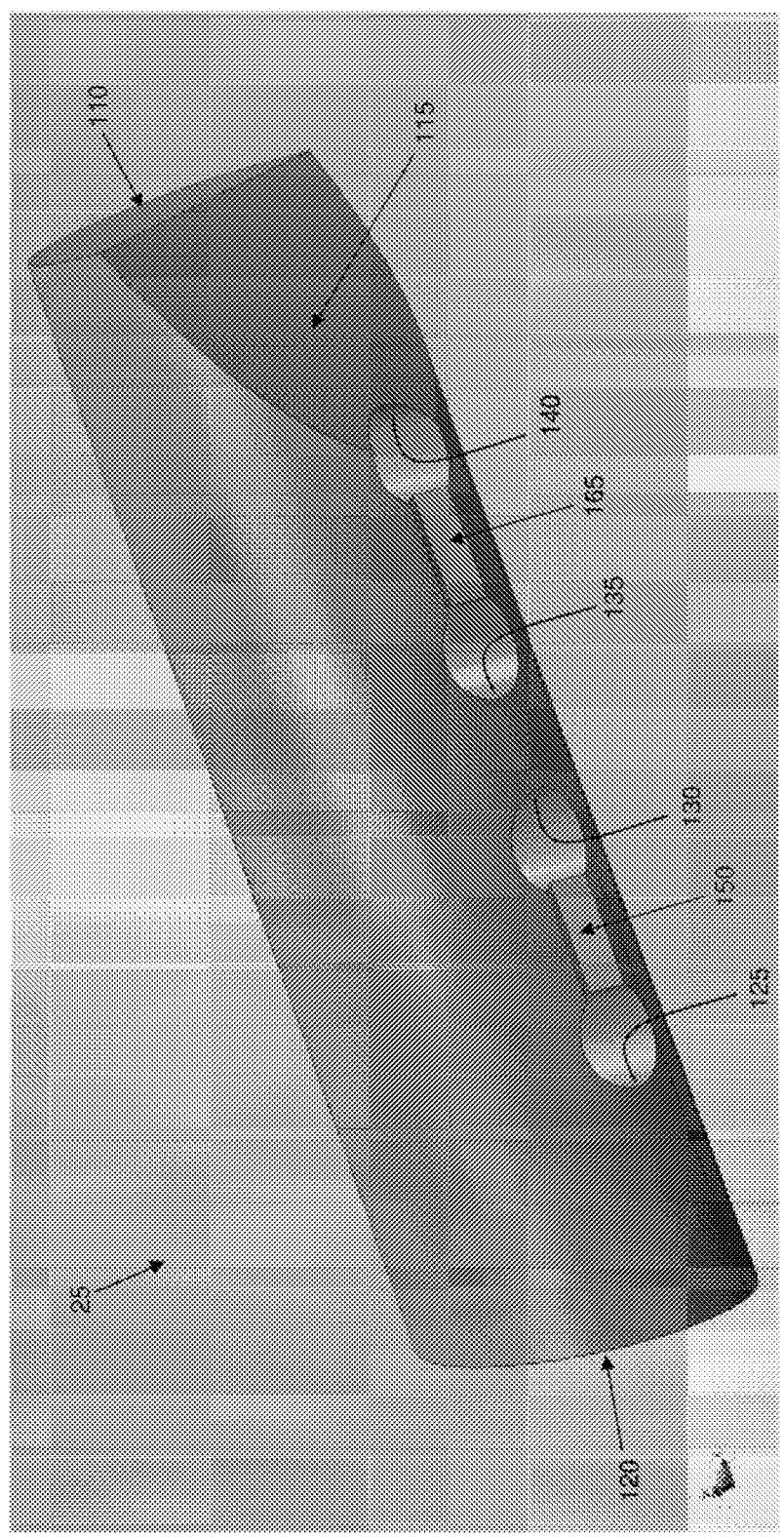
Figure 25:
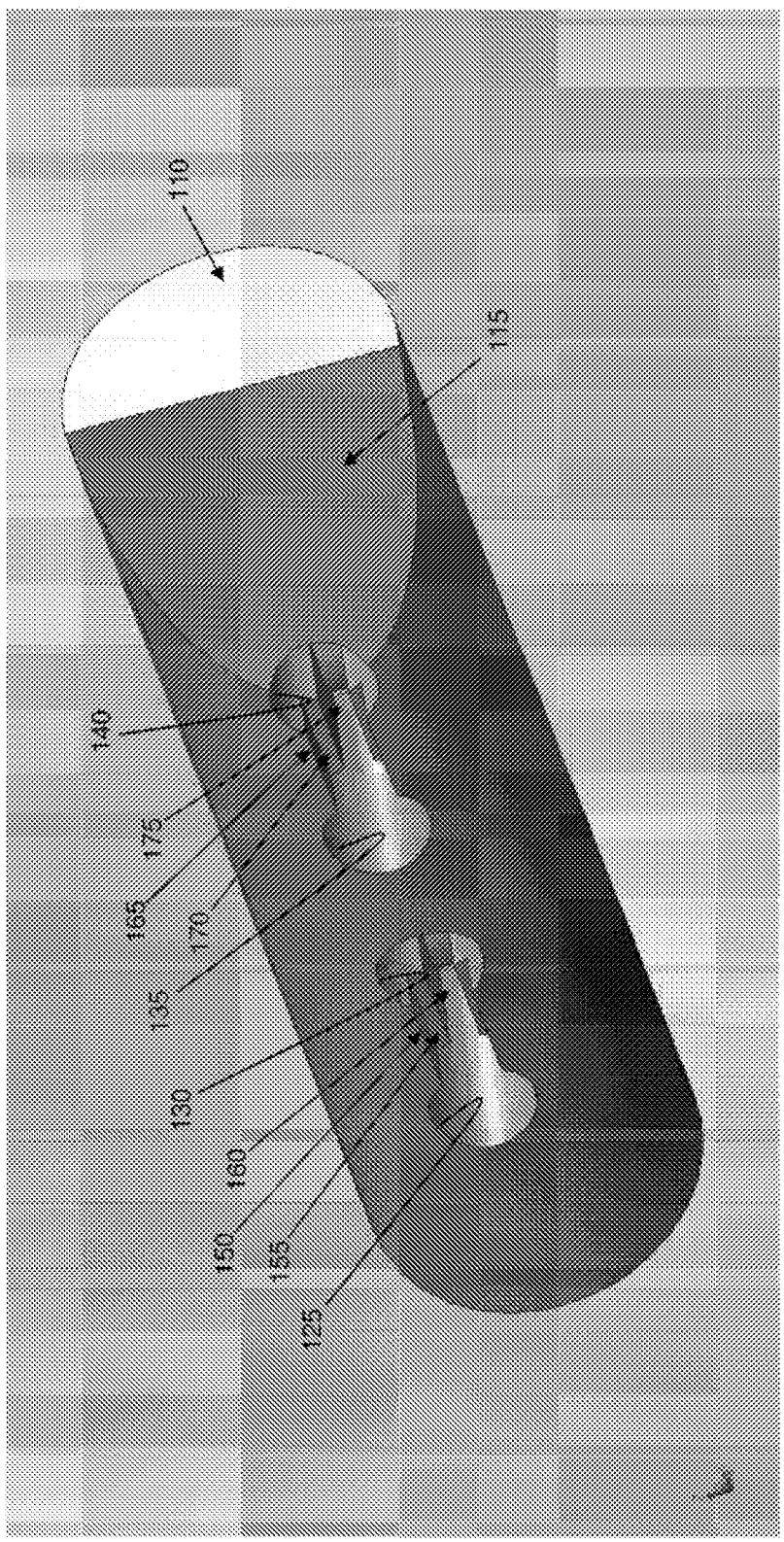
Figure 26:
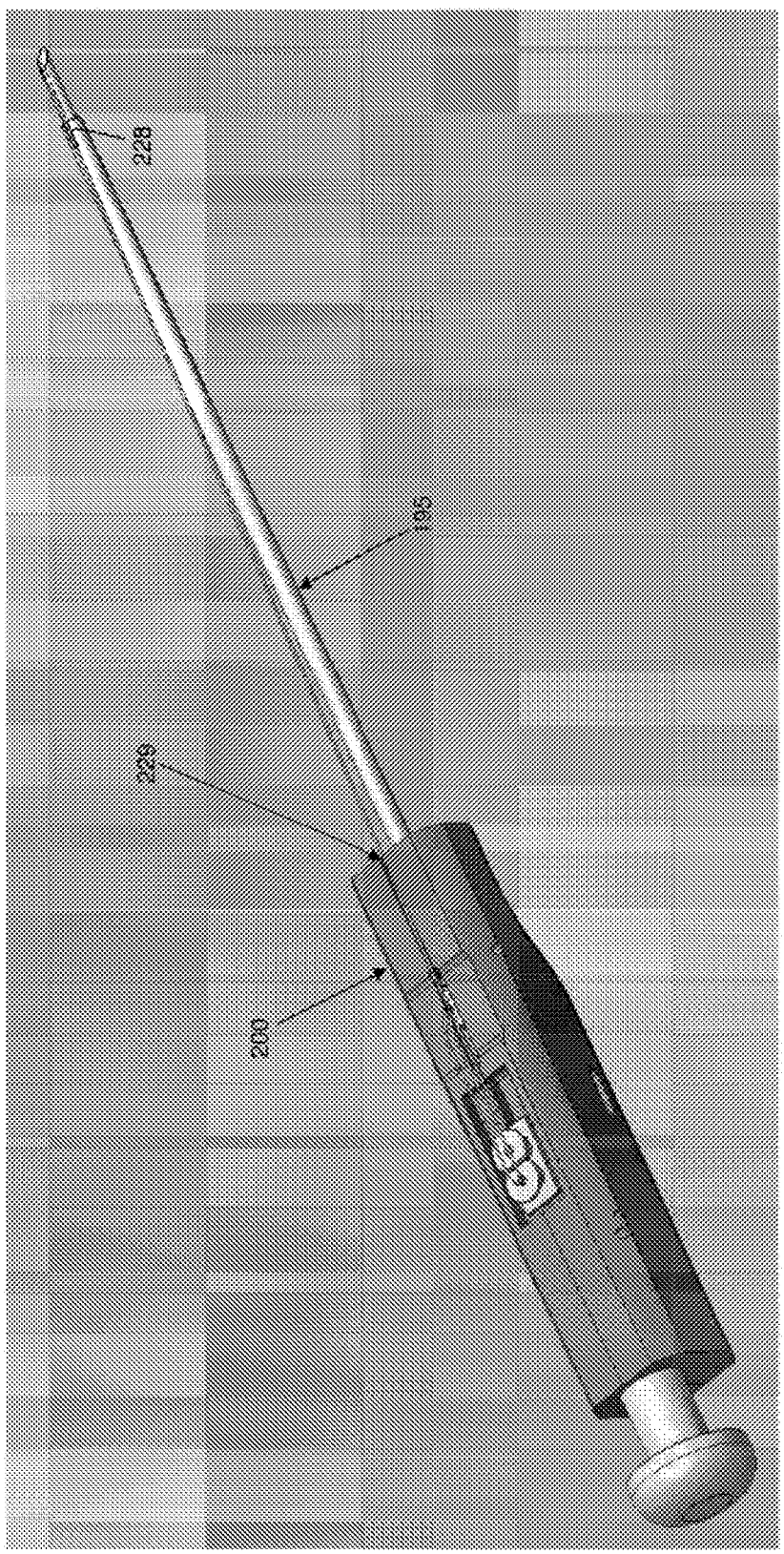
FIGS. 26, 27, 27A and 28-31 are schematic views showing further details of the inserter of FIG. 4.

As seen in FIGS. 3 and 5-8, suture 30 has a distal end 180 terminating in large ball (or knot) 185 and a proximal end 190. As seen in FIG. 6, suture 30 is passed through distal anchor 20 so that the suture extends along horizontal slot 75 of distal anchor 20 and up vertical bore 70 of distal anchor 20. Note that when suture 30 is passed through distal anchor 20 in this manner, distal anchor 20 may be slid along suture 30. As seen in FIG. 8, suture 30 is also passed through proximal anchor 25 so that the suture extends down vertical bore 140, along wider outer portion 170 of bottom horizontal slot 165, up vertical bore 135, forms a loop 320 above top horizontal slot 145, down vertical bore 130, along wider outer portion 155 of bottom horizontal slot 150, and up vertical bore 125. Note that when suture 30 is passed through proximal anchor 25 in this manner, proximal anchor 25 may be slid along suture 30, albeit with some effort due to the serpentine path which suture 30 follows through proximal anchor 25. Note also that, if bottom horizontal slot 165 comprises a narrower inner portion 175 and/or if bottom horizontal slot 150 comprises a narrower inner portion 160, a small amount of additional impedance may be introduced into the system when suture 30 is drawn into narrower inner portion 175 of bottom horizontal slot 165 and/or suture 30 is drawn into narrower inner portion 160 of bottom horizontal slot 150. In addition, it should be appreciated that while top horizontal slot 145 of proximal anchor 25 is sized to slidingly receive one strand of suture 30 therein, two or more overlapping strands of suture 30 will form a construct of greater diameter which may be snugly received within top horizontal slot 145, which may also provide a light hold on the two or more overlapping strands of suture when the two or more overlapping strands of suture are disposed within top horizontal slot 145.

The Inserter

As seen in FIGS. 4 and 26, 27 and 28, inserter 15 generally comprises a shaft 195, a handle 200 and a pushrod 205.

Shaft 195 generally comprises a hollow tube having a distal end 210, a proximal end 215 and a lumen 220 extending therebetween. Distal end 210 of shaft 195 terminates in a sharp point 225. A slot 227 is formed in distal end 210 of shaft 195 and may terminate in a shoulder 228. Alternatively, and more preferably, slot 227 extends proximally along shaft 195 so that it is coextensive with a slot 229 formed in inserter 15 (FIG. 26), whereby to allow suture 30 to separate from inserter 15 after distal anchor 20 and proximal anchor 25 have been set. Lumen 220 is sized to slidably receive distal anchor 20 (FIG. 28) and proximal anchor 25 (as will hereinafter be discussed). A mount 230 is secured to proximal end 215 of shaft 195.

Figure 27:
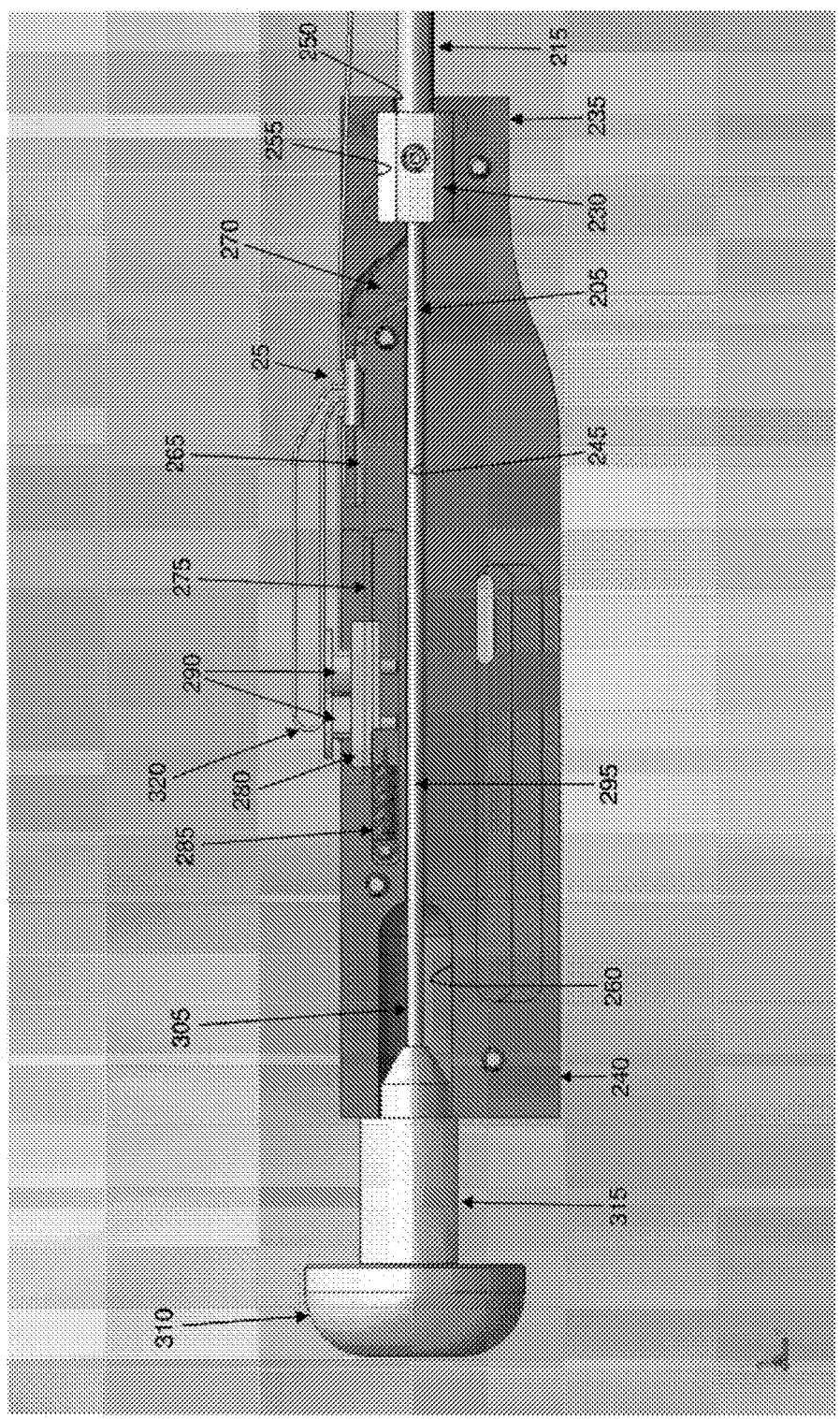

Handle 200 comprises a distal end 235, a proximal end 240, and a bore 245 extending therebetween. A first counterbore 250 is formed at the distal end of handle 200, and a second counterbore 255 is formed just proximal to first counterbore 250, with first counterbore 250 being sized to receive shaft 195 and second counterbore 255 being sized to receive mount 230, whereby to secure shaft 195 to handle 200. A third counterbore 260 is formed at the proximal end of handle 200. A groove 265 is formed on the top side of handle 200 for receiving proximal anchor 25 (FIG. 27). Groove 265 communicates with bore 245 via a passageway 270, whereby to allow proximal anchor 25 to be advanced into bore 245, as will hereinafter be discussed. Another groove 275 is formed on the top side of handle 200 for slidably receiving a suture sled 280. Suture sled 280 is biased proximally by a spring 285. Suture sled 280 includes a pair of suture cleats 290 for releasably securing loop 320 of suture 30 to suture sled 280, as will hereinafter be discussed.

Figure 27A:
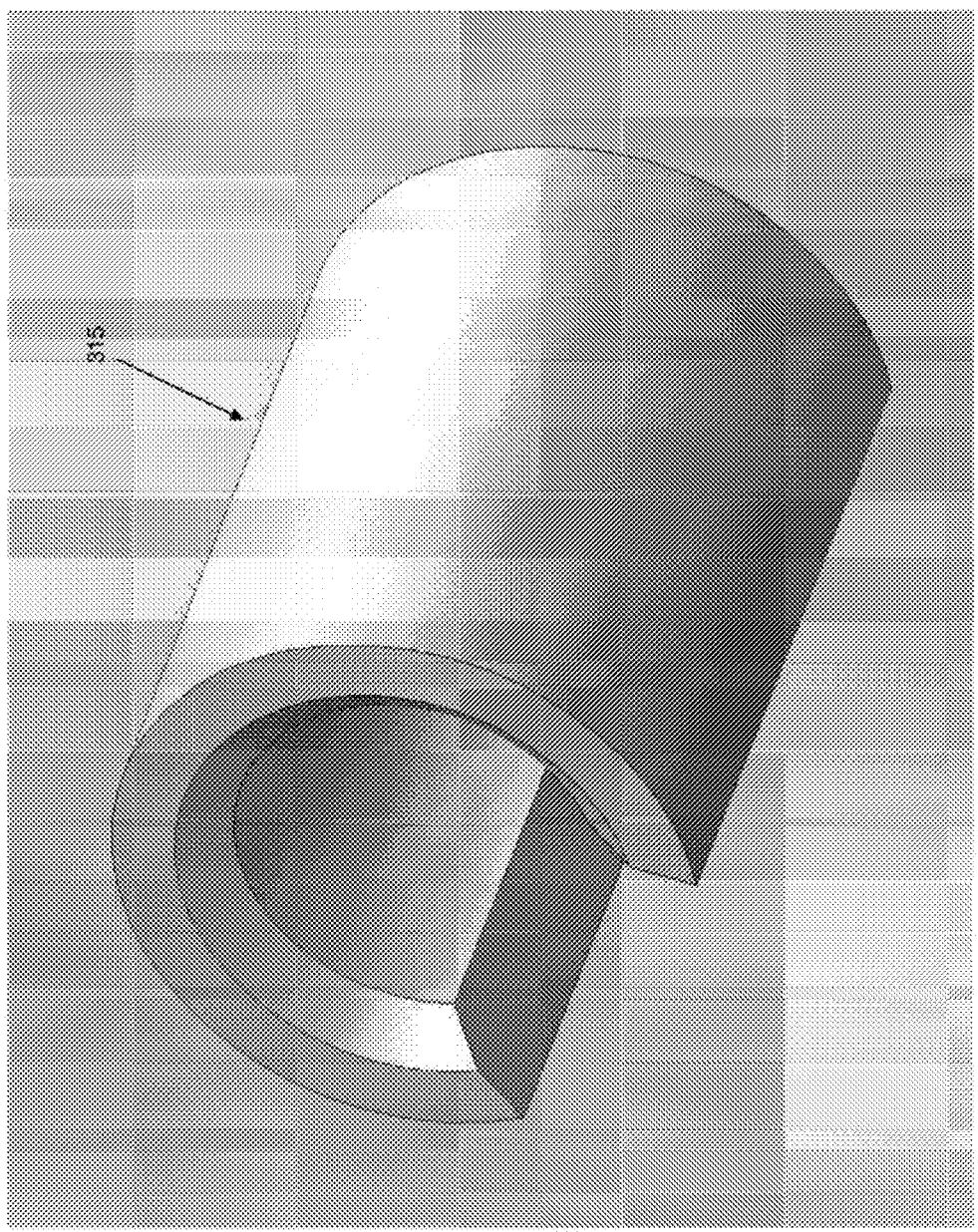

Pushrod 205 comprises a pusher 295 which is sized to be slidably received within bore 245 of handle 200 and lumen 220 of shaft 195. Pusher 295 comprises a distal end 300 (FIG. 28) and a proximal end 305 (FIG. 27). Distal end 300 of pusher 295 is preferably rounded so as to facilitate turning of distal anchor 20 and/or proximal anchor 25 when they are advanced out of shaft 195 of inserter 15, as will hereinafter be discussed. A thumb button 310 is secured to proximal end 305 of pusher 295, whereby to allow pusher 295 to be advanced distally by pressing on thumb button 310. Alternatively, thumb button 310 may be used to retract pusher 295, e.g., by gripping thumb button 310 between the thumb and forefinger of the user and pulling proximally, whereby to retract pusher 295 proximally. A removable stop 315 (FIG. 27A) may be fitted about thumb button 310, proximal to handle 200, so as to prevent distal movement of thumb button 310 and hence prevent distal movement of pusher 295.

Figure 28:
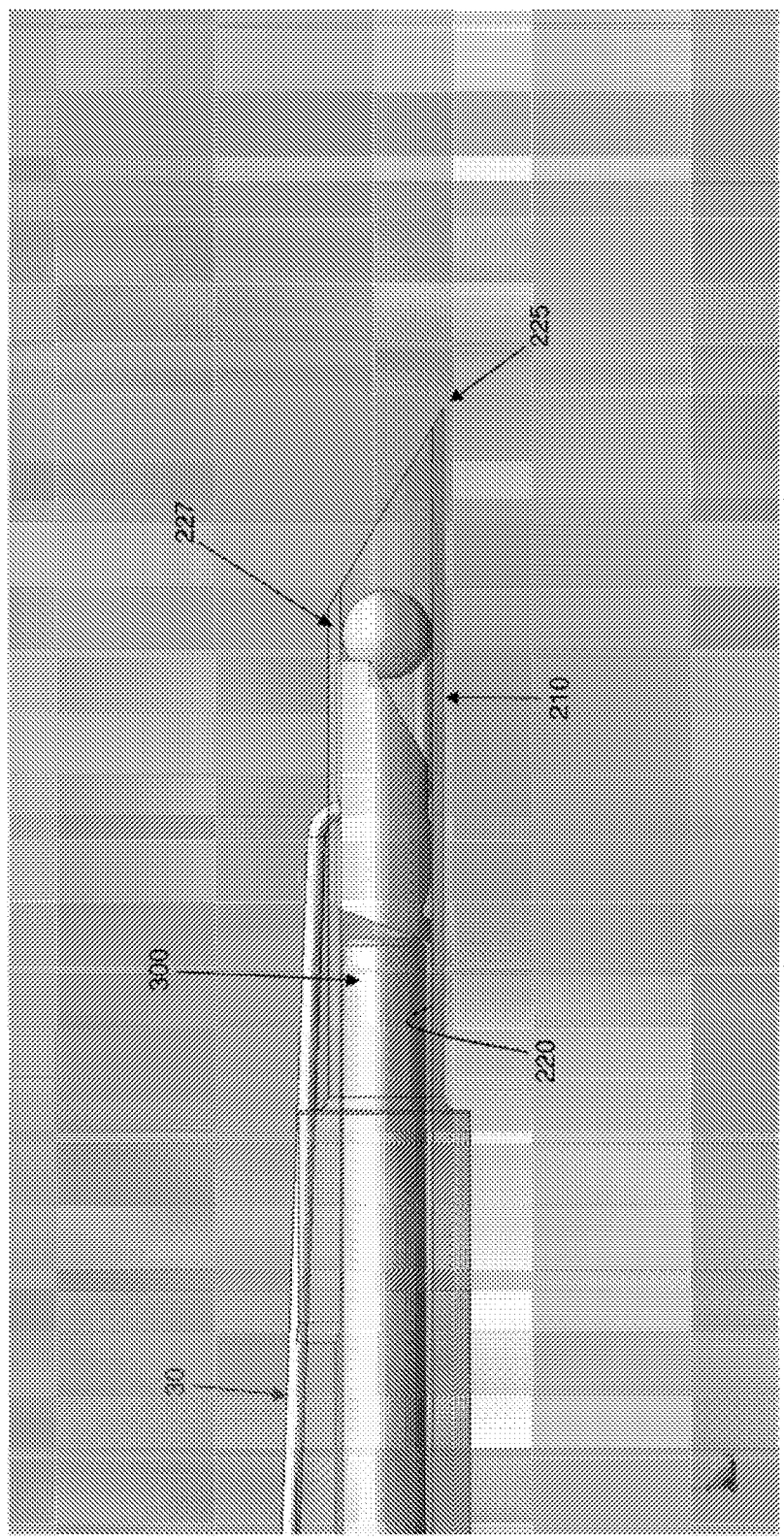

Prior to use, anchor assembly 10 is mounted to inserter 15. More particularly, distal anchor 20 is loaded into distal end 210 of shaft 195 so that suture 30 extends out slot 227 of shaft 195 (FIG. 28). Proximal anchor 25 is loaded into groove 265 of handle 200, suture 30 is drawn taut by pulling on loop 320, and then loop 320 of suture 30 is secured to suture cleats 290. Note that loop 320 is the portion of suture 30 which extends between where the suture exits vertical bore 135 of proximal anchor 25 and re-enters vertical bore 130 of proximal anchor 25. Pushrod 205 is inserted into bore 245 of handle 200 and lumen 220 of shaft 195 until removable stop 315 engages the proximal end of handle 200. At this point, distal end 300 of pusher 295 abuts distal anchor 20 (FIG. 28).

Preferably suture assembly 10 is mounted to inserter 15 at the time of manufacture and prior to packaging and sterilization, although suture assembly 10 may also be mounted to inserter 15 at the time of use if desired.

Exemplary Use of the Novel System to Close a Fissure in the Annulus of an Intervertebral Disc In use, in order to close a fissure in the annulus of an intervertebral disc, distal anchor 20 is intended to be positioned on one side of a fissure, proximal anchor 25 is intended to be positioned on another side of the fissure, and suture 30 is thereafter tensioned so as to close the fissure, whereby to treat degenerative disc disease.

Figure 32:
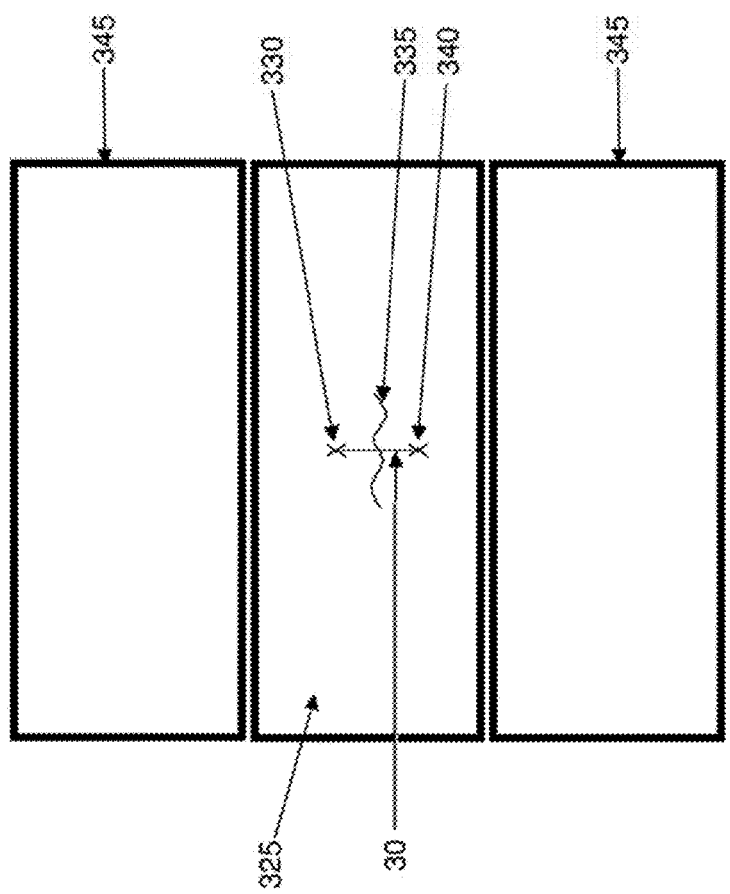

By way of example but not limitation, and looking now at FIG. 32, distal anchor 20 may be passed through the annulus of an intervertebral disc 325 at a location 330 on one side of a fissure 335, and proximal anchor 25 may be passed through the annulus of the same intervertebral disc 325 at a location 340 on the opposite side of a fissure 335, so that the suture 30 spans fissure 335 and holds it closed.

Figure 33:
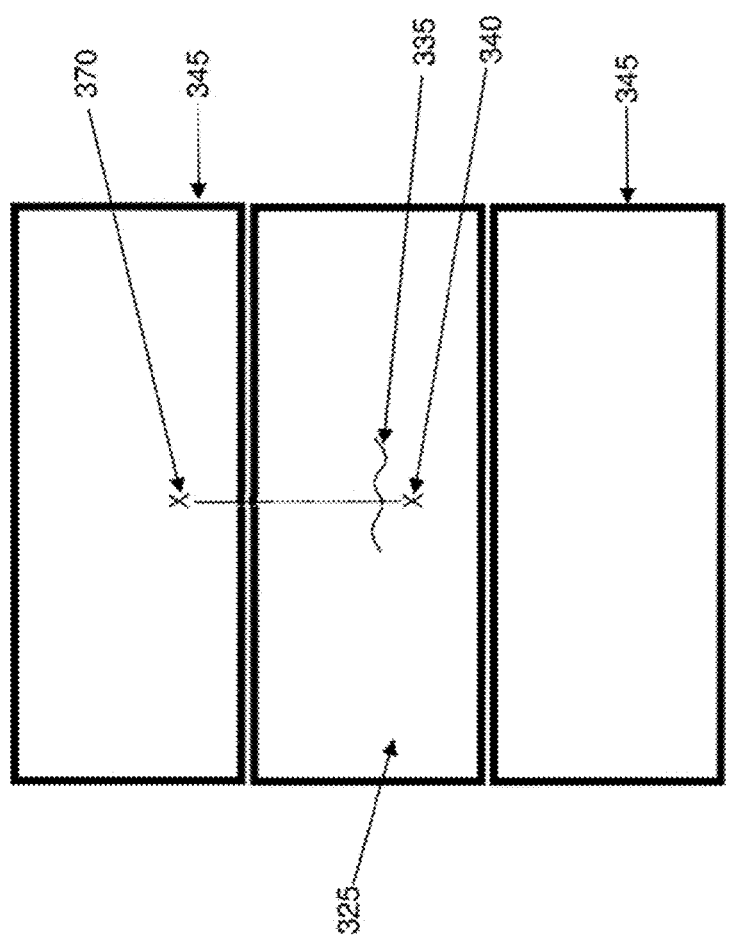

By way of further example but not limitation, and looking now at FIG. 33, distal anchor 20 may be inserted into a vertebral body 345 adjacent to an intervertebral disc 325 having a fissure 335, and proximal anchor 25 may be passed through the annulus of that intervertebral disc 325 at a location 340 on the opposite side of a fissure 335, so that the suture 30 spans fissure 335 and holds it closed. Where distal anchor 320 is to be inserted into vertebral body 345, a hole may be pre-formed in the vertebral body (e.g., by drilling, tapping, punching, etc.).

For purposes of illustrating the present invention, an annulus reconstruction will now be discussed in the context of positioning distal anchor 20 in a vertebral body and proximal anchor 25 in the intervertebral disc.

Figure 29:
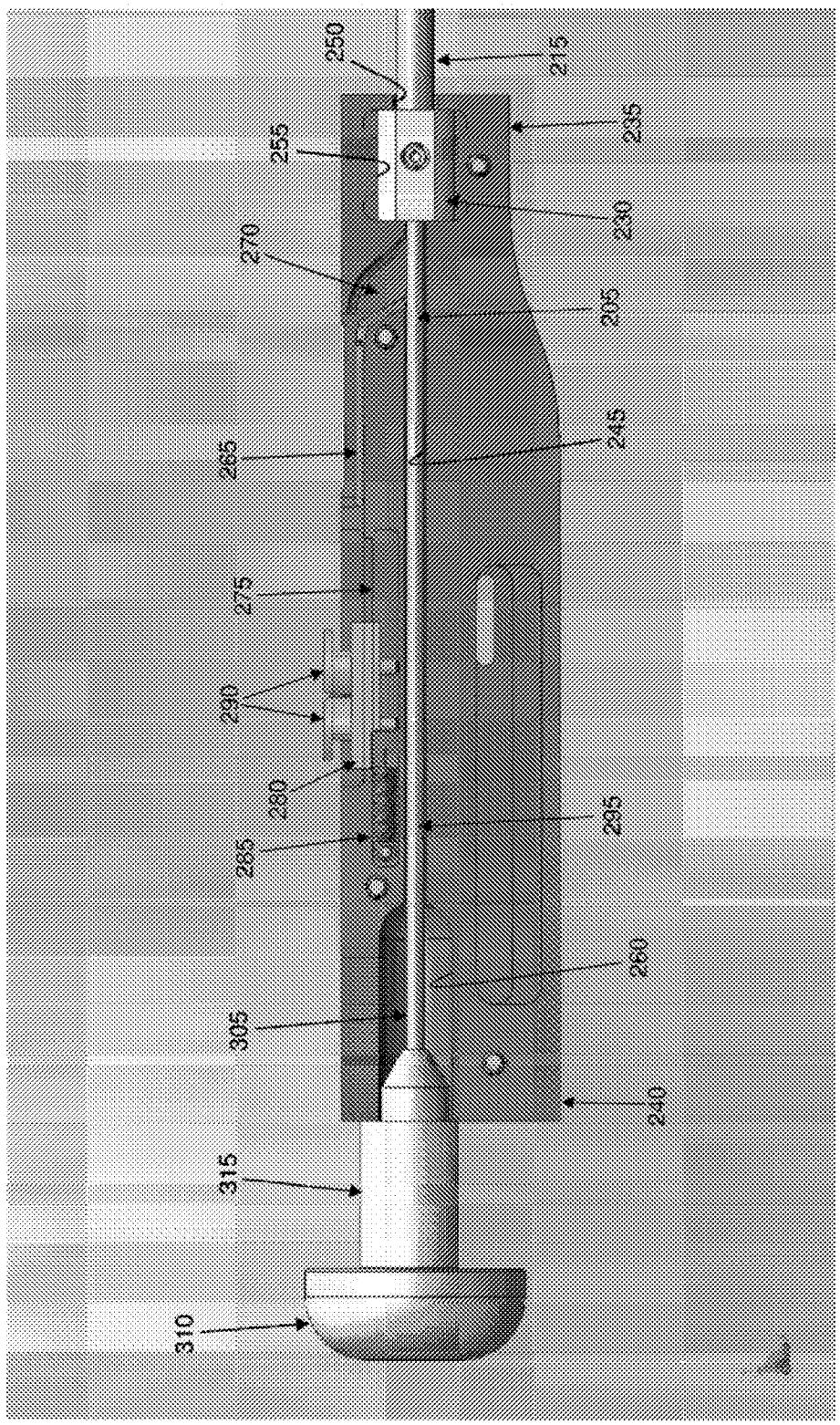
Figure 30:
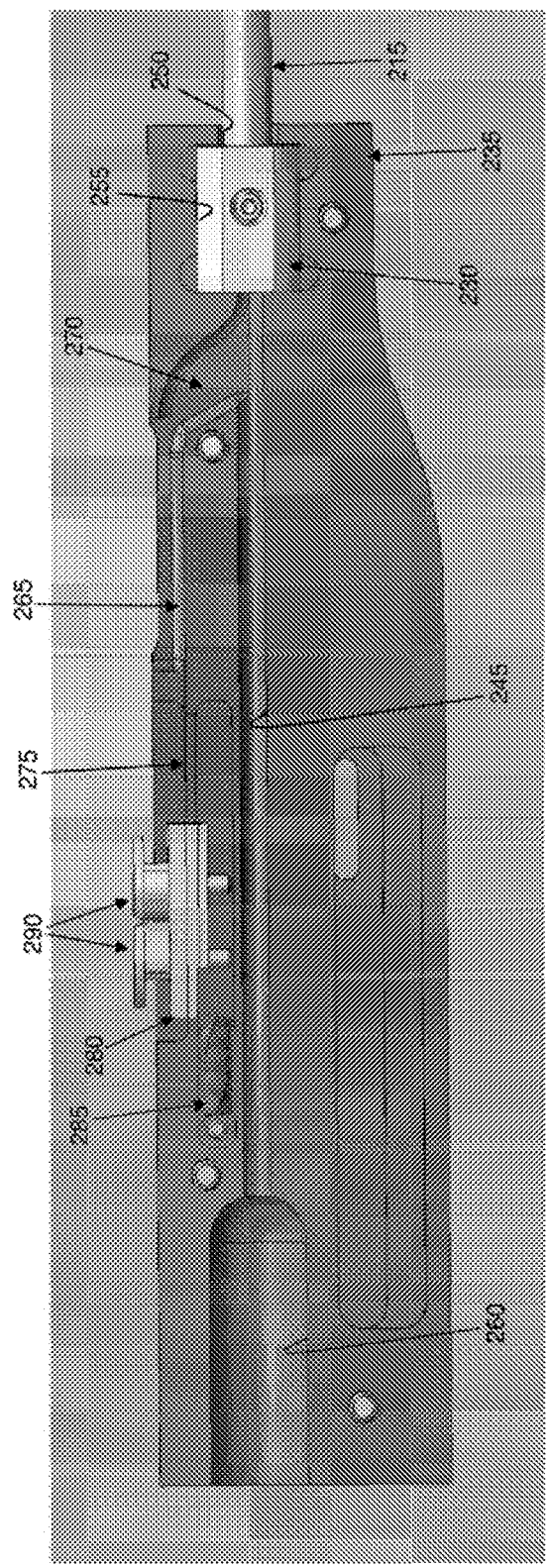
Figure 31:
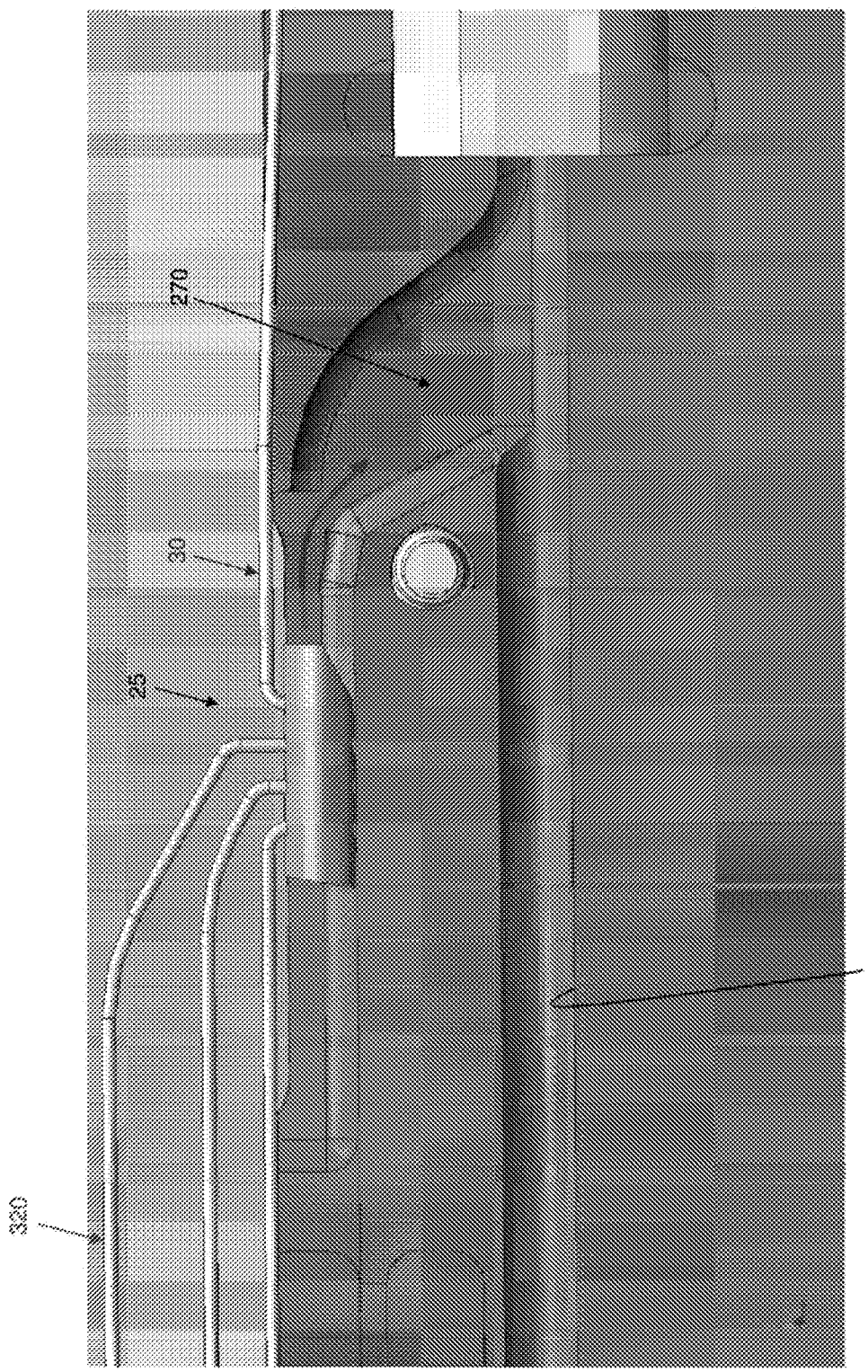
Figure 38:
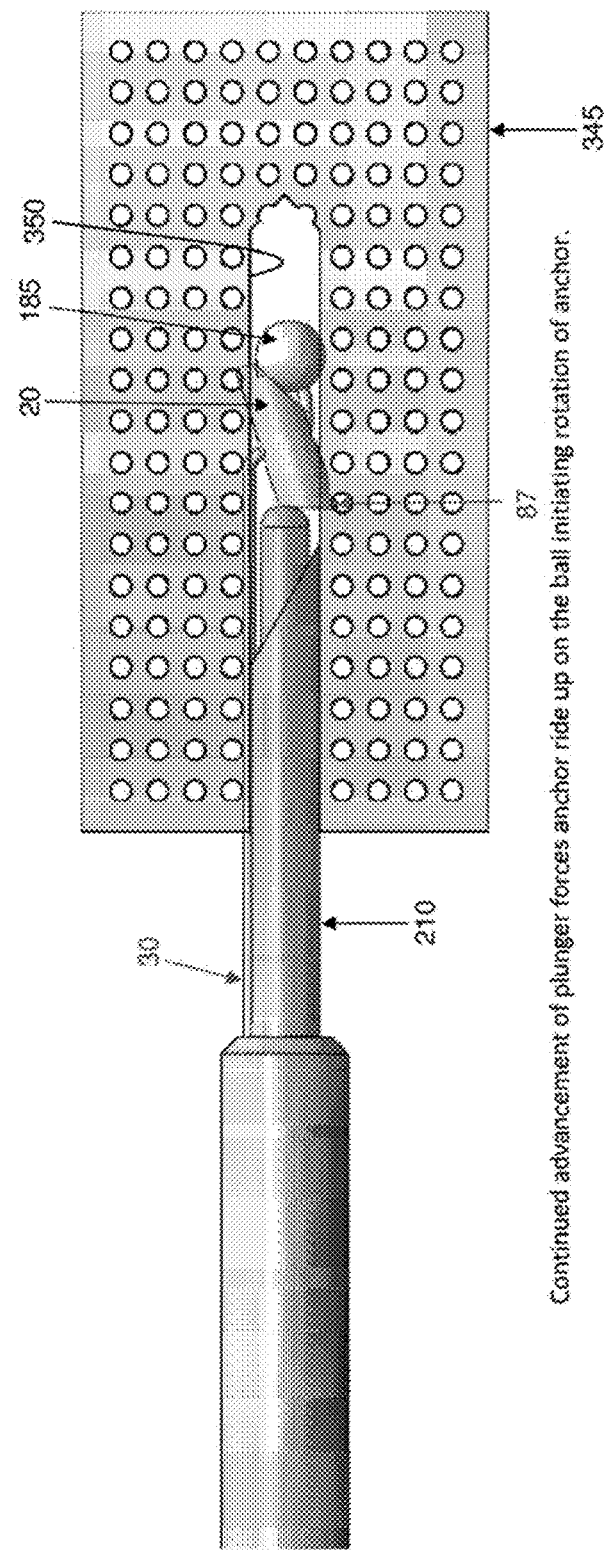

More particularly, and looking now at FIGS. 34-38, a hole 350 is formed (e.g., by drilling, tapping, punching, etc.) in a vertebral body 345 (FIG. 34), the distal end of shaft 195 is inserted into hole 350 to an appropriate depth (FIG. 35), and then removable stop 315 (FIG. 29) is removed from thumb button 310. Then thumb button 310 is advanced toward handle 200, causing the distal end of pusher 295 to advance distal anchor 20 out of shaft 195 (FIG. 36). Note that as distal anchor 20 is advanced out of shaft 195, suture sled 280 moves distally along handle 200, against the power of spring 285, thereby allowing suture 30 (and hence ball 185 set at the distal end of suture 30) to also move distally with distal anchor 20. As thumb button 310 continues to advance distally toward handle 200, suture sled 280 reaches the end of its stroke in groove 275, thereby preventing further distal movement of suture 30 (and hence preventing further distal movement of ball 185 set at the distal end of suture 30). See FIG. 37. Thereafter, continued advancement of thumb button 310 toward handle 200 causes distal anchor 20 to pivot on ball 185 as distal inclined surface 60 of distal anchor 20 rides upward on ball 185, thereby causing distal anchor 20 to rotate within the bone (FIG. 38). In essence, as pusher 295 forces distal anchor 20 against the now-stationary ball 185, the camming engagement of inclined distal surface 60 of distal anchor 20 with ball 185 causes distal anchor 20 to turn within vertebral body 345. Thus, the "throw" of suture sled 280 effectively sets the depth of distal anchor 20, since it effectively sets the position of ball 185 within the vertebral body 345. Inserter 15 is then moved proximally so as to apply a proximal force to distal anchor 20 via suture 30, whereby to set distal anchor 20 into vertebral body 345. Among other things, the pointed heel 87 formed by inclined proximal surface 65 and proximal notch 85 is set into the vertebral body, whereby to facilitate setting of distal anchor 20 as suture 30 is pulled proximally. This completes setting of distal anchor 20.

In this respect it should be appreciated that the provision of the novel apparatus of the present invention (i.e., distal anchor 20, suture 30 and inserter 15) provides a significant advantage over conventional toggle anchors of the prior art, since the present invention permits the toggle-type distal anchor 20 to be reliably toggled and set in dense tissue such as an intervertebral body and/or an intervertebral disc. As noted above, conventional toggle-type anchors have had limited success when set within the interior of tissue in general, and particularly when set within the interior of dense tissue such as an intervertebral body and/or an intervertebral disc, since they provide inconsistent toggling and low pull-out strengths. By contrast, with the present invention, the unique camming engagement of inclined distal surface 60 of distal anchor 20 with the restrained ball 85 causes distal anchor 20 to turn even when it is within the interior of dense tissue such as an intervertebral body and/or an intervertebral disc. Furthermore, the pointed heel 87 of distal anchor 20 facilitates setting of the anchor when suture 30 is tensioned.

Thereafter, loop 320 of suture 30 is released from suture cleats 290, pushrod 205 is removed from shaft 195 and handle 200, and inserter 15 is withdrawn from the bone (if it has not already been withdrawn from the bone). As this occurs, proximal anchor 25 is drawn distally through passageway 270 and into bore 245 in handle 200 (due to the fact that proximal anchor 25 encounters some impedance to sliding along suture 30 since suture 30 follows a serpentine path through proximal anchor 25, and due to the fact that inserter 15 is being withdrawn proximally).

Then removable stop 315 is replaced on thumb button 310, and pushrod 205 is advanced into bore 245 of handle 200 and into lumen 220 of shaft 195. This action advances proximal anchor 25 along lumen 220 of shaft 195. Pushrod 205 is advanced until removable stop 315 engages the proximal end of handle 200. At this point, proximal anchor 25 is disposed in the distal end of shaft 195, but is prevented from being ejected out of the distal end of shaft 195 due to the engagement of removable stop 315 with the proximal end of handle 200.

Figure 38A:
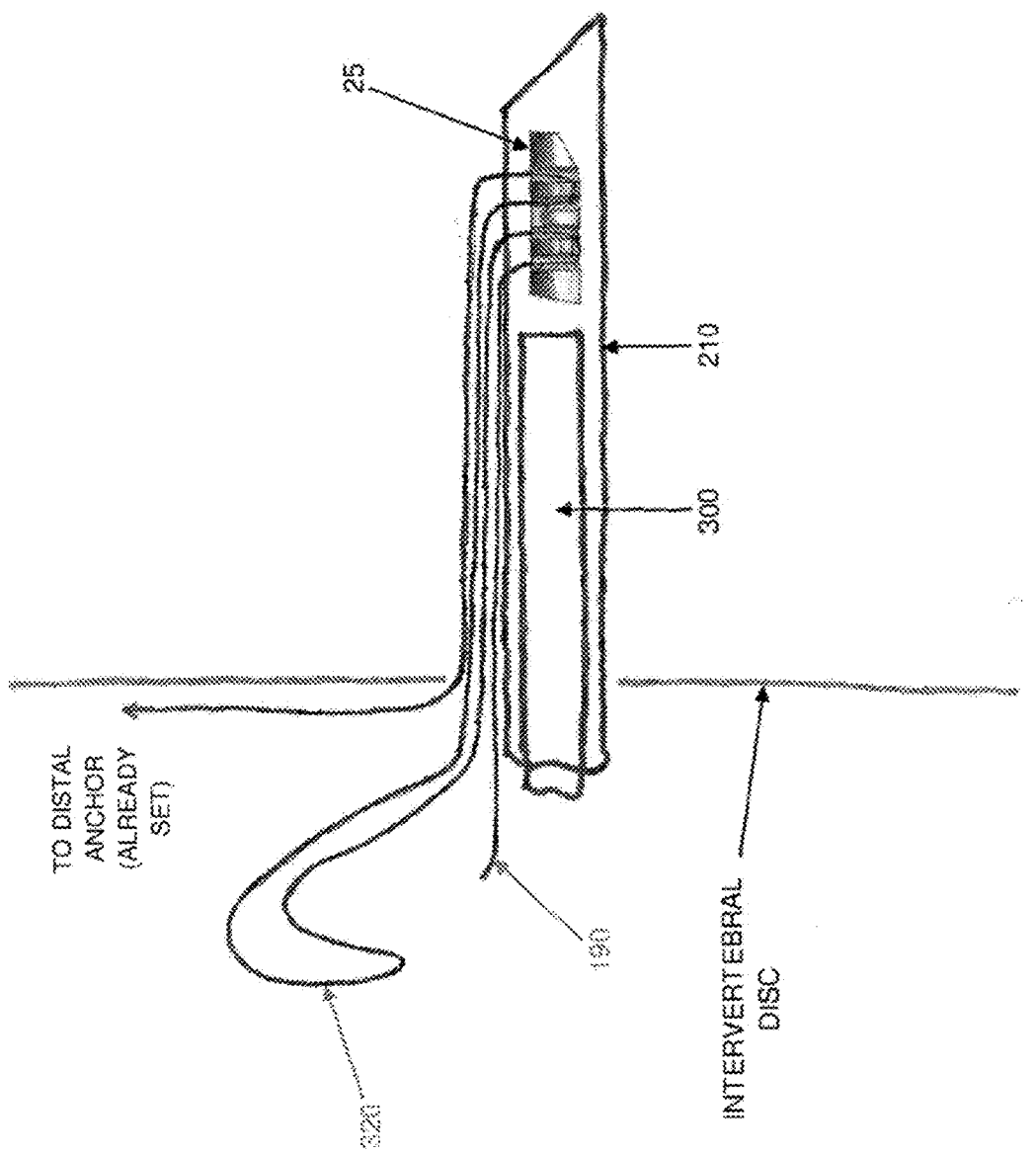
Figure 38B:
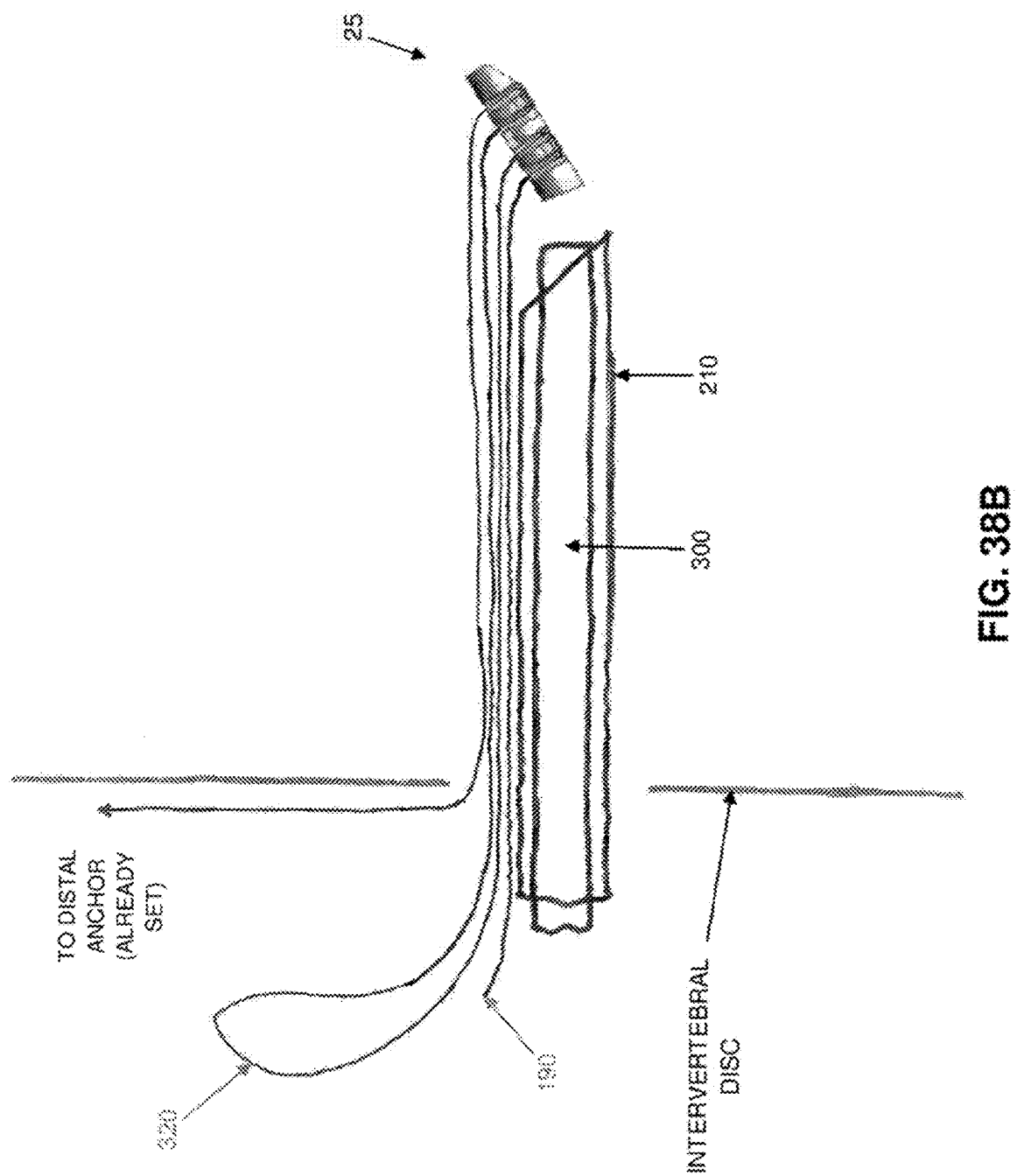
Figure 38D:
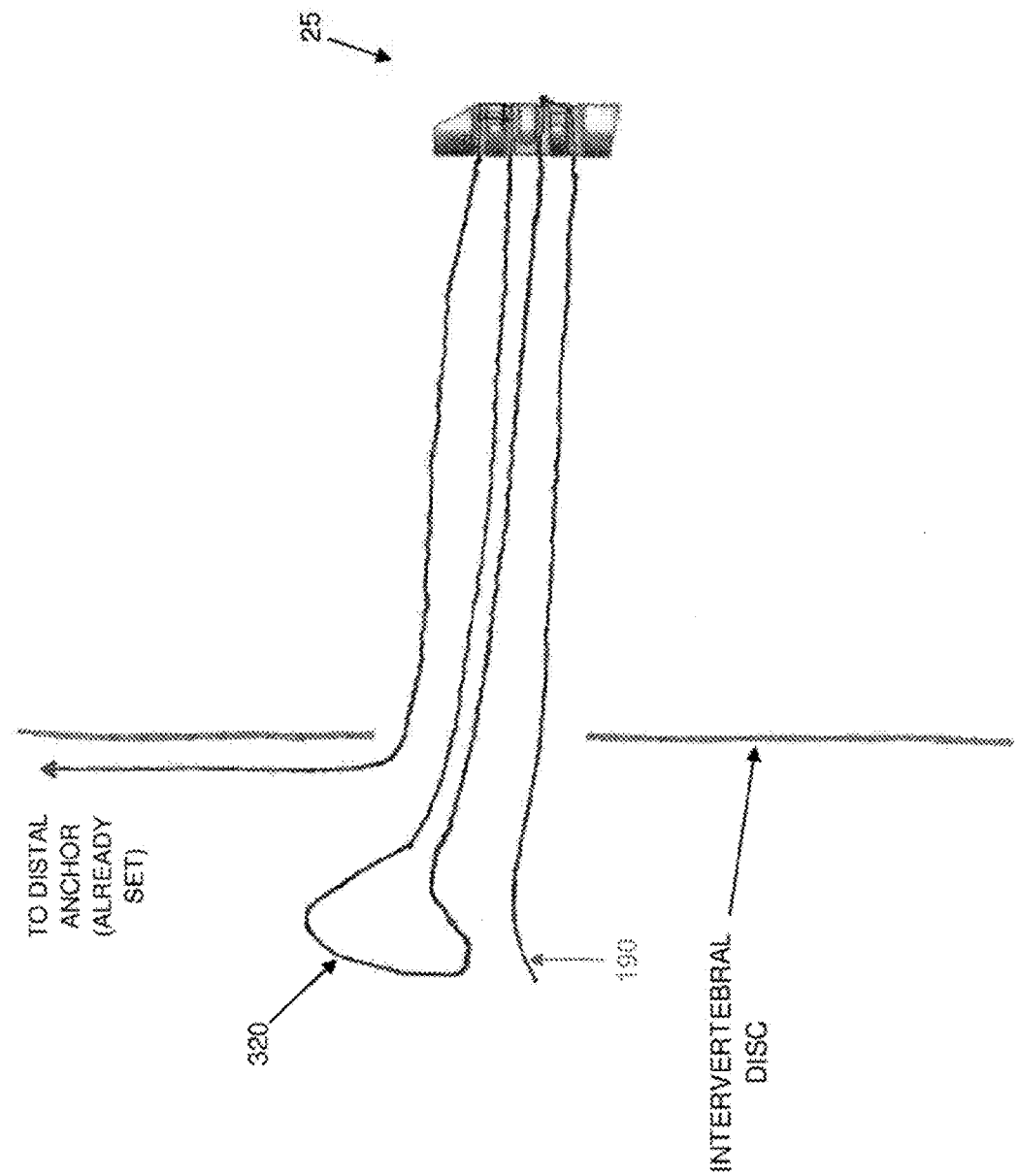
Figure 38E:
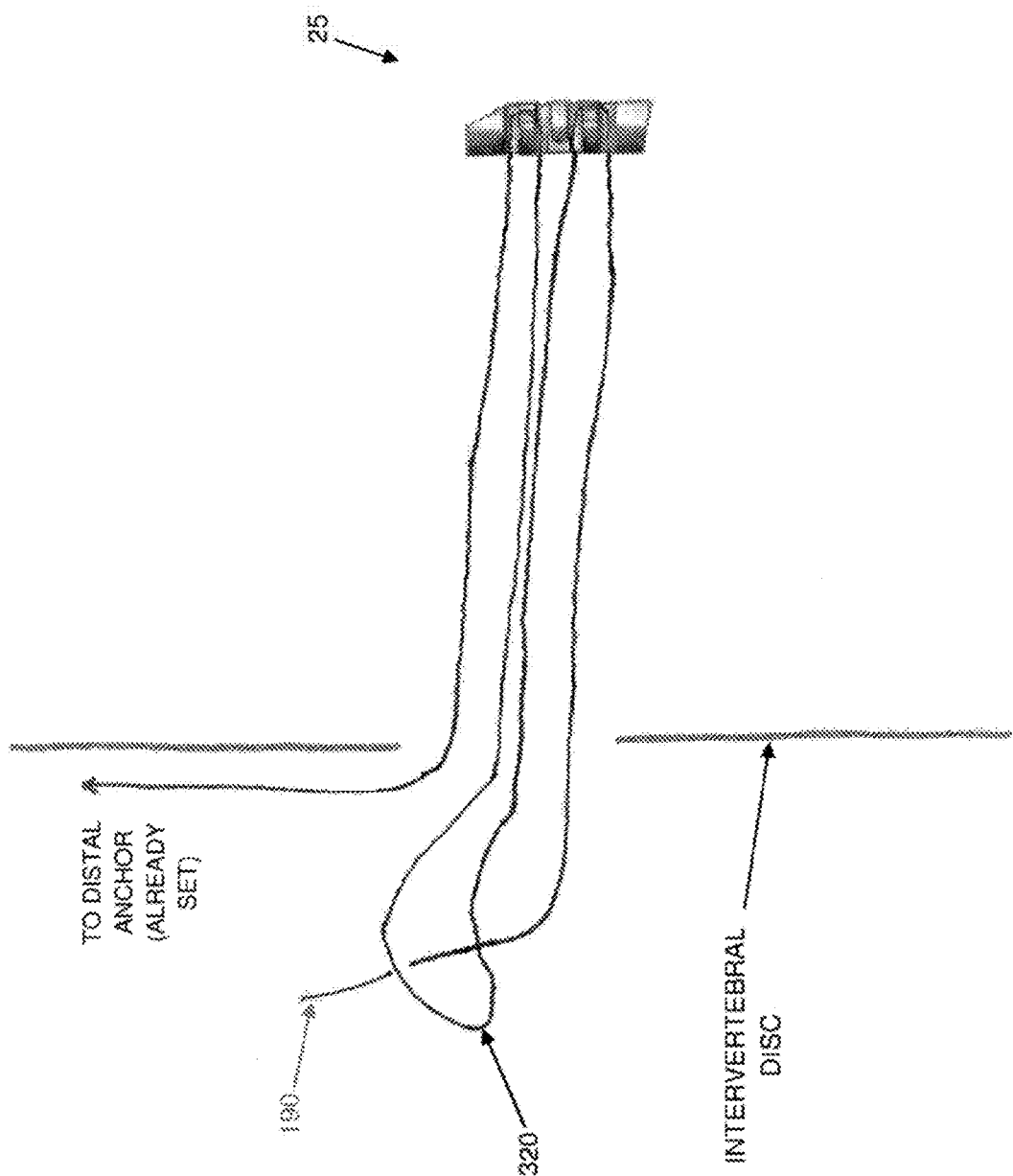
Figure 38F:
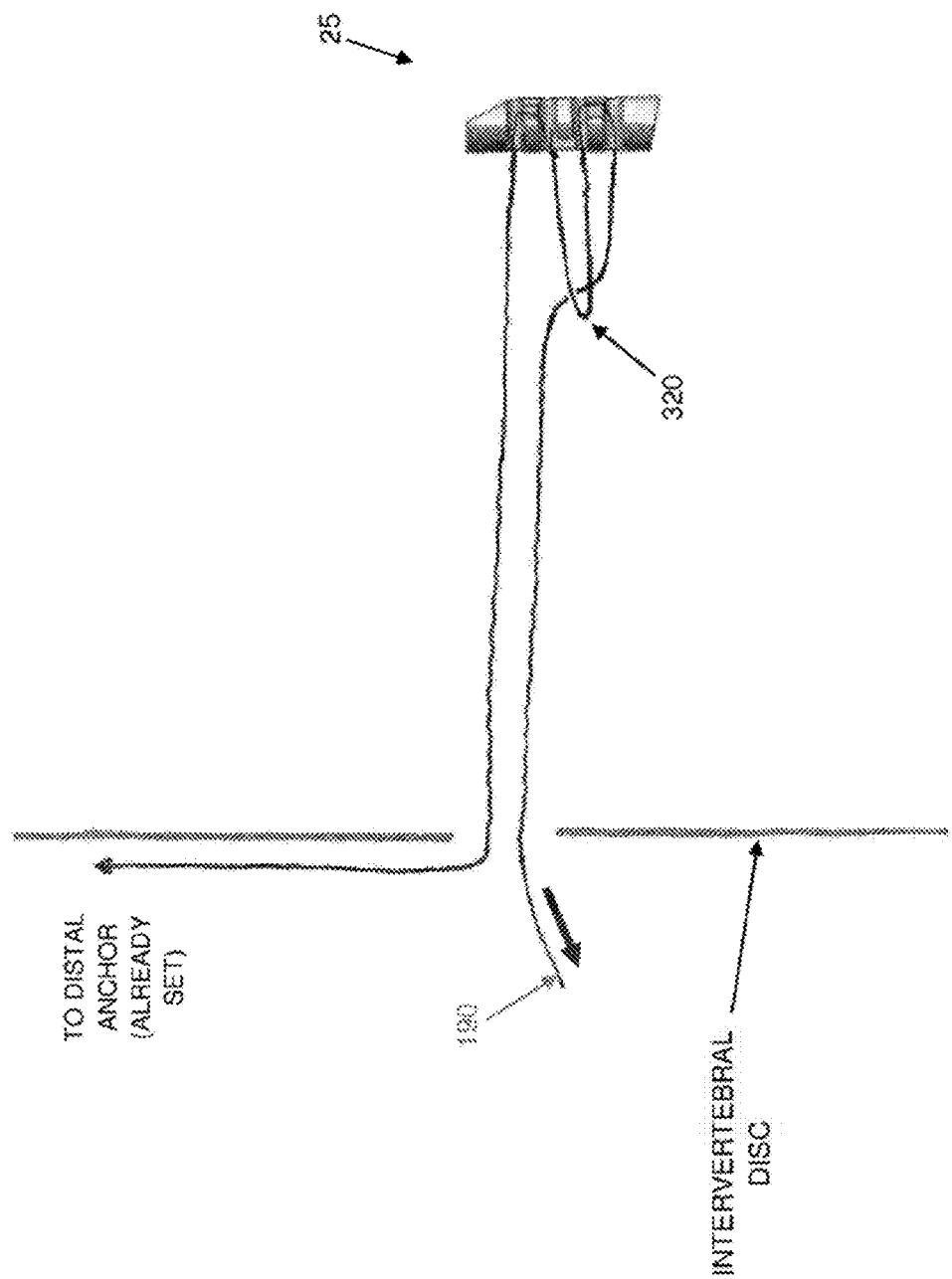
Figure 38G:
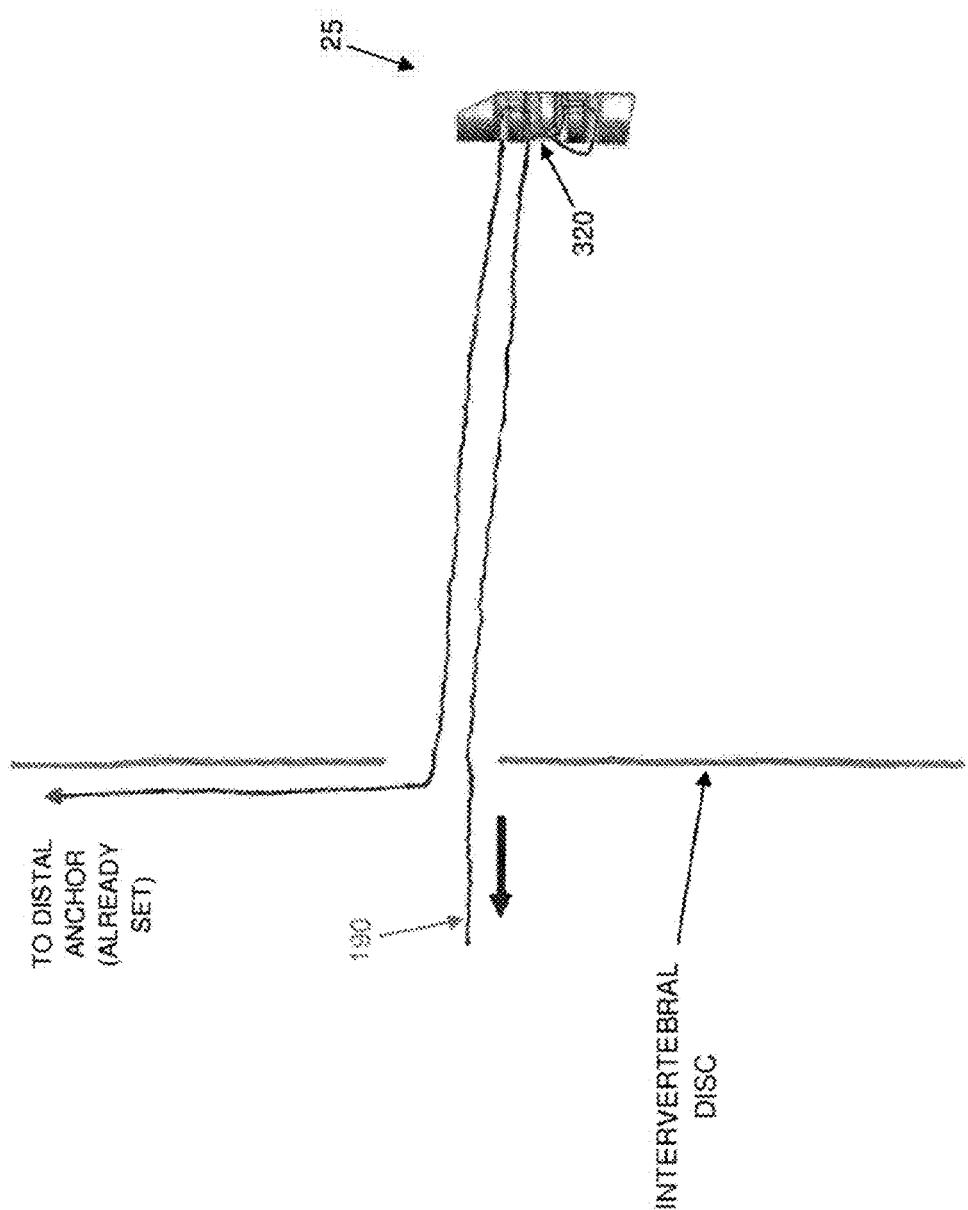

Next, shaft 195 of inserter 15 is inserted through the annulus on the far side of the fissure, so that suture 30 spans the fissure. See FIG. 38A. Then removable stop 315 is removed from thumb button 310, and thumb button 310 is advanced distally so as to cause pusher 295 to eject proximal anchor 25 out of shaft 195 and into the nucleus of the intervertebral disc. As this occurs, the geometry of proximal anchor 25 and the tension on suture 30 causes proximal anchor 25 to begin turning within the nucleus of the intervertebral disc. See FIG. 38B. Next, shaft 195 of inserter 15 is removed from the annulus, and then loop 320 of suture 30 is pulled proximally, causing suture 30 to be pulled taut, whereby to cause proximal anchor 25 to turn further within the nucleus. Where horizontal slot 165 includes a narrower inner portion 175, pulling proximally on loop 320 of suture 30 also causes suture 30 to be drawn into narrower inner portion 175 of bottom horizontal slot 165. This action can introduce additional impedance into the system, and this combined impedance (i.e., the combined impedance provided by (i) the serpentine path of suture 30 through proximal anchor 25, and (ii) the light hold imposed on the suture by narrower inner portion 175 of bottom horizontal slot 165) is sufficient to temporarily hold suture 30 to proximal anchor 25. See FIG. 38C. Thereafter, the proximal end 190 of suture 30 is pulled lightly so as to close down loop 320 of suture 30 somewhat. See FIG. 38D. Then proximal end 190 of suture 30 is passed through loop 320 of suture 30, whereby to form a so-called "half-hitch" configuration. See FIG. 38E. Next, proximal end 190 of suture 30 is pulled so as to draw loop 320 of suture 30 down into the nucleus of the intervertebral disc. See FIG. 38F. Pulling continues until the half-hitch configuration of loop 320 and proximal end 190 of suture 30 are drawn into top horizontal slot 145 of proximal anchor 25, i.e., so that the aforementioned half-hitch is disposed in top horizontal slot 145 of proximal anchor 25, whereby to prevent the half-hitch from slipping through itself and hence securing suture 30 to proximal anchor 25. As this occurs, suture 30 is also pulled into bottom horizontal slot 150 and, where bottom horizontal slot 150 includes narrower inner portion 160, into the narrower inner portion 160 of bottom horizontal slot 150, whereby to further hold suture 30 to proximal anchor 25. See FIG. 38G.

The proximal end 190 of suture 30 may then be trimmed away, whereby to complete the repair.

In this respect it should be appreciated that the unique construction of proximal anchor 25 provides a significant advantage over the conventional toggle anchors of the prior art, since it provides novel means for knotlessly securing suture 30 to proximal anchor 25, whereby to allow the tension of suture 30 to be reliably set between distal anchor 20 and proximal anchor 25. Significantly, the novel construction provided by proximal anchor 25 provides a unique solution to the problem of knotlessly securing suture to an anchor. More particularly, the knotless securement mechanism of proximal anchor 25 avoids the deficiencies of prior art toggle anchor systems using cinch knots (see Cauthen III et al. as discussed above) and/or filament enlargements/anchor narrowings (see Cauthen III et al. as discussed above).

In addition, the knotless securement mechanism of proximal anchor 25 provides a significant improvement over the prior art serpentine suture securement mechanisms sometimes found in prior art bone anchors. More particularly, various prior art bone anchors (e.g., screw-type bone anchors) have previously attempted to use serpentine passageways through the bone anchor to knotlessly secure a suture to the bone anchor. However, such prior art serpentine suture securement mechanisms have traditionally required the designer to choose between low holding strength (but relative ease in pulling the suture through the serpentine passageways) or high holding strength (and significant difficulty in pulling the suture through the serpentine passageways). The present invention avoids this problem, providing both high holding strength and relative ease of pulling the suture through the serpentine passageways, by (i) allowing the suture to be accessed at a midpoint within the anchor's serpentine pathway (e.g., by pulling on loop 320), and (ii) providing additional holding means to supplement the holding power of the serpentine suture pathway (i.e., the aforementioned half-hitch and, to a significantly lesser extent, the friction fit of suture 30 within narrower inner portion 175 of bottom horizontal slot 165 and narrower inner portion 160 of bottom horizontal slot 150 (to the extent that bottom horizontal slot 165 comprises a narrower inner portion 175 and bottom horizontal slot 150 comprises a narrower inner portion 160).

Thus, with the present invention, the distal anchor 20 is set into tissue on one side of the fissure, the proximal anchor is deployed into tissue on the other side of the fissure, and then the suture is appropriately tensioned and made fast to the proximal anchor, whereby to effect the repair with the degree of tension selected by the user. Furthermore, with the present invention, the distal anchor can be reliably turned and set within the interior of relatively dense tissue such as bone (as well as within the interior of other tissue) due to its unique construction and deployment mechanism. And with the present invention, the proximal anchor is capable of providing high holding strengths, e.g., on the order of 16 pounds of holding strength. In this respect it should be appreciated that proximal anchor 25 is held to suture 30 to a large extent by the impedance provided by the half-hitch construct (which is aided against slipping by virtue of its disposition in top horizontal slot 145), and to a lesser extent by the serpentine suture path through proximal anchor 25, and to a much smaller extent by the light hold imposed on suture 30 by narrower inner portion 175 of bottom horizontal slot 165 and narrower inner portion 155 of bottom horizontal slot 150 (to the extent that bottom horizontal slot 165 comprises a narrower inner portion 175 and bottom horizontal slot 150 comprises a narrower inner portion 160).

Note that where bottom horizontal slot 165 comprises a narrower inner portion 175, the hold imposed on suture 30 by narrower inner portion 175 of bottom horizontal slot 165 may be relatively nominal, inasmuch as it provides a useful impedance on suture 30 only during the brief period of time that loop 320 is being reduced and the aforementioned half-hitch is being formed—after loop 320 has been reduced and the aforementioned half-hitch has been set, the significant holding power on suture 30 is provided by the half-hitch construct and the serpentine suture path extending through proximal anchor 25. In this respect it should also be appreciated that, where bottom horizontal slot 165 comprises a narrower inner portion 175, and during the brief period of time that narrower inner portion 175 is providing a useful impedance on suture 30, the patient is lying stationary on the operating table and only a nominal load is imposed on the suture—unlike when the patient is upright and moving about, when a substantial load is imposed on the suture.

By way of example but not limitation, in one form of the present invention, where bottom horizontal slot 165 comprises a narrower inner portion 175 and bottom horizontal slot 150 comprises a narrower inner portion 160, the serpentine suture path through proximal anchor 25, plus the light impedance imposed on suture 30 by narrower inner portion 175 of bottom horizontal slot 165 and narrower inner portion 155 of bottom horizontal slot 150, collectively provide about 4-6 pounds of holding strength, and the half-hitch construct of proximal end 190 of suture 30 passing through loop 320, with the half-hitch construct being drawn into top horizontal slot 145 of proximal anchor 25, brings the total holding strength to about 16 pounds of holding strength.

Tensioner(s) Which May be Used in Conjunction with the Novel System

It will be appreciated that, due to the tortuous path of suture 30 through proximal anchor 25, as well as the need to pull the half-hitch construct into top horizontal slot 145 and, where bottom horizontal slot 165 comprises a narrower inner portion 175 and bottom horizontal slot 150 comprises a narrower inner portion 160, to pull suture 30 into the narrower inner portion 175 of bottom horizontal slot 165 and narrower inner portion 160 of bottom horizontal slot 150, substantial force must be applied to the proximal end of suture 30 in order to pull the length of suture between the anchors 20, 25 taut and secure the suture in position. This level of force is significantly greater than the level of force required to set distal anchor 20. Where the annulus of the vertebral disc is weak, the application of such a force to the proximal end of suture 30 presents the possibility of pulling proximal anchor 25 through the annulus. Therefore, in order to eliminate the possibility of this occurrence, it may be desirable to utilize a tensioner 375 (FIGS. 39-41) to hold the annulus in place while applying proximal tension to suture 30.

Figure 39:
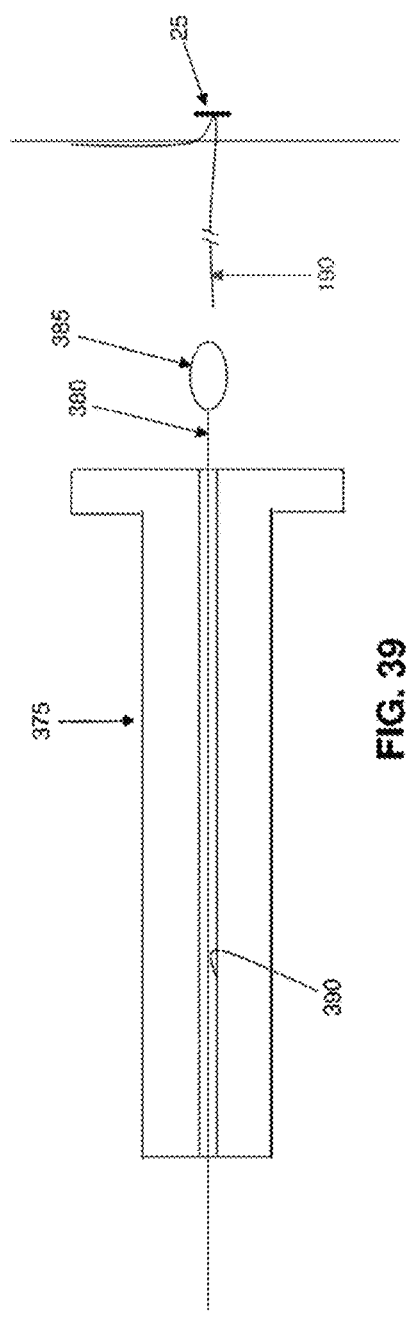
FIGS. 39-41 are schematic views showing a tensioner which may be used in conjunction with the novel system of FIGS. 1 and 2.
Figure 40:
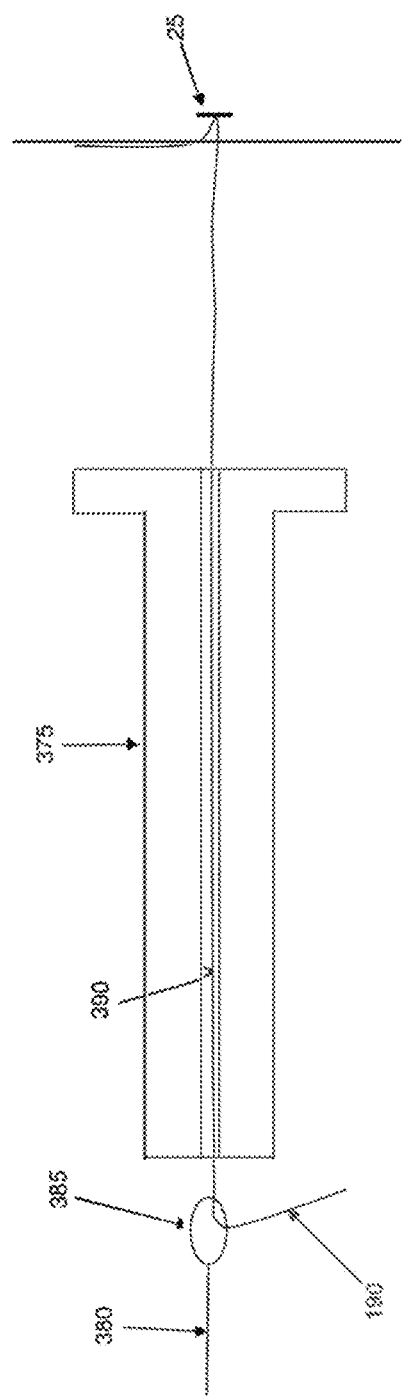
Figure 41:
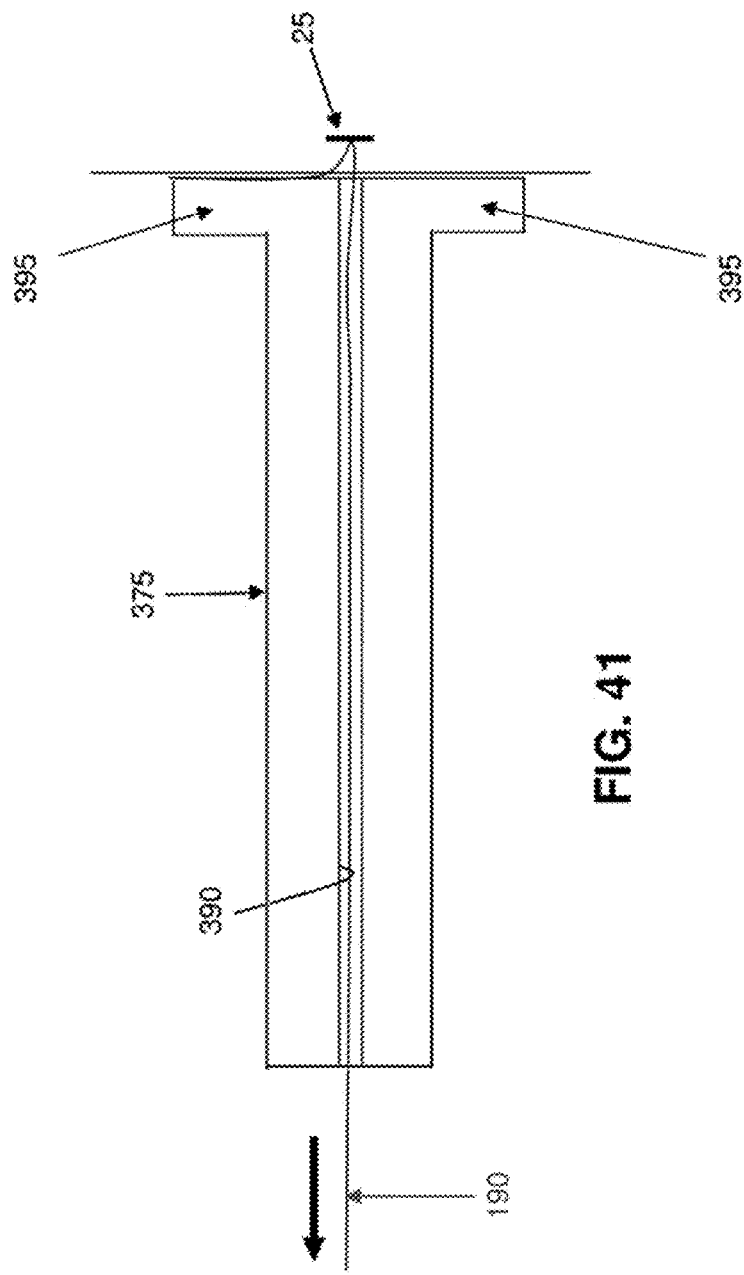

More particularly, a suture retriever 380, having a loop 385 at its distal end, is advanced through a lumen 390 of tensioner 375 (FIG. 39). The proximal end of suture 30 is fed through loop 385, which is then pulled proximally through the tensioner so as to draw suture 30 through the tensioner (FIG. 40). The feet 395 of tensioner 375 are then placed against the annulus adjacent to where suture 30 exits the annulus, and suture 30 is then pulled proximally, whereby to tension the suture and set it in position. As this occurs, feet 395 of tensioner 375 prevent the annulus from bowing outward, which could enable proximal anchor 25 to pass through the annulus.

Figure 41A:
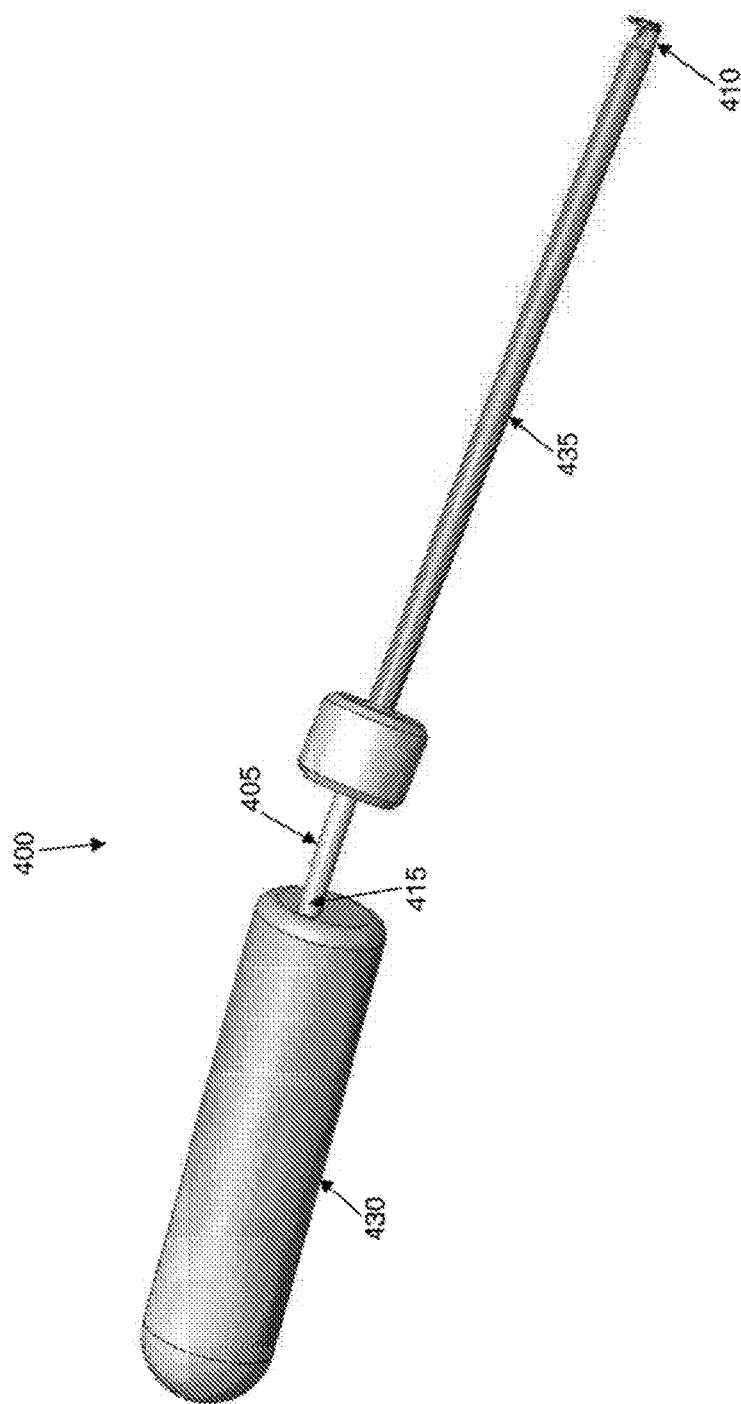
FIGS. 41A and 41B are schematic views showing another form of tensioner which may be used in conjunction with the novel system of FIGS. 1 and 2.
Figure 41B:
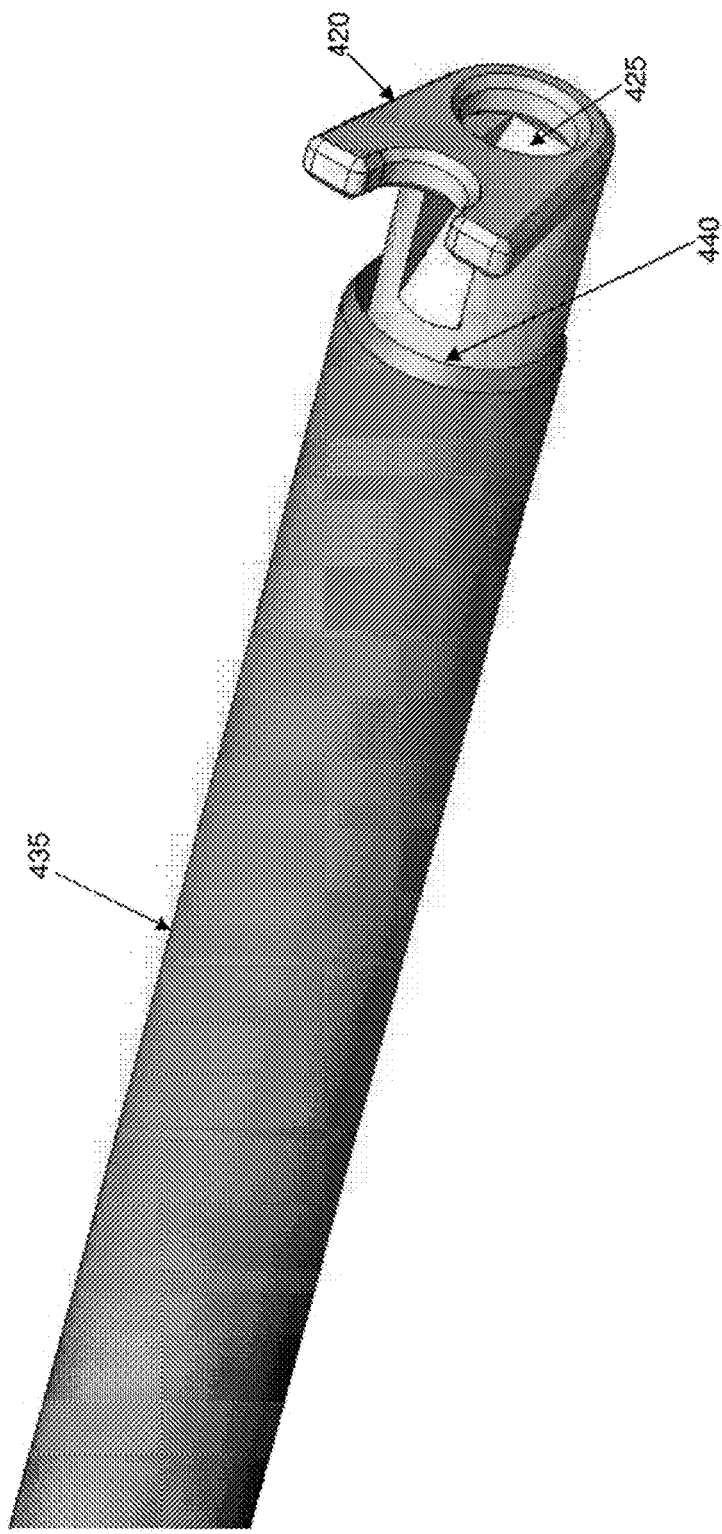

Alternatively, and looking now at FIGS. 41A and 41B, a tensioner 400 may be provided. Tensioner 400 generally comprises a shaft 405 having a distal end 410 and a proximal end 415. Distal end 410 terminates in a foot 420. A ramped suture pathway 425 extends through distal end 410 of shaft 405 and through foot 420. Proximal end 415 of shaft 405 is mounted to a handle 430. A cutter tube 435 is slidably mounted on shaft 405. Cutter tube 435 has a sharpened distal rim 440.

In use, when suture 30 is to be tensioned, the proximal end 190 of suture 30 is fed through ramped suture pathway 425, foot 420 is placed against the annulus adjacent to where suture 30 exits the annulus, and then suture 30 is tensioned, with foot 420 of the tensioner preventing the annulus from bowing outward. Thereafter, excess suture may be cut away by moving cutter tube 435 distally along shaft 405 until its sharpened distal rim 440 engages and trims away excess suture.

Further Applications of the Novel System

In the foregoing description, system 5 is discussed in the context of closing a fissure in the annulus of an intervertebral disc. However, it should be appreciated that system 5 may also be used to effect other anatomical repairs and/or fixations.

Figure 42:
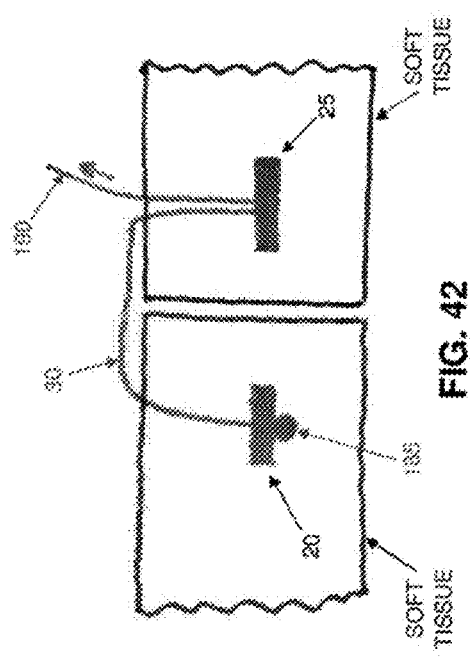
Figure 43:
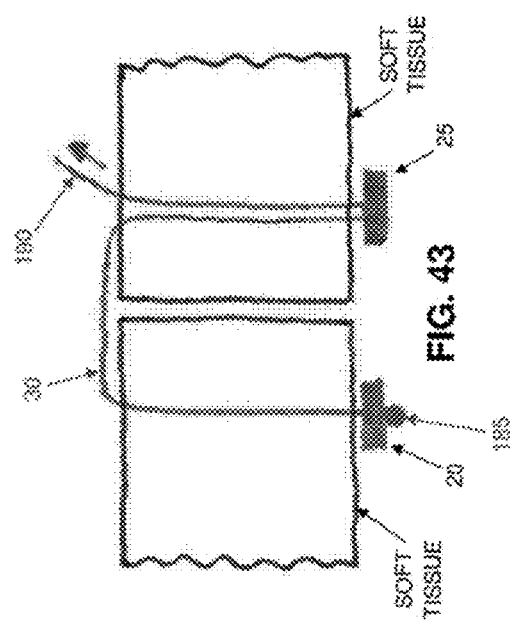
Figure 46:
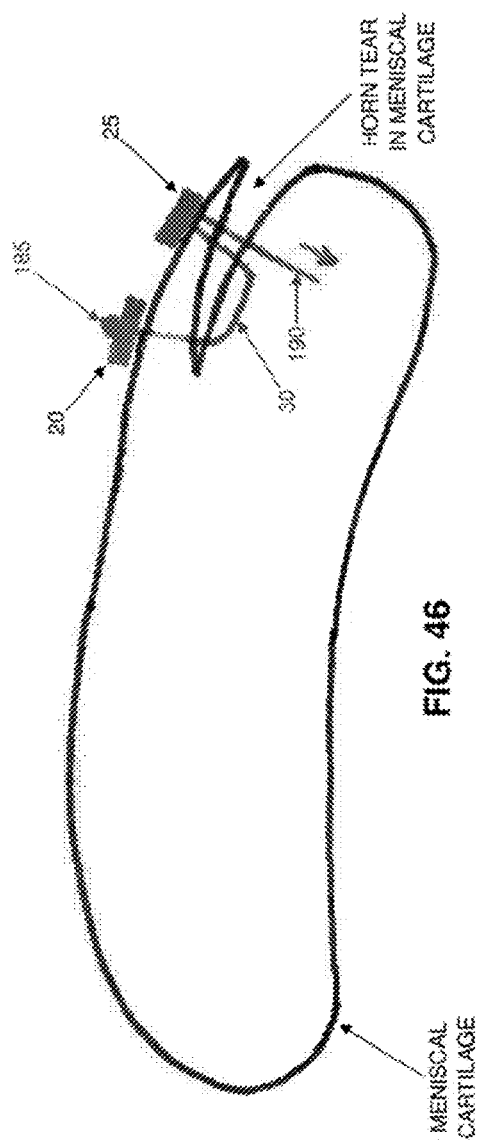
Figure 47:
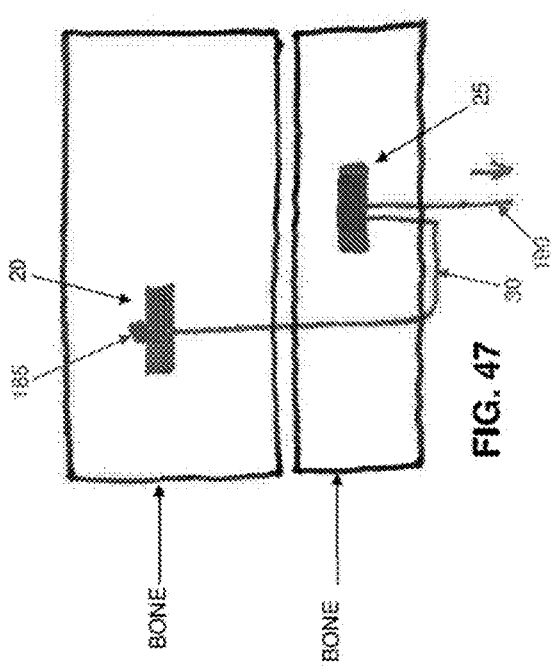

By way of example but not limitation, the present invention may be used to hold two pieces of soft tissue in apposition to one another to effect a repair (e.g., so as to close an incision in the skin). See, for example, FIG. 42, where distal anchor 20 is shown disposed within the interior of one piece of soft tissue and proximal anchor 25 is shown disposed within the interior of another piece of soft tissue; and FIG. 43, where distal anchor 20 is shown disposed against an outer surface of one piece of soft tissue and proximal anchor 25 is shown disposed against an outer surface of another piece of soft tissue. Or the present invention may be used to hold two pieces of cartilage in apposition to one another to effect a repair (e.g., so as to close a tear in meniscal cartilage). See, for example, FIG. 44, where distal anchor 20 is shown disposed within the interior of one section of meniscal cartilage and proximal anchor 25 is shown disposed within the interior of another section of the same meniscal cartilage; and FIGS. 45 and 46, where distal anchor 20 is shown disposed against an outer surface of one section of meniscal cartilage and proximal anchor 25 is shown disposed against an outer surface of another section of the same meniscal cartilage. Or the present invention may be used to hold two pieces of bone in apposition to one another so as to effect a repair (e.g., so as to fuse together bone). See FIG. 47.

By way of further example but not limitation, the present invention may be used to hold a piece of soft tissue in apposition to bone to effect a repair (e.g., so as to attach soft tissue to bone). See, for example, FIG. 48. Or the present invention may be used to hold a piece of cartilage in apposition to bone to effect a repair (e.g., so as to attach labrum to bone or to attach meniscal cartilage to bone). See FIG. 49.

By way of further example but not limitation, the present invention may be used to hold a prosthesis in apposition to soft tissue or bone, or to hold soft tissue or bone in apposition to a prosthesis, and/or to hold any first object in apposition to any second object.

It is also possible to use just distal anchor 20 and suture 30 to effect anatomical repairs and/or fixations, with proximal anchor 25 being omitted altogether. See, for example, FIG. 50, where a knot is used to hold soft tissue to a bone receiving distal anchor 20, and FIG. 51, where a knot is used to hold a labrum to an acetabular rim receiving distal anchor 20. If desired, multiple suture strands may be attached to the large ball (or knot) 185 which is positioned distal to distal anchor 20, which can facilitate repair and/or fixation procedures.

It is also possible to use proximal anchor 25 and suture 30 with an anchor other than distal anchor 20 to effect anatomical repairs and/or fixations. By way of example but not limitation, proximal anchor 25 and suture 30 may be used in conjunction with a conventional bone anchor (e.g., a conventional screw-type bone anchor or by a conventional barb-type bone anchor), with the conventional bone anchor replacing the aforementioned distal anchor 20 of the present invention.

The following is a list of just some of the indications in which the present invention may be used:

Foot/Ankle
Hallux Valgus Repair
Hallux Varus Repair
Lisframe Repair
Correction Of The Intermediate Tarsal Angle
Brostrum Repair
Achilles Tendon Repair/Reconstruction
Medial Capsuloraphy Hallus Valgus
Lateral Stabilization
Medial Stabilization
Great Toe Tendon Repair
Mid—And Forefoot Tendon Reconstruction
Hand/Wrist
CMC—Thumb Instability
CMC—Ligament Reconstruction
Ulnar—Collateral Ligament Repair
Scaphonlunate Repair
TFCC
Flexor Tendon Repair
Plastics/Maxillofacial
Brow Lift
Face/Forehead Lift
Breast Lift
Breast Reconstruction
Crows Feet Repair
Blepharoplasty
Hip
Hip Labrum Repair
Shoulder
Rotator Cuff Repair Partial Rotator Cuff Repair
Instability Repair (SLAP, Bankhart)
Capsular Shift
Capsular Plication
Tendon Transfers For Arthroplasty
Reverse Shoulder Arthroplasty Soft Tissue Management
Acromio-Clavicular Separation
Deltoid Repair
Biceps Tenodesis
Knee
Meniscus Repair
Medial Collateral Ligament Repair
Lateral Collateral Ligament Repair
Elbow
Distal Biceps Repair
Medial And Lateral Repairs
Tennis Elbow Repair Use in Anchoring Sensory Nerve Stimulator (SNS) Leads As noted above, novel system 5 may be used to close a fissure in the annulus of an intervertebral disc, and/or to effect other anatomical repairs and/or other anatomical fixations.

Figure 52:
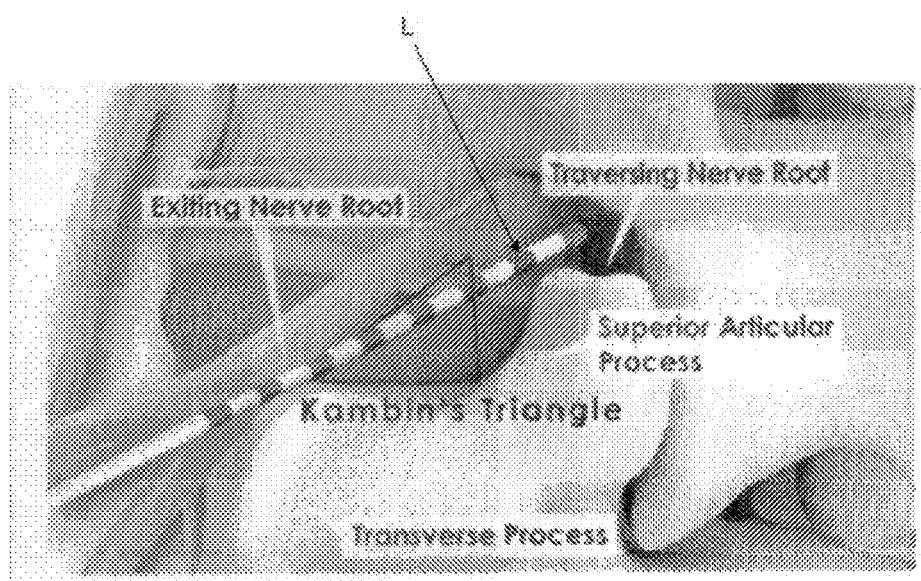
FIG. 52 is a schematic view showing a sensory nerve stimulator (SNS) lead positioned within a spine.

In one preferred form of the invention, novel system 5 may be used in a novel approach to anchor sensory nerve stimulator (SNS) leads. More particularly, in sensory nerve stimulation therapy, electrical leads are positioned adjacent to nerves and used to deliver electrical stimulation to those nerves so as to provide pain relief to a patient. In one significant application of nerve stimulation therapy, sensory nerve stimulator (SNS) leads are disposed adjacent to nerves in the spinal column, whereby to deliver electrical stimulation to those nerves and provide pain relief to the patient. See, for example, FIG. 52, which shows an SNS lead disposed adjacent to a nerve in the spinal column.

In practice, it has been found extremely difficult to reliably anchor an SNS lead adjacent to a nerve in the spinal column. This is due to, among other things, the highly complex and varying anatomy of the spinal column, the need to fabricate the SNS lead with an atraumatic configuration, and the need to ensure that the SNS lead is reliably fixed in position. These factors, and others, combine to make it extremely difficult to reliably anchor an SNS lead adjacent to a specific nerve in the spinal column.

Novel system 5 provides a new and improved approach for stabilizing an SNS lead adjacent to a nerve in the spinal column, by anchoring the SNS lead to one mass of material using the distal anchor of system 5 and by anchoring the SNS lead to another mass of material using the proximal anchor of system 5, with the intervening suture securing the SNS lead reliably in position. Among other things, novel system 5 comprises a distal anchor 20 which is deployable, using a minimally-invasive approach, against the exterior of a hard or soft object (e.g., a bone, soft tissue, a hard prosthesis, a soft prosthesis, etc.), or within the interior of a hard or soft object (e.g., a bone, soft tissue, a hard prosthesis, a soft prosthesis, etc.), thereby providing a wide range of objects to which the distal anchor may be secured. Novel system 5 also comprises a proximal anchor 25 which is deployable, using a minimally-invasive approach, against the exterior of a hard or soft object (e.g., a bone, soft tissue, a hard prosthesis, a soft prosthesis, etc.), or within the interior of a soft object (e.g., soft tissue, a soft prosthesis, etc.), thereby providing a wide range of objects to which the distal anchor may be secured. And novel system 5 comprises a connecting suture 30 which may be used to atraumatically, but reliably, secure an SNS lead in position.

Note that for the purposes of the present invention, the term "bone" is intended to include any bone or bone-like structure including, but not limited to, a vertebral body, a pedicle, a transverse process, a facet structure, a lamina, a spinous process, etc. Note also that for the purposes of the present invention, the term "soft tissue" is intended to include any relatively "soft" structure including, but not limited to, an intervertebral disc, a muscle, a ligament, a tendon, etc.

Figure 53:
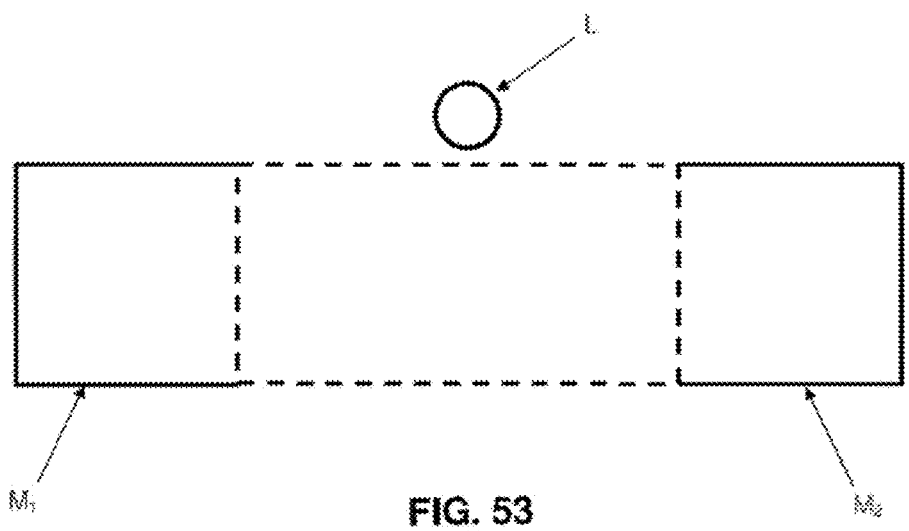
FIGS. 53-62 are schematic views showing how the novel system may be used to hold an SNS lead in position within anatomy.
Figure 54:
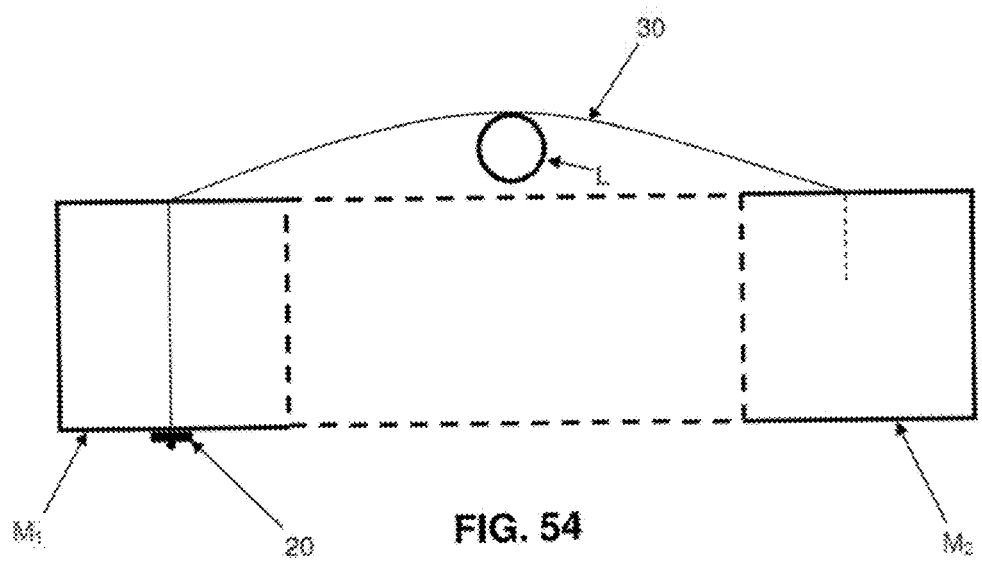
Figure 55:
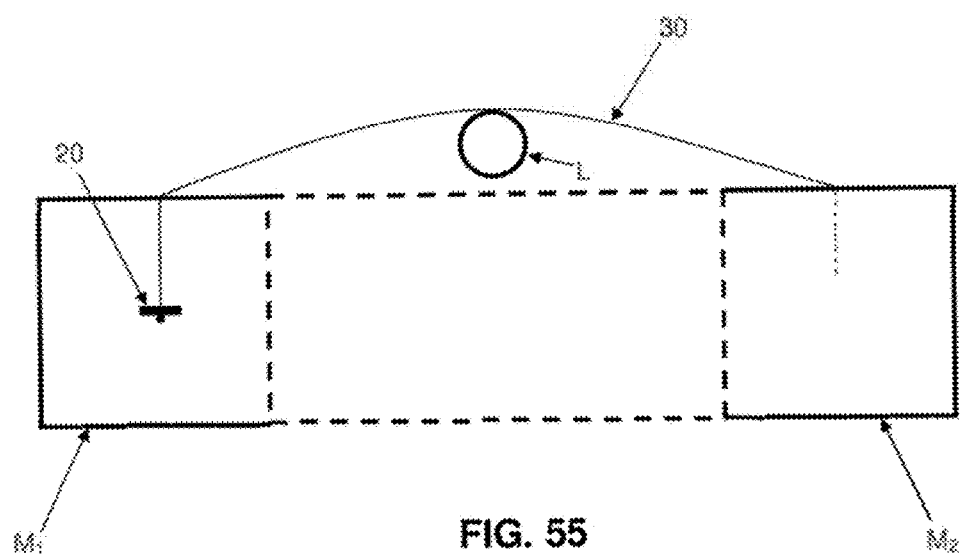
Figure 56:
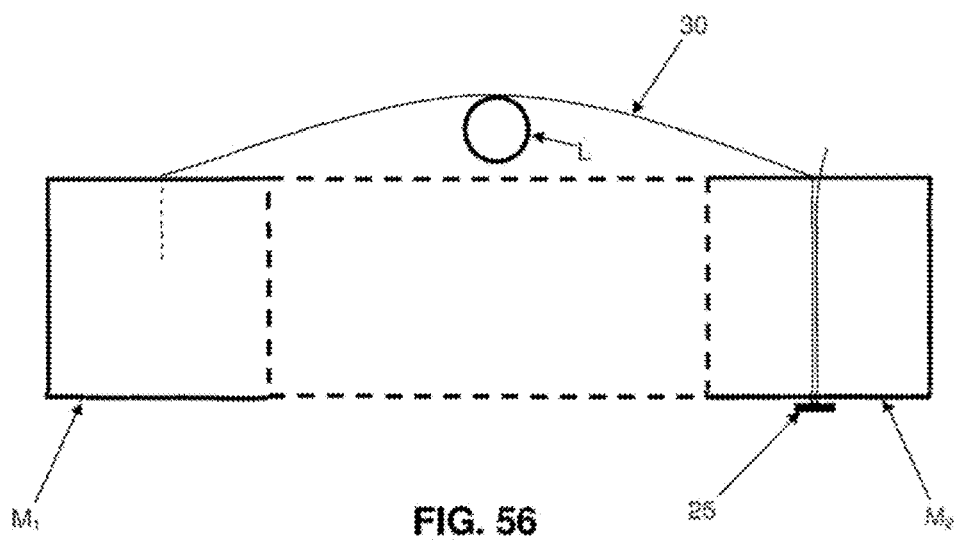
Figure 57:
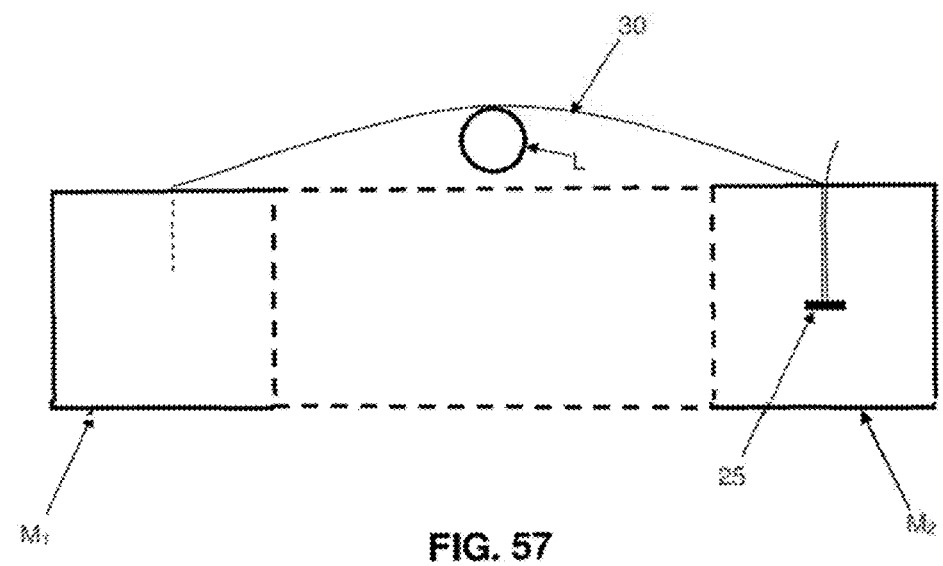

See, for example, FIG. 53, which shows an SNS lead L adjacent to one mass of material $M_1$ for receiving distal anchor 20 of system 5, and adjacent to another mass of material $M_2$ for anchoring proximal anchor 25 of system 5. FIG. 54 shows distal anchor 20 deployed against the exterior of a hard or soft mass of material $M_1$ (e.g., a bone, soft tissue, a hard prosthesis, a soft prosthesis, etc). FIG. 55 shows distal anchor 20 deployed within the interior of a hard or soft mass of material $M_1$ (e.g., a bone, soft tissue, a hard prosthesis, a soft prosthesis, etc.). FIG. 56 shows proximal anchor 25 deployed against the exterior of a hard or soft mass of material $M_2$ (e.g., a bone, soft tissue, a hard prosthesis, a soft prosthesis, etc). FIG. 57 shows proximal anchor 25 deployed within the interior of a soft mass of material $M_2$ (e.g., soft tissue, a soft prosthesis, etc.).

Thus, with the present invention, distal anchor 20 may be deployed through, or deployed within, any appropriate anatomical or prosthetic structure, and proximal anchor 25 may be deployed through, or deployed within, any appropriate anatomical or prosthetic structure, whereby to enable suture 30 to secure SNS lead L in the desired position within the patient's anatomy.

Figure 58:
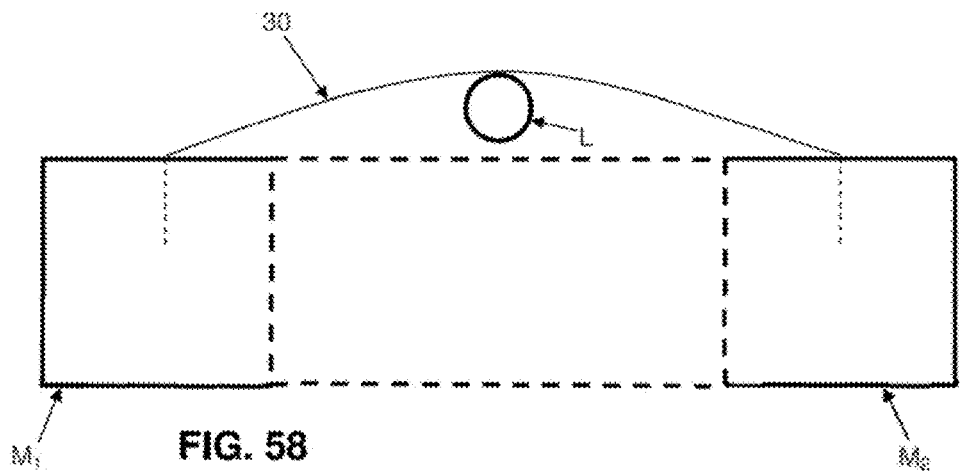
Figure 59:
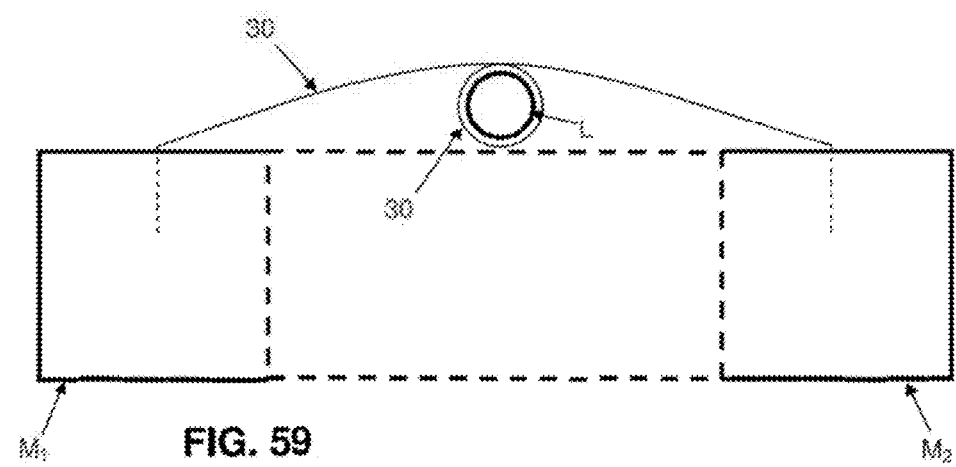
Figure 60:
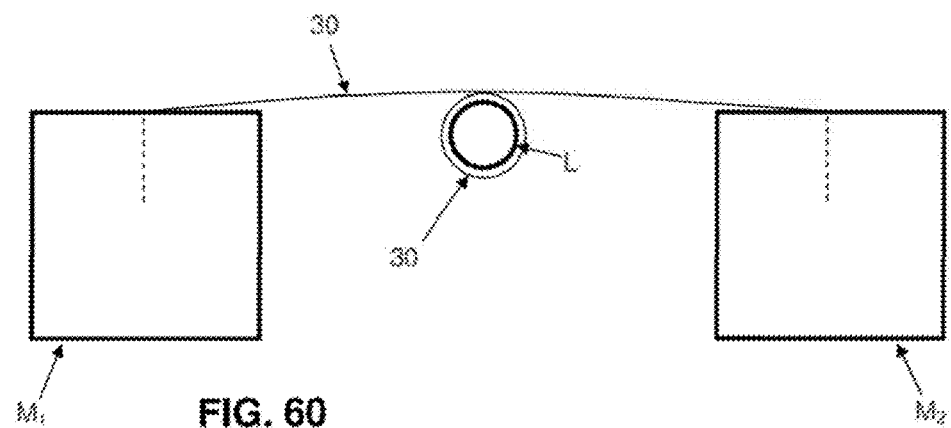
Figure 61:
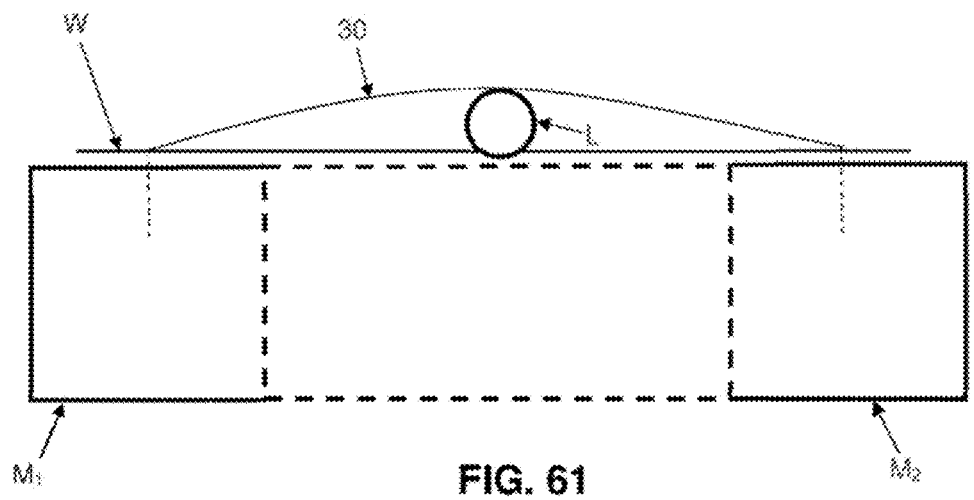
Figure 62:
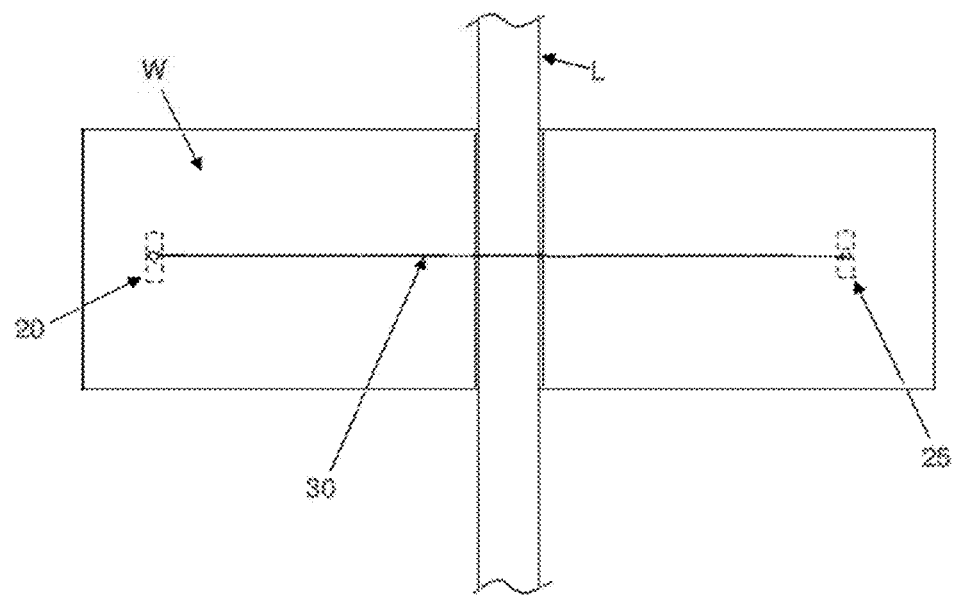
Figure 63:
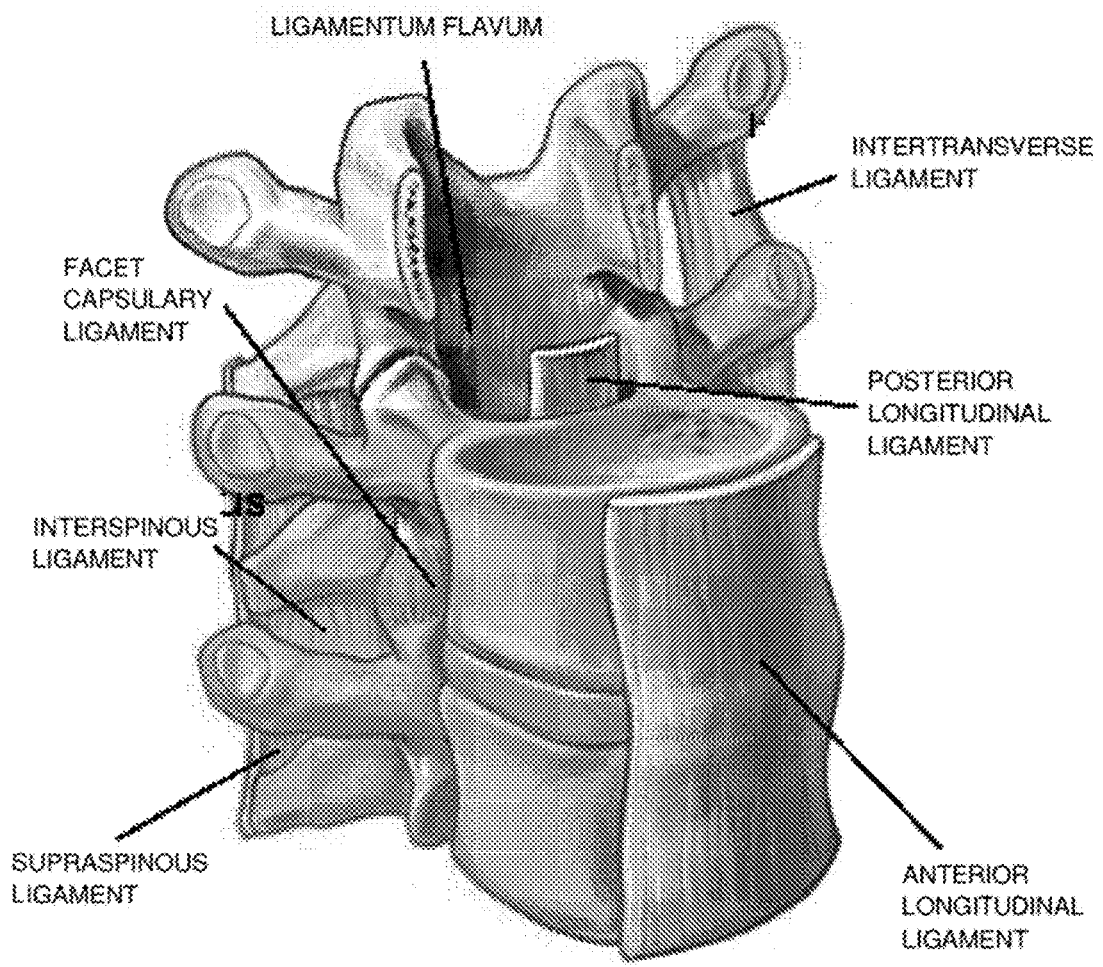
FIGS. 63-70 are schematic views showing various ways in which the novel system may be used to secure an SNS lead adjacent to spinal structures.
Figure 64:
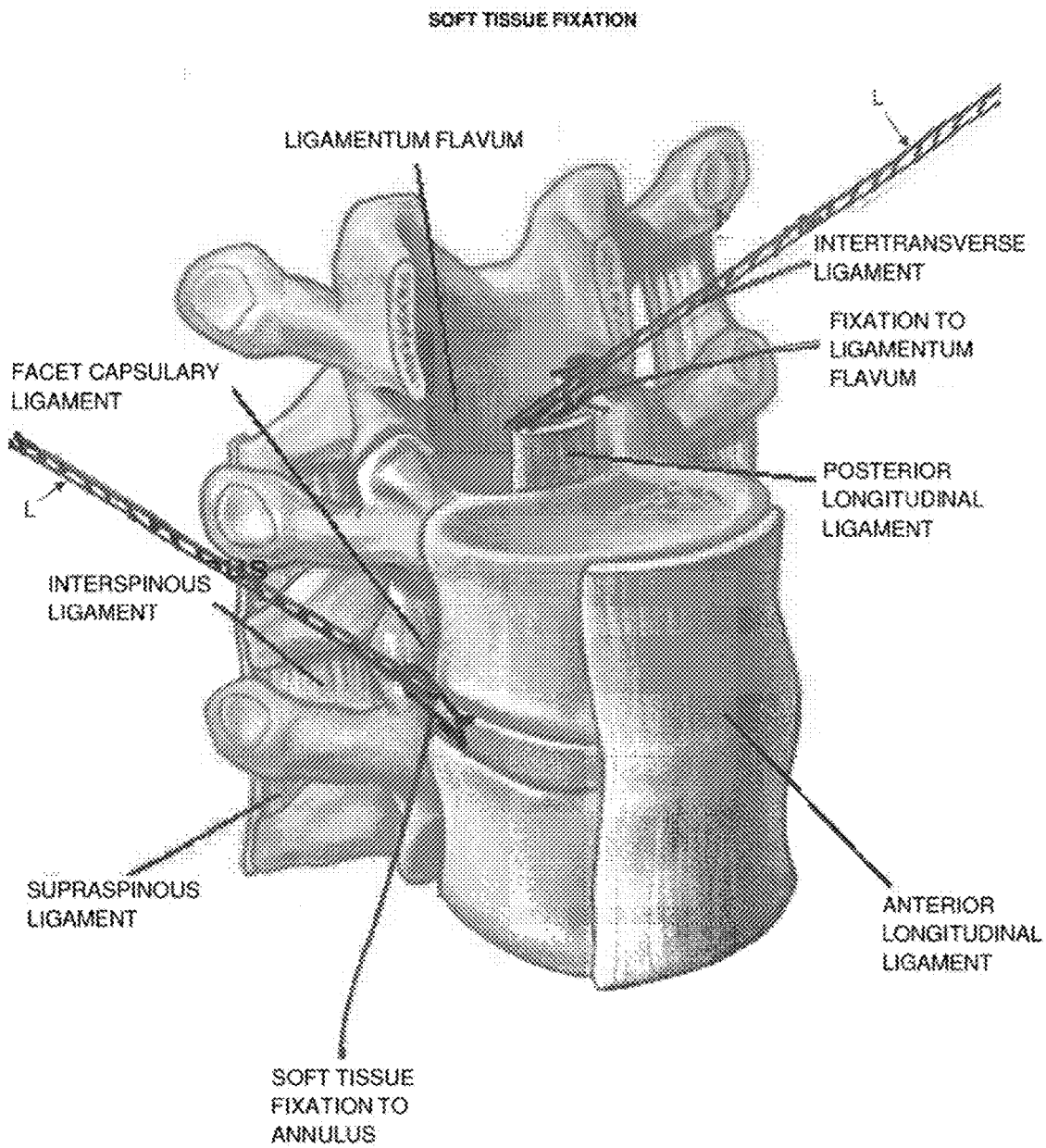
Figure 65:
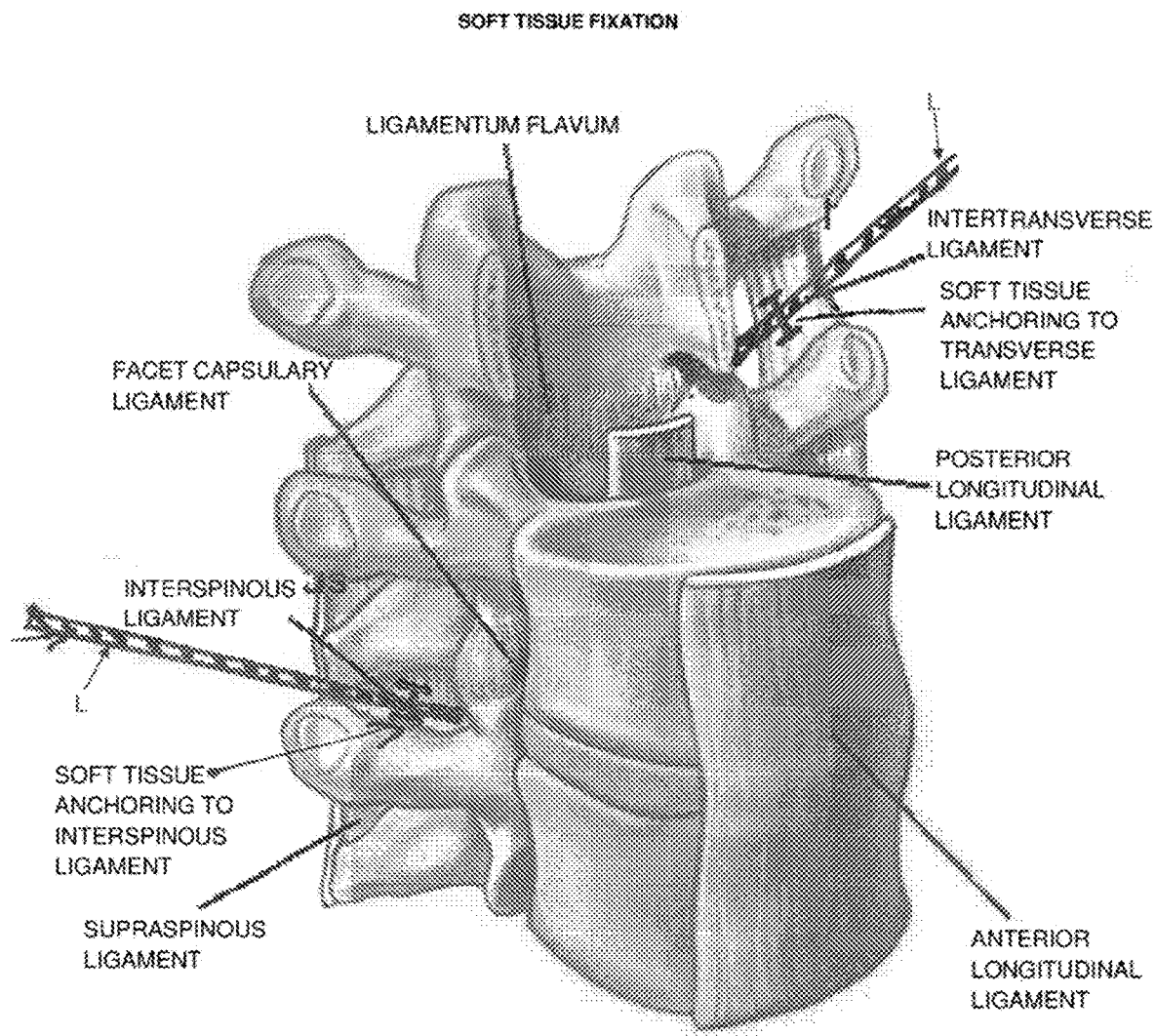
Figure 66:
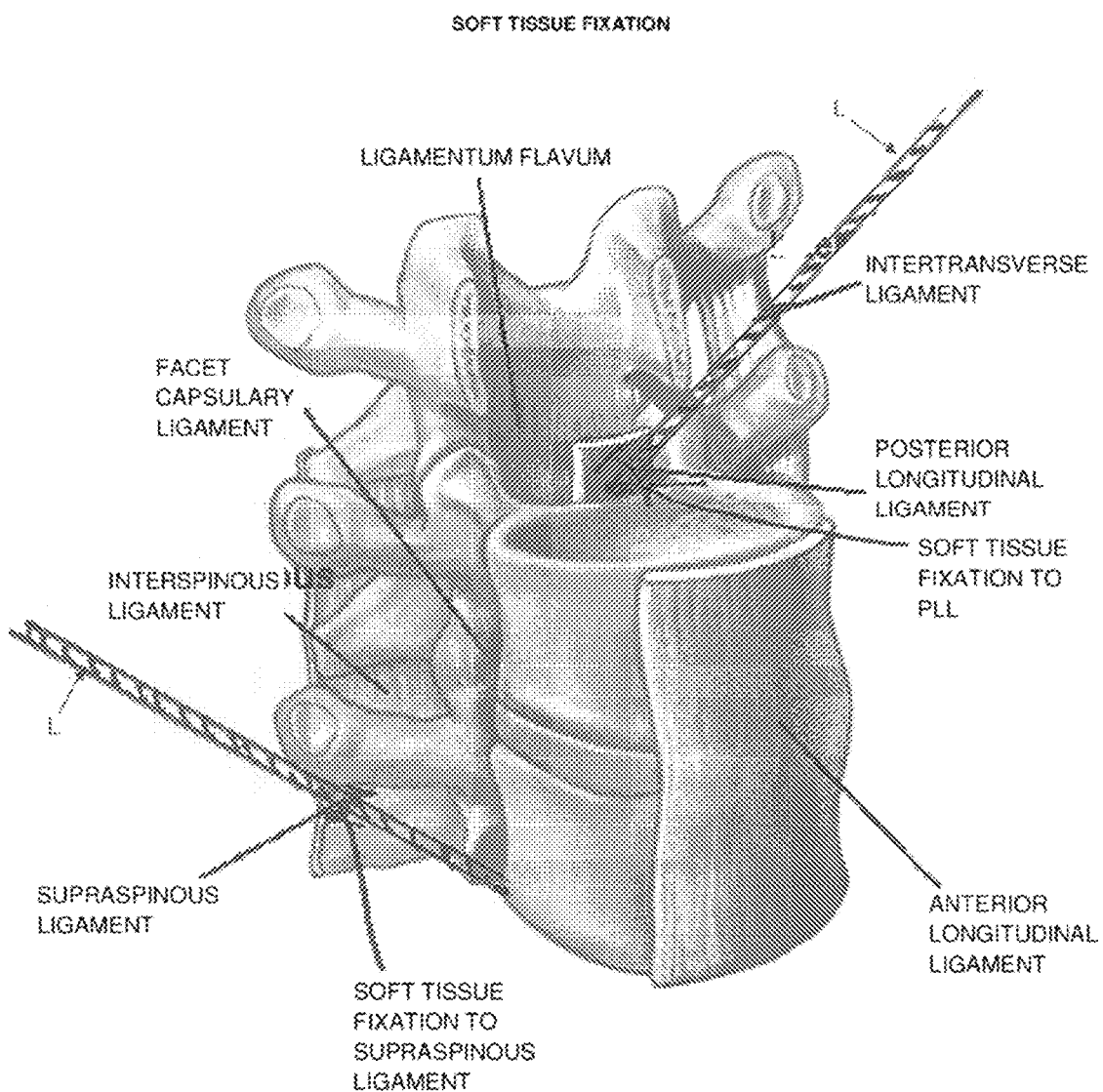
Figure 67:
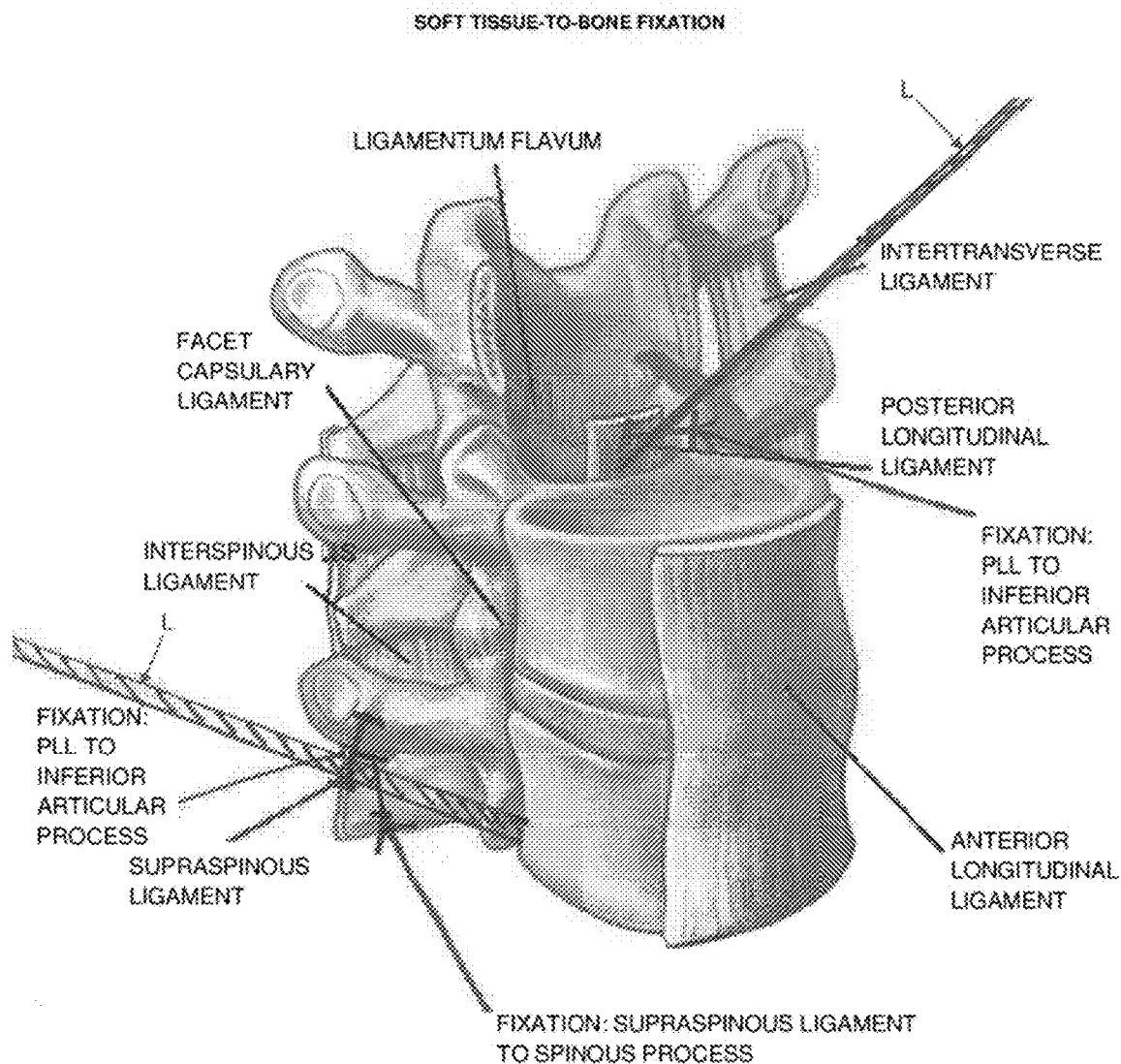
Figure 68:
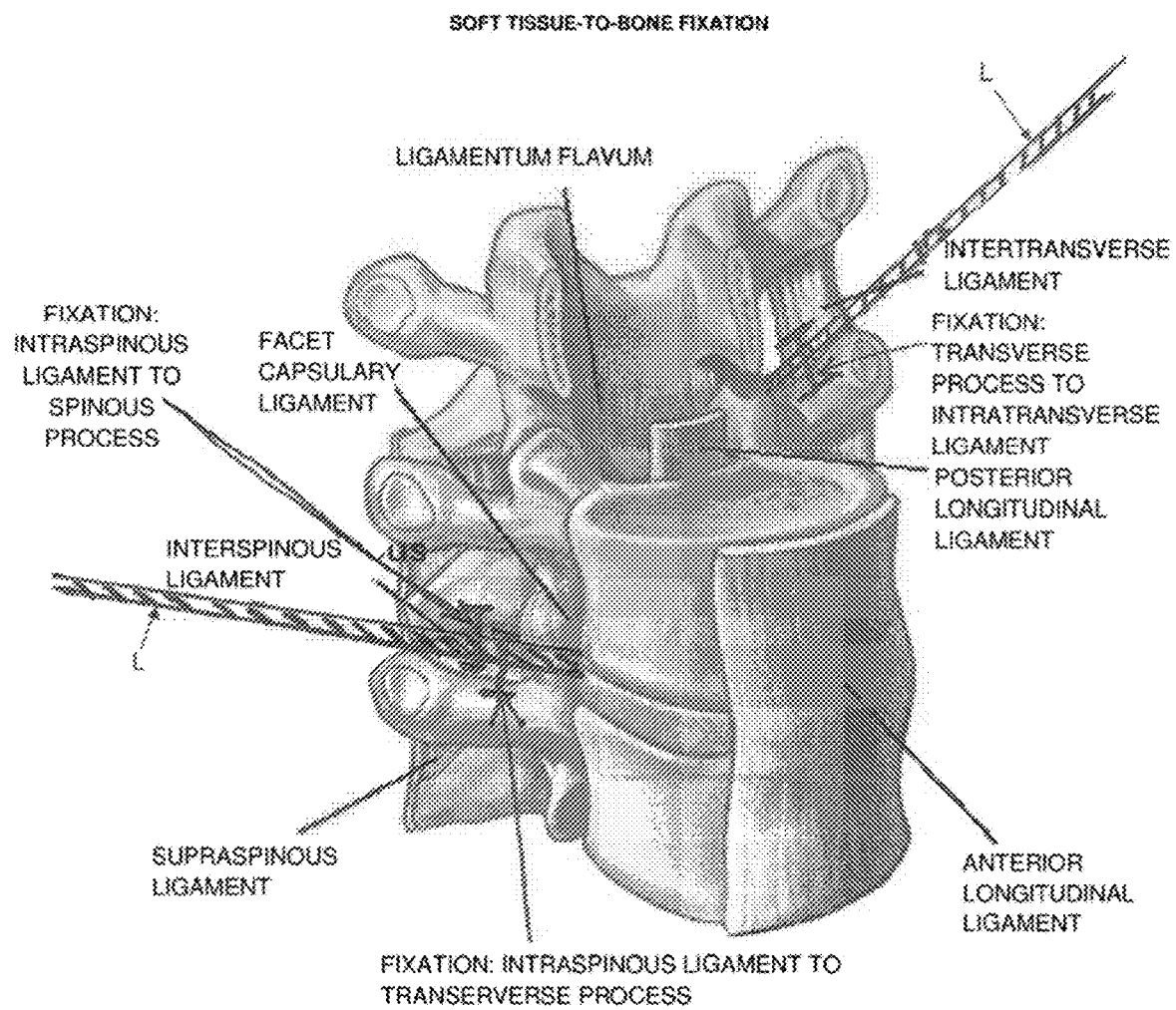
Figure 69:
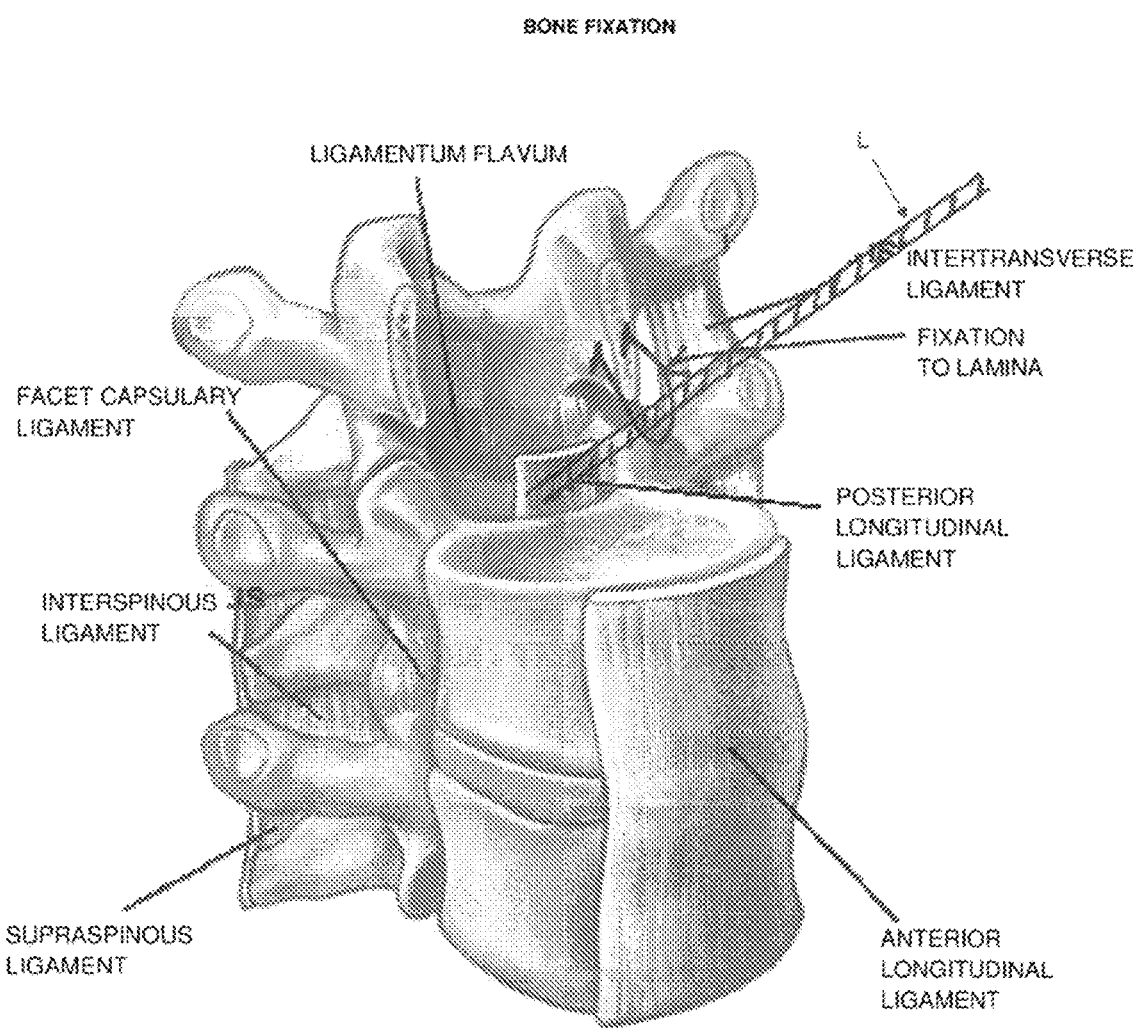
Figure 70:
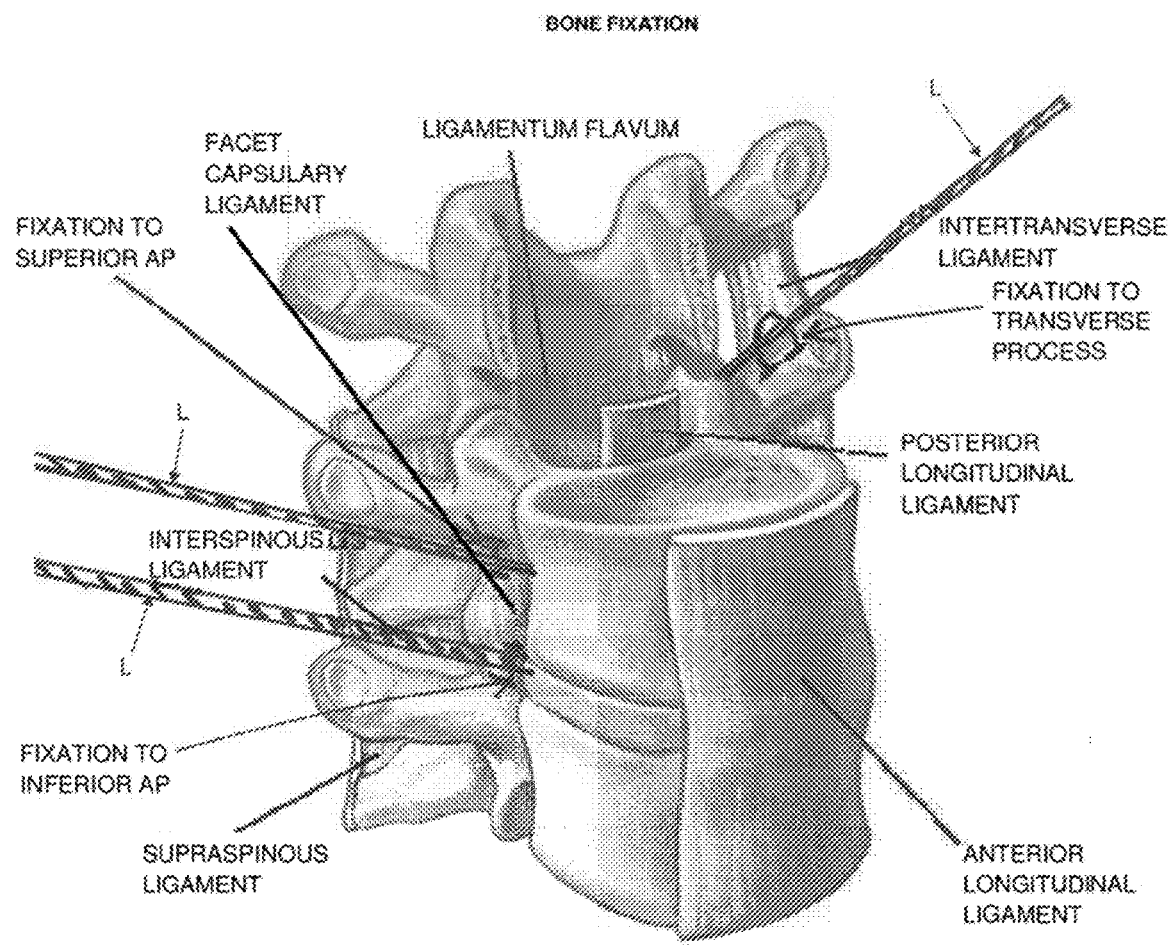

As seen in FIG. 58, suture 30 may simply extend over SNS lead L, holding the SNS lead against underlying tissue. Alternatively, as shown in FIG. 59, suture 30 may be wrapped around SNS lead L. Where suture 30 is wrapped around the SNS lead, it may be possible to support the SNS lead in position even in the absence of underlying tissue, since suture 30 can be used to suspend SNS lead L over a gap in the tissue. Furthermore, if desired, SNS lead L may include an associated mount, e.g., in the form of a web W extending laterally about the SNS lead, and distal anchor 20 and proximal anchor 25 may be advanced through web W prior to deployment through or into a mass of material (e.g., $M_1$ or $M_2$), in the manner shown in FIGS. 61 and 62.

FIGS. 63-70 show a variety of ways in which system 5 may be used to secure SNS lead L to adjacent structures.

Proximal Anchor Comprising Flexible Finger

As noted above, novel system 5 may be used to close a fissure in the annulus of an intervertebral disc, and/or to effect other anatomical repairs and/or other anatomical fixations, including anchoring sensory nerve stimulator (SNS) leads.

In another preferred form of the present invention, novel system 5 utilizes the aforementioned distal anchor 20 and the aforementioned suture 30 (and also the aforementioned inserter 15), but substitutes an alternative proximal anchor 25A (FIGS. 71 and 72) for the aforementioned proximal anchor 25.

More particularly, in this form of the invention, proximal anchor 25A comprises a generally cylindrical body 90A having a distal end 95A, a proximal end 100A and a generally circular side wall 105A. Distal end 95A terminates in a distal surface 110A. Proximal end 100A terminates in a proximal surface 120A. A vertical bore 126A passes completely through proximal anchor 25A. Vertical bore 126A is sized to slidably receive suture 30 therein. A recess 131A passes part way through proximal anchor 25A. A U-shaped slot 136A passes part way through proximal anchor 25A. Recess 131A and U-shaped slot 136A together define a flexible finger 141A. In this form of the invention, a gap 142A is formed between the inner tip 143A of flexible finger 141A and the edge 144A formed at the convergence of recess 131A and U-shaped slot 136A. Preferably gap 142A is sized so as to be approximately 50% of the width of suture 30 when flexible finger 141A is in its relaxed, unbiased condition (i.e., in the position shown in FIGS. 71 and 72) and when suture 30 is in its normal, uncompressed condition. A bottom horizontal slot 151A extends between vertical bore 126A and recess 131A. Bottom horizontal slot 151A may be stepped, comprising a wider outer portion 156A and a narrower inner portion 161A. If desired, wider outer portion 156A may be sized to slidably receive suture 30 therein so as to help keep proximal anchor 25A and suture 30 from binding when they are disposed within the aforementioned inserter 15, but narrower portion 161A may be sized to snugly receive suture 30 therein whereby to provide a light hold on suture 30 when suture 30 is disposed therein.

Figure 71:
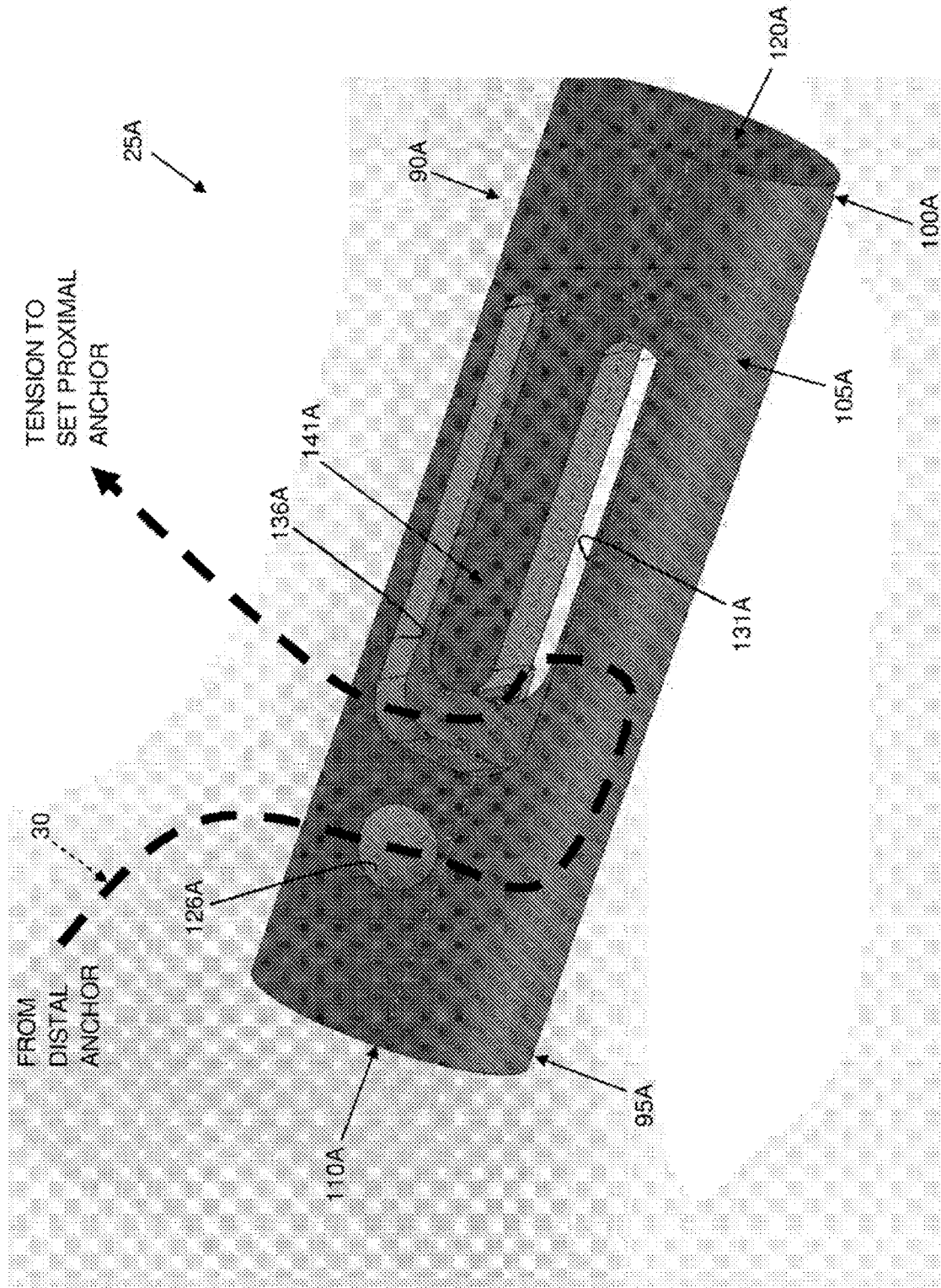
FIGS. 71 and 72 are schematic views showing a proximal anchor comprising a flexible finger.
Figure 72:
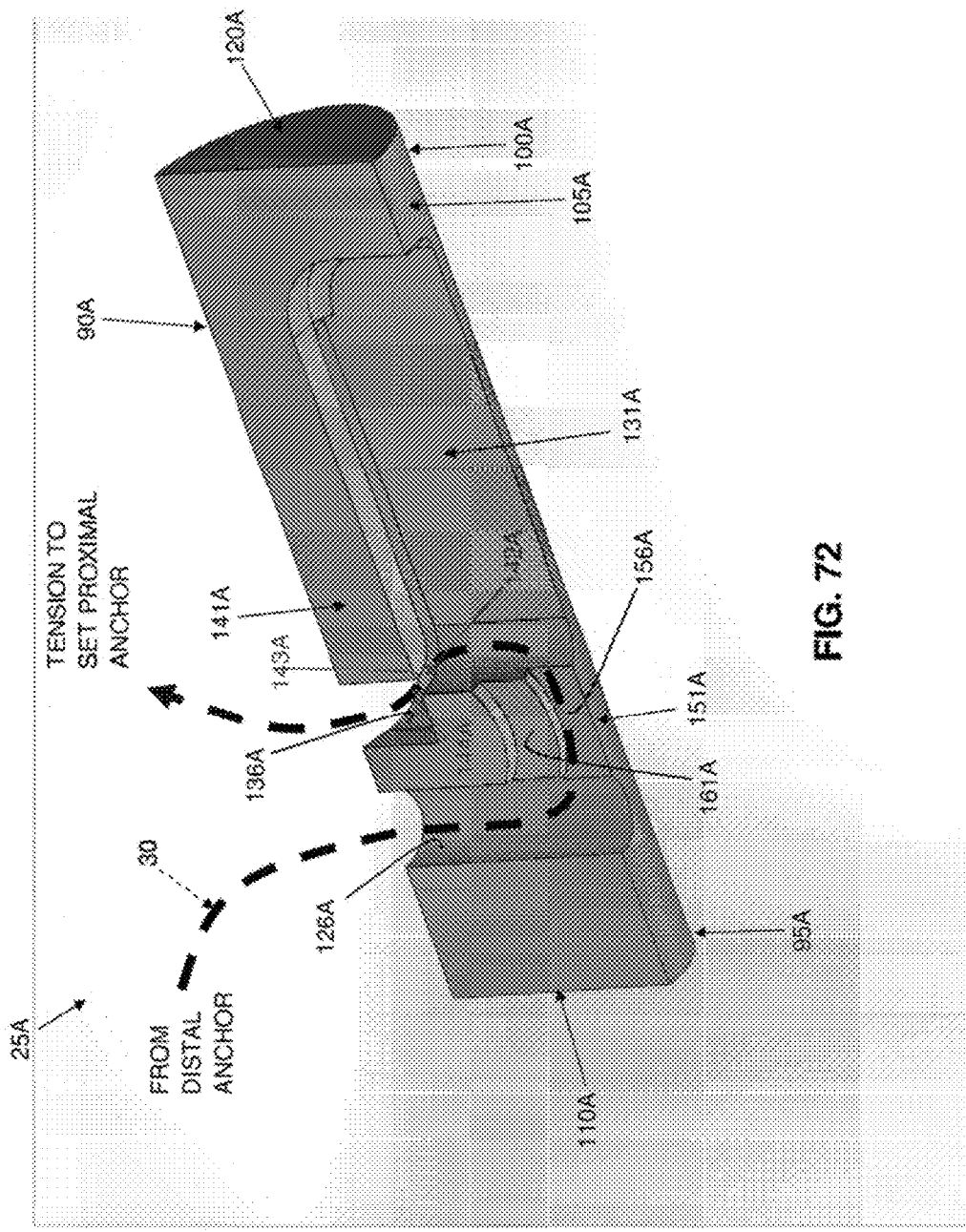

As seen in FIGS. 71 and 72, suture 30 is passed through proximal anchor 25A so that suture 30 extends down vertical bore 126A, through wider outer portion 156A of bottom horizontal slot 151A, up through recess 131A and out U-shaped slot 136A. Note that inasmuch as suture 30 has a diameter which is approximately twice the size of gap 142A formed between inner tip 143A of flexible finger 141A and edge 144A of proximal anchor 25A, flexible finger 141A will normally bear against the suture disposed in gap 142A. In this condition, the presence of the "oversized" suture 30 in the "undersized" gap 142A will cause flexible finger 141A to be flexed upwardly (from the angle of view of FIGS. 71 and 72) so as to accommodate suture 30, with inner tip 143A of flexible finger 141A capturing the suture against edge 144A of proximal anchor 25A. Note that some compression of suture 30 may occur in this condition.

In addition to the foregoing, it should be appreciated that suture 30 follows a non-linear path through proximal anchor 25A, and this non-linear path creates impedance to the passage of suture 30 through proximal anchor 25A.

In use, after the aforementioned distal anchor 20 has been deployed at the surgical site (preferably using the aforementioned inserter 15), proximal anchor 25A is also deployed at the surgical site (again, preferably using the aforementioned inserter 15), and then suture 30 is set by pulling proximally on suture 30. As suture 30 is pulled proximally, flexible finger 141A flexes away from the body of proximal anchor 25A, thereby allowing suture 30 to slide through recess 131A and U-shaped slot 136A (as well as through vertical bore 126A and wider outer portion 156A of bottom horizontal slot 151A). When the slack in suture 30 has been taken up, and suture 30 is thereafter tensioned further, where bottom horizontal slot 151A comprises a narrower portion 161A, suture 30 is pulled from wider outer portion 156A of bottom horizontal slot 151A into narrower portion 161A of bottom horizontal slot 151A so that suture 30 is snugly received therein, such that proximal anchor 25A provides a light hold on suture 30. When tension on the free end of suture 30 is thereafter relaxed, flexible finger 141A flexes back toward the body of proximal anchor 25A, whereby to lock suture 30 to proximal anchor 25A (i.e., with inner tip 143A of flexible finger 141A capturing the suture against edge 144A of proximal anchor 25A). In addition, inasmuch as suture 30 follows a non-linear path through proximal anchor 25A, the non-linear path creates impedance to the passage of suture 30 through proximal anchor 25A. In this way, suture 30 is secured to proximal anchor 25A. Thereafter, a half-hitch may be formed in suture 30 on the proximal side of proximal anchor 25A so as to further secure suture 30 to proximal anchor 25A.

Single Anchor Fixation

Figure 73:
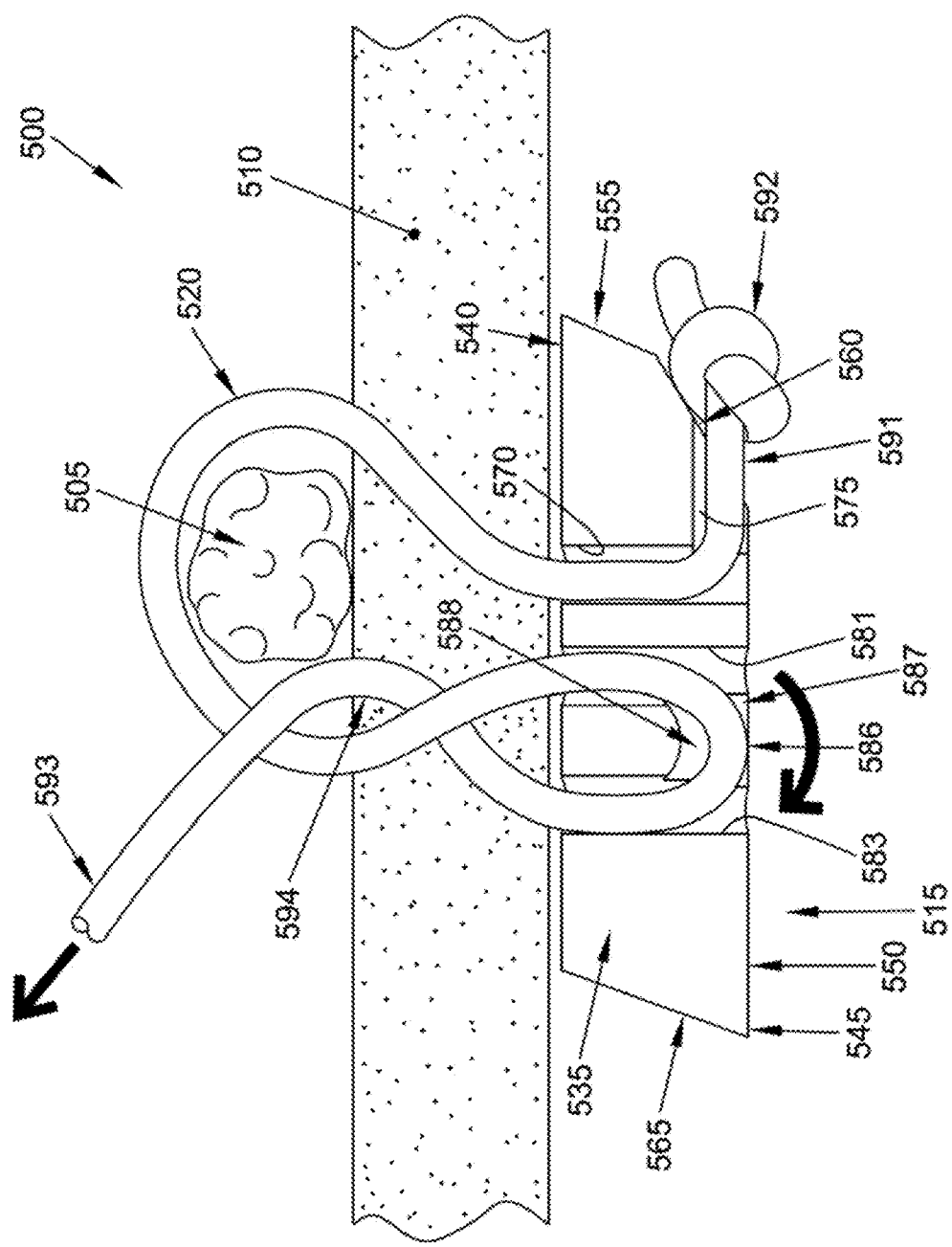
FIG. 73 is a schematic view showing a single anchor system formed in accordance with the present invention.
Figure 74:
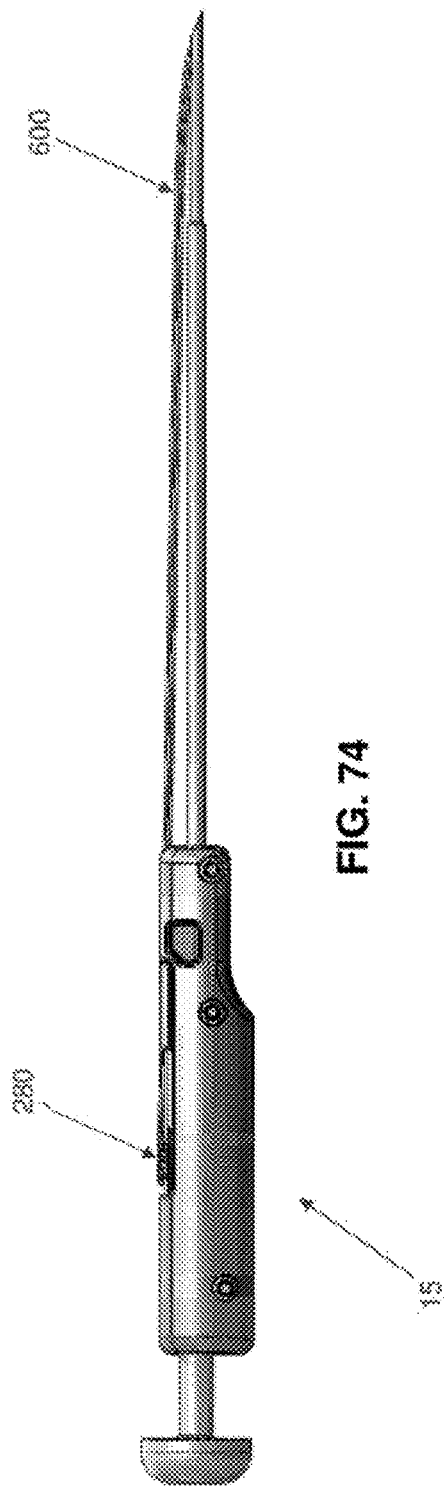
FIGS. 74-85 are schematic views showing another single anchor system formed in accordance with the present invention, wherein the system comprises an anchor comprising a flexible finger.
Figure 75:
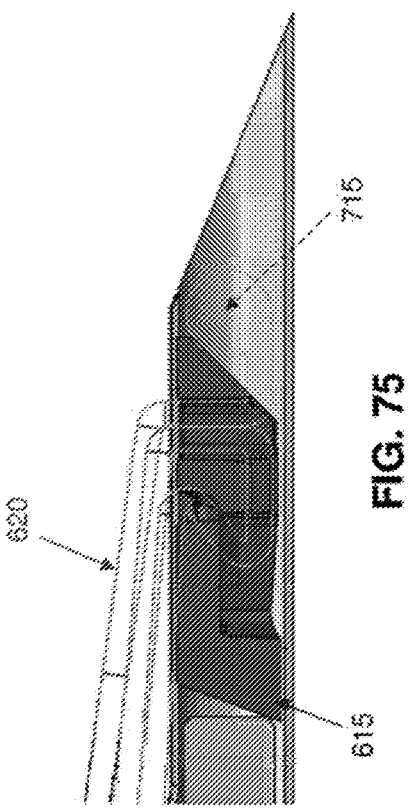
Figure 76:
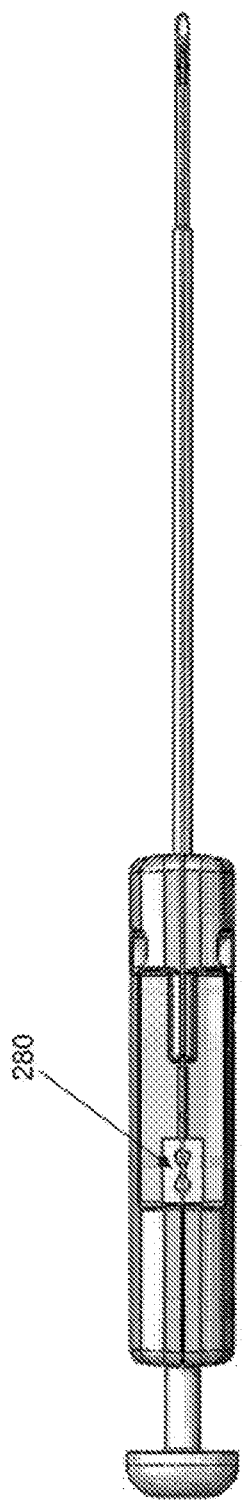
Figure 77:
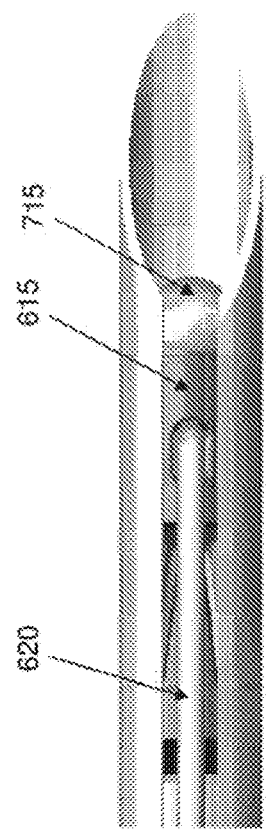
Figure 78:
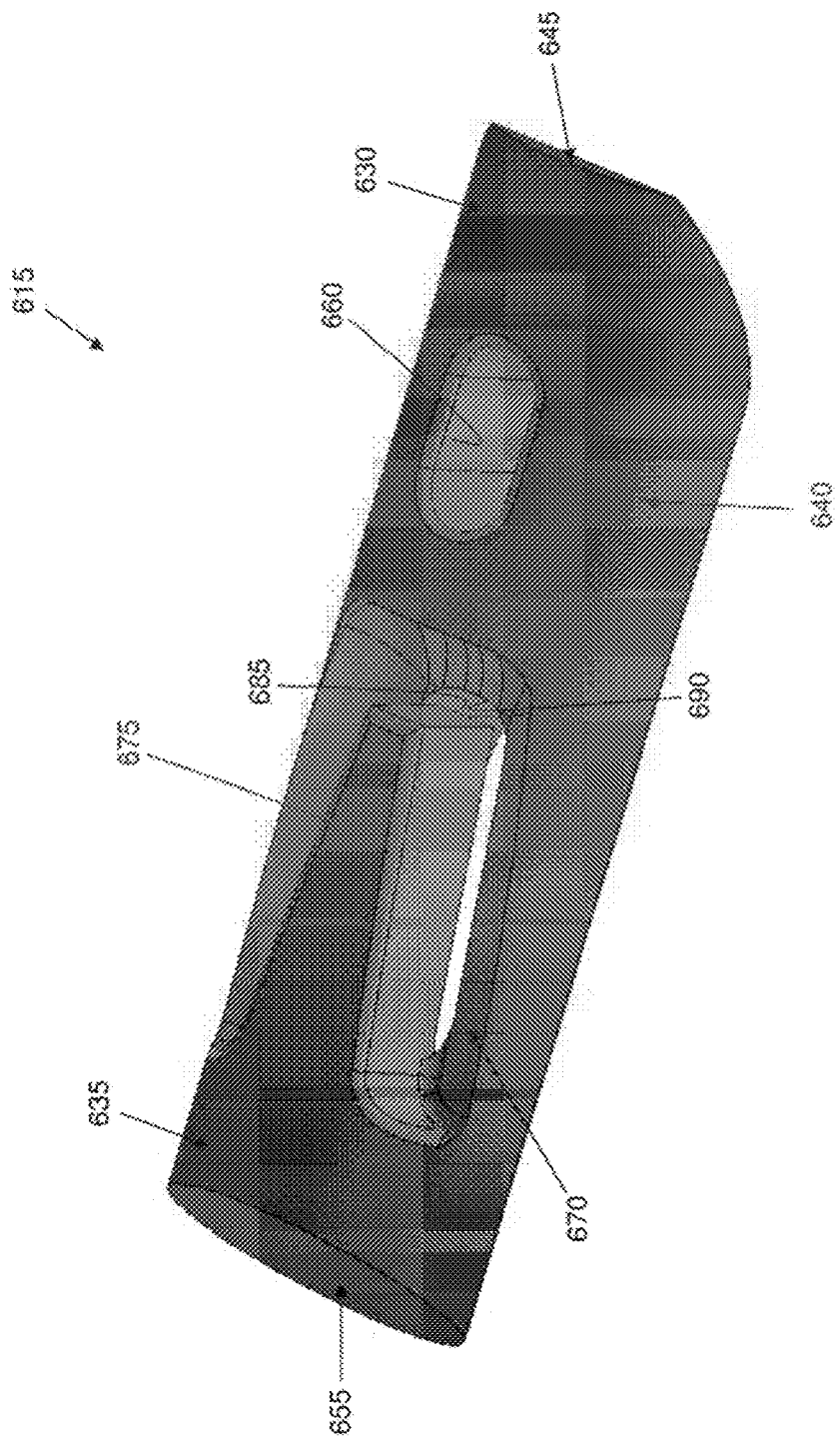
Figure 79:
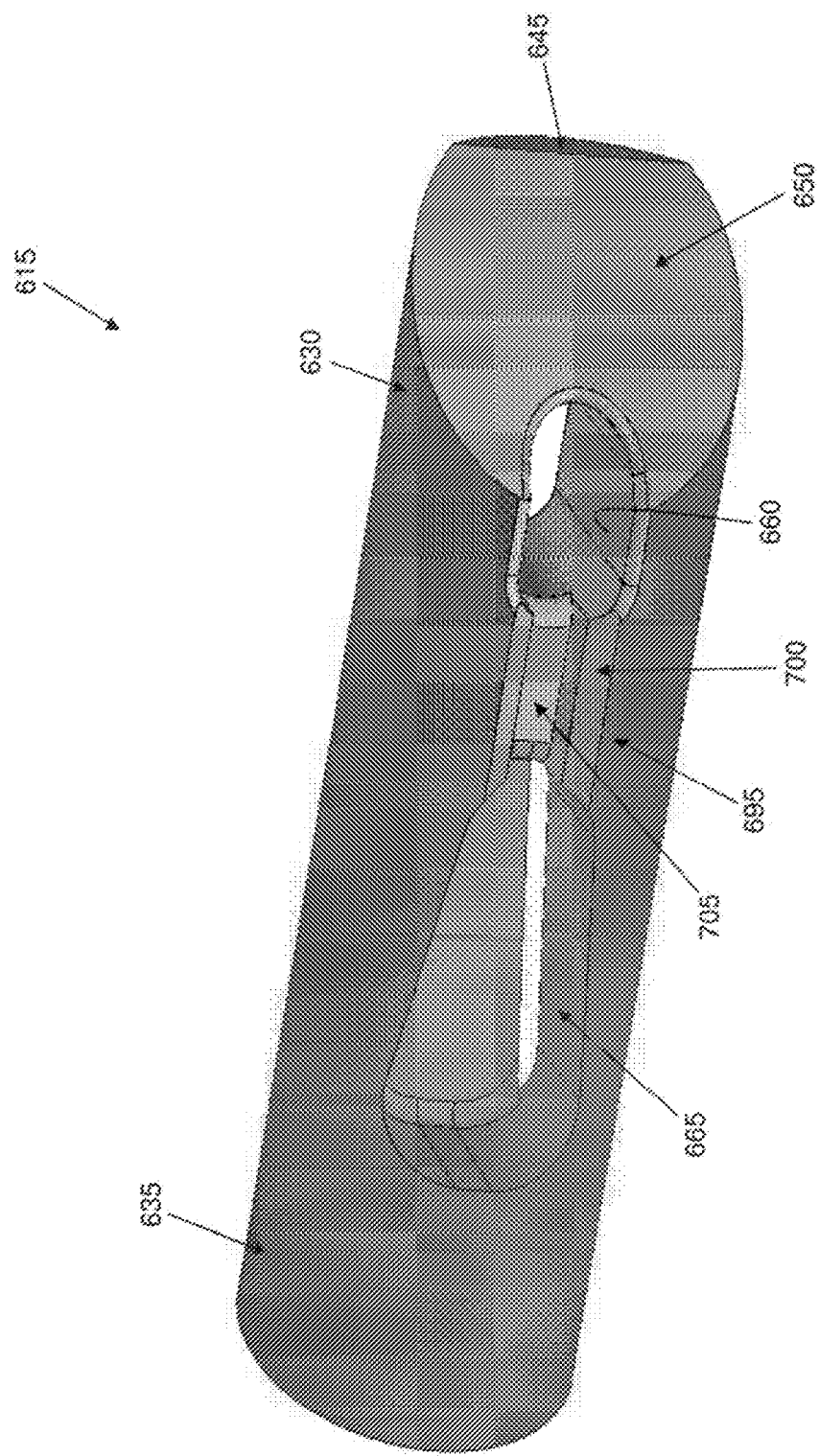
Figure 80:
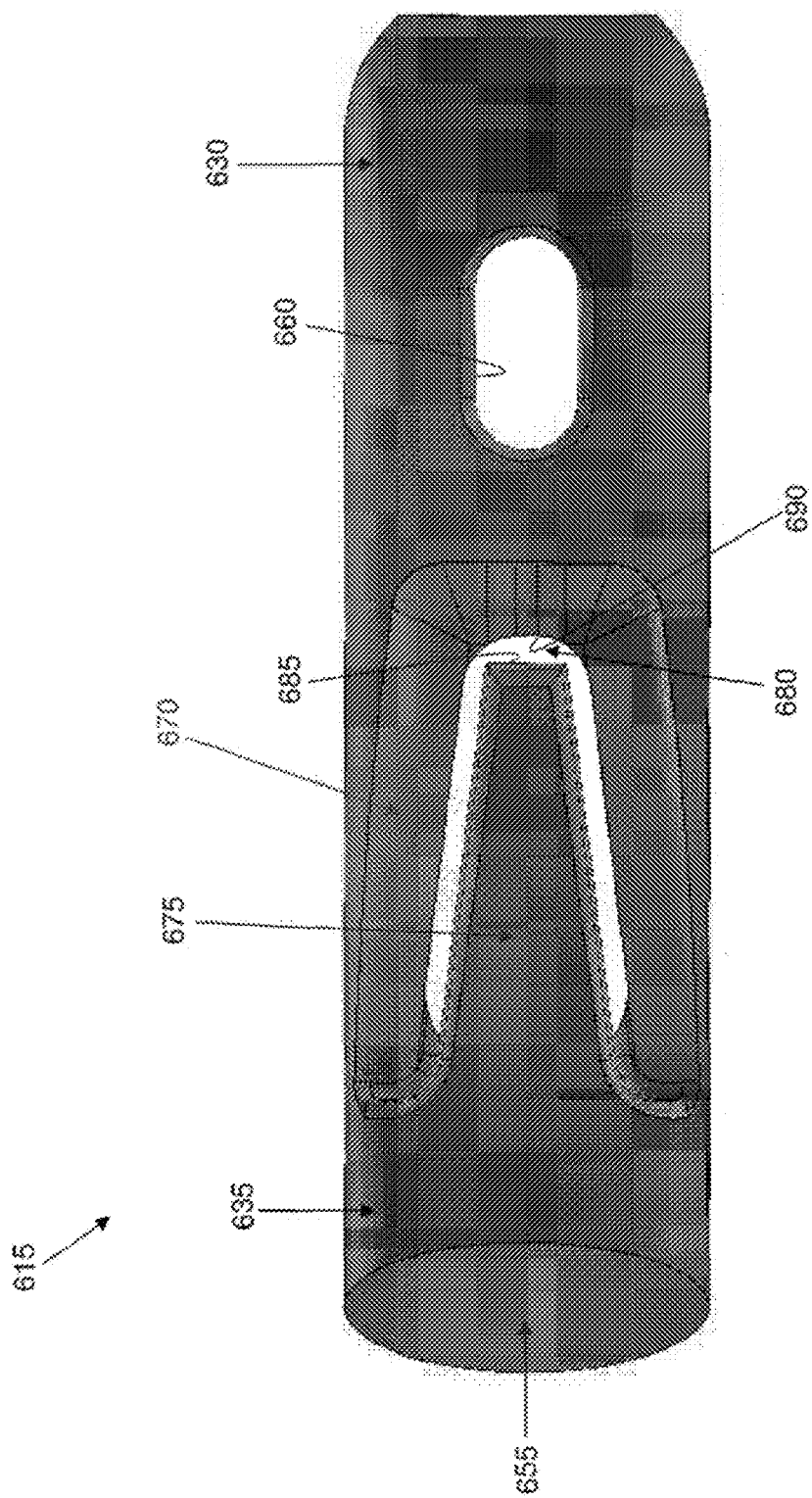
Figure 81:
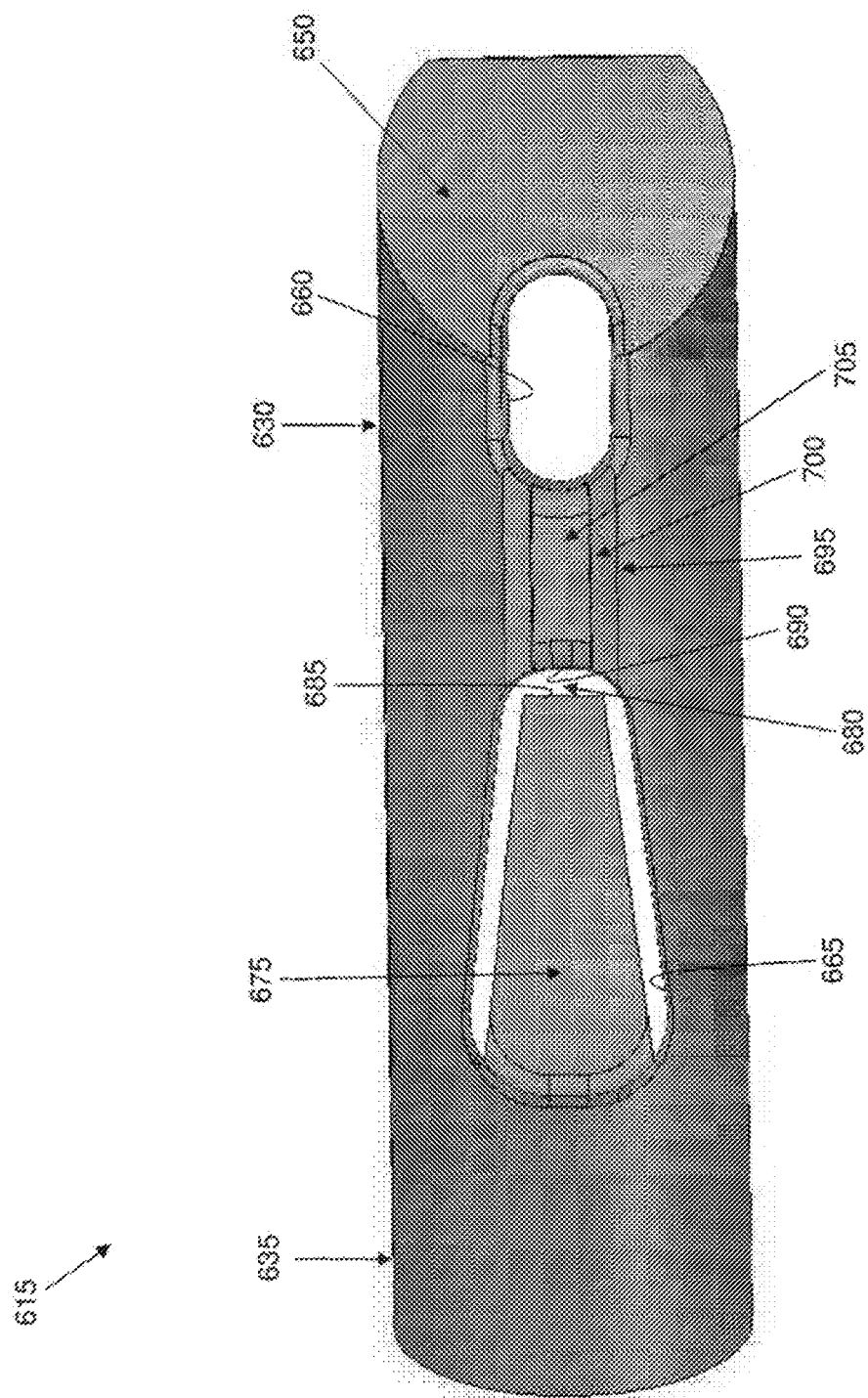
Figure 82:
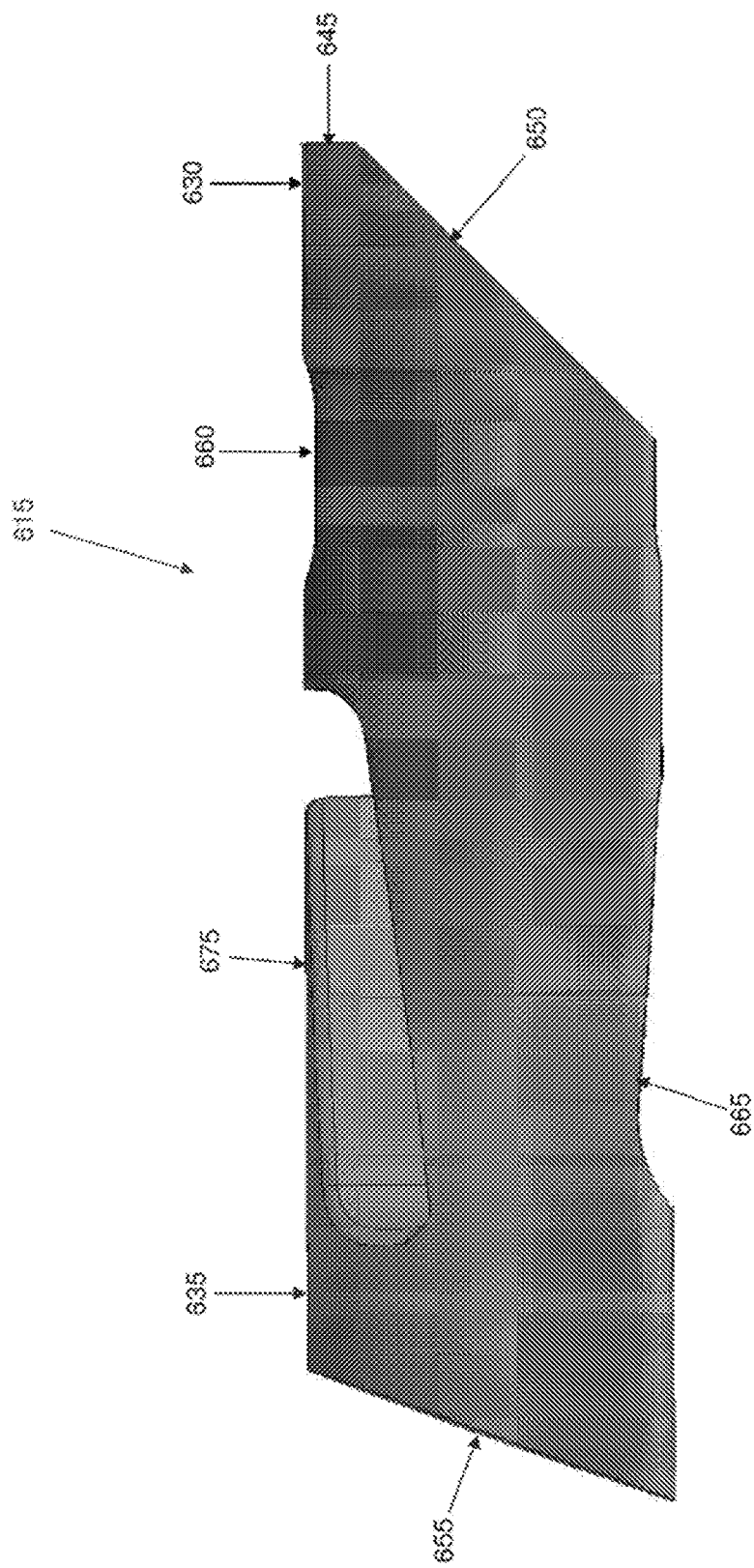

In another preferred form of the present invention, and looking now at FIG. 73, a single anchor system 500 may be used to secure an object (e.g., a sensory nerve stimulator "SNS" lead 505) to tissue (e.g., fascia 510). In this form of the invention, single anchor system 500 comprises a novel anchor 515 and a suture 520. Single anchor system 500 is preferably deployed using the aforementioned inserter 15 (or another appropriate inserter).

More particularly, anchor 515 comprises a generally cylindrical body 535 having a distal end 540, a proximal end 545 and a generally circular side wall 550. Distal end 540 terminates in a flat or somewhat inclined distal end surface 555 and a more inclined distal end surface 560. Flat or somewhat inclined distal end surface 555 is sufficiently large so as to render distal end 540 of anchor 515 substantially blunt (but, where distal end surface 555 is somewhat inclined, also having a tapered lead-in). Inclined distal end surface 560 is pitched at an appropriate angle (e.g., 30 degrees, 45 degrees, etc.) so as to cause anchor 515 to turn during deployment (in the same manner that the aforementioned distal anchor 20 comprises a corresponding inclined distal surface 60 for causing turning), as will hereinafter be discussed. Proximal end 545 terminates in an inclined proximal end surface 565.

A vertical bore 570 passes through anchor 515. Vertical bore 570 is sized to slidably receive suture 520 therein. A horizontal slot 575 extends between inclined distal end surface 560 and vertical bore 570. Horizontal slot 575 is preferably also sized to slidably receive suture 520 therein, and helps keep anchor 515 and suture 520 from binding when they are disposed within the aforementioned inserter 15. A pair of vertical bores 581, 583 are also disposed in anchor 515, proximal to vertical bore 570. Vertical bores 581, 583 are also sized to slidably receive suture 520 therein. A bottom horizontal slot 586 extends between vertical bore 581 and vertical bore 583.

Significantly, suture 520 follows a non-linear path through anchor 515, and this non-linear path creates impedance to the passage of suture 520 through anchor 515.

If desired, bottom horizontal slot 586 may be stepped, comprising a wider outer portion 587 and a narrower inner portion 588. Wider outer portion 587 may be sized to slidably receive suture 520 therein so as to help keep anchor 515 and suture 520 from binding when they are disposed within the aforementioned inserter 15, but narrower portion 588 may be sized to snugly receive suture 520 therein, whereby to provide a light hold on suture 520 when suture 520 is disposed therein.

As seen in FIG. 73, suture 520 has a distal end 591 terminating in a large ball (or knot) 592, and a proximal segment 593. Suture 520 is passed through anchor 515 so that so that large ball (or knot) 592 is disposed against the more inclined distal end surface 560, and the suture extends along horizontal slot 575 of anchor 515, up vertical bore 570 of anchor 515, around the object (e.g., a sensory nerve stimulator "SNS" lead 505) which is to be secured to tissue (e.g., fascia 510), down vertical bore 581, through bottom horizontal slot 586 (i.e., through wider outer portion 587 of bottom horizontal slot 586 where bottom horizontal slot is stepped), and up vertical bore 583.

In use, anchor 515 is deployed at the surgical site with suture 520 under tension so that anchor 515 is turned as it is ejected from the aforementioned inserter 15 (in the same manner that the aforementioned distal anchor 20 is turned as it is ejected from the aforementioned inserter 15), then suture 520 is tensioned by pulling proximally on proximal end 593 of suture 520. As suture 520 is tensioned, sensory nerve stimulator "SNS" lead 505 is secured against fascia 510 (i.e., by virtue of anchor 515 being set in fascia 510 and by virtue of lead 505 being captured to anchor 515 via suture 520). Note that suture 520 will be held against slippage relative to anchor 515 by virtue of the fact that suture 520 follows a non-linear path through anchor 515, and this non-linear path creates impedance to the passage of suture 520 through anchor 515. When suture 520 is thereafter tensioned further, and where bottom horizontal slot 586 comprises a narrower portion 588, suture 520 will be pulled from wider outer portion 587 of bottom horizontal slot 586 into narrower portion 588 of bottom horizontal slot 586 so that suture 520 is snugly received therein. This can provide an additional hold on suture 520. Thereafter, a half-hitch 594 is formed in suture 520 on the proximal side of anchor 520 so as to secure the fixation. In this form of the invention, half hitch 594 will provide the primary fixation of suture 520 to anchor 515, and the impedance created by the non-linear path of suture 520 through anchor 515 will provide significant additional fixation of suture 520. Where bottom horizontal slot 586 comprises a narrower portion 588, movement of suture 520 into narrower portion 588 can also provide a small additional holding force.

Single Anchor Fixation Utilizing Anchor Comprising Flexible Finger

In another preferred form of the present invention, and looking now at FIGS. 74-85, a single anchor system 600 may be used (e.g., with the aforementioned inserter 15) to secure an object (e.g., a sensory nerve stimulator SNS lead 605) to tissue (e.g., fascia 610). In this form of the invention, single anchor system 600 comprises a novel anchor 615 and a suture 620. Single anchor system 600 is preferably deployed using the aforementioned inserter 15 (or another appropriate inserter).

More particularly, anchor 615 comprises a generally cylindrical body 625 having a distal end 630, a proximal end 635 and a generally circular side wall 640. Distal end 630 terminates in a flat or somewhat inclined distal end surface 645 and a more inclined distal end surface 650. Flat or somewhat inclined distal end surface 645 is sufficiently large so as to render distal end 630 of anchor 615 substantially blunt (but, where distal end surface 645 is somewhat inclined, also having a tapered lead-in). Inclined distal end surface 650 is pitched at an appropriate angle (e.g., 30 degrees, 45 degrees, etc.) so as to cause anchor 615 to turn during deployment (in the same manner that the aforementioned distal anchor 20 comprises a corresponding inclined distal surface 60 for causing turning), as will hereinafter be discussed. Proximal end 635 terminates in an inclined proximal end surface 655.

A vertical bore 660 passes completely through anchor 615. Vertical bore 660 preferably intersects inclined distal end surface 650 and is sized to slidably receive suture 620 therein. A recess 665 passes part way through anchor 615. A U-shaped slot 670 passes part way through anchor 615. Recess 665 and U-shaped slot 670 together define a flexible finger 675. In this form of the invention, a gap 680 is formed between the inner tip 685 of flexible finger 675 and the edge 690 formed at the convergence of recess 665 and U-shaped slot 670. Preferably gap 680 is sized so as to be approximately 50% of the width of suture 620 when flexible finger 675 is in its relaxed, unbiased condition (i.e., in the position shown in FIGS. 78 and 83) and when suture 620 is in its normal, uncompressed condition. A bottom horizontal slot 695 extends between vertical bore 660 and recess 665. Bottom horizontal slot 695 may be stepped, comprising a wider outer portion 700 and a narrower inner portion 705. If desired, wider outer portion 700 may be sized to slidably receive suture 620 therein so as to help keep anchor 615 and suture 620 from binding when they are disposed within the aforementioned inserter 15, but narrower portion 705 may be sized to snugly receive suture 620 therein whereby to provide a light hold on suture 620 when suture 620 is disposed therein. Alternatively, bottom horizontal slot 695 may comprise a slot of uniform width with a chamfer lead-in.

Figure 83:
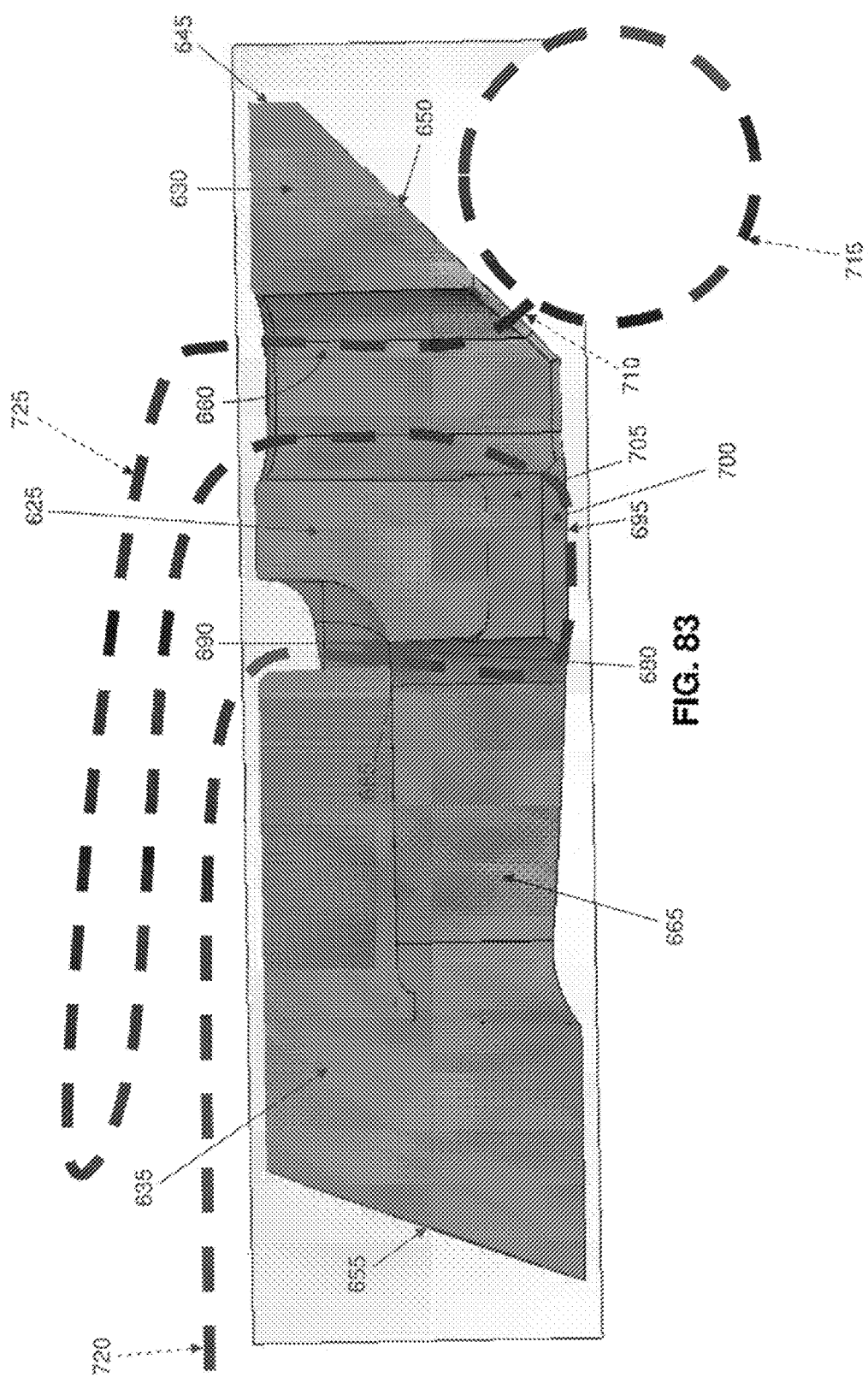
Figure 84:
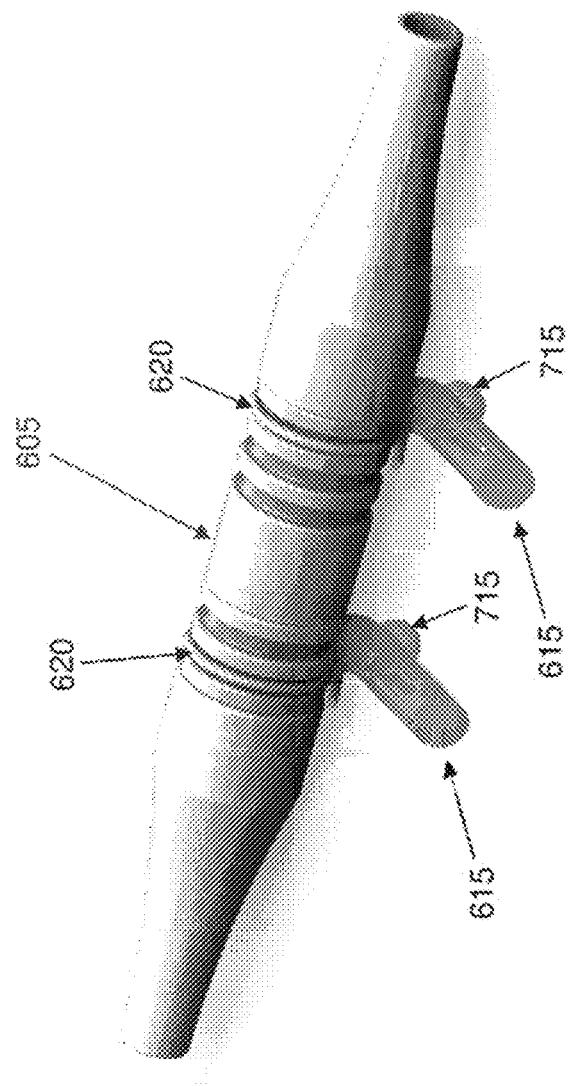
Figure 85:
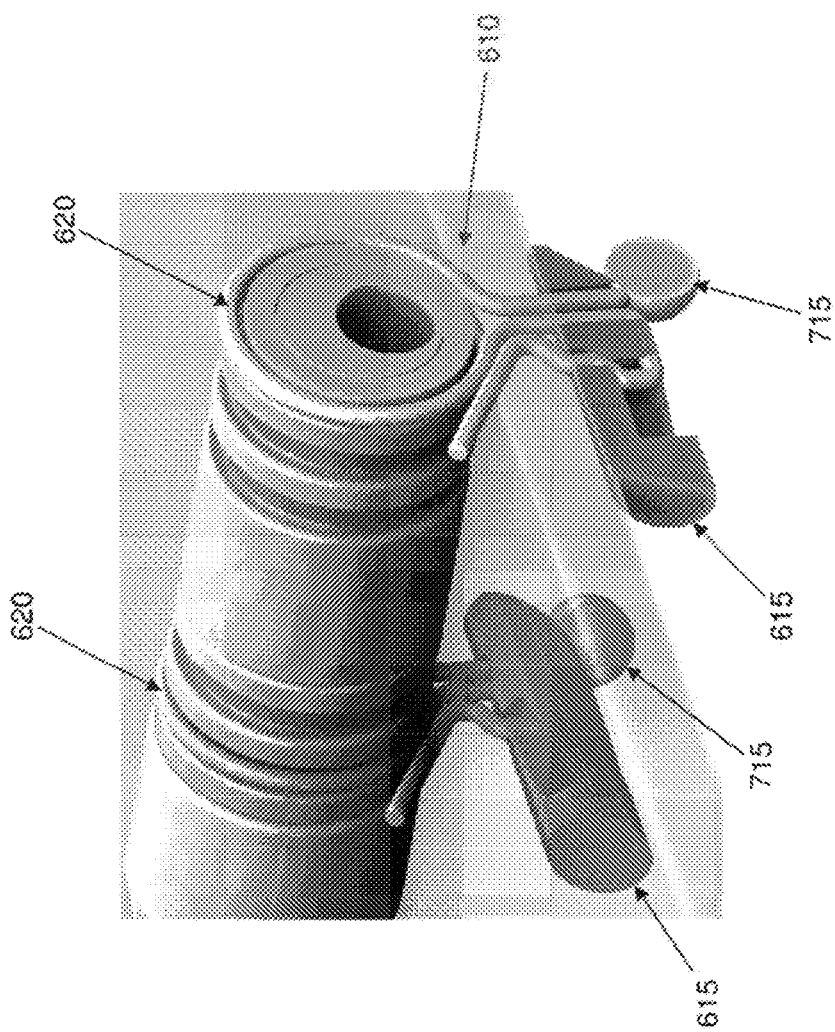

As seen in FIG. 83, suture 620 has a distal end 710 terminating in a large ball or knot 715, a proximal segment 720, and an intermediate loop 725 which may be releasably secured to suture sled 280 of inserter 15. Suture 620 is passed through anchor 615 so that large ball or knot 715 is disposed against the more inclined distal end surface 650, and the suture extends into vertical bore 660, loops around to form loop 725 (which is preferably releasably secured to suture sled 280 of inserter 15) and extends back down vertical bore 660, through wider outer portion 700 of bottom horizontal slot 695 (if bottom horizontal slot 695 is stepped), up through recess 665 and out U-shaped slot 670. Note that inasmuch as suture 620 has a diameter which is approximately twice the size of gap 680 formed between inner tip 685 of flexible finger 675 and edge 690 of anchor 615, flexible finger 675 will normally bear against the suture disposed in gap 680. In this condition, the presence of the "oversized" suture 620 in the "undersized" gap 680 will cause flexible finger 675 to be flexed upwardly (from the angle of view of FIG. 83) so as to accommodate suture 620, with inner tip 685 of flexible finger 675 capturing the suture against edge 690 of anchor 615. Note that some compression of suture 620 may occur in this condition.

In addition to the foregoing, it should be appreciated that suture 620 follows a non-linear path through anchor 615, and this non-linear path creates impedance to the passage of suture 620 through anchor 615.

In use, anchor 615 is deployed at the surgical site with suture 620 under tension so that anchor 615 is turned as it is ejected from the aforementioned inserter 15 (in the same manner that the aforementioned distal anchor 20 is turned as it is ejected from the aforementioned inserter 15). In one preferred form of the invention, this is accomplished by releasably mounting loop 725 of suture 620 to suture sled 280 of inserter 15 during insertion of anchor 615. Then loop 725 of suture 620 is released from suture sled 280, SNS lead 605 is passed through loop 725, and then suture 620 is tensioned by pulling proximally on proximal end 720 of suture 620. As suture 620 is tensioned, flexible finger 675 flexes away from the body of anchor 615, thereby allowing suture 620 to slide through recess 680 and U-shaped slot 670 (as well as through vertical bore 660 and wider outer portion 700 of bottom horizontal slot 695). When the slack in suture 620 has been taken up, whereby to pull SNS lead 605 tight against fascia 610, and suture 620 is thereafter tensioned further, where bottom horizontal slot 695 comprises a narrower portion 705, suture 620 is pulled from wider outer portion 700 of bottom horizontal slot 695 into narrower portion 705 of bottom horizontal slot 695 so that suture 620 is snugly received therein, such that anchor 615 provides a light hold on suture 620. When tension on the free end of suture 620 is thereafter relaxed, flexible finger 675 flexes back toward the body of anchor 615, whereby to lock suture 620 to anchor 615 (i.e., with inner tip 685 of flexible finger 675 capturing the suture against edge 690 of anchor 615). In addition, inasmuch as suture 620 follows a non-linear path through anchor 615, the non-linear path creates impedance to the passage of suture 620 through anchor 615. In this way, suture 620 is secured to anchor 615. Thereafter, if desired, a half-hitch may be formed in suture 620 on the proximal side of anchor 615 so as to further secure suture 620 to anchor 615, and hence secure SNS lead 605 to fascia 610.

In one preferred form of the invention, single anchor system 600 is configured so that its failure mode comprises slipping, not breaking (i.e., suture 620 will slip relative to anchor 615 before anchor 615 will break).

And in one preferred form of the invention, anchor 615 comprises carbon fiber-reinforced PEEK (30%).

Furthermore, if desired, anchor 615 may comprise a radiopaque material so that anchor 615 is visible under X-ray visualization. By way of example but not limitation, a radiopaque element may be incorporated in the body of anchor 615. By way of further example but not limitation, a piece of Nitinol wire may be molded into anchor 615 so that the Nitinol wire extends through flexible finger 675 and into the adjoining body of anchor 615—in this form of the invention, the Nitinol wire reinforces flexible finger 675 at the same time that it provides a radiopaque element in anchor 615.

Inserter with Alternative Suture Sled

In the foregoing disclosure, inserter 15 is characterized as having a suture sled 280 which is spring mounted to handle 200. Suture sled 280 serves as a movable mount for securing the proximal portion of suture loop 320 (or suture loop 725) to handle 200, such that suture sled 280 can slide along handle 200 as distal anchor 20 (or anchor 615) is advanced into a mass of material (e.g., an intervertebral disc, a bone, soft tissue, etc.), and then be stopped relative to handle 200 so that distal anchor 20 (or anchor 615) is driven against ball 185 (or ball 715), whereby to facilitate turning of distal anchor 20 (or anchor 615) within the mass of material.

To this end, in the foregoing disclosure, suture sled 280 is characterized as being spring mounted to handle 200 so that suture sled 280 initially remains in a proximal position, whereby to hold suture 30 (or suture 620) under tension, until distal anchor 20 (or anchor 615) is driven distally by push rod 205 of inserter 15, whereupon suture sled 280 is permitted to move distally, against the power of spring 285, until distal anchor 20 (or anchor 615) is at the proper depth within the mass of material, whereupon distal movement of suture sled 280 is stopped, thereby stopping distal movement of ball 185 (or ball 715) and hence setting the depth of distal anchor 20 (or anchor 615).

However, if desired, spring 285 may be omitted, and other means may be provided for releasably holding suture sled 280 in a proximal position until distal anchor 20 (or anchor 615) is driven distally by push rod 205. By way of example but not limitation, suture sled 280 may be releasably held in a proximal position by means of a yielding stop finger, a ball-and-detent mechanism, or other releasable holding mechanism of the sort well known in the art.

Inserter with Impulse Driver

In the foregoing disclosure, inserter 15 is characterized as having a push rod 205 which is moved distally by manually pressing on thumb button 310 (e.g., in the manner of manually pressing on the plunger of a syringe), whereby to drive distal anchor 20 (or anchor 615) distally.

However, in some circumstances it can be desirable to drive distal anchor 20 (or anchor 615) with an impulse mechanism, so that an impulse of drive energy is applied to distal anchor 20 (or anchor 615). By way of example but not limitation, where distal anchor 20 (or anchor 615) is formed out of a material having limited strength (e.g., PEEK or PLLA), and where distal anchor 20 (or anchor 615) is to be set in a harder mass of material (e.g., bone), it can be helpful to set distal anchor 20 (or anchor 615) with an impulse mechanism.

Figure 86:
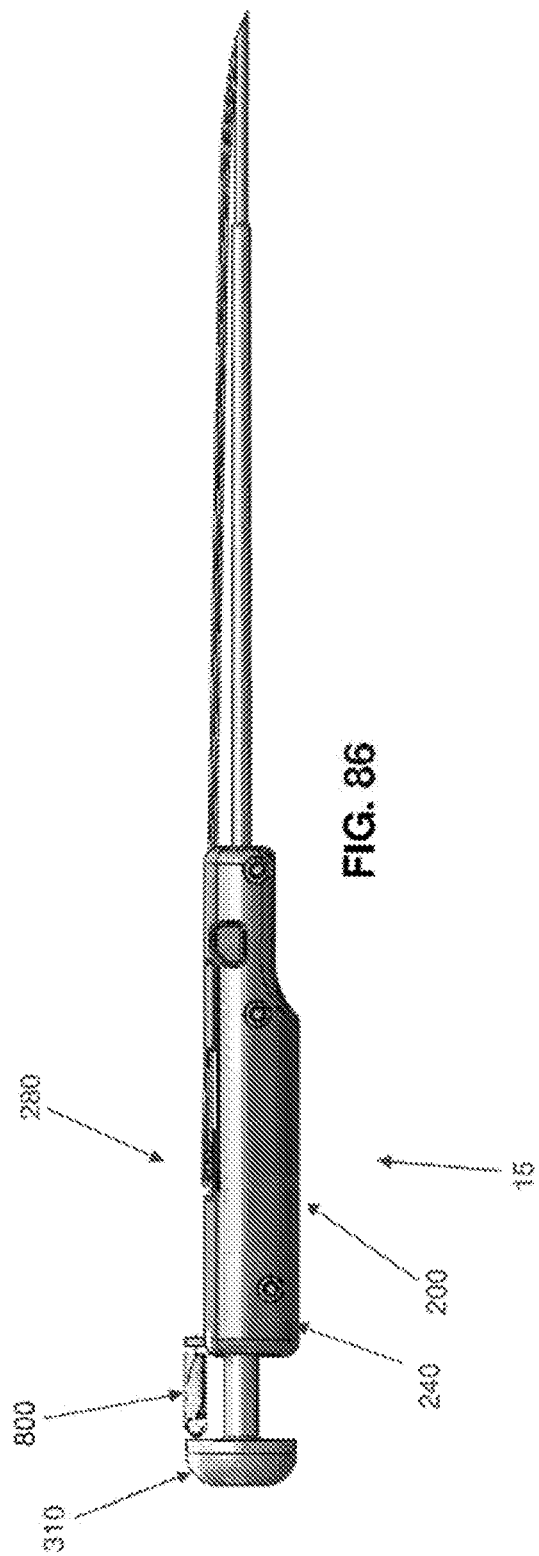
FIG. 86 is a schematic view showing an alternative form of inserter with impulse driver.
Figure 87:
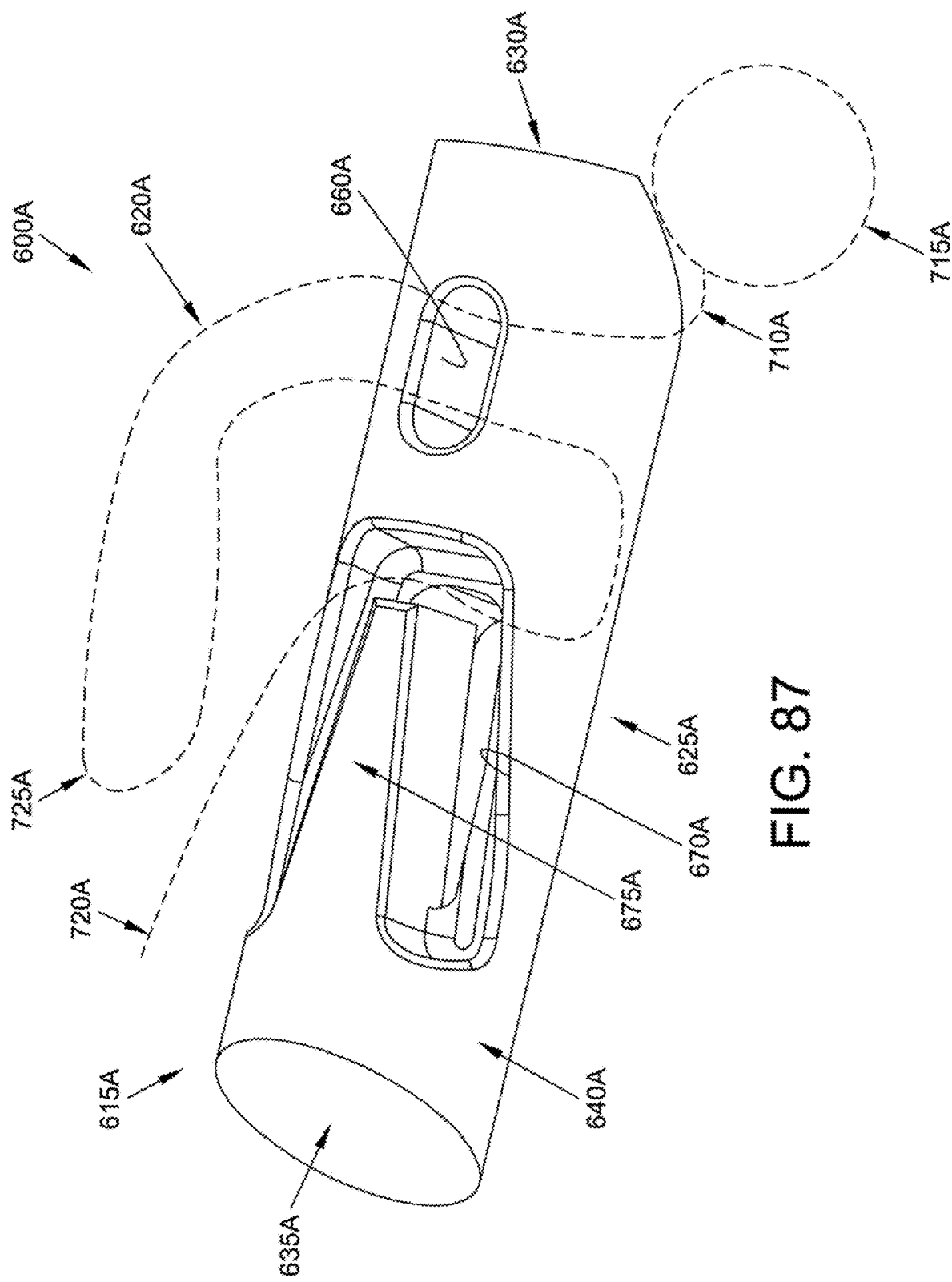
FIGS. 87-92 are schematic views showing another single anchor system formed in accordance with the present invention, wherein the system comprises an anchor comprising a flexible finger.
Figure 88:
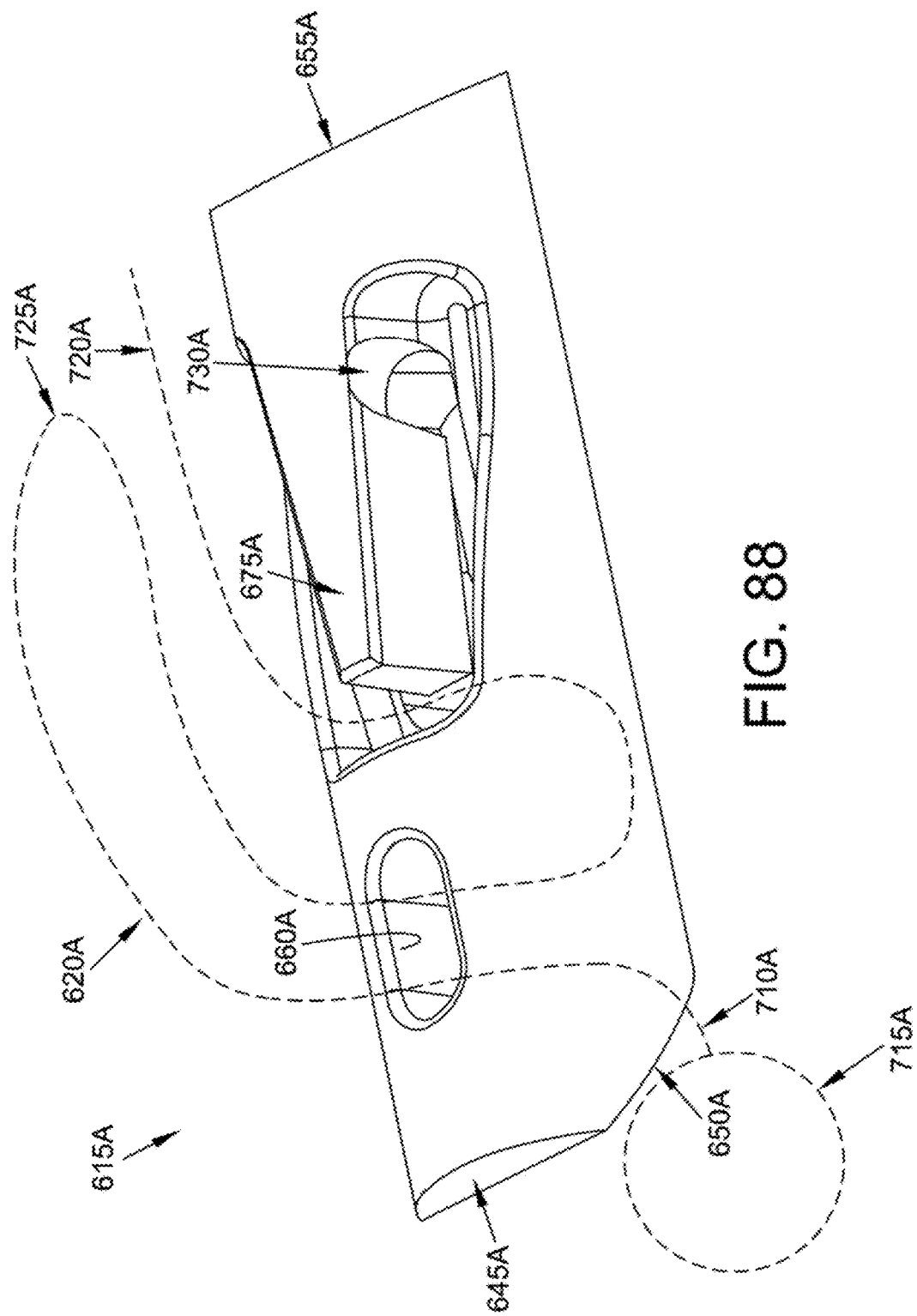
Figure 89:
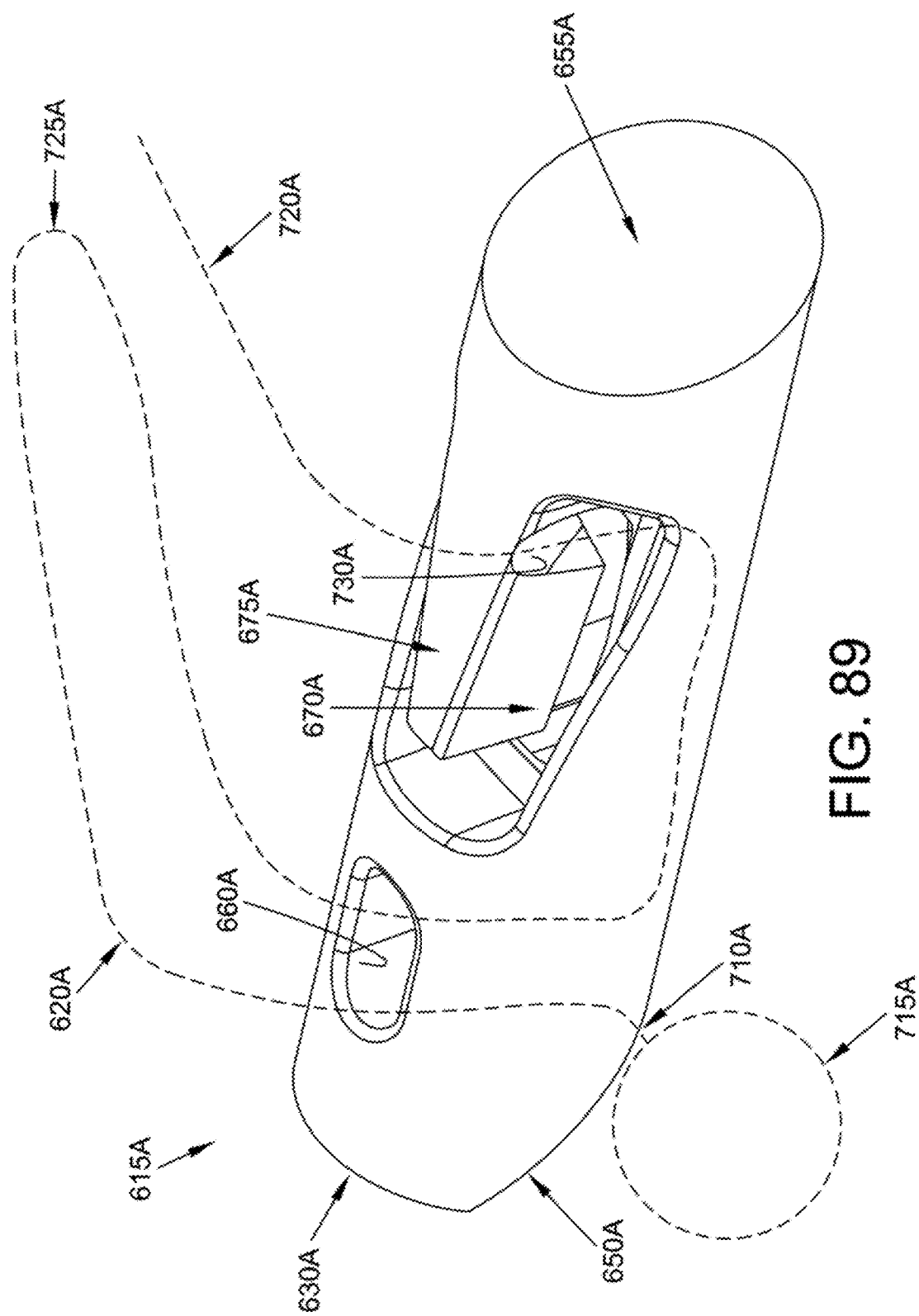
Figure 90:
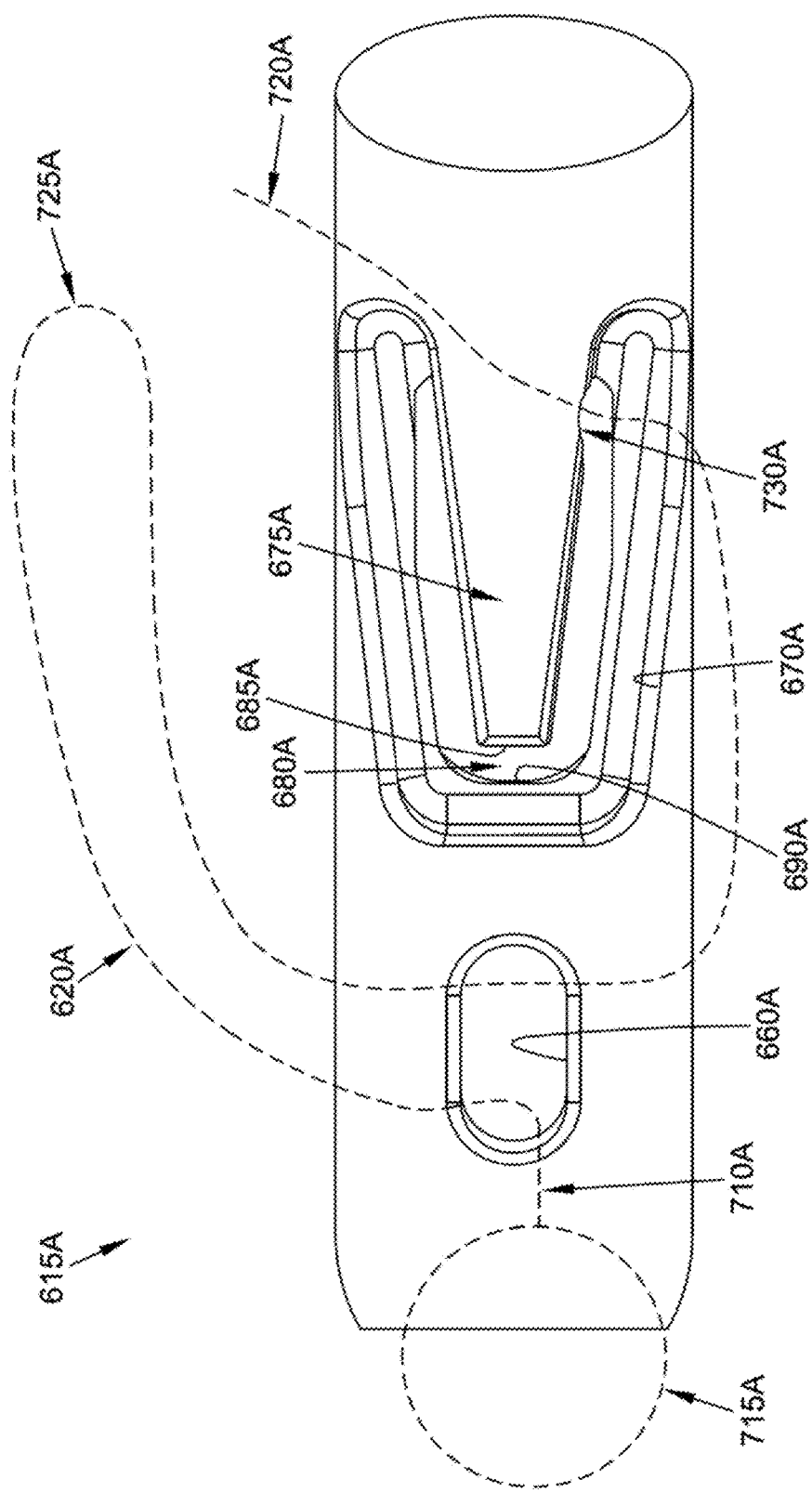
Figure 91:
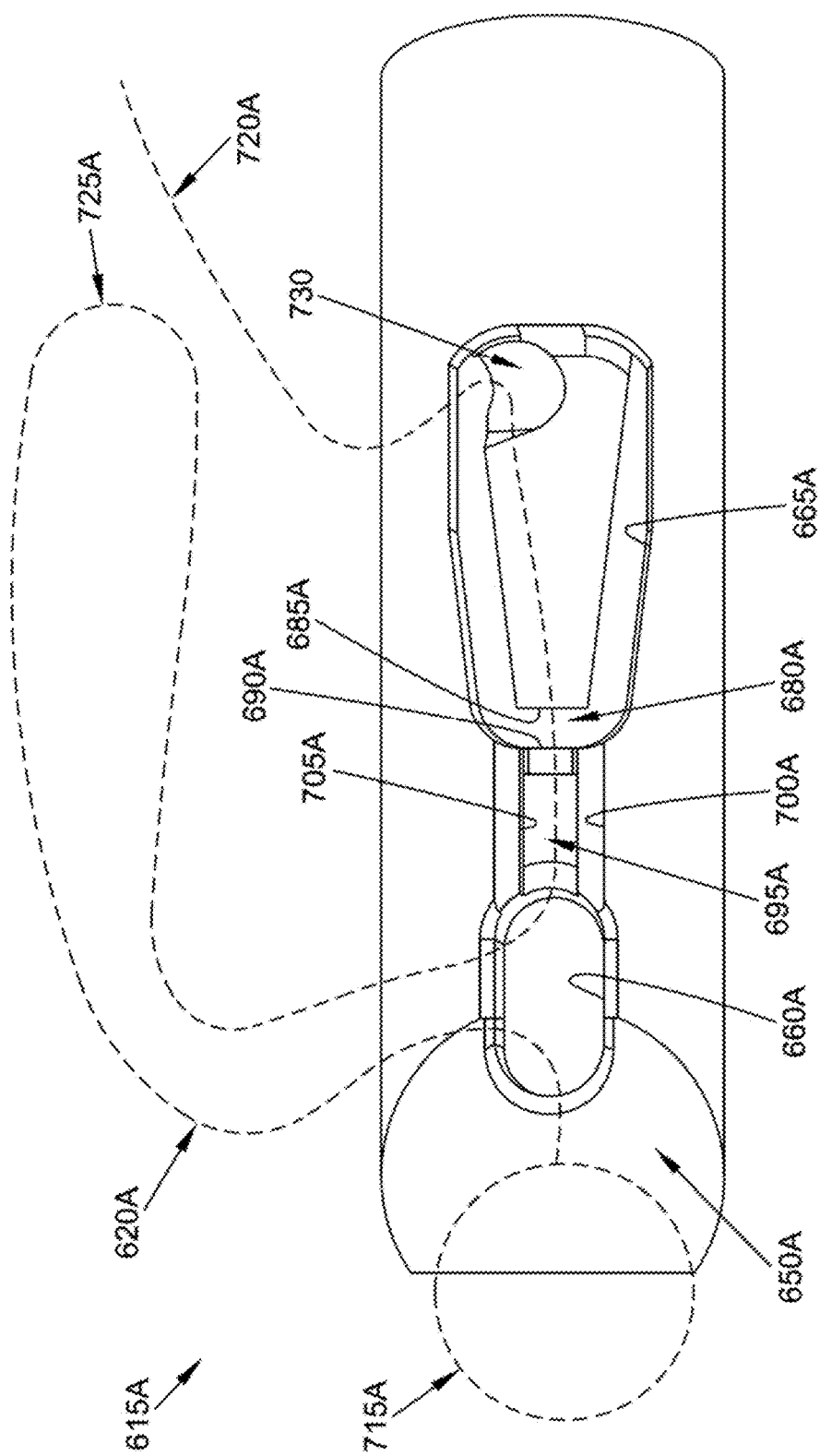
Figure 92:
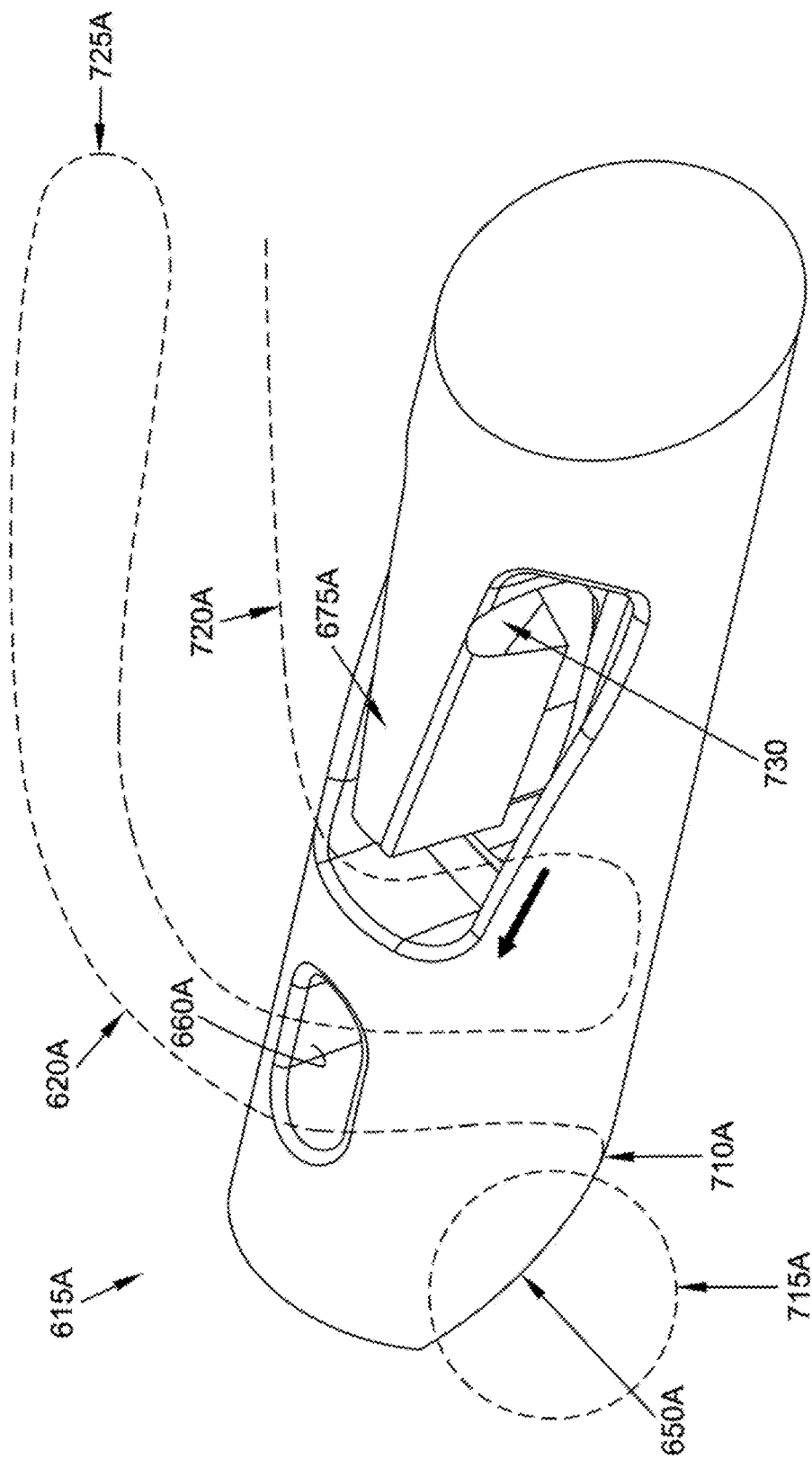
Figure 93:
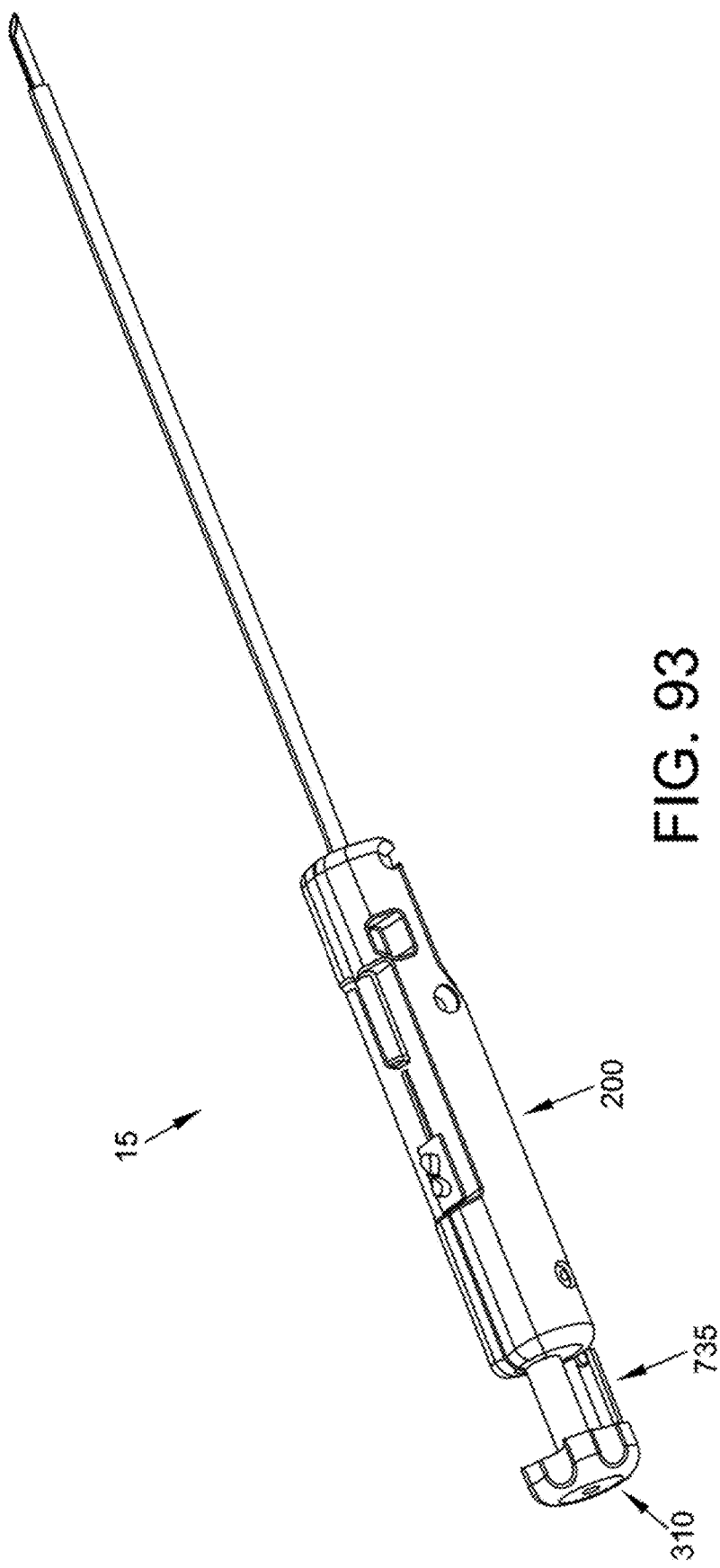
FIGS. 93-97 are schematic views showing another form of stop for selectively preventing deployment of an anchor from an inserter.
Figure 94:
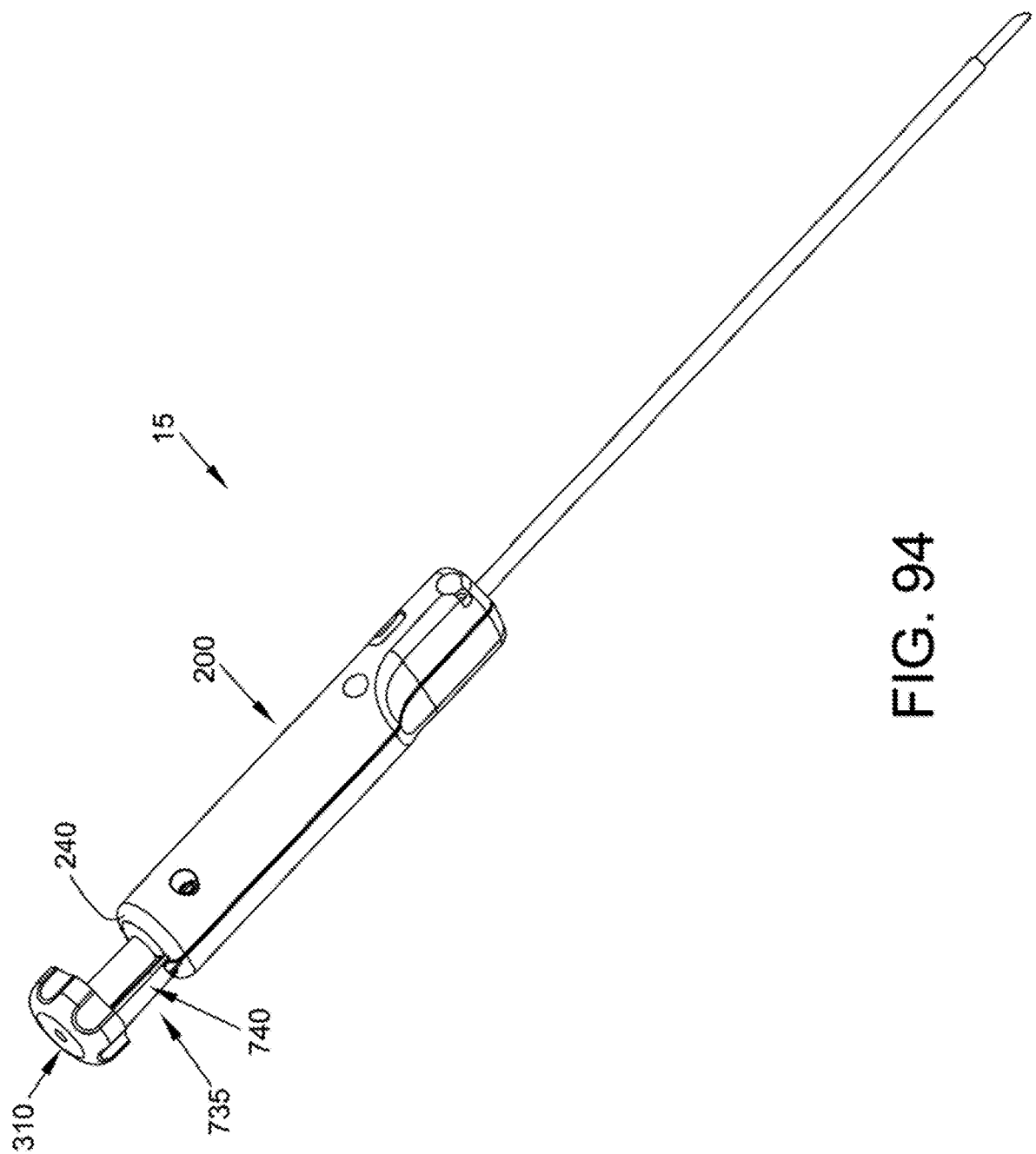

To this end, and looking now at FIG. 86, inserter 15 may be provided with a tension spring 800 which is secured to proximal end 240 of handle 200 and to thumb button 310 of push rod 205. With such a construction, thumb button 310 may be pulled proximally, away from handle 200, so that tension spring 800 is stretched and then, when impulse energy is to be applied to distal anchor 20 (or anchor 615) via push rod 205, thumb button 310 is simply released, so that tension spring 800 applies impulse energy to thumb button 310 and hence causes push rod 205 to apply impulse energy to distal anchor 20 (or anchor 615).

Single Anchor Fixation Utilizing Anchor Comprising Flexible Finger And Suture Loading Hole As discussed above, the free end of suture 620 is passed through suture anchor 615 (i.e., up through vertical bore 660, back down through vertical bore 660, across bottom horizontal slot 695, up recess 665 and out U-shaped slot 670) along a tortuous path. See FIG. 83.

However, it has been found that it is often challenging to thread a suture through a narrow opening (e.g., through recess 665 and through U-shaped slot 670) without employing a suture threader (not shown). A suture threader is well known in the field of sutures and medical devices utilizing sutures, and generally comprises a substantially resilient device (e.g., a flexible wire) which can be passed through the narrow opening and then used to draw the suture back through the opening (e.g., by passing the suture through an opening in the suture threader, and then pulling the suture threader, including the suture, back through the narrow opening).

Thus it would be desirable to provide a suture anchor which facilitates loading a suture into the suture anchor, and which avoids the need for using a separate suture threader, and which facilitates quick and easy loading of a suture through the tortuous path of the suture anchor.

To this end, and looking now at FIGS. 87-92, there is shown an alternative novel anchor 615A. Anchor 615A is generally similar to the aforementioned anchor 615 discussed above, however, anchor 615A is configured to facilitate simplified loading of a suture through anchor 615A, as will hereinafter be discussed.

Anchor 615A preferably comprises a generally cylindrical body 625A having a distal end 630A, a proximal end 635A and a generally circular side wall 640A. Distal end 630A terminates in a flat or somewhat inclined distal end surface 645A and a more inclined distal end surface 650A. Flat or somewhat inclined distal end surface 645A is sufficiently large so as to render distal end 630A of anchor 615A substantially blunt (but, where distal end surface 645A is somewhat inclined, flat or somewhat inclined distal end surface 645A is sufficient to provide anchor 615A with a tapered lead-in). Inclined distal end surface 650A is pitched at an appropriate angle (e.g., 30 degrees, 45 degrees, etc.) so as to cause anchor 615A to turn during deployment (i.e., in the same manner that the aforementioned distal anchor 20 comprises a corresponding inclined distal surface 60 for causing turning), as will hereinafter be discussed. Proximal end 635A preferably terminates in an inclined proximal end surface 655A.

A vertical bore 660A passes completely through anchor 615A. Vertical bore 660A preferably extends substantially perpendicular to the longitudinal axis of anchor 615A. Vertical bore 660A preferably intersects inclined distal end surface 650A and is sized to slidably receive suture 620A therein. A recess 665A is formed on one side of generally cylindrical body 625A and passes part way through anchor 615A. Recess 665A preferably extends substantially perpendicular to the longitudinal axis of anchor 615A. A U-shaped slot 670A is formed on the opposite side of generally cylindrical body 625A (i.e., opposite to recess 665A) and passes part way through anchor 615A. U-shaped slot 670A preferably extends substantially perpendicular to the longitudinal axis of anchor 615A. Recess 665A and U-shaped slot 670A together define a flexible finger 675A which preferably extends distally within generally cylindrical body 625A. In this form of the invention, a gap 680A is formed between the inner tip 685A of flexible finger 675A and the edge 690A formed at the convergence of recess 665A and U-shaped slot 670A. Preferably gap 680A is sized so as to be approximately 50% of the width of suture 620A when flexible finger 675A is in its relaxed, unbiased condition (i.e., in the position shown in FIGS. 87-92) and when suture 620A is in its normal, uncompressed condition. It should be appreciated that recess 665A communicates with U-shaped slot 670A such that a suture can be passed through generally cylindrical body 625A of anchor 615A, as will hereinafter be discussed. A bottom horizontal slot 695A preferably extends between vertical bore 660A and recess 665A. Bottom horizontal slot 695A may be stepped, comprising a wider outer portion 700A and a narrower inner portion 705A. If desired, wider outer portion 700A may be sized to slidably receive suture 620A therein so as to help keep anchor 615A and suture 620A from binding when they are disposed within the aforementioned inserter 15, but narrower portion 705A may be sized to snugly receive suture 620A therein whereby to provide a light hold on suture 620A when suture 620A is disposed therein. Alternatively, bottom horizontal slot 695A may comprise a slot of uniform width with a chamfer lead-in.

A suture loading hole 730A is formed near the proximal end of U-shaped slot 670A in the proximal portion of flexible finger 675A. More particularly, a portion of flexible finger 675A is cut away (e.g., so as to form a hemicylindrical cutout) near the proximal end of flexible finger 675A to form suture loading hole 730A which passes through U-shaped slot 670A and into recess 665A. Suture loading hole 730A is configured to be wider than gap 680A (i.e., wider than the gap between inner tip 685A of flexible finger 675A and edge 690A formed at the convergence of recess 665A and U-shaped slot 670A) so as to facilitate passage of the free end of suture 620A therethrough.

Note that, if desired, suture loading hole 730A may be formed in generally cylindrical body 625A rather than in flexible finger 675A (i.e., a hemicylindrical cutout may be formed in generally cylindrical body 625A rather than in flexible finger 675A); or suture loading hole 730A may be formed in both flexible finger 675A and in generally cylindrical body 625A rather than in just flexible finger 675A or in just generally cylindrical body 625A (i.e., hemicylindrical cutouts may be formed in both flexible finger 675A and in generally cylindrical body 625A rather than in just flexible finger 675A or in just generally cylindrical body 625A).

Suture 620A is generally the same as the aforementioned suture 620, however, suture 620A preferably comprises a stiffened free end for facilitating threading of the free end through vertical bore 660A and through suture loading hole 730A, as will hereinafter be discussed in further detail. More particularly, as seen in FIGS. 87-92, suture 620A has a distal end 710A terminating in a large ball or knot 715A, a proximal segment 720A, and an intermediate loop 725A which may be releasably secured to suture sled 280 of inserter 15. Suture 620A is passed through anchor 615A so that large ball or knot 715A is disposed against the more inclined distal end surface 650A, and the suture extends into vertical bore 660A, loops around to form loop 725A (which is preferably releasably secured to suture sled 280 of inserter 15) and extends back down vertical bore 660A, through wider outer portion 700A of bottom horizontal slot 695A (if bottom horizontal slot 695A is stepped), and up through suture loading hole 730A. It will be appreciated that inasmuch as suture loading hole 730A comprises a diameter slightly larger than the diameter of suture 620A, suture loading hole 730A facilitates easy passage of suture 620A through recess 665A and out U-shaped slot 670A.

After suture 620A has been threaded through suture loading hole 730A, the suture is pulled distally so as to lodge suture 620A in gap 680A between inner tip 685A of flexible finger 675A and edge 690A formed at the convergence of recess 665A and U-shaped slot 670A. Note that inasmuch as suture 620A has a diameter which is approximately twice the size of gap 680A formed between inner tip 685A of flexible finger 675A and edge 690A of anchor 615A, flexible finger 675A will normally bear against the suture disposed in gap 680A. In this condition, the presence of the "oversized" suture 620A in the "undersized" gap 680A will cause flexible finger 675A to be flexed upwardly (from the angle of view of FIG. 87) so as to accommodate suture 620A, with inner tip 685A of flexible finger 675A capturing the suture against edge 690A of anchor 615A. Note that some compression of suture 620A may occur in this condition.

In addition to the foregoing, it should be appreciated that suture 620A follows a non-linear path through anchor 615A, and this non-linear path creates impedance to the passage of suture 620A through anchor 615A.

It should be appreciated that while suture 620A is preferably formed with a stiffened free end in order to facilitate passage of the free end of the suture through vertical bore 660A and/or through suture loading hole 730A, the stiffened free end may be omitted, and/or, if desired, a suture threader may be passed through suture loading hole 730A, used to grasp suture 620A, and then used to pull suture 620A through suture loading hole 730A.

It will be appreciated that novel anchor 615A and suture 620A together form a single anchor system 600A, and single anchor system 600A may be used (e.g., with the aforementioned inserter 15) to secure an object (e.g., a sensory nerve stimulator SNS lead 605) to tissue (e.g., fascia 610) in substantially the same manner that single anchor system 600 (and the aforementioned inserter 15) may be used.

Inserter with Alternative Stop

As discussed above, it is generally desirable to provide inserter 15 with a stop (e.g., removable stop 315, FIGS. 27 and 27A) to prevent thumb button 310 from being inadvertently actuated. In one form of the invention, inserter 15 comprises the aforementioned removable stop 315 which is removably mounted to the shaft of thumb button 310 between the proximal end of handle 200 and thumb button 310. When it is desired to actuate thumb button 310, removable stop 315 is removed from the shaft of thumb button 310 so as to allow thumb button 310 to move distally. However, it has been found that it is sometimes desirable to allow movement of thumb button 310 and then thereafter prevent movement of thumb button 310, and/or to provide a stop which does not require a removable component.

Figure 95:
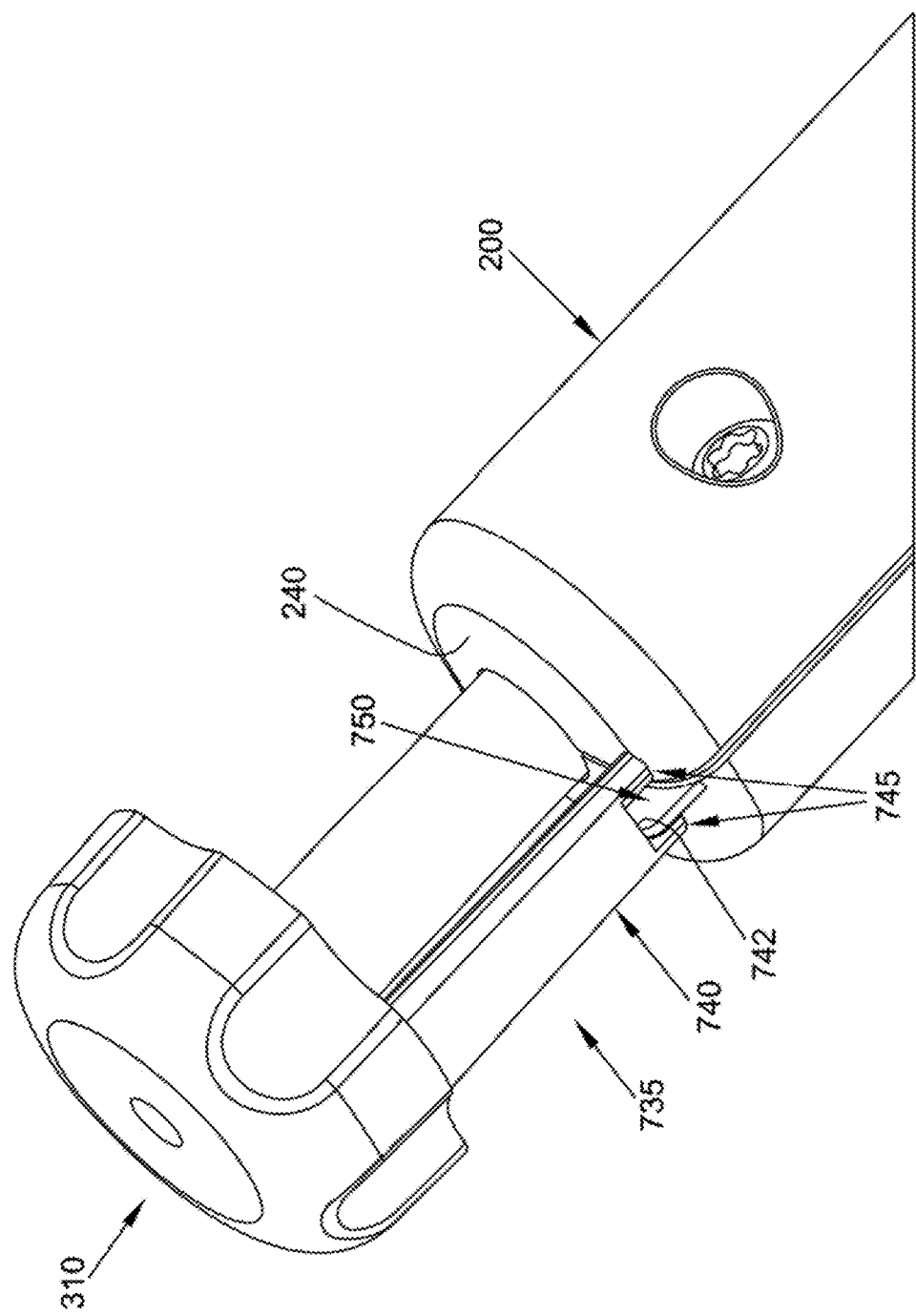
Figure 96:
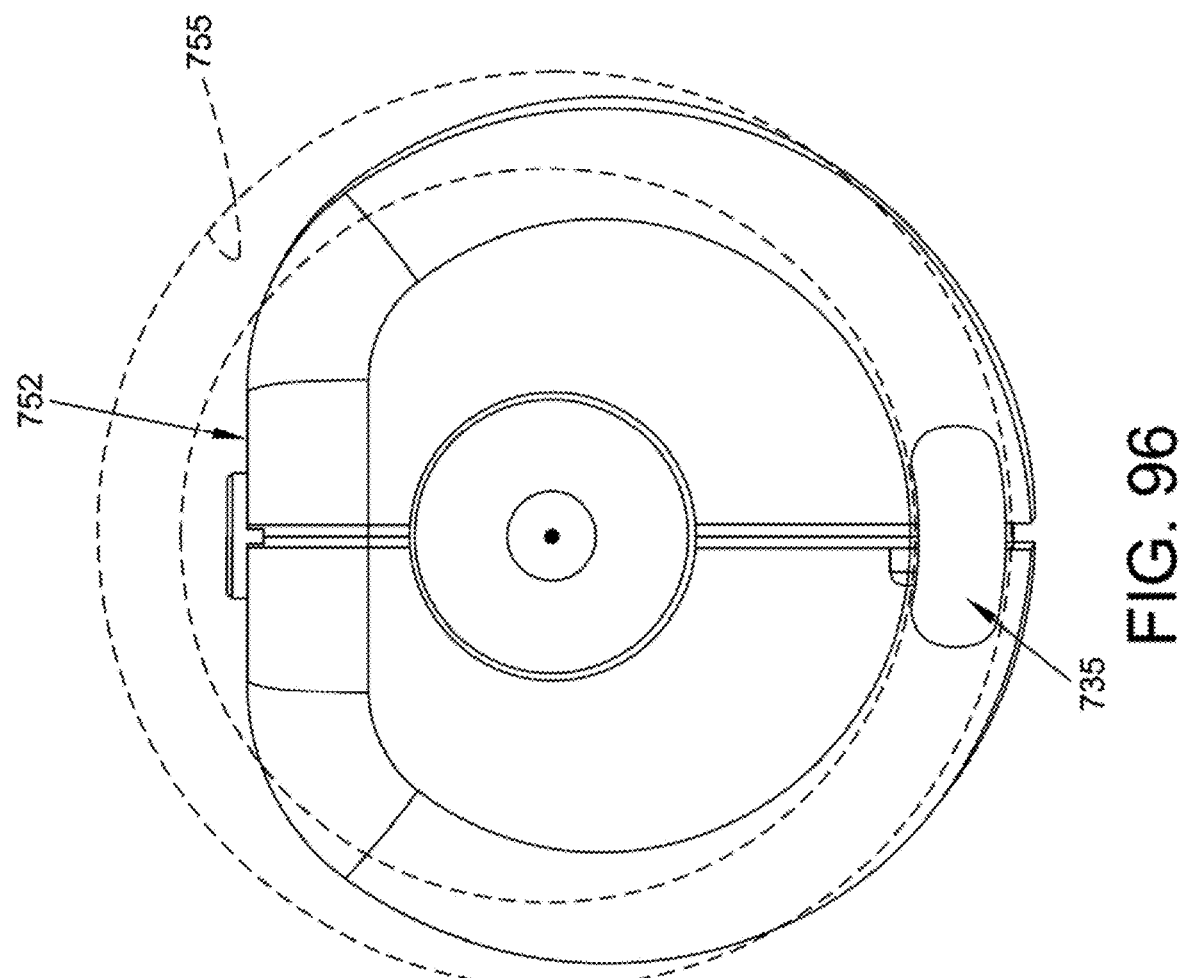
Figure 97:
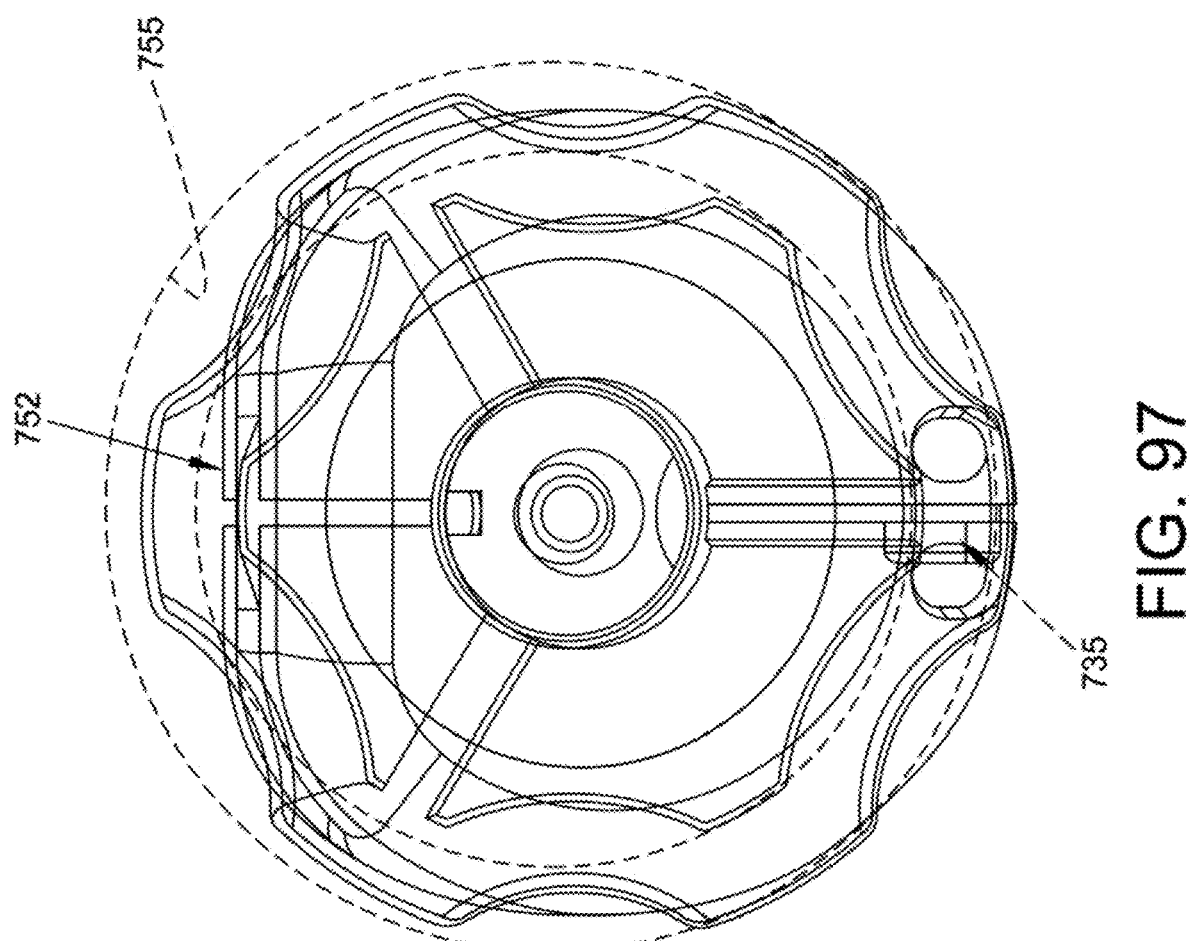

To this end, and looking now at FIGS. 93-97, there is provided an alternative stop 735 which may be incorporated into handle 200 and thumb button 310. Stop 735 generally comprises a distally-extending member 740 which is mounted to (or formed integral with) thumb button 310 and extends distally therefrom. When thumb button 310 is in its unbiased proximal position, the distal end of member 740 of stop 735 contacts proximal end 240 of handle 200. In one preferred form of the invention, the distal end of member 740 comprises a seat 742 disposed between a pair of distally-extending fingers 745 (FIG. 95) for engaging a tab 750 mounted to proximal end 240 of handle 200 (FIG. 95).

In this form of the invention, handle 200 preferably has a non-circular cross-section, comprising a recessed flat 752.

When it is desired to actuate thumb button 310, thumb button 310 is pulled proximally to release seat 742 from engagement with tab 750 (i.e., by moving seat 742 proximally such that seat 742 no longer contacts tab 750), and thumb button 310 is rotated 180 degrees (i.e., along an arc 755) so that member 740 is arcuately aligned with recessed flat 752 of handle 200. See FIG. 96. As this occurs, distally-extending member 740 of stop 735 no longer contacts proximal end 240 of handle 200 and distally-extending member 740 is able to move distally along one side of handle 200 (i.e., along recessed flat 752). If it is desired to thereafter re-engage stop 735, thumb button 310 can be again pulled proximally and then rotated 180 degrees so that seat 742 of distally-extending member 740 is aligned with tab 750 of handle 200, such that seat 742 will re-engage tab 750 if thumb button 310 should be moved distally.

In another form of the invention, and looking now at FIG. 98, an alternative stop 760 may be provided. Stop 760 comprises a tab 765 which is hingedly mounted to thumb button 310. Tab 765 comprises a cutout 770 for releasably engaging the shaft of thumb button 310 as tab 765 is swung toward the shaft of thumb button 310. In this manner, tab 765 can be selectively interposed between the head of thumb button 310 and proximal end 240 of handle 200, whereby to prevent undesired actuation of thumb button 310.

When it is desired to actuate thumb button 310, tab 765 is swung radially away from the shaft of thumb button 310, cutout 770 disengages from the shaft of thumb button 310 and the body of tab 765 is no longer interposed between proximal end 240 of handle 200 and the head of thumb button 310, whereby to allow thumb button 310 to be actuated as desired. If it is thereafter desired to lock thumb button 310 against actuation, tab 765 can be swung inwardly such that cutout 770 re-engages the shaft of thumb button 310 and is re-interposed between thumb button 310 and proximal end 240 of handle 200.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. Apparatus for attaching a suture to an object, said apparatus comprising:
    an anchor comprising a body having a distal end and a proximal end, and a vertical bore extending through said body substantially perpendicular to the longitudinal axis of said body;
    wherein said anchor further comprises a recess formed on one side of said body and a U-shaped slot formed on the opposing side of said body, wherein the recess and the U-shaped slot together form a flexible finger extending distally within said body, and further wherein said distal end of said flexible finger is spaced from a bottom edge of the U-shaped slot; and
    wherein at least one of said flexible finger and said body comprises a cutout extending therethrough, with said cutout cooperating with said U-shaped slot and said recess so as to together form a suture loading hole extending through said body, with said suture loading hole being sized larger than the space between the distal end of said flexible finger and the bottom edge of the U-shaped slot so as to receive a suture in the suture loading hole without displacing the flexible finger relative to the body.

2. Apparatus according to claim 1 wherein said cutout is formed in said flexible finger.

3. Apparatus according to claim 1 wherein said cutout extends substantially perpendicular to the longitudinal axis of said body.

4. Apparatus according to claim 1 wherein said body is generally cylindrical.

5. Apparatus according to claim 1 wherein said distal end of said body comprises an inclined distal end surface.

6. Apparatus according to claim 1 wherein said distal end of said flexible finger is spaced from the bottom edge of the U-shaped slot by a distance which is less than the diameter of the suture, such that said flexible finger applies a compressive force against the suture when a suture extends between said flexible finger and the bottom edge of the U-shaped slot.

7. Apparatus according to claim 6 wherein the distance is approximately 50% of the width of the suture.

8. Apparatus according to claim 1 wherein said anchor further comprises a horizontally-extending slot formed in said anchor and in communication with said vertical bore and said recess.

9. Apparatus according to claim 8 wherein said horizontally-extending slot comprises a wider outer portion and a narrower inner portion.

10. Apparatus according to claim 9 wherein the wider outer portion is sized to slidably receive the suture, and further wherein the narrower inner portion is sized to snugly receive the suture.

11. Apparatus according to claim 1 wherein the apparatus further comprises the suture, said suture having a proximal end and a distal end, with an enlargement formed at said distal end.

12. Apparatus according to claim 11 wherein said suture extends through said vertical bore of said anchor.

13. Apparatus according to claim 12 wherein said proximal end of said suture extends through said recess and through said U-shaped slot.

14. Apparatus according to claim 12 wherein said suture extends through said recess and said cutout before said suture extends through said recess and through said U-shaped slot.

15. Apparatus according to claim 1 further comprising an inserter, said inserter comprising:
a handle;
a tube mounted to said handle and extending distally therefrom, said tube being sized to receive said anchor;
a push rod slidably disposed within said tube; and
a suture sled movably mounted to said handle, said suture sled comprising means for releasably securing said suture to said suture sled.

16. Apparatus according to claim 15 wherein said handle comprises a distal end and a proximal end, wherein said tube extends distally from said distal end of said handle, and further wherein a thumb button is disposed on said proximal end of said handle, said thumb button being configured to selectively move said push rod distally when said thumb button is moved distally.

17. Apparatus according to claim 16 wherein said handle comprises at least one flat edge and said thumb button comprises a stop extending distally from said thumb button, wherein said thumb button is rotatably mounted to said handle, and further wherein said thumb button can only be moved distally when said stop is aligned with said at least one flat edge of said handle.

18. Apparatus according to claim 17 wherein said thumb button is locked against rotation relative to said handle until said thumb button is pulled proximally.

19. Apparatus according to claim 15 wherein said handle comprises a distal end and a proximal end, wherein said tube extends distally from said distal end of said handle, wherein a thumb button shaft extends proximally from the proximal end of said handle, and further wherein a thumb button is disposed on the proximal end of said thumb button shaft, said thumb button being configured to selectively move said push rod distally when said thumb button is moved distally.

20. Apparatus according to claim 19 wherein said thumb button comprises a tab hingedly mounted to said thumb button, wherein said tab is configured to engage said thumb button shaft and prevent distal movement of said thumb button when said tab is disposed in a first position, and wherein said tab is configured to disengage said thumb button shaft and allow distal movement of said thumb button when said tab is disposed in a second position.

21. A method for attaching a suture to an object, said method comprising
providing apparatus comprising:
an anchor comprising a body having a distal end and a proximal end, and a vertical bore extending through said body substantially perpendicular to the longitudinal axis of said body;
wherein said anchor further comprises a recess formed on one side of said body and a U-shaped slot formed on the opposing side of said body, wherein the recess and the U-shaped slot together form a flexible finger extending distally within said body, and further wherein said distal end of said flexible finger is spaced from a bottom edge of the U-shaped slot; and
wherein at least one of said flexible finger and said body comprises a cutout extending therethrough, with said cutout cooperating with said U-shaped slot and said recess so as to together form a suture loading hole extending through said body, with said suture loading hole being sized larger than the space between the distal end of said flexible finger and the bottom edge of the U-shaped slot so as to receive a suture in the suture loading hole without displacing the flexible finger relative to the body; and
a suture comprising a proximal end and a distal end; and
passing said suture through said vertical bore of said anchor, forming a loop, passing said suture back through said vertical bore of said anchor, and passing said suture through said suture loading hole without displacing the flexible finger relative to the body.

22. A method according to claim 21 wherein said cutout is formed in said flexible finger.

23. A method according to claim 21 wherein said cutout extends substantially perpendicular to the longitudinal axis of said body.

24. A method according to claim 21 further comprising:
pulling said suture out of said suture loading hole so that said suture extends into the space between the distal end of the flexible finger and the bottom edge of the U-shaped slot.

25. A method according to claim 24 further comprising:
advancing said anchor into the object; and
pulling on said proximal end of said suture.

26. A method according to claim 21 wherein said body is generally cylindrical.

27. A method according to claim 21 wherein said distal end of said body comprises an inclined distal end surface.

28. A method according to claim 27 wherein an enlargement is formed at said distal end of said suture.

29. A method according to claim 21 wherein said distal end of said flexible finger is spaced from the bottom edge of the U-shaped slot by a distance which is less than the diameter of the suture, such that said flexible finger applies a compressive force against the suture when a suture extends between said flexible finger and the bottom edge of the U-shaped slot.

30. A method according to claim 29 wherein the distance is approximately 50% of the width of the suture.

31. A method according to claim 21 wherein said anchor further comprises a horizontally-extending slot formed in said anchor and in communication with said vertical bore and said recess.

32. A method according to claim 31 wherein said horizontally-extending slot comprises a wider outer portion and a narrower inner portion.

33. A method according to claim 32 wherein the wider outer portion is sized to slidably receive the suture, and further wherein the narrower inner portion is sized to snugly receive the suture.

* * * * *